(12) United States Patent
Poole et al.

(10) Patent No.: US 10,564,239 B2
(45) Date of Patent: *Feb. 18, 2020

(54) LOW-FIELD MAGNETIC RESONANCE IMAGING METHODS AND APPARATUS

(71) Applicant: Hyperfine Research, Inc., Guilford, CT (US)

(72) Inventors: Michael Stephen Poole, Guilford, CT (US); Cedric Hugon, Guilford, CT (US); Christopher Thomas McNulty, Guilford, CT (US)

(73) Assignee: Hyperfine Research, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/275,295

(22) Filed: Feb. 13, 2019

(65) Prior Publication Data

US 2019/0178963 A1 Jun. 13, 2019

Related U.S. Application Data

(63) Continuation of application No. 15/956,554, filed on Apr. 18, 2018, now Pat. No. 10,281,541, which is a
(Continued)

(51) Int. Cl.
*G01V 3/00* (2006.01)
*G01R 33/385* (2006.01)
(Continued)

(52) U.S. Cl.
CPC ........ *G01R 33/3852* (2013.01); *A61B 5/0555* (2013.01); *A61B 6/4405* (2013.01);
(Continued)

(58) Field of Classification Search
CPC .............................................. G01R 33/3852
(Continued)

(56) References Cited

U.S. PATENT DOCUMENTS 5,153,546 A 10/1992 Laskaris
5,194,810 A 3/1993 Breneman
(Continued)

FOREIGN PATENT DOCUMENTS

WO WO 2016/183284 A1 11/2016

OTHER PUBLICATIONS

International Search Report and Written Opinion for International Application No. PCT/US2017/63000 dated Apr. 9, 2018.
(Continued)

*Primary Examiner* — Louis M Arana
(74) *Attorney, Agent, or Firm* — Wolf, Greenfield & Sacks, P.C.

(57) ABSTRACT

According to some aspects, a low-field magnetic resonance imaging system is provided. The low-field magnetic resonance imaging system comprises a magnetics system having a plurality of magnetics components configured to produce magnetic fields for performing magnetic resonance imaging, the magnetics system comprising, a B0 magnet configured to produce a B0 field for the magnetic resonance imaging system at a low-field strength of less than 0.2 Tesla (T), a plurality of gradient coils configured to, when operated, generate magnetic fields to provide spatial encoding of magnetic resonance signals, and at least one radio frequency coil configured to, when operated, transmit radio frequency signals to a field of view of the magnetic resonance imaging system and to respond to magnetic resonance signals emitted from the field of view, a power system comprising one or more power components configured to provide power to the magnetics system to operate the magnetic resonance imaging system to perform image acquisition, and a power connection configured to connect to a single-phase outlet to receive mains electricity and deliver the mains electricity to the power system to provide power needed to operate the
(Continued)

magnetic resonance imaging system. According to some aspects, the power system operates the low-field magnetic resonance imaging system using an average of less than 1.6 kilowatts during image acquisition.

30 Claims, 74 Drawing Sheets

Related U.S. Application Data continuation-in-part of application No. 15/821,207, filed on Nov. 22, 2017, which is a continuation-in-part of application No. 15/640,369, filed on Jun. 30, 2017.

(60) Provisional application No. 62/425,465, filed on Nov. 22, 2016.

(51) Int. Cl.

| | |
|---|---|
| G01R 33/383 | (2006.01) |
| G01R 33/44 | (2006.01) |
| A61B 50/13 | (2016.01) |
| G01R 33/389 | (2006.01) |
| G01R 33/421 | (2006.01) |
| G01R 33/56 | (2006.01) |
| G01R 33/38 | (2006.01) |
| A61B 5/055 | (2006.01) |
| A61B 6/00 | (2006.01) |
| A61G 13/10 | (2006.01) |
| G01R 33/34 | (2006.01) |
| G01R 33/48 | (2006.01) |
| A61B 90/00 | (2016.01) |
| G01R 33/3873 | (2006.01) |
| G01R 33/36 | (2006.01) |
| G01R 33/422 | (2006.01) |

(52) U.S. Cl.
CPC .............. *A61B 50/13* (2016.02); *A61B 90/00* (2016.02); *A61G 13/104* (2013.01); *G01R 33/34092* (2013.01); *G01R 33/38* (2013.01); *G01R 33/383* (2013.01); *G01R 33/389* (2013.01); *G01R 33/4215* (2013.01); *G01R 33/445* (2013.01); *G01R 33/48* (2013.01); *G01R 33/5608* (2013.01); *A61B 2560/0431* (2013.01); *G01R 33/3642* (2013.01); *G01R 33/3657* (2013.01); *G01R 33/3802* (2013.01); *G01R 33/385* (2013.01); *G01R 33/3806* (2013.01); *G01R 33/3854* (2013.01); *G01R 33/3873* (2013.01); *G01R 33/422* (2013.01)

(58) Field of Classification Search
USPC ................................................ 324/319, 320
See application file for complete search history.

(56) References Cited

U.S. PATENT DOCUMENTS

| | | | |
|---|---|---|---|
| 5,203,332 A | 4/1993 | Leunbach | |
| 5,382,904 A | 1/1995 | Pissanetzky | |
| 5,390,673 A | 2/1995 | Kikinis | |
| 5,423,315 A | 6/1995 | Margosian et al. | |
| 5,659,281 A | 8/1997 | Pissanetzky et al. | |
| 5,808,376 A | 9/1998 | Gordon et al. | |
| 6,131,690 A | 10/2000 | Galando et al. | |
| 6,317,618 B1 | 11/2001 | Livni et al. | |
| 6,452,472 B1 | 9/2002 | Aoki et al. | |
| 6,611,702 B2 | 8/2003 | Rohling et al. | |
| 7,019,610 B2 | 3/2006 | Creighton, IV et al. | |
| 7,116,102 B2 | 10/2006 | Clarke et al. | |
| 7,218,104 B2 | 5/2007 | Clarke et al. | |
| 7,417,426 B2 | 8/2008 | Race et al. | |
| 7,538,553 B2 | 5/2009 | Trequattrini et al. | |
| 7,759,938 B2 | 7/2010 | Prado et al. | |
| 7,834,270 B2 | 11/2010 | Zhu et al. | |
| 7,966,059 B2 | 6/2011 | Creighton, IV et al. | |
| 8,120,358 B2 | 2/2012 | Du | |
| 8,335,359 B2 | 12/2012 | Fidrich et al. | |
| 8,368,402 B2 | 2/2013 | Lee et al. | |
| 8,378,682 B2 | 2/2013 | Subbarao | |
| 8,570,042 B2 | 10/2013 | Pines et al. | |
| 8,614,575 B2 | 12/2013 | Demas et al. | |
| 8,699,199 B2 | 4/2014 | Blakes | |
| 8,901,928 B2 | 12/2014 | Alexiuk et al. | |
| 8,993,898 B2 | 3/2015 | Weibler et al. | |
| 9,222,998 B2 | 12/2015 | Teklemariam et al. | |
| 9,500,727 B2 | 11/2016 | Sohn et al. | |
| 9,541,616 B2 | 1/2017 | Rothberg et al. | |
| 9,547,057 B2 | 1/2017 | Rearick et al. | |
| 9,625,543 B2 | 4/2017 | Rearick et al. | |
| 9,625,544 B2 | 4/2017 | Poole et al. | |
| 9,638,773 B2 | 5/2017 | Poole et al. | |
| 9,645,210 B2 | 5/2017 | McNulty et al. | |
| 9,797,971 B2 | 10/2017 | Rearick et al. | |
| 9,817,093 B2 | 11/2017 | Rothberg et al. | |
| 9,897,668 B2 | 2/2018 | Piron et al. | |
| 9,910,115 B2 | 3/2018 | Wald et al. | |
| 10,139,464 B2 | 11/2018 | Rearick et al. | |
| 10,145,913 B2 | 12/2018 | Hugon et al. | |
| 10,145,922 B2 | 12/2018 | Rothberg et al. | |
| 10,222,434 B2 | 3/2019 | Poole et al. | |
| 10,222,435 B2 | 3/2019 | Mileski et al. | |
| 10,241,177 B2 | 3/2019 | Poole et al. | |
| 10,274,561 B2 | 4/2019 | Poole et al. | |
| 10,281,540 B2 | 5/2019 | Mileski et al. | |
| 10,281,541 B2 * | 5/2019 | Poole | A61B 90/00 |
| 10,295,628 B2 | 5/2019 | Mileski et al. | |
| 10,310,037 B2 | 6/2019 | McNulty et al. | |
| 10,324,147 B2 | 6/2019 | McNulty et al. | |
| 10,330,755 B2 | 6/2019 | Poole et al. | |
| 10,353,030 B2 | 7/2019 | Poole et al. | |
| 2002/0175792 A1 | 11/2002 | Laskaris et al. | |
| 2005/0218896 A1 | 10/2005 | Gortler | |
| 2006/0077027 A1 | 4/2006 | Aoki | |
| 2006/0241333 A1 | 10/2006 | Hunter | |
| 2007/0120631 A1 | 5/2007 | Hobbs et al. | |
| 2007/0285197 A1 | 12/2007 | Shi et al. | |
| 2009/0099444 A1 | 4/2009 | Bogdanov | |
| 2009/0167304 A1 | 7/2009 | Prado et al. | |
| 2010/0000780 A1 | 1/2010 | Zhu et al. | |
| 2010/0219833 A1 | 9/2010 | McGinley et al. | |
| 2011/0088940 A1 | 4/2011 | Nordling et al. | |
| 2011/0115485 A1 | 5/2011 | Subbarao | |
| 2011/0210739 A1 | 9/2011 | Ham | |
| 2011/0248715 A1 | 10/2011 | Telemariam et al. | |
| 2012/0196753 A1 | 8/2012 | Laskaris et al. | |
| 2012/0323110 A1 | 12/2012 | Blake et al. | |
| 2013/0271142 A1 | 10/2013 | Penanen et al. | |
| 2013/0278255 A1 | 10/2013 | Khalighi et al. | |
| 2013/0285659 A1 | 10/2013 | Sohn et al. | |
| 2014/0111202 A1 | 4/2014 | Wald et al. | |
| 2014/0155732 A1 | 6/2014 | Patz et al. | |
| 2014/0347053 A1 | 11/2014 | Dempsey et al. | |
| 2015/0141799 A1 | 5/2015 | Rapoport et al. | |
| 2015/0177343 A1 | 6/2015 | Wald et al. | |
| 2015/0230810 A1 | 8/2015 | Creighton et al. | |
| 2015/0253401 A1 | 9/2015 | Rapoport | |
| 2015/0285882 A1 | 10/2015 | Mezrich et al. | |
| 2015/0301134 A1 | 10/2015 | Hoshino et al. | |
| 2015/0342177 A1 | 12/2015 | Hassanein et al. | |
| 2016/0011290 A1 | 1/2016 | Iannello | |
| 2016/0069968 A1 | 3/2016 | Rothberg et al. | |
| 2016/0069970 A1 | 3/2016 | Rearick et al. | |
| 2016/0069971 A1 | 3/2016 | McNulty et al. | |
| 2016/0069972 A1 | 3/2016 | Poole et al. | |
| 2016/0069975 A1 | 3/2016 | Rothberg et al. | |
| 2016/0128592 A1 | 5/2016 | Rosen et al. | |
| 2016/0131727 A1 | 5/2016 | Sacolick et al. | |
| 2016/0169992 A1 | 6/2016 | Rothberg et al. | |
| 2016/0169993 A1 | 6/2016 | Rearick et al. | |

(56) References Cited

U.S. PATENT DOCUMENTS

| | | |
|---|---|---|
| 2016/0187436 A1 | 6/2016 | Piron et al. |
| 2016/0223631 A1 | 8/2016 | Poole et al. |
| 2016/0231399 A1 | 8/2016 | Rothberg et al. |
| 2016/0231402 A1 | 8/2016 | Rothberg et al. |
| 2016/0231403 A1 | 8/2016 | Rothberg et al. |
| 2016/0231404 A1 | 8/2016 | Rothberg et al. |
| 2016/0299203 A1 | 10/2016 | Mileski et al. |
| 2016/0334479 A1 | 11/2016 | Poole et al. |
| 2016/0356869 A1 | 12/2016 | Dempsey et al. |
| 2017/0007148 A1 | 1/2017 | Kaditz et al. |
| 2017/0011255 A1 | 1/2017 | Kaditz et al. |
| 2017/0102443 A1 | 4/2017 | Rearick et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2017/0285122 A1 | 10/2017 | Kaditz et al. |
| 2018/0024208 A1 | 1/2018 | Rothberg et al. |
| 2018/0038931 A1 | 2/2018 | Rearick et al. |
| 2018/0088193 A1 | 3/2018 | Rearick et al. |
| 2018/0136292 A1 | 5/2018 | Piron et al. |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0210047 A1 | 7/2018 | Poole et al. |
| 2018/0224512 A1 | 8/2018 | Poole et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2019/0004130 A1 | 1/2019 | Poole et al. |
| 2019/0011510 A1 | 1/2019 | Hugon et al. |
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0086497 A1 | 3/2019 | Rearick et al. |
| 2019/0101607 A1 | 4/2019 | Rothberg et al. |
| 2019/0162806 A1 | 5/2019 | Poole et al. |
| 2019/0178962 A1 | 6/2019 | Poole et al. |
| 2019/0178963 A1 | 6/2019 | Poole et al. |

OTHER PUBLICATIONS

International Preliminary Report on Patentability for International Application No. PCT/US2017/63000 dated Jun. 6, 2019.
U.S. Appl. No. 15/956,554, filed Apr. 18, 2018, Poole.

* cited by examiner

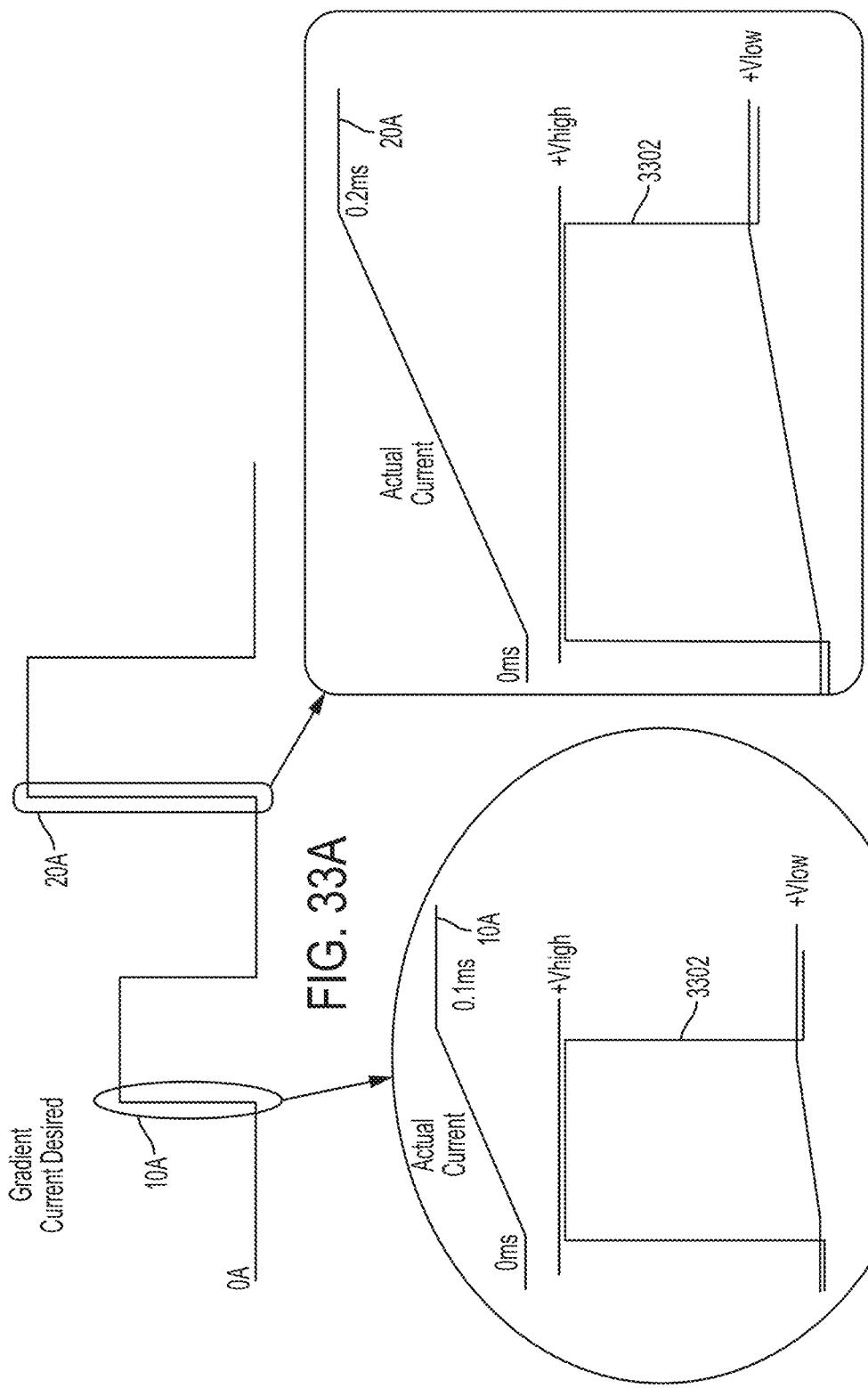

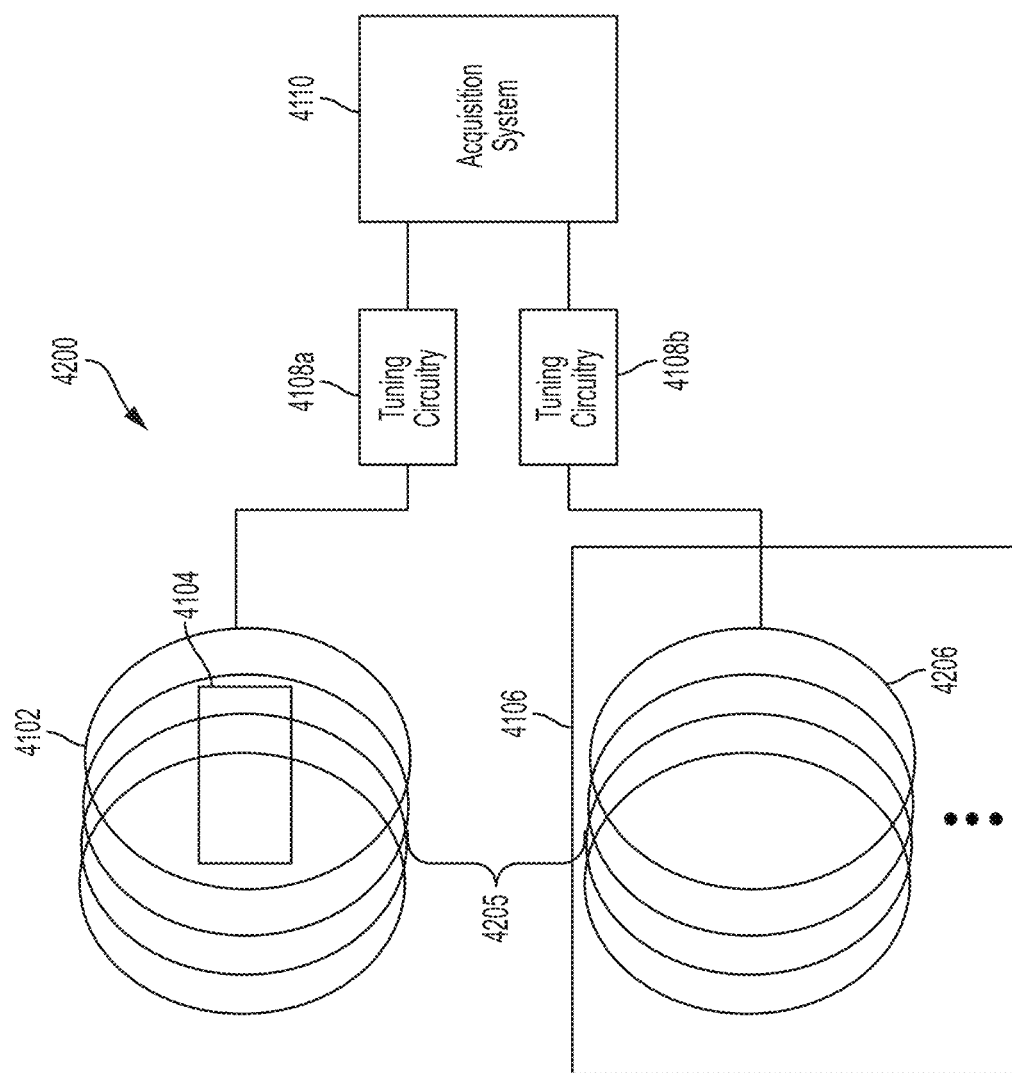

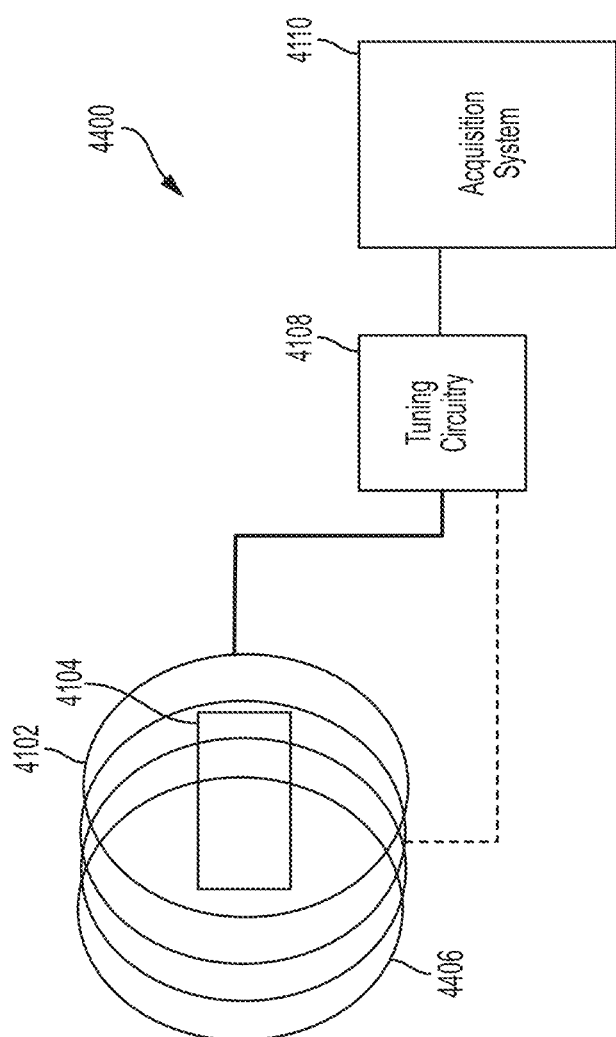

LOW-FIELD MAGNETIC RESONANCE IMAGING METHODS AND APPARATUS

CROSS REFERENCE TO RELATED APPLICATIONS

This application claims priority under 35 U.S.C. § 120 and is a continuation (CON) of U.S. application Ser. No. 15/956,554, filed Apr. 18, 2018 and titled "Low-Field Magnetic Resonance Imaging Methods and Apparatus," which claims priority under 35 U.S.C. § 120 and is a continuation-in-part (CIP) of U.S. application Ser. No. 15/821,207, filed Nov. 22, 2017 and titled "Low-Field Magnetic Resonance Imaging Methods and Apparatus," which claims priority under 35 U.S.C. § 119 to U.S. Provisional Application Ser. No. 62/425,465, filed Nov. 22, 2016, and titled LOW-FIELD MAGNETIC RESONANCE IMAGING METHODS AND APPARATUS, and which claims priority under 35 U.S.C. § 120 and is a continuation-in-part (CIP) of U.S. application Ser. No. 15/640,369, filed Jun. 30, 2017 and titled "Low-Field Magnetic Resonance Imaging Methods and Apparatus," which also claims priority under 35 U.S.C. § 119 to U.S. Provisional Application Ser. No. 62/425,465, filed Nov. 22, 2016, and titled LOW-FIELD MAGNETIC RESONANCE IMAGING METHODS AND APPARATUS, each application of which is herein incorporated by reference in its entirety.

BACKGROUND

Magnetic resonance imaging (MRI) provides an important imaging modality for numerous applications and is widely utilized in clinical and research settings to produce images of the inside of the human body. As a generality, MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to the ability to produce non-invasive images having relatively high resolution and contrast without the safety concerns of other modalities (e.g., without needing to expose the subject to ionizing radiation, e.g., x-rays, or introducing radioactive material to the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to MRI that, for a given imaging application, may involve the relatively high cost of the equipment, limited availability and/or difficulty in gaining access to clinical MRI scanners and/or the length of the image acquisition process.

The trend in clinical MRI has been to increase the field strength of MRI scanners to improve one or more of scan time, image resolution, and image contrast, which, in turn, continues to drive up costs. The vast majority of installed MRI scanners operate at 1.5 or 3 tesla (T), which refers to the field strength of the main magnetic field $B_0$. A rough cost estimate for a clinical MRI scanner is approximately one million dollars per tesla, which does not factor in the substantial operation, service, and maintenance costs involved in operating such MRI scanners.

Additionally, conventional high-field MRI systems typically require large superconducting magnets and associated electronics to generate a strong uniform static magnetic field ($B_0$) in which an object (e.g., a patient) is imaged. The size of such systems is considerable with a typical MRI installment including multiple rooms for the magnet, electronics, thermal management system, and control console areas. The size and expense of MRI systems generally limits their usage to facilities, such as hospitals and academic research centers, which have sufficient space and resources to purchase and maintain them. The high cost and substantial space requirements of high-field MRI systems results in limited availability of MRI scanners. As such, there are frequently clinical situations in which an MRI scan would be beneficial, but due to one or more of the limitations discussed above, is not practical or is impossible, as discussed in further detail below.

SUMMARY

Some embodiments include a low-field magnetic resonance imaging system comprising a magnetics system having a plurality of magnetics components configured to produce magnetic fields for performing magnetic resonance imaging, the magnetics system comprising a B0 magnet configured to produce a B0 field for the magnetic resonance imaging system at a low-field strength of less than 0.2 Tesla (T), a plurality of gradient coils configured to, when operated, generate magnetic fields to provide spatial encoding of magnetic resonance signals, and at least one radio frequency coil configured to, when operated, transmit radio frequency signals to a field of view of the magnetic resonance imaging system and to respond to magnetic resonance signals emitted from the field of view. The low-field magnetic resonance system further comprises a power system comprising one or more power components configured to provide power to the magnetics system to operate the magnetic resonance imaging system to perform image acquisition, and a power connection configured to connect to a single-phase outlet to receive mains electricity and deliver the mains electricity to the power system to provide power needed to operate the magnetic resonance imaging system.

Some embodiments include a low-field magnetic resonance imaging system comprising a magnetics system having a plurality of magnetics components configured to produce magnetic fields for performing magnetic resonance imaging, the magnetics system comprising a B0 magnet configured to produce a B0 field for the magnetic resonance imaging system at a low-field strength of less than 0.2 Tesla (T), a plurality of gradient coils configured to, when operated, generate magnetic fields to provide spatial encoding of emitted magnetic resonance signals, and at least one radio frequency coil configured to, when operated, transmit radio frequency signals to a field of view of the magnetic resonance imaging system and to respond to magnetic resonance signals emitted from the field of view, and a power system comprising one or more power components configured to provide power to the magnetics system to operate the magnetic resonance imaging system to perform image acquisition, wherein the power system operates the low-field magnetic resonance imaging system using an average of less than 5 kilowatts during image acquisition.

Some embodiments include a low-field magnetic resonance imaging system comprising a magnetics system having a plurality of magnetics components configured to produce magnetic fields for performing magnetic resonance imaging, the magnetics system comprising a $B_0$ magnet configured to produce a $B_0$ field for the magnetic resonance imaging system, a plurality of gradient coils configured to, when operated, generate magnetic fields to provide spatial encoding of emitted magnetic resonance signals, and at least one radio frequency coil configured to, when operated, transmit radio frequency signals to the field of view of the magnetic resonance imaging system and to respond to magnetic resonance signals emitted from the field of view. The low-field magnetic resonance imaging system further comprises a power system comprising one or more power components configured to provide power to the magnetics system to operate the magnetic resonance imaging system to perform image acquisition, wherein the power system operates the low-field magnetic resonance imaging system using an average of less than 1.6 kilowatts during image acquisition.

Some embodiments include a portable magnetic resonance imaging system comprising a magnetics system having a plurality of magnetics components configured to produce magnetic fields for performing magnetic resonance imaging, the magnetics system comprising a permanent B0 magnet configured to produce a B0 field for the magnetic resonance imaging system and a plurality of gradient coils configured to, when operated, generate magnetic fields to provide spatial encoding of emitted magnetic resonance signals. The portable magnetic resonance imaging system further comprises a power system comprising one or more power components configured to provide power to the magnetics system to operate the magnetic resonance imaging system to perform image acquisition, and a base that supports the magnetics system and houses the power system, the base comprising at least one conveyance mechanism allowing the portable magnetic resonance imaging system to be transported to different locations.

Some embodiments include a portable magnetic resonance imaging system comprising a magnetics system having a plurality of magnetics components configured to produce magnetic fields for performing magnetic resonance imaging, the magnetics system comprising a permanent $B_0$ magnet configured to produce a $B_0$ field for the magnetic resonance imaging system, a plurality of gradient coils configured to, when operated, generate magnetic fields to provide spatial encoding of emitted magnetic resonance signals, and at least one radio frequency transmit coil. The portable magnetic resonance imaging system further comprises power system comprising one or more power components configured to provide power to the magnetics system to operate the magnetic resonance imaging system to perform image acquisition, and a base that supports the magnetics system and houses the power system, the base having a maximum horizontal dimension of less than or equal to approximately 50 inches.

Some embodiments include a portable magnetic resonance imaging system comprising a magnetics system having a plurality of magnetics components configured to produce magnetic fields for performing magnetic resonance imaging, the magnetics system comprising a permanent $B_0$ magnet configured to produce a $B_0$ field for the magnetic resonance imaging system, a plurality of gradient coils configured to, when operated, generate magnetic fields to provide spatial encoding of emitted magnetic resonance signals, and at least one radio frequency transmit coil. The portable magnetic resonance imaging system further comprises power system comprising one or more power components configured to provide power to the magnetics system to operate the magnetic resonance imaging system to perform image acquisition, and a base that supports the magnetics system and houses the power system, wherein the portable magnetic resonance imaging system weighs less than 1,500 pounds.

Some embodiments include a low-field magnetic resonance imaging system comprising a magnetics system having a plurality of magnetics components configured to produce magnetic fields for performing magnetic resonance imaging, the magnetics system comprising a permanent $B_0$ magnet configured to produce a $B_0$ field having a field strength of less than or equal to approximately 0.1 T, and a plurality of gradient coils configured to, when operated, generate magnetic fields to provide spatial encoding of magnetic resonance signals; and at least one radio frequency coil configured to, when operated, transmit radio frequency signals to a field of view of the magnetic resonance imaging system and to respond to magnetic resonance signals emitted from the field of view. The low-field magnetic resonance imaging system further comprises at least one controller configured to operate the magnetics system in accordance with a predetermined pulse sequence to acquire at least one image.

Some embodiments include a low-field magnetic resonance imaging system comprising a magnetics system having a plurality of magnetics components configured to produce magnetic fields for performing magnetic resonance imaging, the magnetics system comprising a permanent $B_0$ magnet configured to produce a $B_0$ field having a field strength of less than or equal to approximately 0.1 T, and a plurality of gradient coils configured to, when operated, generate magnetic fields to provide spatial encoding of magnetic resonance signals; and at least one radio frequency coil configured to, when operated, transmit radio frequency signals to a field of view of the magnetic resonance imaging system and to respond to magnetic resonance signals emitted from the field of view, wherein the low-field magnetic resonance imaging system has a 5-Gauss line that has a maximum dimension of less than or equal to five feet.

Some embodiment include a magnetic resonance imaging system comprising a $B_0$ magnet configured to produce a $B_0$ field for the magnetic resonance imaging system, and a positioning member coupled to the $B_0$ magnet and configured to allow the $B_0$ magnet to be manually rotated to a plurality of positions, each of the plurality of positions placing the $B_0$ magnet at a different angle.

Some embodiments include a portable magnetic resonance imaging system comprising a magnetics system having a plurality of magnetics components configured to produce magnetic fields for performing magnetic resonance imaging, the magnetics system comprising a B0 magnet configured to produce a $B_0$ field for the magnetic resonance imaging system, and a plurality of gradient coils configured to, when operated, generate magnetic fields to provide spatial encoding of emitted magnetic resonance signals. The portable magnetic resonance imaging system further comprises a power system comprising one or more power components configured to provide power to the magnetics system to operate the magnetic resonance imaging system to perform image acquisition, a base that supports the magnetics system and houses the power system, the base comprising at least one conveyance mechanism allowing the portable magnetic resonance imaging system to be transported desired locations, and a positioning member coupled to the B0 magnet and configured to allow the B0 magnet to be rotated to a desired angle.

Some embodiments include a portable magnetic resonance imaging system comprising a B0 magnet configured to produce a B0 field for an imaging region of the magnetic resonance imaging system, a housing for the B0 magnet, and at least one electromagnetic shield adjustably coupled to the housing to provide electromagnetic shielding for the imaging region in an amount that is configurable by adjusting the at least one electromagnetic shield about the imaging region.

Some embodiments include a portable magnetic resonance imaging system comprising a $B_0$ magnet configured to produce a $B_0$ magnetic field for an imaging region of the magnetic resonance imaging system, a noise reduction system configured to detect and suppress at least some electromagnetic noise in an operating environment of the portable magnetic resonance imaging system, and electromagnetic shielding provided to attenuate at least some of the electromagnetic noise in the operating environment of the portable magnetic resonance imaging system, the electromagnetic shielding arranged to shield a fraction of the imaging region of the portable magnetic resonance imaging system.

Some embodiments include a portable magnetic resonance imaging system comprising a $B_0$ magnet configured to produce a $B_0$ field for an imaging region of the magnetic resonance imaging system, a noise reduction system configured to detect and suppress at least some electromagnetic noise in an operating environment of the portable magnetic resonance imaging system, and electromagnetic shielding for at least a portion of the portable magnetic resonance imaging system, the electromagnetic shielding providing substantially no shielding of the imaging region of the portable magnetic resonance imaging system.

Some embodiments include a portable magnetic resonance imaging system comprising a $B_0$ magnet configured to produce a $B_0$ field for an imaging region of the magnetic resonance imaging system, a housing for the $B_0$ magnet, and at least one electromagnetic shield structure adjustably coupled to the housing to provide electromagnetic shielding for the imaging region in an amount that can be varied by adjusting the at least one electromagnetic shield structure about the imaging region.

BRIEF DESCRIPTION OF THE DRAWINGS

Various aspects and embodiments of the disclosed technology will be described with reference to the following figures. It should be appreciated that the figures are not necessarily drawn to scale.

FIGS. 33A-D show a gradient coil current waveform, gradient coil voltage waveform, and power supply terminal voltage waveforms, according to some embodiments.

FIG. 41A-D illustrate exemplary respective examples of a noise reduction system, in accordance with some embodiments;

DETAILED DESCRIPTION

Figure 1:
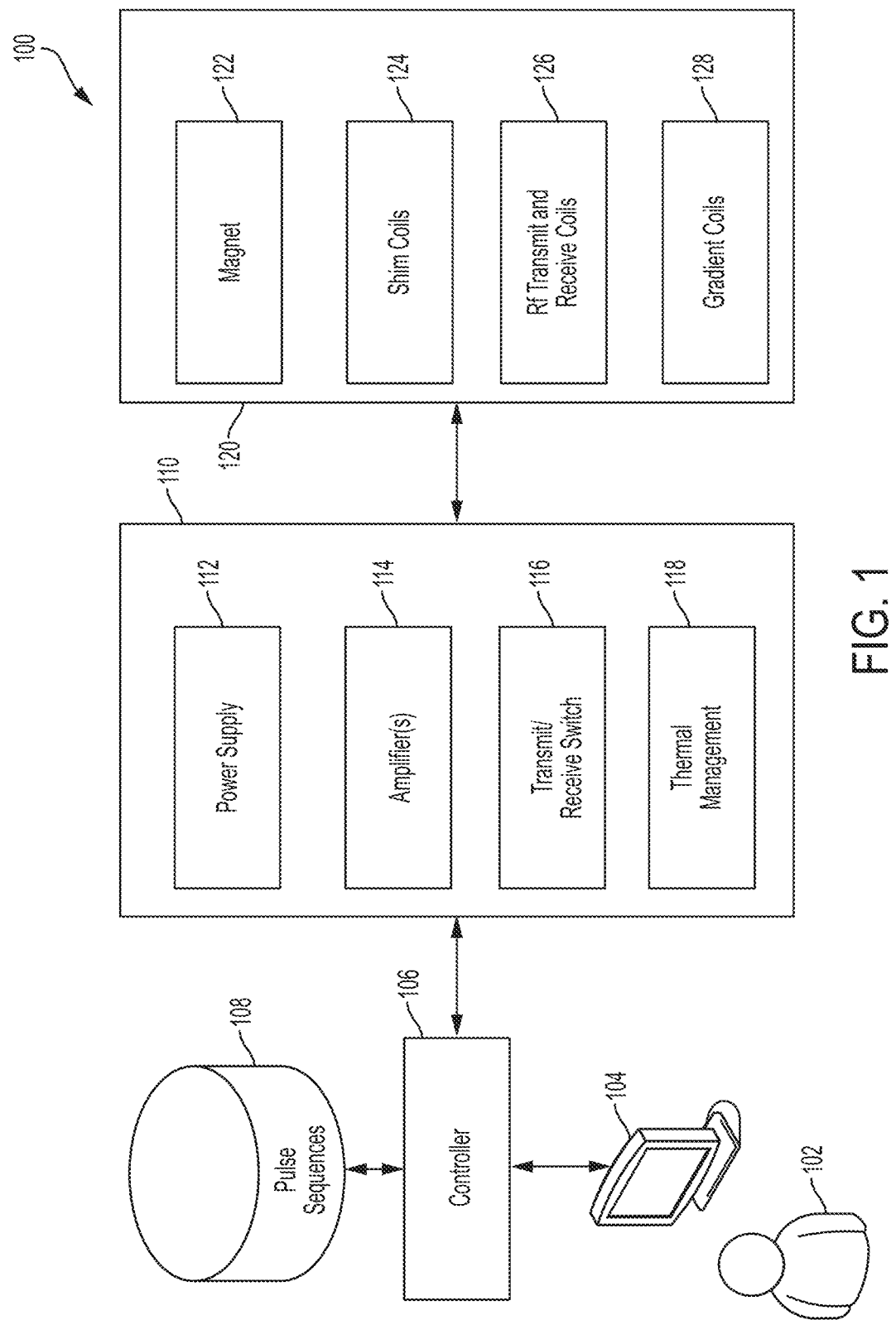
FIG. 1 illustrates exemplary components of a magnetic resonance imaging system.

The MRI scanner market is overwhelmingly dominated by high-field systems, and particularly for medical or clinical MRI applications. As discussed above, the general trend in medical imaging has been to produce MRI scanners with increasingly greater field strengths, with the vast majority of clinical MRI scanners operating at 1.5 T or 3 T, with higher field strengths of 7 T and 9 T used in research settings. As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 T and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1 T have also been characterized as mid-field. By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI systems operating with a $B_0$ field of less than 0.1 T are referred to herein as "very low-field" and low-field MRI systems operating with a $B_0$ field of less than 10 mT are referred to herein as "ultra-low field."

As discussed above, conventional MRI systems require specialized facilities. An electromagnetically shielded room is required for the MRI system to operate and the floor of the room must be structurally reinforced. Additional rooms must be provided for the high-power electronics and the scan technician's control area. Secure access to the site must also be provided. In addition, a dedicated three-phase electrical connection must be installed to provide the power for the electronics that, in turn, are cooled by a chilled water supply. Additional HVAC capacity typically must also be provided. These site requirements are not only costly, but significantly limit the locations where MRI systems can be deployed. Conventional clinical MRI scanners also require substantial expertise to both operate and maintain. These highly trained technicians and service engineers add large on-going operational costs to operating an MRI system. Conventional MRI, as a result, is frequently cost prohibitive and is severely limited in accessibility, preventing MRI from being a widely available diagnostic tool capable of delivering a wide range of clinical imaging solutions wherever and whenever needed. Typically, patient must visit one of a limited number of facilities at a time and place scheduled in advance, preventing MRI from being used in numerous medical applications for which it is uniquely efficacious in assisting with diagnosis, surgery, patient monitoring and the like.

As discussed above, high-field MRI systems require specially adapted facilities to accommodate the size, weight, power consumption and shielding requirements of these systems. For example, a 1.5 T MRI system typically weighs between 4-10 tons and a 3 T MRI system typically weighs between 8-20 tons. In addition, high-field MRI systems generally require significant amounts of heavy and expensive shielding. Many mid-field scanners are even heavier, weighing between 10-20 tons due, in part, to the use of very large permanent magnets and/or yokes. Commercially available low-field MRI systems (e.g., operating with a $B_0$ magnetic field of 0.2 T) are also typically in the range of 10 tons or more due to the large amounts of ferromagnetic material used to generate the $B_0$ field, with additional tonnage in shielding. To accommodate this heavy equipment, rooms (which typically have a minimum size of 30-50 square meters) have to be built with reinforced flooring (e.g., concrete flooring), and must be specially shielded to prevent electromagnetic radiation from interfering with operation of the MRI system. Thus, available clinical MRI systems are immobile and require the significant expense of a large, dedicated space within a hospital or facility, and in addition to the considerable costs of preparing the space for operation, require further additional on-going costs in expertise in operating and maintaining the system.

In addition, currently available MRI systems typically consume large amounts of power. For example, common 1.5 T and 3 T MRI systems typically consume between 20-40 kW of power during operation, while available 0.5 T and 0.2 T MRI systems commonly consume between 5-20 kW, each using dedicated and specialized power sources. Unless otherwise specified, power consumption is referenced as average power consumed over an interval of interest. For example, the 20-40 kW referred to above indicates the average power consumed by conventional MRI systems during the course of image acquisition, which may include relatively short periods of peak power consumption that significantly exceeds the average power consumption (e.g., when the gradient coils and/or RF coils are pulsed over relatively short periods of the pulse sequence). Intervals of peak (or large) power consumption are typically addressed via power storage elements (e.g., capacitors) of the MRI system itself. Thus, the average power consumption is the more relevant number as it generally determines the type of power connection needed to operate the device. As discussed above, available clinical MRI systems must have dedicated power sources, typically requiring a dedicated three-phase connection to the grid to power the components of the MRI system. Additional electronics are then needed to convert the three-phase power into single-phase power utilized by the MRI system. The many physical requirements of deploying conventional clinical MRI systems creates a significant problem of availability and severely restricts the clinical applications for which MRI can be utilized.

Accordingly, the many requirements of high-field MRI render installations prohibitive in many situations, limiting their deployment to large institutional hospitals or specialized facilities and generally restricting their use to tightly scheduled appointments, requiring the patient to visit dedicated facilities at times scheduled in advance. Thus, the many restrictions on high field MRI prevent MRI from being fully utilized as an imaging modality. Despite the drawbacks of high-field MRI mentioned above, the appeal of the significant increase in SNR at higher fields continues to drive the industry to higher and higher field strengths for use in clinical and medical MRI applications, further increasing the cost and complexity of MRI scanners, and further limiting their availability and preventing their use as a general-purpose and/or generally-available imaging solution.

The low SNR of MR signals produced in the low-field regime (particularly in the very low-field regime) has prevented the development of a relatively low cost, low power and/or portable MRI system. Conventional "low-field" MRI systems operate at the high end of what is typically characterized as the low-field range (e.g., clinically available low-field systems have a floor of approximately 0.2 T) to achieve useful images. Though somewhat less expensive than high-field MRI systems, conventional low-field MRI systems share many of the same drawbacks. In particular, conventional low-field MRI systems are large, fixed and immobile installments, consume substantial power (requiring dedicated three-phase power hook-ups) and require specially shielded rooms and large dedicated spaces. The challenges of low-field MRI have prevented the development of relatively low cost, low power and/or portable MRI systems that can produce useful images.

The inventors have developed techniques enabling portable, low-field, low power and/or lower-cost MRI systems that can improve the wide-scale deployability of MRI technology in a variety of environments beyond the current MRI installments at hospitals and research facilities. As a result, MRI can be deployed in emergency rooms, small clinics, doctor's offices, in mobile units, in the field, etc. and may be brought to the patient (e.g., bedside) to perform a wide variety of imaging procedures and protocols. Some embodiments include very low-field MRI systems (e.g., 0.1 T, 50 mT, 20 mT, etc.) that facilitate portable, low-cost, low-power MRI, significantly increasing the availability of MRI in a clinical setting.

There are numerous challenges to developing a clinical MRI system in the low-field regime. As used herein, the term clinical MRI system refers to an MRI system that produces clinically useful images, which refers to an images having sufficient resolution and adequate acquisition times to be useful to a physician or clinician for its intended purpose given a particular imaging application. As such, the resolutions/acquisition times of clinically useful images will depend on the purpose for which the images are being obtained. Among the numerous challenges in obtaining clinically useful images in the low-field regime is the relatively low SNR. Specifically, the relationship between SNR and $B_0$ field strength is approximately $B_0^{5/4}$ at field strength above 0.2 T and approximately $B_0^{3/2}$ at field strengths below 0.1 T. As such, the SNR drops substantially with decreases in field strength with even more significant drops in SNR experienced at very low field strength. This substantial drop in SNR resulting from reducing the field strength is a significant factor that has prevented development of clinical MRI systems in the very low-field regime. In particular, the challenge of the low SNR at very low field strengths has prevented the development of a clinical MRI system operating in the very low-field regime. As a result, clinical MRI systems that seek to operate at lower field strengths have conventionally achieved field strengths of approximately the 0.2 T range and above. These MRI systems are still large, heavy and costly, generally requiring fixed dedicated spaces (or shielded tents) and dedicated power sources.

The inventors have developed low-field and very low-field MRI systems capable of producing clinically useful images, allowing for the development of portable, low cost and easy to use MRI systems not achievable using state of the art technology. According to some embodiments, an MRI system can be transported to the patient to provide a wide variety of diagnostic, surgical, monitoring and/or therapeutic procedures, generally, whenever and wherever needed.

FIG. 1 is a block diagram of typical components of a MRI system 100. In the illustrative example of FIG. 1, MRI system 100 comprises computing device 104, controller 106, pulse sequences store 108, power management system 110, and magnetics components 120. It should be appreciated that system 100 is illustrative and that a MRI system may have one or more other components of any suitable type in addition to or instead of the components illustrated in FIG. 1. However, a MRI system will generally include these high level components, though the implementation of these components for a particular MRI system may differ vastly, as discussed in further detail below.

As illustrated in FIG. 1, magnetics components 120 comprise $B_0$ magnet 122, shim coils 124, RF transmit and receive coils 126, and gradient coils 128. Magnet 122 may be used to generate the main magnetic field $B_0$. Magnet 122 may be any suitable type or combination of magnetics components that can generate a desired main magnetic $B_0$ field. As discussed above, in the high field regime, the $B_0$ magnet is typically formed using superconducting material generally provided in a solenoid geometry, requiring cryogenic cooling systems to keep the $B_0$ magnet in a superconducting state. Thus, high-field $B_0$ magnets are expensive, complicated and consume large amounts of power (e.g., cryogenic cooling systems require significant power to maintain the extremely low temperatures needed to keep the $B_0$ magnet in a superconducting state), require large dedicated spaces, and specialized, dedicated power connections (e.g., a dedicated three-phase power connection to the power grid). Conventional low-field $B_0$ magnets (e.g., $B_0$ magnets operating at 0.2 T) are also often implemented using superconducting material and therefore have these same general requirements. Other conventional low-field $B_0$ magnets are implemented using permanent magnets, which to produce the field strengths to which conventional low-field systems are limited (e.g., between 0.2 T and 0.3 T due to the inability to acquire useful images at lower field strengths), need to be very large magnets weighing 5-20 tons. Thus, the $B_0$ magnet of conventional MRI systems alone prevents both portability and affordability.

Gradient coils 128 may be arranged to provide gradient fields and, for example, may be arranged to generate gradients in the $B_0$ field in three substantially orthogonal directions (X, Y, Z). Gradient coils 128 may be configured to encode emitted MR signals by systematically varying the $B_0$ field (the $B_0$ field generated by magnet 122 and/or shim coils 124) to encode the spatial location of received MR signals as a function of frequency or phase. For example, gradient coils 128 may be configured to vary frequency or phase as a linear function of spatial location along a particular direction, although more complex spatial encoding profiles may also be provided by using nonlinear gradient coils. For example, a first gradient coil may be configured to selectively vary the $B_0$ field in a first (X) direction to perform frequency encoding in that direction, a second gradient coil may be configured to selectively vary the $B_0$ field in a second (Y) direction substantially orthogonal to the first direction to perform phase encoding, and a third gradient coil may be configured to selectively vary the $B_0$ field in a third (Z) direction substantially orthogonal to the first and second directions to enable slice selection for volumetric imaging applications. As discussed above, conventional gradient coils also consume significant power, typically operated by large, expensive gradient power sources, as discussed in further detail below.

MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same coils for transmitting and receiving. Thus, a transmit/receive component may include one or more coils for transmitting, one or more coils for receiving and/or one or more coils for transmitting and receiving. Transmit/receive coils are also often referred to as Tx/Rx or Tx/Rx coils to generically refer to the various configurations for the transmit and receive magnetics component of an MRI system. These terms are used interchangeably herein. In FIG. 1, RF transmit and receive coils 126 comprise one or more transmit coils that may be used to generate RF pulses to induce an oscillating magnetic field $B_1$. The transmit coil(s) may be configured to generate any suitable types of RF pulses.

Power management system 110 includes electronics to provide operating power to one or more components of the low-field MRI system 100. For example, as discussed in more detail below, power management system 110 may include one or more power supplies, gradient power components, transmit coil components, and/or any other suitable power electronics needed to provide suitable operating power to energize and operate components of MRI system 100. As illustrated in FIG. 1, power management system 110 comprises power supply 112, power component(s) 114, transmit/receive switch 116, and thermal management components 118 (e.g., cryogenic cooling equipment for superconducting magnets). Power supply 112 includes electronics to provide operating power to magnetic components 120 of the MRI system 100. For example, power supply 112 may include electronics to provide operating power to one or more $B_0$ coils (e.g., $B_0$ magnet 122) to produce the main magnetic field for the low-field MRI system. Transmit/receive switch 116 may be used to select whether RF transmit coils or RF receive coils are being operated.

Power component(s) 114 may include one or more RF receive (Rx) pre-amplifiers that amplify MR signals detected by one or more RF receive coils (e.g., coils 126), one or more RF transmit (Tx) power components configured to provide power to one or more RF transmit coils (e.g., coils 126), one or more gradient power components configured to provide power to one or more gradient coils (e.g., gradient coils 128), and one or more shim power components configured to provide power to one or more shim coils (e.g., shim coils 124).

In conventional MRI systems, the power components are large, expensive and consume significant power. Typically, the power electronics occupy a room separate from the MRI scanner itself. The power electronics not only require substantial space, but are expensive complex devices that consume substantial power and require wall mounted racks to be supported. Thus, the power electronics of conventional MRI systems also prevent portability and affordability of MRI.

As illustrated in FIG. 1, MRI system 100 includes controller 106 (also referred to as a console) having control electronics to send instructions to and receive information from power management system 110. Controller 106 may be configured to implement one or more pulse sequences, which are used to determine the instructions sent to power management system 110 to operate the magnetic components 120 in a desired sequence (e.g., parameters for operating the RF transmit and receive coils 126, parameters for operating gradient coils 128, etc.). As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information. In conventional MRI systems, computing device 104 typically includes one or more high performance work-stations configured to perform computationally expensive processing on MR data relatively rapidly. Such computing devices are relatively expensive equipment on their own.

As should be appreciated from the foregoing, currently available clinical MRI systems (including high-field, mid-field and low-field systems) are large, expensive, fixed installations requiring substantial dedicated and specially designed spaces, as well as dedicated power connections. The inventors have developed low-field, including very-low field, MRI systems that are lower cost, lower power and/or portable, significantly increasing the availability and applicability of MRI. According to some embodiments, a portable MRI system is provided, allowing an MRI system to be brought to the patient and utilized at locations where it is needed.

As discussed above, some embodiments include an MRI system that is portable, allowing the MRI device to be moved to locations in which it is needed (e.g., emergency and operating rooms, primary care offices, neonatal intensive care units, specialty departments, emergency and mobile transport vehicles and in the field). There are numerous challenges that face the development of a portable MRI system, including size, weight, power consumption and the ability to operate in relatively uncontrolled electromagnetic noise environments (e.g., outside a specially shielded room). As discussed above, currently available clinical MRI systems range from approximately 4-20 tons. Thus, currently available clinical MRI systems are not portable because of the sheer size and weight of the imaging device itself, let alone the fact that currently available systems also require substantial dedicated space, including a specially shielded room to house the MRI scanner and additional rooms to house the power electronics and the technician control area, respectively. The inventors have developed MRI systems of suitable weight and size to allow the MRI system to be transported to a desired location, some examples of which are discussed in further detail below.

A further aspect of portability involves the capability of operating the MRI system in a wide variety of locations and environments. As discussed above, currently available clinical MRI scanners are required to be located in specially shielded rooms to allow for correct operation of the device and is one (among many) of the reasons contributing to the cost, lack of availability and non-portability of currently available clinical MRI scanners. Thus, to operate outside of a specially shielded room and, more particularly, to allow for generally portable, cartable or otherwise transportable MRI, the MRI system must be capable of operation in a variety of noise environments. The inventors have developed noise suppression techniques that allow the MRI system to be operated outside of specially shielded rooms, facilitating both portable/transportable MRI as well as fixed MRI installments that do not require specially shielded rooms. While the noise suppression techniques allow for operation outside specially shielded rooms, these techniques can also be used to perform noise suppression in shielded environments, for example, less expensive, loosely or ad-hoc shielding environments, and can be therefore used in conjunction with an area that has been fitted with limited shielding, as the aspects are not limited in this respect.

A further aspect of portability involves the power consumption of the MRI system. As also discussed above, current clinical MRI systems consume large amounts of power (e.g., ranging from 20 kW to 40 kW average power consumption during operation), thus requiring dedicated power connections (e.g., dedicated three-phase power connections to the grid capable of delivering the required power). The requirement of a dedicated power connection is a further obstacle to operating an MRI system in a variety of locations other than expensive dedicated rooms specially fitted with the appropriate power connections. The inventors have developed low power MRI systems capable of operating using mains electricity such as a standard wall outlet (e.g., 120V/20 A connection in the U.S.) or common large appliance outlets (e.g., 220-240V/30 A), allowing the device to be operated anywhere common power outlets are provided. The ability to "plug into the wall" facilitates both portable/transportable MRI as well as fixed MRI system installations without requiring special, dedicated power such as a three-phase power connection.

Figure 39A:
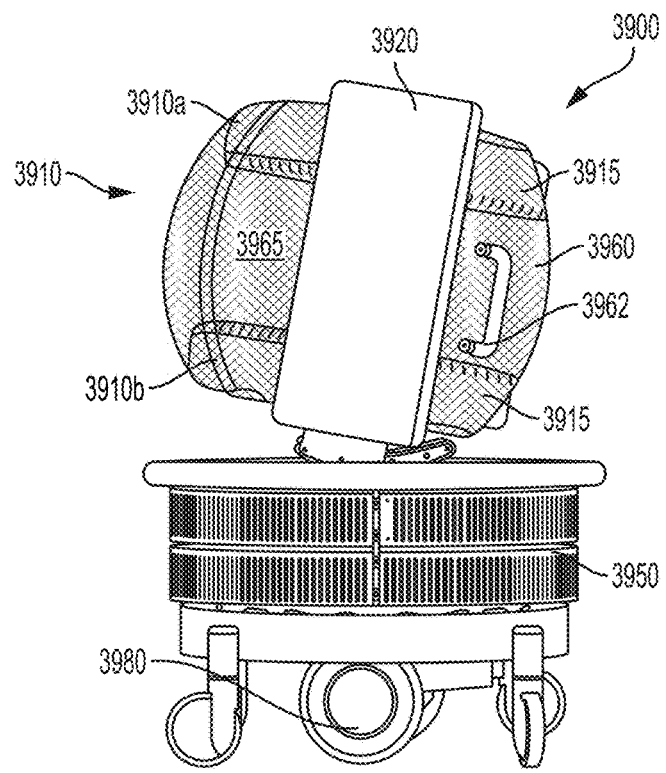
FIGS. 39A and 39B illustrate views of a portable MRI system, in accordance with some embodiments.
Figure 39B:
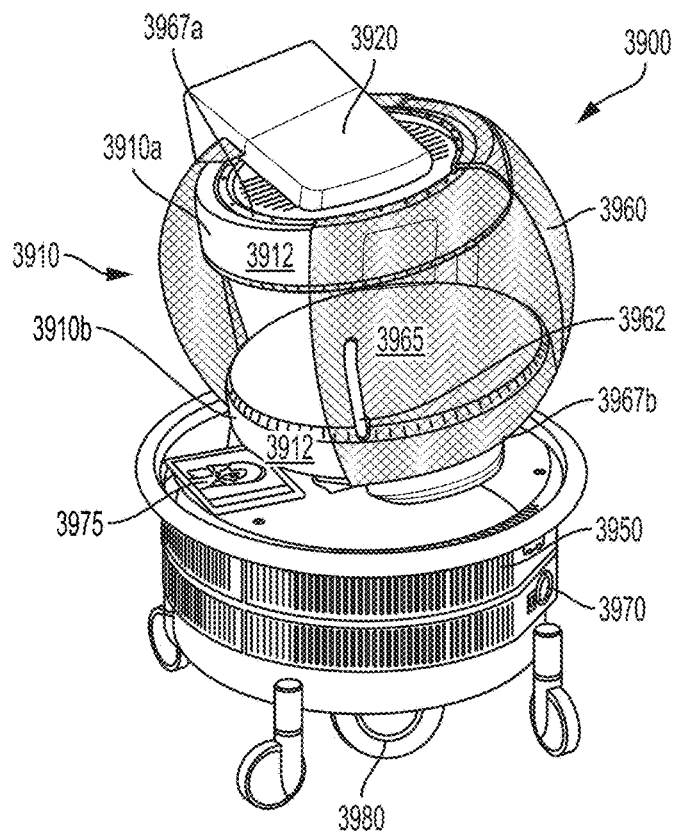

According to some embodiments, a portable MRI system (e.g., any of the portable MRI systems illustrated in FIGS. 19, 39-40 and 44A-D below) is configured to operate using mains electricity (e.g., single-phase electricity provided at standard wall outlets) via a power connection 3970 (see e.g., FIG. 39B). According to some embodiments, a portable MRI system comprises a power connection configured to connect to a single-phase outlet providing approximately between 110 and 120 volts and rated at 15, 20 or 30 amperes, and wherein the power system is capable of providing the power to operate the portable MRI system from power provided by the single-phase outlet. According to some embodiments, a portable MRI system comprises a power connection configured to connect to a single-phase outlet providing approximately between 220 and 240 volts and rated at 15, 20 or 30 amperes, and wherein the power system is capable of providing the power to operate the magnetic resonance imaging system from power provided by the single-phase outlet. According to some embodiments, a portable MRI system is configured using the low power techniques described herein to use an average of less than 3 kilowatts during image acquisition. According to some embodiments, a portable MRI system is configured using the low power techniques described herein to use an average of less than 2 kilowatts during image acquisition. According to some embodiments, a portable MRI system is configured using the low power techniques described herein to use an average of less than 1 kilowatt during image acquisition. For example, a low power MRI system employing a permanent $B_0$ magnet and low power components described herein may operate at 1 kilowatt or less, such as at 750 watts or less.

As discussed above, a significant contributor to the size, cost and power consumption of conventional MRI systems are the power electronics for powering the magnetics components of the MRI system. The power electronics for conventional MRI systems often require a separate room, are expensive and consume significant power to operate the corresponding magnetics components. In particular, the gradient coils and thermal management systems utilized to cool the gradient coils alone generally require dedicated power connections and prohibit operation from standard wall outlets. The inventors have developed low power, low noise gradient power sources capable of powering the gradient coils of an MRI system that can, in accordance with some embodiments, be housed in the same portable, cartable or otherwise transportable apparatus as the magnetics components of the MRI system. According to some embodiments, the power electronics for powering the gradient coils of an MRI system consume less than 50 W when the system is idle and between 100-200 W when the MRI system is operating (i.e., during image acquisition). The inventors have developed power electronics (e.g., low power, low noise power electronics) to operate a portable low field MRI system that all fit within the footprint of the portable MRI scanner. According to some embodiments, innovative mechanical design has enabled the development of an MRI scanner that is maneuverable within the confines of a variety of clinical environments in which the system is needed.

At the core of developing a low power, low cost and/or portable MRI system is the reduction of the field strength of the $B_0$ magnet, which can facilitate a reduction in size, weight, expense and power consumption. However, as discussed above, reducing the field strength has a corresponding and significant reduction in SNR. This significant reduction in SNR has prevented clinical MRI systems from reducing the field strength below the current floor of approximately 0.2 T, which systems remain large, heavy, expensive fixed installations requiring specialized and dedicated spaces. While some systems have been developed that operate between 0.1 T and 0.2 T, these systems are often specialized devices for scanning extremities such as the hand, arm or knee. The inventors have developed MRI systems operating in the low-field and very-low field capable of acquiring clinically useful images. Some embodiments include highly efficient pulse sequences that facilitate acquiring clinically useful images at lower field strengths than previously achievable. The signal to noise ratio of the MR signal is related to the strength of the main magnetic field $B_0$, and is one of the primary factors driving clinical systems to operate in the high-field regime. Pulse sequences developed by the inventors that facilitate acquisition of clinically useful images are described in U.S. patent application Ser. No. 14/938,430, filed Nov. 11, 2015 and titled "Pulse Sequences for Low Field Magnetic Resonance," which is herein incorporated by reference in its entirety.

Further techniques developed by the inventors to address the low SNR of low field strength include optimizing the configuration of radio frequency (RF) transmit and/or receive coils to improve the ability of the RF transmit/receive coils to transmit magnetic fields and detect emitted MR signals. The inventors have appreciated that the low transmit frequencies in the low field regime allow for RF coil designs not possible at higher fields strengths and have developed RF coils with improved sensitivity, thereby increasing the SNR of the MRI system. Exemplary RF coil designs and optimization techniques developed by the inventors are described in U.S. patent application Ser. No. 15/152,951, filed May 12, 2016 and titled "Radio Frequency Coil Methods and Apparatus," which is herein incorporated by reference in its entirety.

Another technique for addressing the relatively low SNR characteristic of the low-field regime is to improve the homogeneity of the $B_0$ field by the $B_0$ magnet. In general, a $B_0$ magnet requires some level of shimming to produce a $B_0$ magnetic field with a profile (e.g., a $B_0$ magnetic field at the desired field strength and/or homogeneity) satisfactory for use in MRI. In particular, production factors such as design, manufacturing tolerances, imprecise production processes, environment, etc., give rise to field variation that produces a $B_0$ field having unsatisfactory profile after assembly/manufacture. For example, after production, exemplary $B_0$ magnets 200, 300 and/or 3200 described above may produce a $B_0$ field with an unsatisfactory profile (e.g., inhomogeneity in the $B_0$ field unsuitable for imaging) that needs to be improved or otherwise corrected, typically by shimming, to produce clinically useful images. Shimming refers to any of various techniques for adjusting, correcting and/or improving a magnetic field, often the $B_0$ magnetic field of a magnetic resonance imaging device. Similarly, a shim refers to something (e.g., an object, component, device, system or combination thereof) that performs shimming (e.g., by producing a magnetic field).

Conventional techniques for shimming are relatively time and/or cost intensive, often requiring significant manual effort by an expert in order to adjust the $B_0$ magnetic field so that it is suitable for its intended purpose, which incurs significant post-production time and expense. For example, conventional shimming techniques typically involve an iterative process by which the $B_0$ magnetic field is measured, the necessary corrections are determined and deployed, and the process repeated until a satisfactory $B_0$ magnetic field is produced. This iterative process is conventionally performed with substantial manual involvement, requiring expertise and significant time (e.g., a day at a minimum, and more typically, longer). Thus, conventional post-production field correction of a $B_0$ magnetic field significantly contributes to the expense and complexity of conventional MRI systems.

The inventors have developed a number of techniques that, according to some embodiments, facilitate more efficient and/or cost effective shimming for a $B_0$ magnet for MRI. Some embodiments are suitable for use in low-field MRI, but the techniques described herein are not limited for use in the low-field context. For example, the inventors have developed techniques to minimize the manual effort involved in correcting the $B_0$ field produced by a $B_0$ magnet, for example, correcting at least some field inhomogeneity resulting from imperfect manufacturing processes. In particular, the inventors have developed automated techniques for patterning magnetic material to provide accurate and precise field correction to the $B_0$ field produced by a $B_0$ magnet. Exemplary shimming techniques developed by the inventors are described in U.S. patent application Ser. No. 15/466,500, filed Mar. 22, 2017 and titled "Methods and Apparatus for Magnetic Field Shimming," which is herein incorporated by reference in its entirety.

Another aspect of increasing the availability of MRI is to make MRI affordable. The development of a portable low-field MRI system by the inventors eliminates many of the costs associated with conventional clinical MRI systems, including expensive superconducting materials and cryogenic cooling systems, expensive site preparation of large and complex dedicated facilities, highly trained personnel to operate and maintain the system to name a few. In addition, the inventors have developed further cost reduction techniques and designs, including, according to some embodiments, integrated power electronics, designs that reduce materials, optimize or otherwise minimize the use of expensive materials and/or reduce production costs. The inventors have developed automated shimming techniques to allow for correction of field inhomogeneity of the $B_0$ magnet after manufacture, reducing the cost of both production and post-production processes.

According to some embodiments, designs developed by the inventors also reduce the cost and complexity of operating and maintaining the MRI scanner. For example, conventional clinical MRI systems require significant expertise to both operate and maintain, resulting in significant on-going costs of these systems. The inventors have developed easy-to-use MRI systems that allow minimally trained or untrained personnel to operate and/or maintain the system. According to some embodiments, automated setup processes allow the MRI scanner to automatically probe and adapt to its environment to prepare for operation. Network connectivity allows the MRI system to be operated from a mobile device such as a tablet, notepad or smart phone with easy-to-use interfaces configured to automatically run desired scanning protocols. Acquired images are immediately transferred to a secure cloud server for data sharing, telemedicine and/or deep learning.

Following below are more detailed descriptions of various concepts related to, and embodiments of, lower cost, lower power and/or portable low-field MRI. It should be appreciated that the embodiments described herein may be implemented in any of numerous ways. Examples of specific implementations are provided below for illustrative purposes only. It should be appreciated that the embodiments and the features/capabilities provided may be used individually, all together, or in any combination of two or more, as aspects of the technology described herein are not limited in this respect.

A significant contributor to the high cost, size, weight and power consumption of high-field MRI is the $B_0$ magnet itself along with the apparatus required to power the $B_0$ magnet and to perform thermal management thereof. In particular, to produce the field strengths characteristic of high-field MRI, the $B_0$ magnet is typically implemented as an electromagnet configured in a solenoid geometry using superconducting wires that need a cryogenic cooling system to keep the wires in a superconducting state. Not only is the superconducting material itself expensive, but the cryogenic equipment to maintain the superconducting state is also expensive and complex.

The inventors have recognized that the low-field context allows for $B_0$ magnet designs not feasible in the high-field regime. For example, due at least in part to the lower field strengths, superconducting material and the corresponding cryogenic cooling systems can be eliminated. Due in part to the low-field strengths, $B_0$ electromagnets constructed using non-superconducting material (e.g., copper) may be employed in the low-field regime. However, such electromagnets still may consume relatively large amounts of power during operation. For example, operating an electromagnet using a copper conductor to generate a magnetic field of 0.2 T or more requires a dedicated or specialized power connection (e.g., a dedicated three-phase power connection). The inventors have developed MRI systems that can be operated using mains electricity (i.e., standard wall power), allowing the MRI system to be powered at any location having common power connection, such as a standard wall outlet (e.g., 120V/20 A connection in the U.S.) or common large appliance outlets (e.g., 220-240V/30 A). Thus, a low-power MRI system facilitates portability and availability, allowing an MRI system to be operated at locations where it is needed (e.g., the MRI system can be brought to the patient instead of vice versa), examples of which are discussed in further detail below. In addition, operating from standard wall power eliminates the electronics conventionally needed to convert three-phase power to single-phase power and to smooth out the power provided directly from the grid. Instead, wall power can be directly converted to DC and distributed to power the components of the MRI system.

Figure 2A:
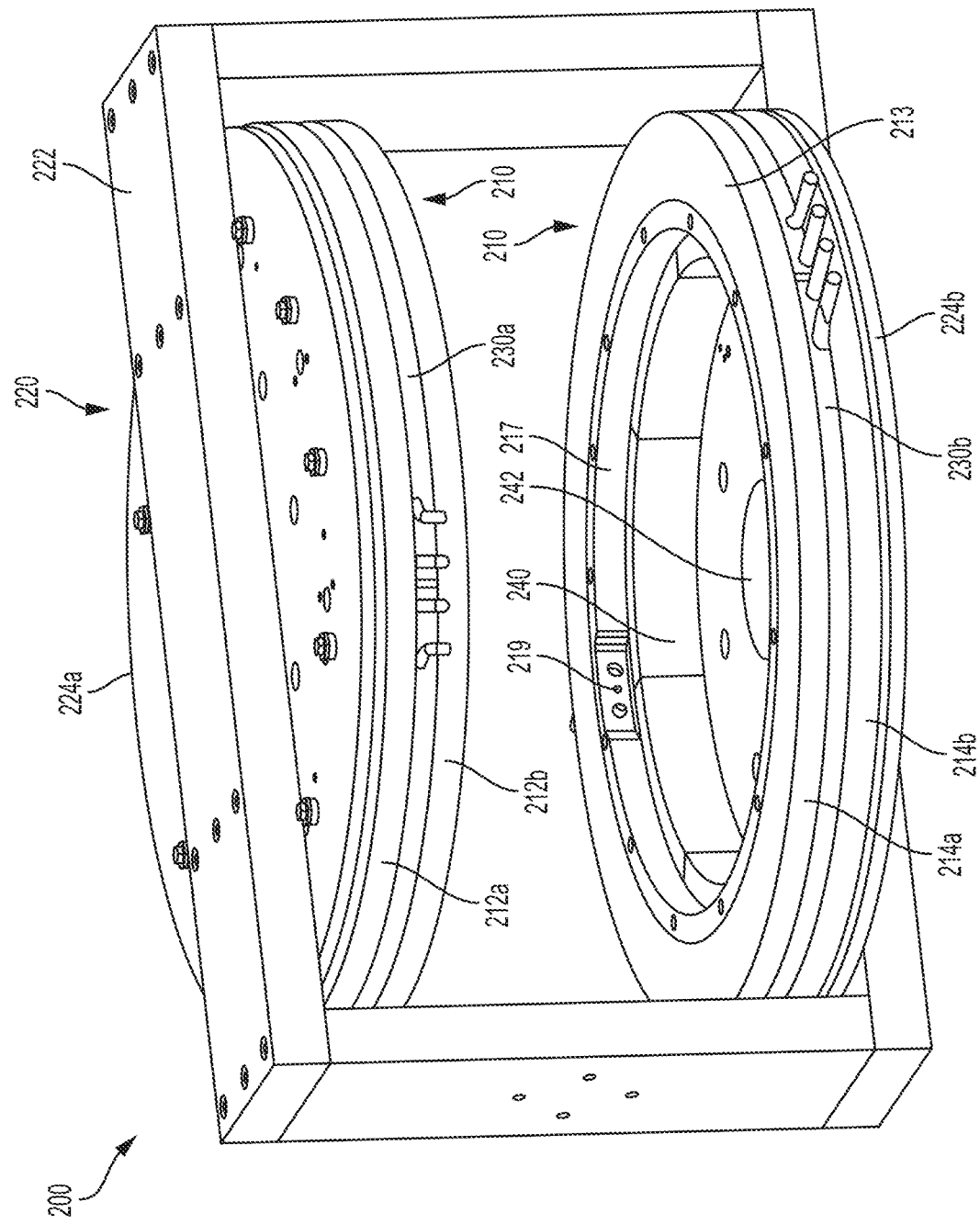
FIGS. 2A and 2B illustrate a $B_0$ magnet comprising a plurality of electromagnets, in accordance with some embodiments.
Figure 2B:
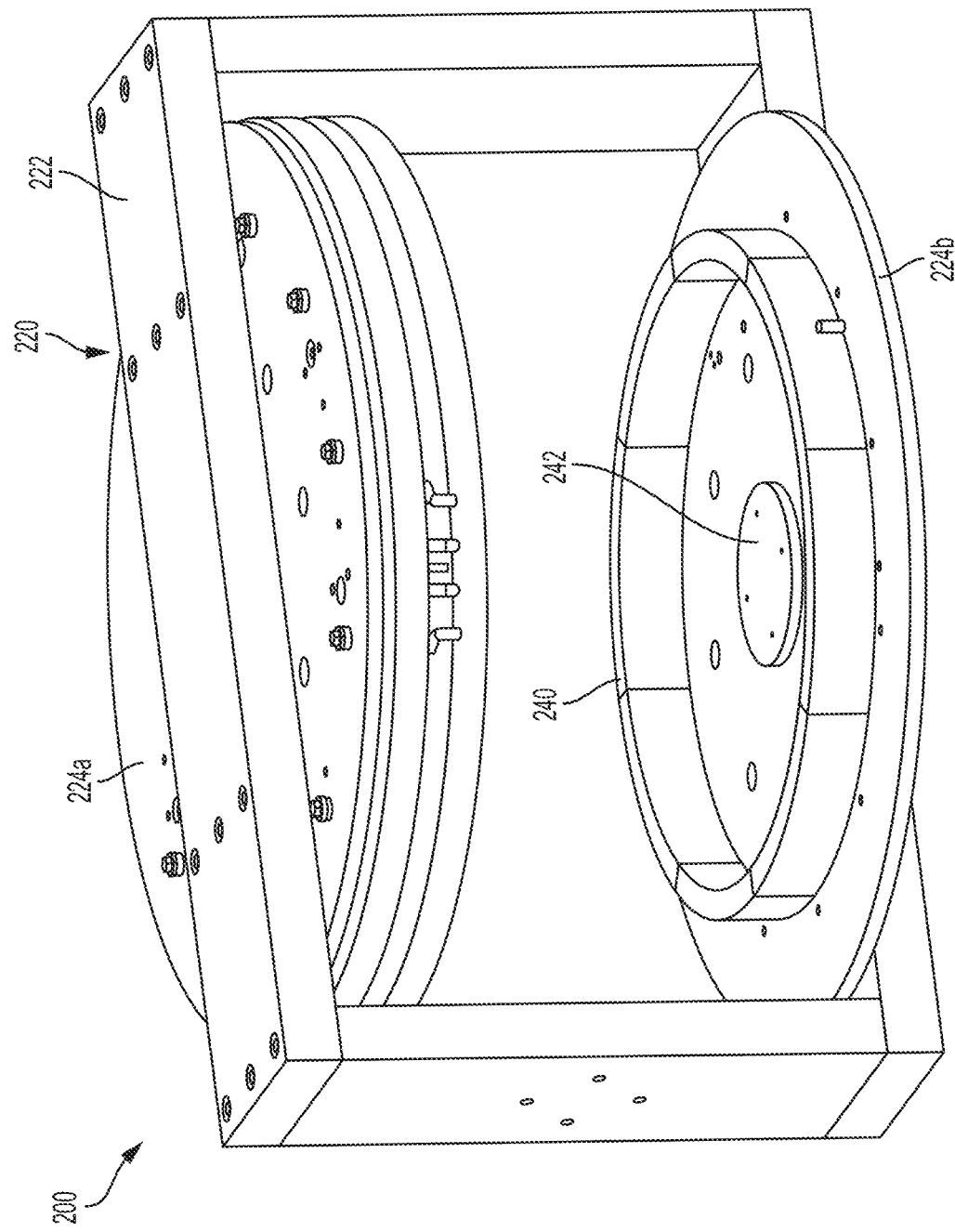

FIGS. 2A and 2B illustrate a $B_0$ magnet formed using an electromagnet and a ferromagnetic yoke. In particular, $B_0$ magnet 200 is formed in part by an electromagnet 210 arranged in a bi-planar geometry comprising electromagnetic coils 212a and 212b on an upper side and electromagnetic coils 214a and 214b on a lower side of $B_0$ magnet 200. According to some embodiments, the coils forming electromagnet 210 may be formed from a number of turns of a copper wire or copper ribbon, or any other conductive material suitable for producing a magnetic field when operated (e.g., when electrical current is driven through the conductor windings). While the exemplary electromagnet illustrated in FIGS. 2A and 2B comprises two pairs of coils, an electromagnet may be formed using any number of coils in any configuration, as the aspects are not limited in this respect. The electromagnetic coils forming electromagnet 210 may be formed, for example, by winding a conductor 213 (e.g., a copper ribbon, wire, paint, etc.) about a fiberglass ring 217. For example, conductor 213 may be a suitable insulated copper wire, or alternatively, conductor 213 may be a copper ribbon wound in conjunction with an insulating layer (e.g., a Mylar layer) to electrically isolate the multiple windings of the coil. A connector 219 may be provided to allow for a power connection to provide current to operate coils 214a and 214b in series. A similar connector on the upper side of the electromagnet (not visible in FIGS. 2A and 2B) may be provided to operate coils 212a and 212b.

It should be appreciated that the electromagnetic coils may be formed from any suitable material and dimensioned in any suitable way so as to produce or contribute to a desired $B_0$ magnetic field, as the aspects are not limited for use with any particular type of electromagnet. As one non-limiting example that may be suitable to form, in part, an electromagnet (e.g., electromagnet 210), an electromagnetic coil may be constructed using copper ribbon and mylar insulator having 155 turns to form an inner diameter of approximately 23-27 inches (e.g., approximately 25 inches), an outer diameter of approximately 30-35 inches (e.g., 32 inches). However, different material and/or different dimensions may be used to construct an electromagnetic coil having desired characteristics, as the aspects are not limited in this respect. The upper and lower coil(s) may be positioned to provide a distance of approximately 10-15 inches (e.g., approximately 12.5 inches) between the lower coil on the upper side and the upper coil on the lower side. It should be appreciated that the dimensions will differ depending on the desired characteristics including, for example, field strength, field of view, etc.

In the exemplary $B_0$ magnet illustrated in FIGS. 2A and 2B, each coil pair 212 and 214 is separated by thermal management components 230a and 230b, respectively, to transfer heat produced by the electromagnetic coils and gradient coils (not illustrated in FIGS. 2A and 2B) away from the magnets to provide thermal management for the MRI device. In particular, thermal management components 230a and 230b may comprise a cooling plate having conduits that allow coolant to be circulated through the cooling plate to transfer heat away from the magnets. The cooling plate 230a, 230b may be constructed to reduce or eliminate eddy currents induced by operating the gradient coils that can produce electromagnetic fields that disrupt the $B_0$ magnetic field produced by the B0 magnet 200. For example, thermal management components 230a and 230b may be the same or similar to any of the thermal management components described in U.S. application Ser. No. 14/846,042 entitled "Thermal Management Methods and Apparatus," filed on Sep. 4, 2015, which is incorporated by reference herein in its entirety. According to some embodiments, thermal management components may be eliminated, as discussed in further detail below.

$B_0$ magnet 200 further comprises a yoke 220 that is magnetically coupled to the electromagnet to capture magnetic flux that, in the absence of yoke 220, would be lost and not contribute to the flux density in the region of interest between the upper and lower electromagnetic coils. In particular, yoke 220 forms a "magnetic circuit" connecting the coils on the upper and lower side of the electromagnet so as to increase the flux density in the region between the coils, thus increasing the field strength within the imaging region (also referred to as the field of view) of the $B_0$ magnet. The imaging region or field of view defines the volume in which the $B_0$ magnetic field produced by a given B0 magnet is suitable for imaging. More particularly, the imaging region or field of view corresponds to the region for which the $B_0$ magnetic field is sufficiently homogeneous at a desired field strength that detectable MR signals are emitted by an object positioned therein in response to application of radio frequency excitation (e.g., a suitable radio frequency pulse sequence). Yoke 220 comprises frame 222 and plates 224a, 224b, which may be formed using any suitable ferromagnetic material (e.g., iron, steel, etc.). Plates 224a, 224b collect magnetic flux generated by the coil pairs of electromagnet 210 and directs it to frame 222 which, in turn, returns the flux back to the opposing coil pair, thereby increasing, by up to a factor of two, the magnetic flux density in the imaging region between the coil pairs (e.g., coil pair 212a, 212b and coil pair 214a, 214b) for the same amount of operating current provided to the coils. Thus, yoke 220 can be used to produce a higher $B_0$ field (resulting in higher SNR) without a corresponding increase in power requirements, or yoke 220 can be used to lower the power requirements of $B_0$ magnet 200 for a given $B_0$ field.

According to some embodiments, the material used for portions of yoke 220 (i.e., frame 222 and/or plates 224a, 224b) is steel, for example, a low-carbon steel, silicon steel, cobalt steel, etc. According to some embodiments, gradient coils (not shown in FIGS. 2A, 2B) of the MRI system are arranged in relatively close proximity to plates 224a, 224b inducing eddy currents in the plates. To mitigate, plates 224a, 224b and/or frame 222 may be constructed of silicon steel, which is generally more resistant to eddy current production than, for example, low-carbon steel. It should be appreciated that yoke 220 may be constructed using any ferromagnetic material with sufficient magnetic permeability and the individual parts (e.g., frame 222 and plates 224a, 224b) may be constructed of the same or different ferromagnetic material, as the techniques of increasing flux density is not limited for use with any particular type of material or combination of materials. Furthermore, it should be appreciated that yoke 220 can be formed using different geometries and arrangements.

It should be appreciated that the yoke 220 may be made of any suitable material and may be dimensioned to provide desired magnetic flux capture while satisfying other design constraints such as weight, cost, magnetic properties, etc. As an example, the frame of the yoke (e.g., frame 222) may be formed of a low-carbon steel of less than 0.2% carbon or silicon steel, with the long beam(s) having a length of approximately 38 inches, a width of approximately 8 inches, and a thickness (depth) of approximately 2 inches, and the short beam(s) having a length of approximately 19 inches, a width of approximately 8 inches and a thickness (depth) of approximately 2 inches. The plates (e.g., plates 224a and 224b) may be formed from a low-carbon steel of less than 0.2% carbon or silicon steel and have a diameter of approximately 30-35 inches (e.g., approximately 32 inches). However, the above provided dimensions and materials are merely exemplary of a suitable embodiment of a yoke that can be used to capture magnetic flux generated by an electromagnet.

As an example of the improvement achieved via the use of yoke 220, operating electromagnet 210 to produce a $B_0$ magnetic field of approximately 20 mT without yoke 220 consumes about 5 kW, while producing the same 20 mT $B_0$ magnetic field with yoke 220 consumes about 750 W of power. Operating electromagnet 210 with the yoke 220, a $B_0$ magnetic field of approximately 40 mT may be produced using 2 kW of power and a $B_0$ magnetic field of approximately 50 mT may be produced using approximately 3 kW of power. Thus, the power requirements can be significantly reduced by use of yoke 220 allowing for operation of a $B_0$ magnet without a dedicated three-phase power connection. For example, mains electrical power in the United States and most of North America is provided at 120V and 60 Hz and rated at 15 or 20 amps, permitting utilization for devices operating below 1800 and 2400 W, respectively. Many facilities also have 220-240 VAC outlets with 30 amp ratings, permitting devices operating up to 7200 W to be powered from such outlets. According to some embodiments, a low-field MRI system utilizing a $B_0$ magnet comprising an electromagnet and a yoke (e.g., $B_0$ magnet 200) is configured to be powered via a standard wall outlet, as discussed in further detail below. According to some embodiments, a low-field MRI system utilizing a $B_0$ magnet comprising an electromagnet and a yoke (e.g., $B_0$ magnet 200) is configured to be powered via a 220-240 VAC outlet, as also discussed in further detail below.

Referring again to FIGS. 2A and 2B, exemplary $B_0$ magnet 200 further comprises shim rings 240a, 240b and shim disks 242a, 242b configured to augment the generated $B_0$ magnetic field to improve homogeneity in the field of view (e.g., in the region between the upper and lower coils of the electromagnet where the $B_0$ field is suitable for sufficient MR signal production), as best seen in FIG. 2B in which the lower coils have been removed. In particular, shim rings 240 and shim disk 242 are dimensioned and arranged to increase the uniformity of the magnetic field generated by the electromagnet at least within the field of view of the $B_0$ magnet. In particular, the height, thickness and material of shim rings 240a, 240b and the diameter, thickness and material of shim disks 242a, 242b may be chosen so as to achieve a $B_0$ field of suitable homogeneity. For example, the shim disk may be provided with a diameter of approximately 5-6 inches and a width of approximately 0.3-0.4 inches. A shim ring may be formed from a plurality of circular arc segments (e.g., 8 circular arc segments) each having a height of approximately 20-22 inches, and a width of approximately 2 inches to form a ring having an inner diameter of approximately between 21-22 inches and an outer diameter of approximately between 23-24 inches.

The weight of the $B_0$ magnet is a significant portion of the overall weight of the MRI system which, in turn, impacts the portability of the MRI system. In embodiments that primarily use low carbon and/or silicon steel for the yoke and shimming components, an exemplary $B_0$ magnet 200 dimensioned similar to that described in the foregoing may weigh approximately 550 kilograms. According to some embodiments, cobalt steel (CoFe) may be used as the primary material for the yoke (and possibly the shim components), potentially reducing the weight of $B_0$ magnet 200 to approximately 450 Kilograms. However, CoFe is generally more expensive than, for example, low carbon steel, driving up the cost of the system. Accordingly, in some embodiments, select components may be formed using CoFe to balance the tradeoff between cost and weight arising from its use. Using such exemplary $B_0$ magnets a portable, cartable or otherwise transportable MRI system may be constructed, for example, by integrating the $B_0$ magnet within a housing, frame or other body to which castors, wheels or other means of locomotion can be attached to allow the MRI system to be transported to desired locations (e.g., by manually pushing the MRI system and/or including motorized assistance). As a result, an MRI system can be brought to the location in which it is needed, increasing its availability and use as a clinical instrument and making available MRI applications that were previously not possible. According to some embodiments, the total weight of a portable MRI system is less than 1,500 pounds and, preferably, less than 1000 pounds to facilitate maneuverability of the MRI system.

The primary contributor to the overall power consumption of a low-field MRI system employing a $B_0$ magnet such as $B_0$ magnet 200 is the electromagnet (e.g., electromagnet 210). For example, in some embodiments, the electromagnet may consume 80% or more of the power of the overall MRI system. To significantly reduce the power requirements of the MRI system, the inventors have developed $B_0$ magnets that utilize permanent magnets to produce and/or contribute to the $B_0$ electromagnetic field. According to some embodiments, $B_0$ electromagnets are replaced with permanent magnets as the main source of the $B_0$ electromagnetic field. A permanent magnet refers to any object or material that maintains its own persistent magnetic field once magnetized. Materials that can be magnetized to produce a permanent magnet are referred to herein as ferromagnetic and include, as non-limiting examples, iron, nickel, cobalt, neodymium (NdFeB) alloys, samarium cobalt (SmCo) alloys, alnico (AlNiCo) alloys, strontium ferrite, barium ferrite, etc. Permanent magnet material (e.g., magnetizable material that has been driven to saturation by a magnetizing field) retains its magnetic field when the driving field is removed. The amount of magnetization retained by a particular material is referred to as the material's remanence. Thus, once magnetized, a permanent magnet generates a magnetic field corresponding to its remanence, eliminating the need for a power source to produce the magnetic field.

Figure 3A:
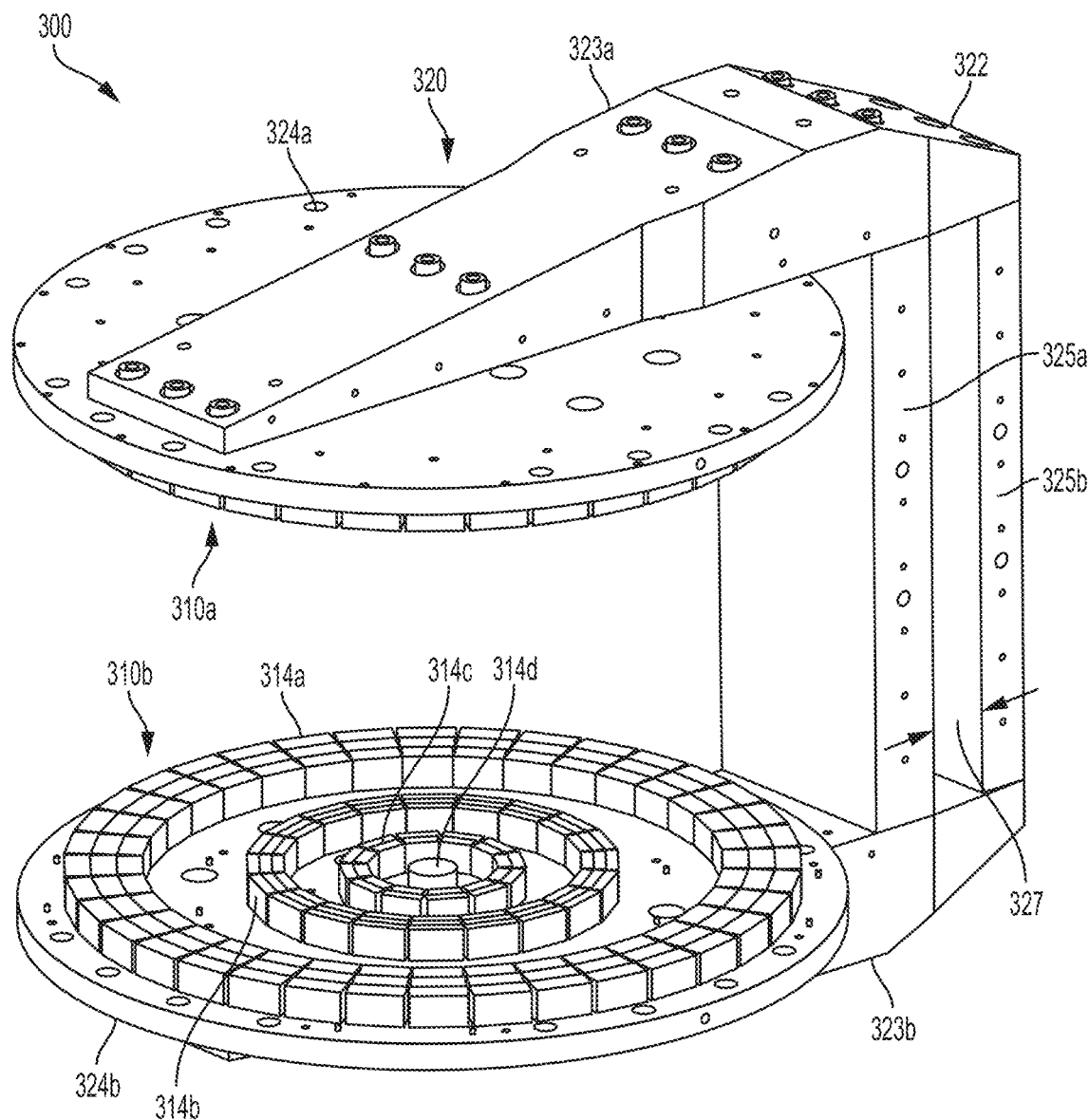
FIG. 3A illustrates a $B_0$ magnet comprising a plurality of permanent magnets, in accordance with some embodiments.

FIG. 3A illustrates a permanent $B_0$ magnet, in accordance with some embodiments. In particular, $B_0$ magnet 300 is formed by permanent magnets 310a and 310b arranged in a bi-planar geometry and a yoke 320 that captures electromagnetic flux produced by the permanent magnets and transfers the flux to the opposing permanent magnet to increase the flux density between permanent magnets 310a and 310b. Each of permanent magnets 310a and 310b are formed from a plurality of concentric permanent magnets. In particular, as visible in FIG. 3, permanent magnet 310b comprises an outer ring of permanent magnets 314a, a middle ring of permanent magnets 314b, an inner ring of permanent magnets 314c, and a permanent magnet disk 314d at the center. Permanent magnet 310a may comprise the same set of permanent magnet elements as permanent magnet 310b.

The permanent magnet material used may be selected depending on the design requirements of the system. For example, according to some embodiments, the permanent magnets (or some portion thereof) may be made of NdFeB, which produces a magnetic field with a relatively high magnetic field per unit volume of material once magnetized. According to some embodiments, SmCo material is used to form the permanent magnets, or some portion thereof. While NdFeB produces higher field strengths (and in general is less expensive than SmCo), SmCo exhibits less thermal drift and thus provides a more stable magnetic field in the face of temperature fluctuations. Other types of permanent magnet material(s) may be used as well, as the aspects are not limited in this respect. In general, the type or types of permanent magnet material utilized will depend, at least in part, on the field strength, temperature stability, weight, cost and/or ease of use requirements of a given $B_0$ magnet implementation.

The permanent magnet rings are sized and arranged to produce a homogenous field of a desired strength in the central region (field of view) between permanent magnets 310a and 310b. In the exemplary embodiment illustrated in FIG. 3A, each permanent magnet ring comprises a plurality segments, each segment formed using a plurality of blocks that are stacked in the radial direction and positioned adjacent to one another about the periphery to form the respective ring. The inventors have appreciated that by varying the width (in the direction tangent to the ring) of each permanent magnet, less waste of useful space may be achieved while using less material. For example, the space between stacks that does not produce useful magnetic fields can be reduced by varying the width of the blocks, for example, as function of the radial position of the block, allowing for a closer fit to reduce wasted space and maximize the amount of magnetic field that can be generated in a given space. The dimensions of the blocks may also be varied in any desired way to facilitate the production of a magnetic field of desired strength and homogeneity, as discussed in further detail below.

$B_0$ magnet 300 further comprises yoke 320 configured and arranged to capture magnetic flux generated by permanent magnets 310a and 310b and direct it to the opposing side of the $B_0$ magnet to increase the flux density in between permanent magnets 310a and 310b, increasing the field strength within the field of view of the $B_0$ magnet. By capturing magnetic flux and directing it to the region between permanent magnets 310a and 310b, less permanent magnet material can be used to achieve a desired field strength, thus reducing the size, weight and cost of the $B_0$ magnet. Alternatively, for given permanent magnets, the field strength can be increased, thus improving the SNR of the system without having to use increased amounts of permanent magnet material. For exemplary $B_0$ magnet 300, yoke 320 comprises a frame 322 and plates 324a and 324b. In a manner similar to that described above in connection with yoke 220, plates 324a and 324b capture magnetic flux generated by permanent magnets 310a and 310b and direct it to frame 322 to be circulated via the magnetic return path of the yoke to increase the flux density in the field of view of the $B_0$ magnet. Yoke 320 may be constructed of any desired ferromagnetic material, for example, low carbon steel, CoFe and/or silicon steel, etc. to provide the desired magnetic properties for the yoke. According to some embodiments, plates 324a and 324b (and/or frame 322 or portions thereof) may be constructed of silicon steel or the like in areas where the gradient coils could most prevalently induce eddy currents.

Exemplary frame 322 comprises arms 323a and 323b that attach to plates 324a and 324b, respectively, and supports 325a and 325b providing the magnetic return path for the flux generated by the permanent magnets. The arms are generally designed to reduce the amount of material needed to support the permanent magnets while providing sufficient cross-section for the return path for the magnetic flux generated by the permanent magnets. Arms 323a has two supports within a magnetic return path for the $B_0$ field produced by the $B_0$ magnet. Supports 325a and 325b are produced with a gap 327 formed between, providing a measure of stability to the frame and/or lightness to the structure while providing sufficient cross-section for the magnetic flux generated by the permanent magnets. For example, the cross-section needed for the return path of the magnetic flux can be divided between the two support structures, thus providing a sufficient return path while increasing the structural integrity of the frame. It should be appreciated that additional supports may be added to the structure, as the technique is not limited for use with only two supports and any particular number of multiple support structures.

As discussed above, exemplary permanent magnets 310a and 310b comprise a plurality of rings of permanent magnetic material concentrically arranged with a permanent magnet disk at the center. Each ring may comprise a plurality of stacks of ferromagnetic material to form the respective ring, and each stack may include one or more blocks, which may have any number (including a single block in some embodiments and/or in some of the rings). The blocks forming each ring may be dimensioned and arranged to produce a desired magnetic field. The inventors have recognized that the blocks may be dimensioned in a number of ways to decrease cost, reduce weight and/or improve the homogeneity of the magnetic field produced, as discussed in further detail in connection with the exemplary rings that together form permanent magnets of a $B_0$ magnet, in accordance with some embodiments.

Figure 3B:
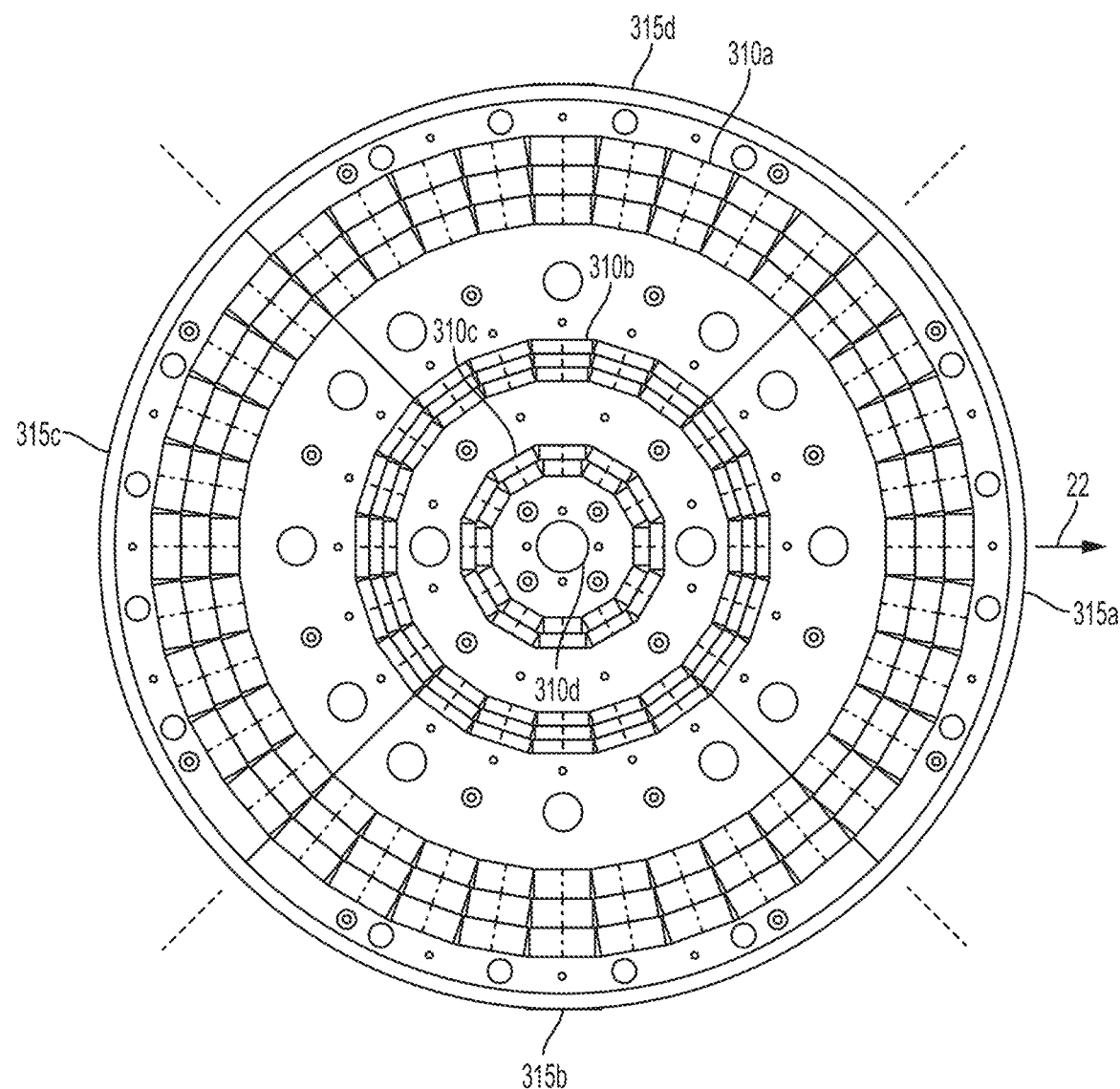
FIG. 3B illustrates a top view of an exemplary configuration of permanent magnet rings forming, in part, the $B_0$ magnet illustrated in FIG. 3A.

FIG. 3B illustrates a top-down view of a permanent magnet 310, which may, for example, be used as the design for permanent magnets 310a and 310b of $B_0$ magnet 300 illustrated in FIG. 3A. Permanent magnet 310 comprises concentric rings 310a, 310b, and 310c, each constructed of a plurality of stacks of ferromagnetic blocks, and a ferromagnetic disk 310d at the center. The direction of the frame of the yoke to which permanent magnet is attached is indicated by arrow 22. In embodiments in which the yoke is not symmetric (e.g., yoke 320), the yoke will cause the magnetic field produced by the permanent magnets for which it captures and focuses magnetic flux to be asymmetric as well, negatively impacting the uniformity of the $B_0$ magnetic field.

According to some embodiments, the block dimensions are varied to compensate for the effects of the yoke on the magnetic field produced by the permanent magnet. For example, dimensions of blocks in the four regions 315a, 315b, 315c and 315d labeled in FIG. 3B may be varied depending on which region the respective block is located. In particular, the height of the blocks (e.g., the dimension of the block normal to the plane of the circular magnet 310) may be greater in region 315c farthest away from the frame than corresponding blocks in region 315a closest to the frame. Block height can be varied in one or more rings or portions thereof, as the technique of compensating for the effects of the yoke are not limited to varying any particular block, set of blocks and/or any particular dimension. One example of varying block dimension to compensate for yoke effects are discussed in further detail below.

Figure 4A:
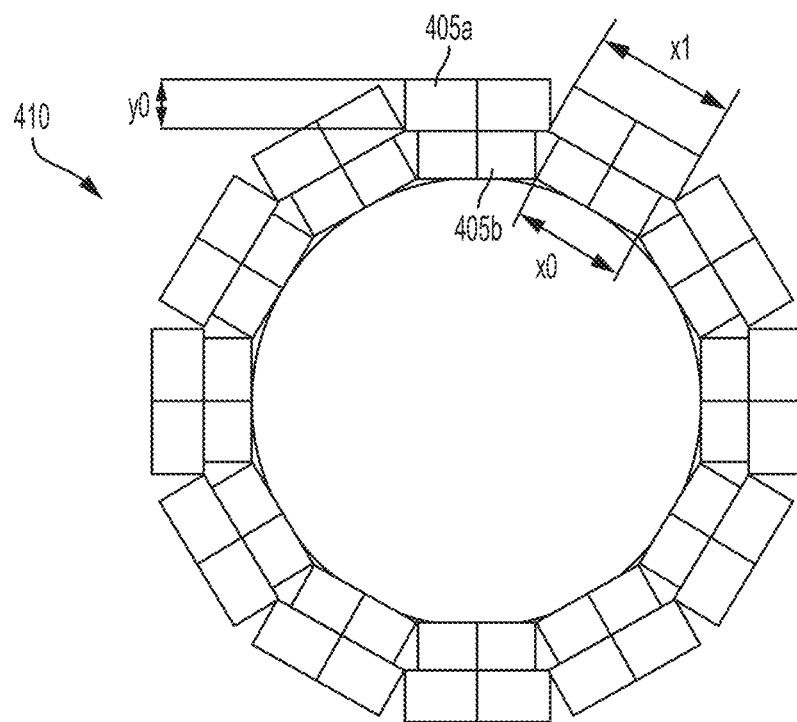
FIGS. 4A and 4B illustrate an exemplary ring of permanent magnets for a $B_0$ magnet, in accordance with some embodiments.
Figure 4B:
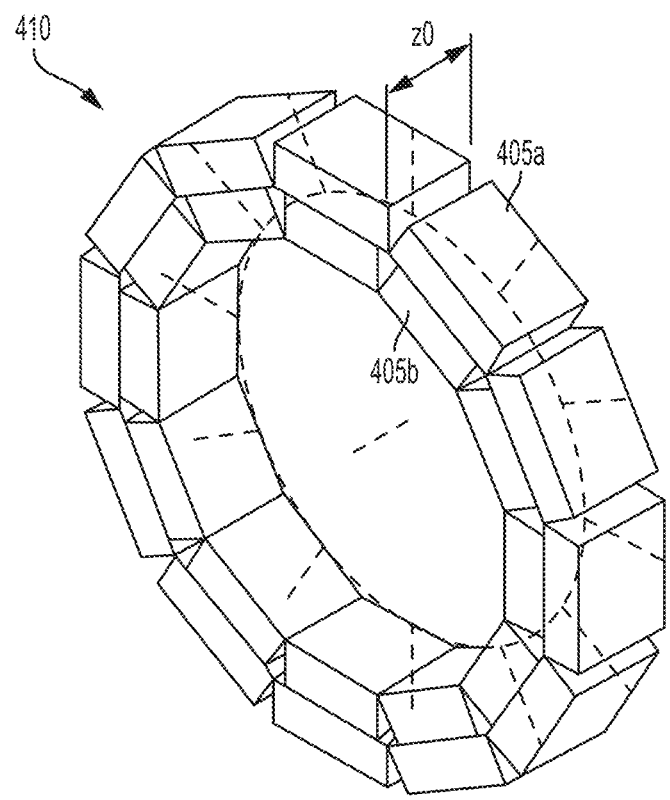
Figure 5A:
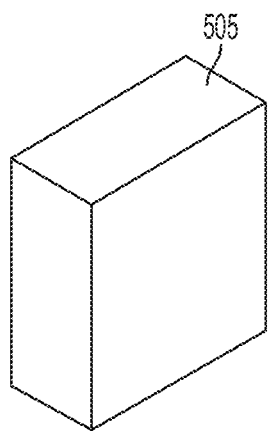
FIGS. 5A-C illustrate exemplary dimensions for permanent magnet blocks for the permanent magnet ring illustrated in FIGS. 4A and 4B, in accordance with some embodiments.
Figure 5B:
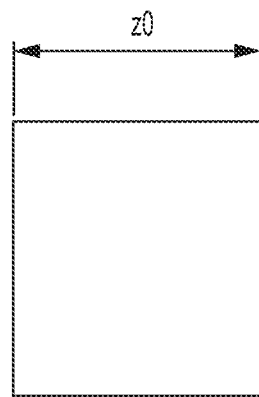
Figure 5C:
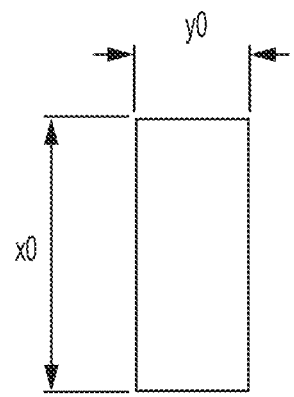
Figure 6A:
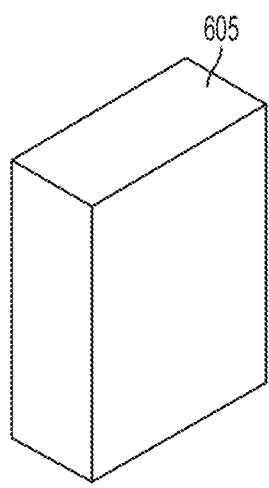
FIGS. 6A-C illustrate exemplary dimensions for permanent magnet blocks for the permanent magnet ring illustrated in FIGS. 4A and 4B, in accordance with some embodiments.
Figure 6B:
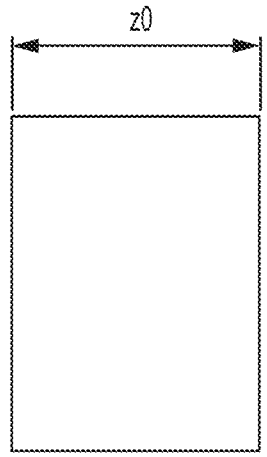
Figure 6C:
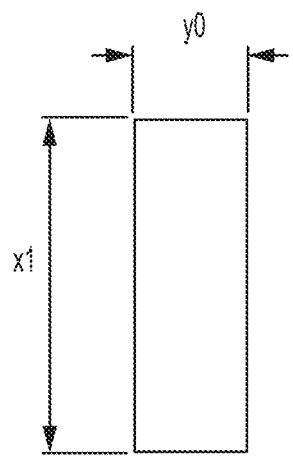

FIGS. 4A and 4B illustrate different views of an inner ring 410 (e.g., ring 310c illustrated in FIG. 3B), in accordance with some embodiments. Exemplary ring 410 includes a plurality (twelve in FIGS. 4A and 4B) of stacks of two blocks each, thus forming two sub-rings of ferromagnetic blocks (e.g., blocks formed of NdFeB, SmCo, etc.). The inner sub-ring is formed of blocks (e.g., exemplary block 405b) having a length $x_0$, a width $y_0$ and a height (or depth) $z_0$. The outer sub-ring is formed of blocks (e.g., exemplary block 405a) having a length $x_1$, a width $y_0$ and a height (or depth) $z_0$. As shown, the blocks in the outer sub-ring have a greater length than block in the inner sub-ring (i.e., $x_0 < x_1$), reducing the amount of empty space between adjacent block than if the blocks in the outer sub-ring were formed with a length $x_0$. As such more of the space in which exemplary ring 410 is contained is occupied by field producing magnetic material, increasing the field strength in the same amount of space. It should be appreciated that the arrangement in exemplary ring 410 is merely illustrative and other arrangements of blocks (e.g., number of stacks and number of blocks within each stack) may be used, as the aspects are not limited in this respect.

FIGS. 5A-C and 6A-C illustrate exemplary dimensions for blocks comprising the inner sub-ring and outer sub-ring of an inner permanent magnet ring (e.g., exemplary dimensions for blocks 405a and 405b forming permanent magnet ring 410). In particular, exemplary block 505 illustrated in FIG. 5A (e.g., a block in the inner sub-ring of inner permanent magnet ring 410 or 310c) may be manufactured to have dimensions $x_0$, $y_0$ and $z_0$. According to some embodiments, $x_0$ has dimensions in a range between 20 and 25 millimeters, $y_0$ has dimensions between 8 and 12 millimeter, and $z_0$ has dimensions between 19 and 23 millimeters. Exemplary block 605 illustrated in FIG. 6A (e.g., a block in the outer sub-ring of inner permanent magnet ring 410) may be manufactured to have dimensions $x_1$, $y_0$ and $z_0$. According to some embodiments, $x_1$ has dimensions in a range between 27 and 32 millimeters. It should be appreciated that the dimensions of exemplary blocks 505 and 605 are merely illustrative and the dimensions may be selected as desired and are not limited in this respect. Additionally, blocks may be formed using any one or combination of ferromagnetic material, as the aspects are not limited for use with any particular type of magnetic material.

Figure 7A:
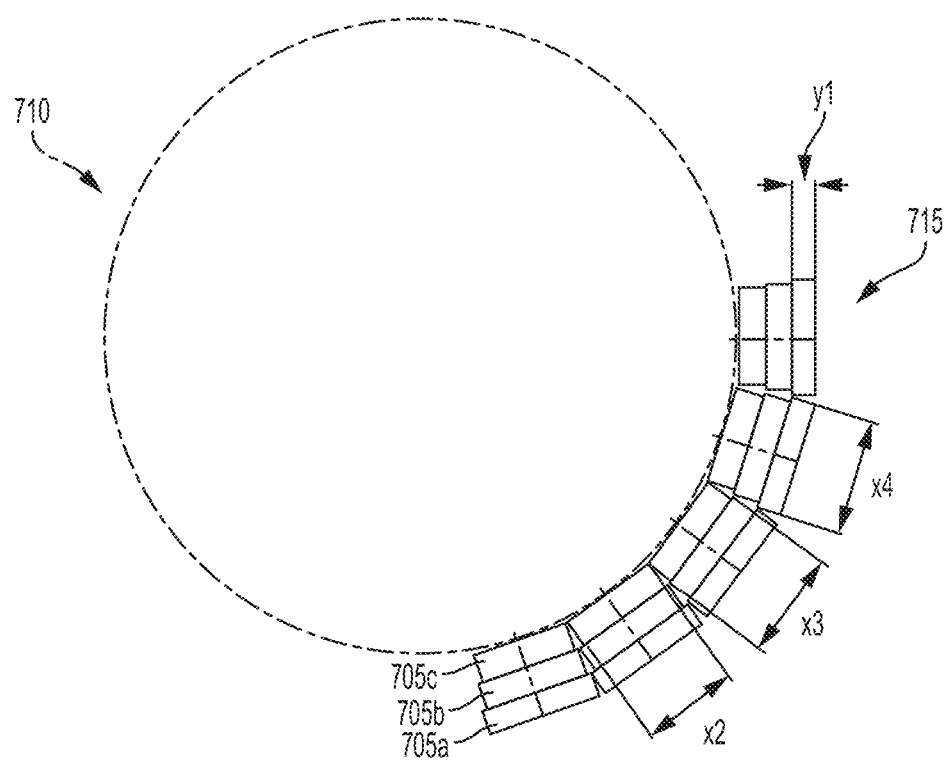
FIGS. 7A-7F illustrate respective portions of an exemplary ring of permanent magnets for a $B_0$ magnet, in accordance with some embodiments.
Figure 7B:
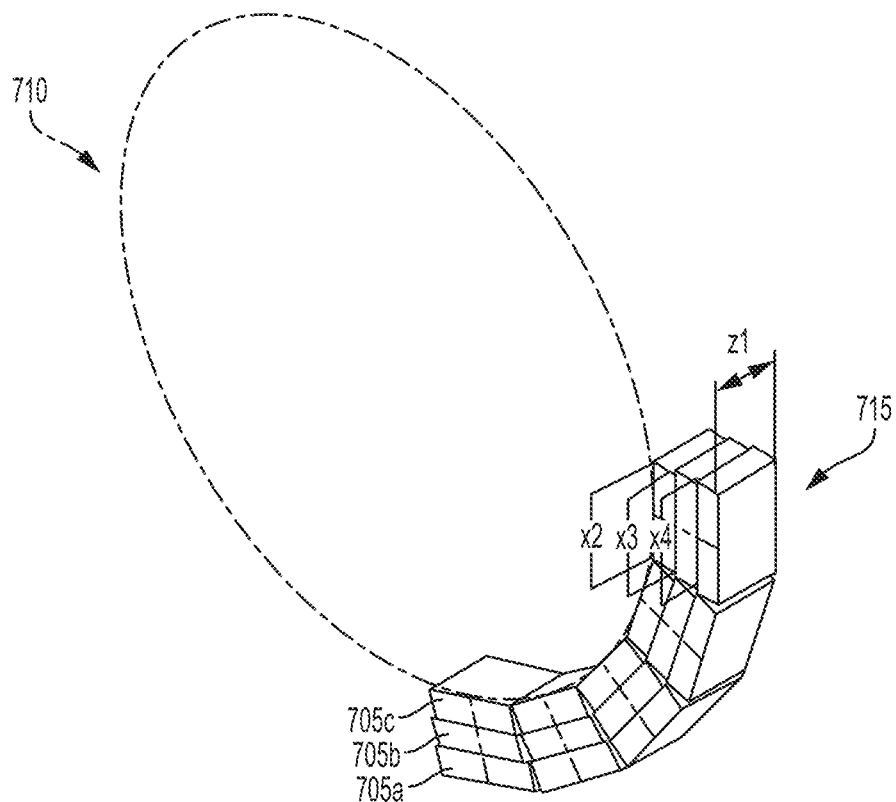

FIGS. 7A and 7B illustrate different views of a portion 715 of middle ring 710 in a quadrant away from the yoke frame (e.g., the portion of ring 310b in quadrant 315c illustrated in FIG. 3B), in accordance with some embodiments. Exemplary portion 715 of ring 710 includes a plurality (five in FIGS. 7A and 7B) of stacks of three blocks each, thus forming three sub-rings of ferromagnetic blocks (e.g., blocks formed of NdFeB, SmCo, etc.). The inner sub-ring is formed of blocks (e.g., exemplary block 705c) having a length $x_2$, a width $y_1$ and a height (or depth) $z_1$. The middle sub-ring is formed of blocks (e.g., exemplary block 705b) having a length $x_3$, a width $y_1$ and a height (or depth) $z_1$. The outer sub-ring is formed of blocks (e.g., exemplary block 705a) having a length $x_4$, a width $y_1$ and a height (or depth) $z_1$. As shown, the blocks in the outer sub-ring have a greater length than blocks in the middle sub-ring which, in turn, have a length greater than the blocks in the inner sub-ring (i.e., $x_2<x_3<x_4$), reducing the amount of empty space between adjacent block than if the blocks in all sub-rings were formed with a length $x_2$. As such more of the space in which exemplary ring 710 is contained is occupied by field producing magnetic material, increasing the field strength in the same amount of space. It should be appreciated that the arrangement in exemplary ring 710 is merely illustrative and other arrangements of blocks (e.g., number of stacks and number of blocks within each stack) may be used, as the aspects are not limited in this respect.

Figure 7C:
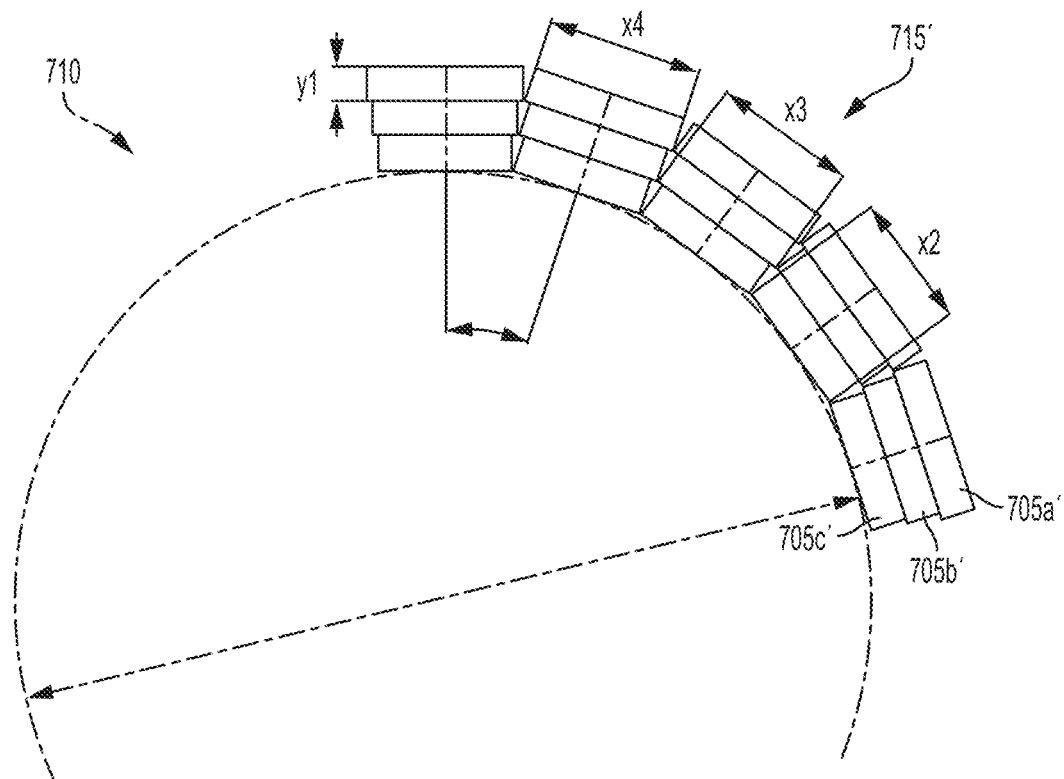
Figure 7D:
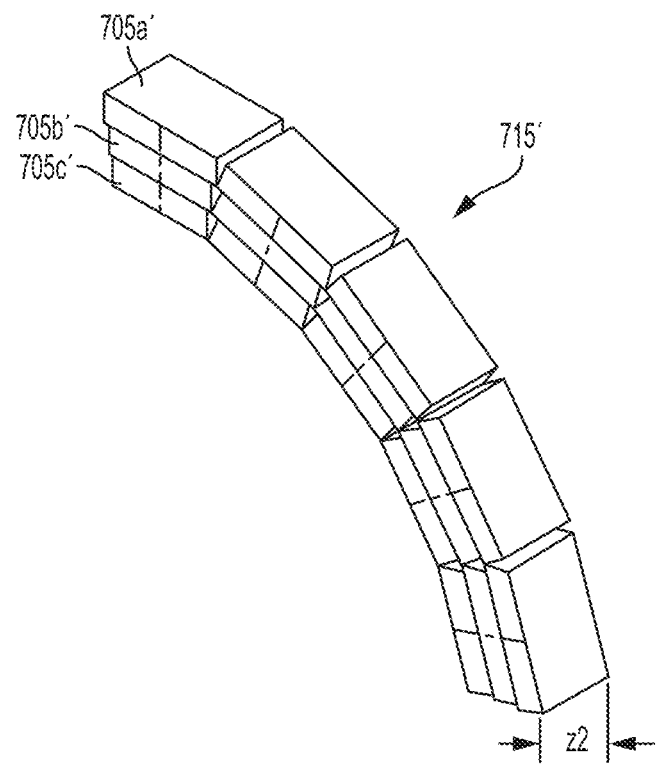

FIGS. 7C and 7D illustrate different views of a portion 715' of middle ring 710 in quadrant(s) in the middle with respect to the yoke frame (e.g., the portion of ring 310b in quadrant 315b and/or 315d illustrated in FIG. 3B), in accordance with some embodiments. That is, portion 715' may be used for both middle quadrants, for example, in embodiments where the middle quadrants are equidistant from the yoke frame. Exemplary portion 715' of ring 710 includes a plurality (five in FIGS. 7C and 7D) of stacks of three blocks each, thus forming three sub-rings of ferromagnetic blocks (e.g., blocks formed of NdFeB, SmCo, etc.). The inner sub-ring is formed of blocks (e.g., exemplary block 705c') having a length $x_2$, a width $y_1$ and a height (or depth) $z_2$. The middle sub-ring is formed of blocks (e.g., exemplary block 705b') having a length $x_3$, a width $y_1$ and a height (or depth) $z_2$. The outer sub-ring is formed of blocks (e.g., exemplary block 705a') having a length $x_4$, a width $y_1$ and a height (or depth) $z_2$. As shown, the blocks in the outer sub-ring have a greater length than blocks in the middle sub-ring which, in turn, have a length greater than the blocks in the inner sub-ring (i.e., $x_2<x_3<x_4$), reducing the amount of empty space between adjacent blocks than if the blocks in all sub-rings were formed with a length $x_2$. As such more of the space in which exemplary ring 710 is contained is occupied by field producing magnetic material, increasing the field strength in the same amount of space. It should be appreciated that the arrangement in exemplary ring 710 is merely illustrative and other arrangements of blocks (e.g., number of stacks and number of blocks within each stack) may be used, as the aspects are not limited in this respect.

Figure 7E:
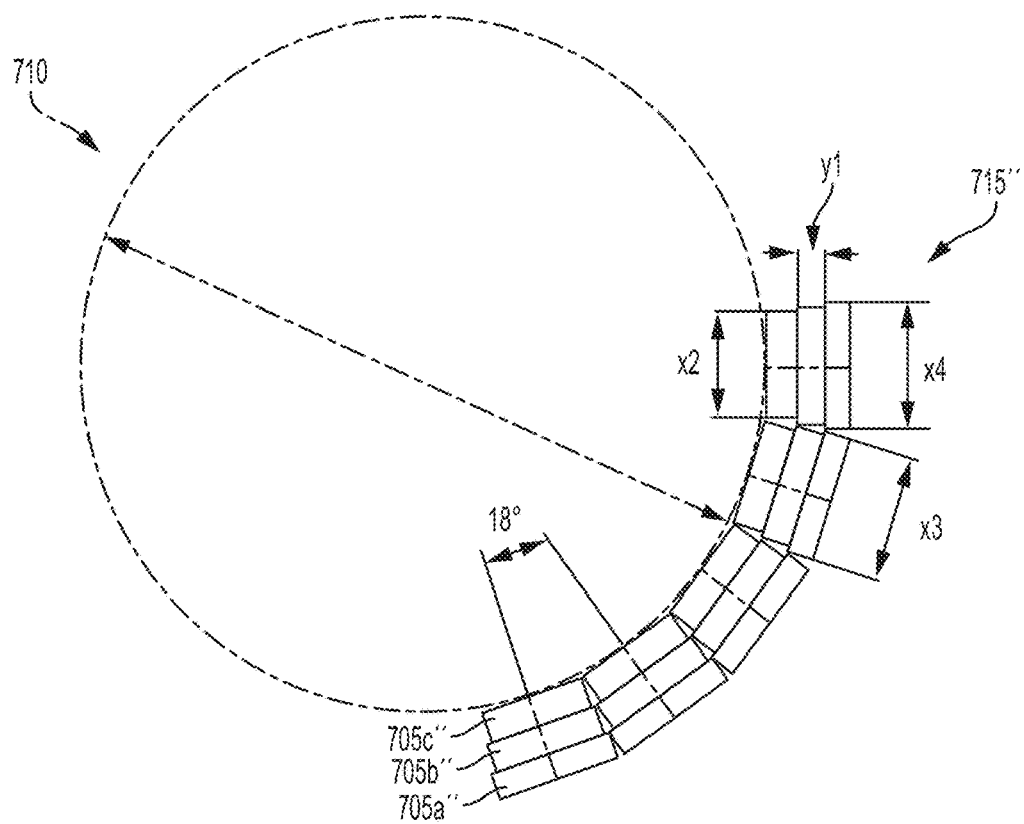
Figure 7F:
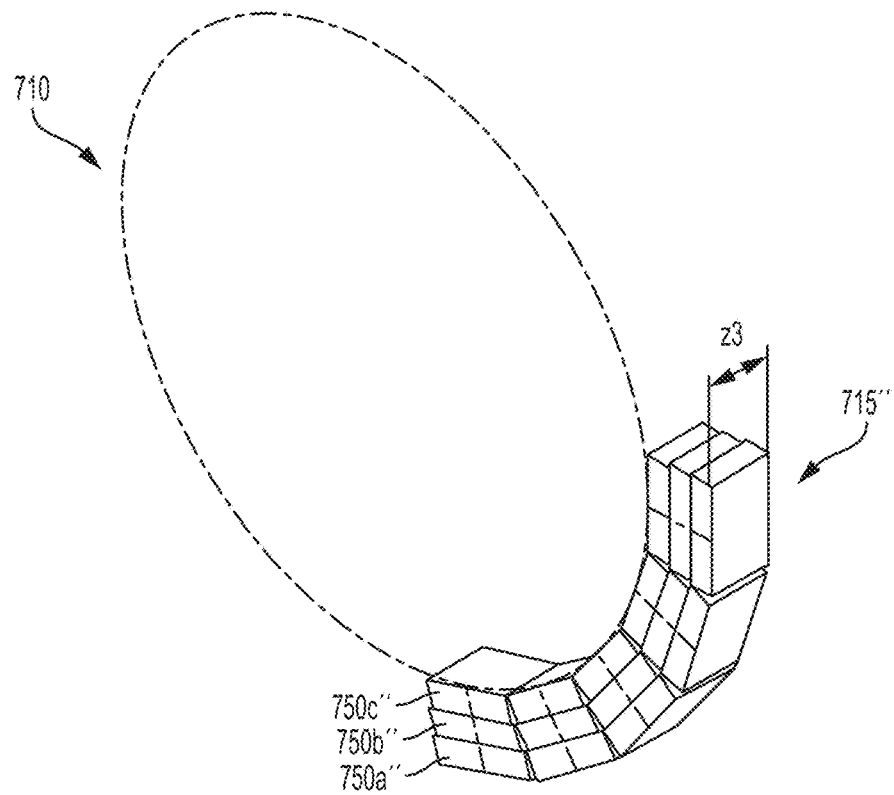
Figure 8A:
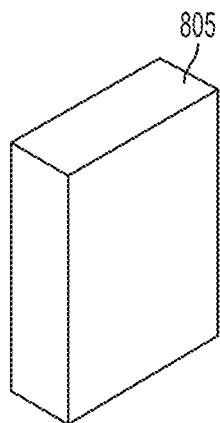
FIGS. 8A-C illustrate exemplary dimensions for permanent magnet blocks for an inner sub-ring of the permanent magnet ring illustrated in FIGS. 7A-F, in accordance with some embodiments.
Figure 8B:
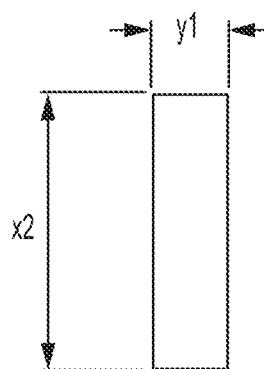
Figure 8C:
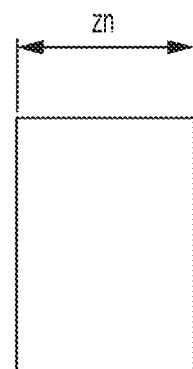
Figure 9A:
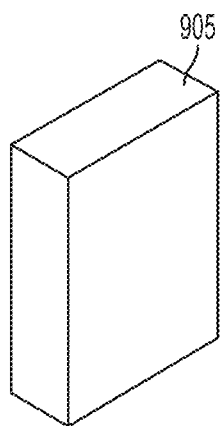
FIGS. 9A-C illustrate exemplary dimensions for permanent magnet blocks for a middle sub-ring of the permanent magnet ring illustrated in FIGS. 7A-F, in accordance with some embodiments.
Figure 9B:
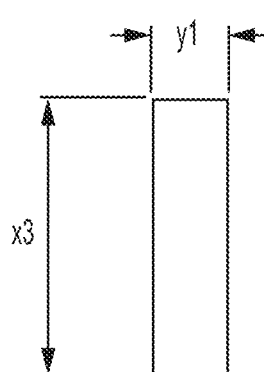
Figure 9C:
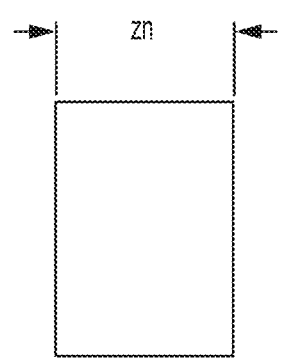
Figure 10A:
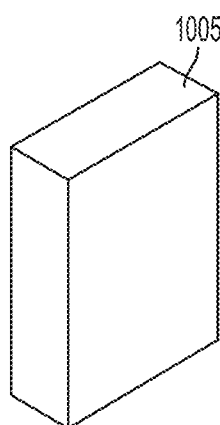
FIGS. 10A-C illustrate exemplary dimensions for permanent magnet blocks for a outer sub-ring of the permanent magnet ring illustrated in FIGS. 7A-F, in accordance with some embodiments.
Figure 10B:
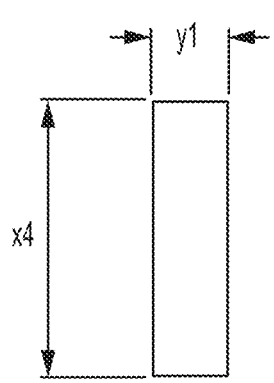
Figure 10C:
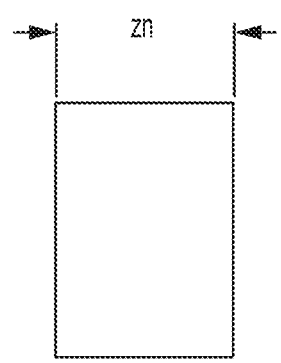

FIGS. 7E and 7F illustrate different views of a portion 715" of middle ring 710 in a quadrant nearest the yoke frame (e.g., the portion of ring 310b in quadrant 315a illustrated in FIG. 3B), in accordance with some embodiments. Exemplary portion 715" of ring 710 includes a plurality (five in FIGS. 7E and 7F) of stacks of three blocks each, thus forming three sub-rings of ferromagnetic blocks (e.g., blocks formed of NdFeB, SmCo, etc.). The inner sub-ring is formed of blocks (e.g., exemplary block 705c") having a length $x_2$, a width $y_1$ and a height (or depth) $z_3$. The middle sub-ring is formed of blocks (e.g., exemplary block 705b") having a length $x_3$, a width $y_1$ and a height (or depth) $z_3$. The outer sub-ring is formed of blocks (e.g., exemplary block 705a") having a length $x_4$, a width $y_1$ and a height (or depth) $z_3$. As shown, the blocks in the outer sub-ring have a greater length than blocks in the middle sub-ring which, in turn, have a length greater than the blocks in the inner sub-ring (i.e., $x_2<x_3<x_4$), reducing the amount of empty space between adjacent block than if the blocks in all sub-rings were formed with a length $x_2$. As such more of the space in which exemplary ring 710 is contained is occupied by field producing magnetic material, increasing the field strength in the same amount of space. It should be appreciated that the arrangement in exemplary ring 710 is merely illustrative and other arrangements of blocks (e.g., number of stacks and number of blocks within each stack) may be used, as the aspects are not limited in this respect.

FIGS. 8A-C, 9A-C and 10A-C illustrate exemplary dimensions for blocks comprising the inner, middle and outer sub-rings of a middle permanent magnet ring (e.g., exemplary dimensions for blocks 705a-705c, 705a'-705c' and 705a"-705c" forming permanent magnet ring 710 illustrated in FIGS. 7A-7F). In particular, exemplary block 805 illustrated in FIG. 8A (e.g., a block in the inner sub-ring of middle permanent magnet ring 710 or 310b) may be manufactured to have dimensions $x_2$, $y_1$ and $z_n$ as labeled in FIGS. 8B and 8C. According to some embodiments, $x_2$ has dimensions in a range between 31 and 35 millimeters, $y_1$ has dimensions between 6 and 10 millimeters, and $z_n$ has dimensions between 21 and 25 millimeters. Exemplary block 905 illustrated in FIG. 9A (e.g., a block in the middle sub-ring of middle permanent magnet ring 710 or 310b) may be manufactured to have dimensions $x_3$, $y_1$ and $z_n$ as labeled in FIGS. 9B and 9C. According to some embodiments, $x_3$ has dimensions in a range between 34 and 38 millimeters. Similarly, exemplary block 1005 illustrated in FIG. 10A (e.g., a block in the outer sub-ring of middle permanent magnet ring 710 or 310b) may be manufactured to have dimensions $x_4$, $y_1$ and $z_n$ as labeled in FIGS. 10B and 10C. According to some embodiments, $x_4$ has dimensions in a range between 37 and 41 millimeters. It should be appreciated that the dimensions of exemplary blocks 805, 905 and 1005 are merely illustrative and the dimensions may be selected as desired and are not limited in this respect. Additionally, blocks may be formed using any one or combination of ferromagnetic material, as the aspects are not limited for use with any particular type of magnetic material. As discussed above, the height of the blocks may be varied to compensate for effects in the homogeneity of the magnetic field resulting from the presence of the yoke. According to some embodiments, $z_n$ is varied depending on which quadrant the block appears in (e.g., whether the block is in quadrant 715, 715' or 715"), further details of which are discussed below.

Figure 11A:
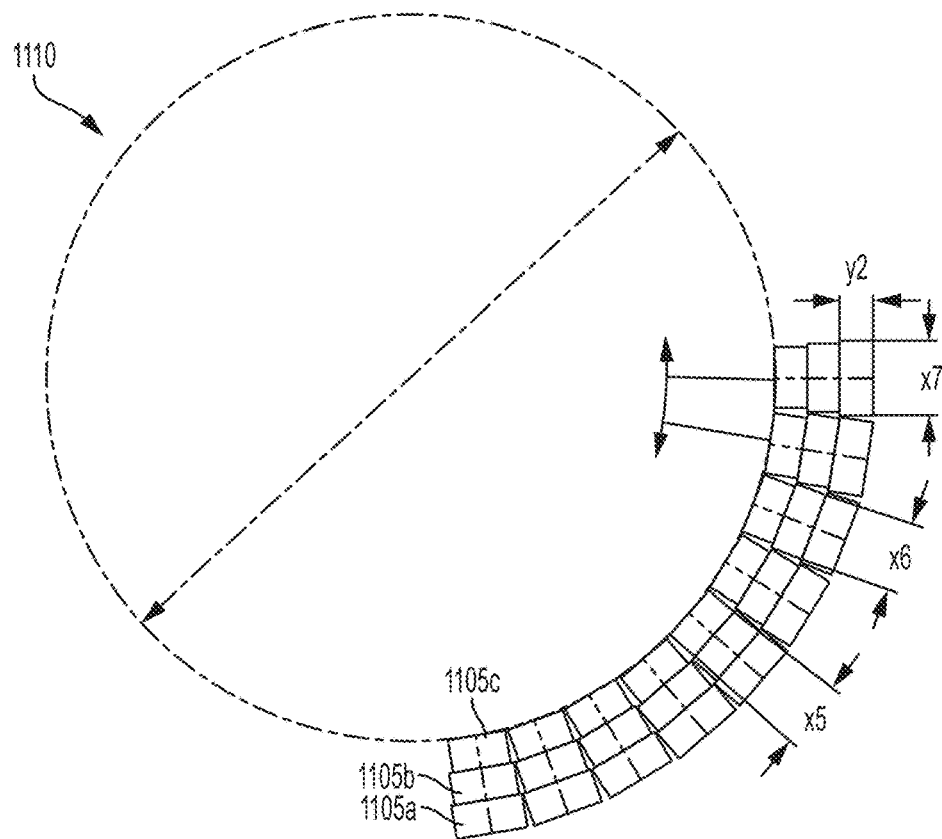
FIGS. 11A-F illustrate portions of an exemplary ring of permanent magnets for a $B_0$ magnet, in accordance with some embodiments.
Figure 11B:
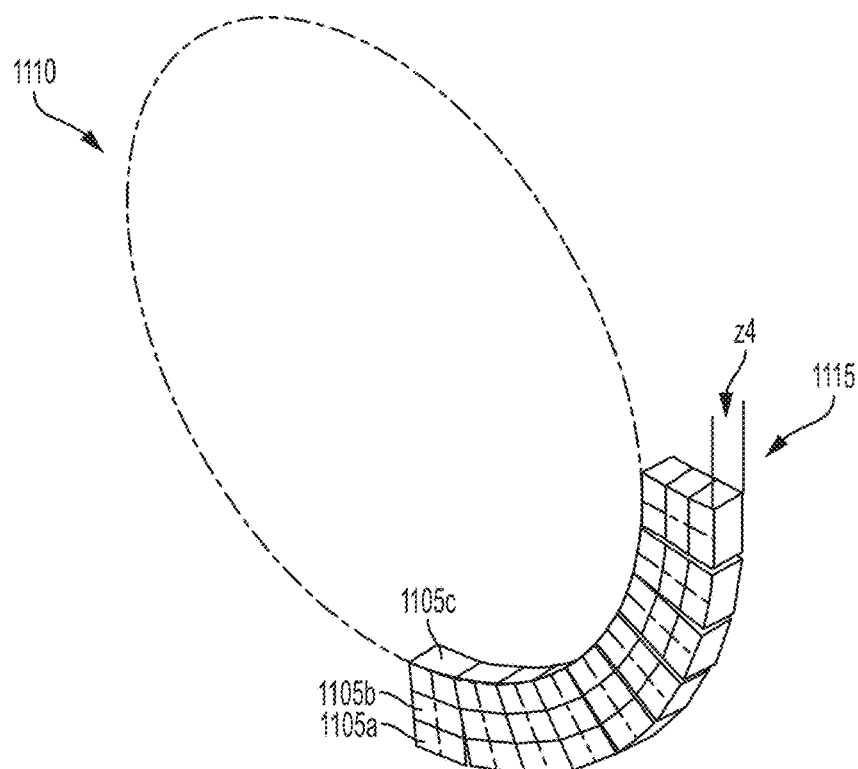

FIGS. 11A and 11B illustrate different views of a portion 1115 of outer ring 1110 in a quadrant away from the yoke frame (e.g., the portion of ring 310a in quadrant 315c illustrated in FIG. 3B), in accordance with some embodiments. Exemplary portion 1115 of ring 1110 includes a plurality (nine in FIGS. 11A and 11B) of stacks of three blocks each, thus forming three sub-rings of ferromagnetic blocks (e.g., blocks formed of NdFeB, SmCo, etc.). The inner sub-ring is formed of blocks (e.g., exemplary block 1105c) having a length $x_5$, a width $y_2$ and a height (or depth) $z_4$. The middle sub-ring is formed of blocks (e.g., exemplary block 1105b) having a length $x_6$, a width $y_2$ and a height (or depth) $z_4$. The outer sub-ring is formed of blocks (e.g., exemplary block 1105a) having a length $x_7$, a width $y_2$ and a height (or depth) $z_4$. As shown, the blocks in the outer sub-ring have a greater length than blocks in the middle sub-ring which, in turn, have a length greater than the blocks in the inner sub-ring (i.e., $x_5<x_6<x_7$), reducing the amount of empty space between adjacent block than if the blocks in all sub-rings were formed with a length $x_5$. As such more of the space in which exemplary ring 1110 is contained is occupied by field producing magnetic material, increasing the field strength in the same amount of space. It should be appreciated that the arrangement in exemplary ring 1110 is merely illustrative and other arrangements of blocks (e.g., number of stacks and number of blocks within each stack) may be used, as the aspects are not limited in this respect.

Figure 11C:
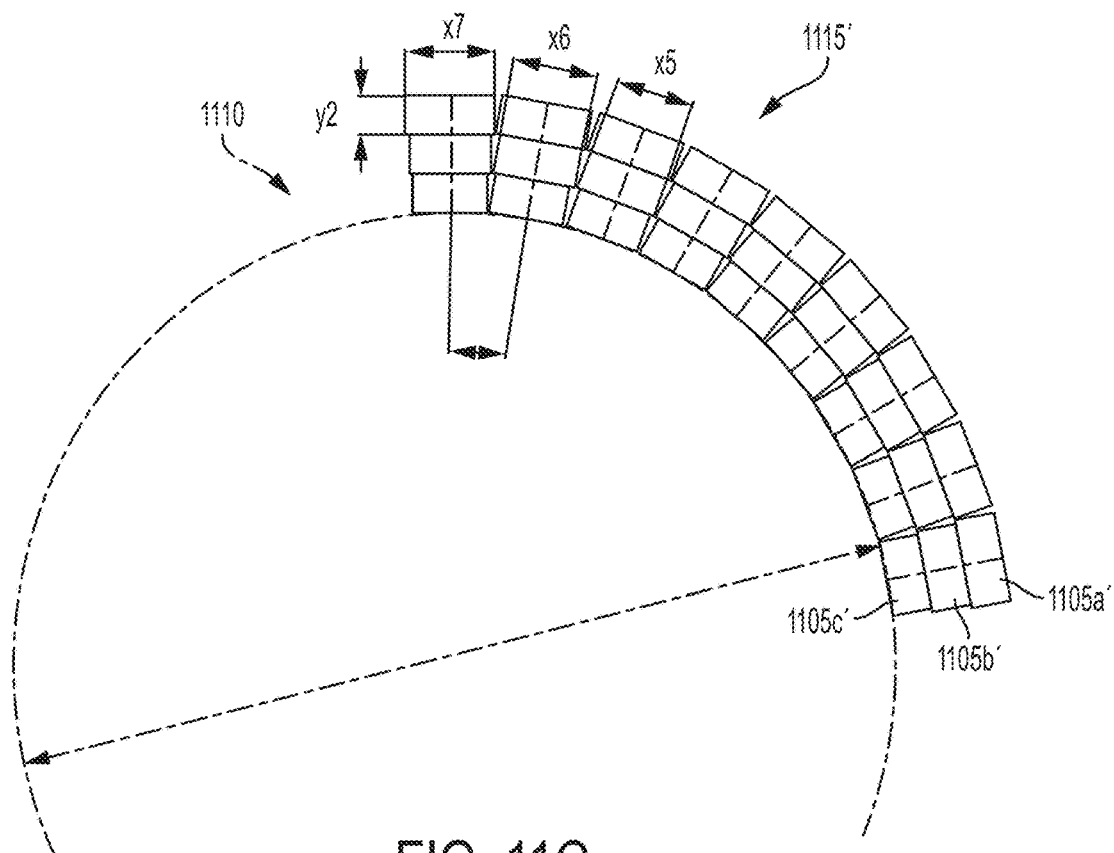
Figure 11D:
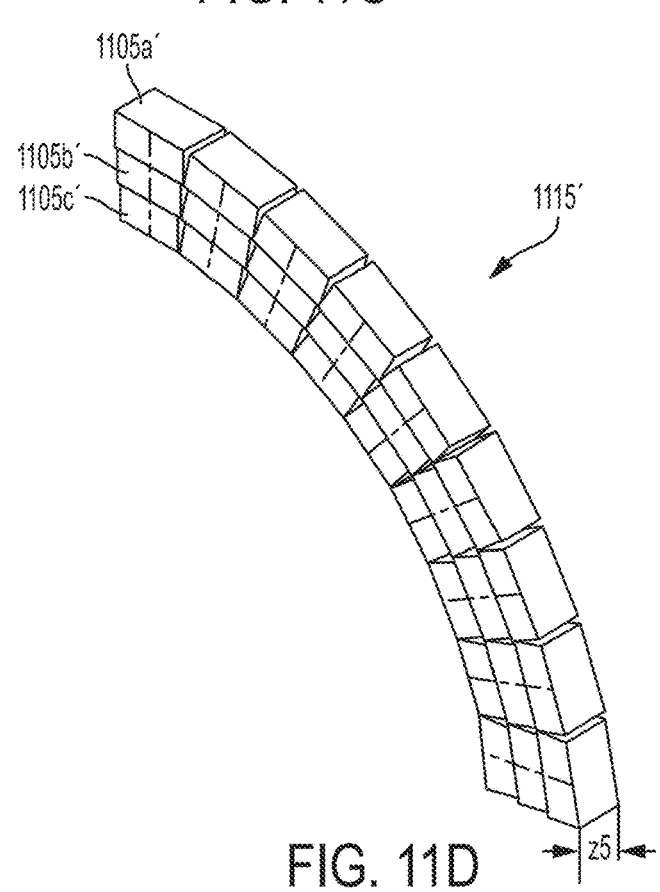

FIGS. 11C and 11D illustrate different views of a portion 1115' of outer ring 1110 in quadrant(s) in the middle with respect to the yoke frame (e.g., the portion of ring 310a in quadrant 315b and/or 315d illustrated in FIG. 3B), in accordance with some embodiments. That is, portion 1115' may be used for both middle quadrants, for example, in embodiments where the middle quadrants are equidistant from the yoke frame. Exemplary portion 1115' of ring 1110 includes a plurality (nine in FIGS. 11C and 11D) of stacks of three blocks each, thus forming three sub-rings of ferromagnetic blocks (e.g., blocks formed of NdFeB, SmCo, etc.). The inner sub-ring is formed of blocks (e.g., exemplary block 1105c') having a length $x_5$, a width $y_2$ and a height (or depth) $z_5$. The middle sub-ring is formed of blocks (e.g., exemplary block 1105b') having a length $x_6$, a width $y_2$ and a height (or depth) $z_5$. The outer sub-ring is formed of blocks (e.g., exemplary block 1105a') having a length $x_7$, a width $y_2$ and a height (or depth) $z_s$. As shown, the blocks in the outer sub-ring have a greater length than blocks in the middle sub-ring which, in turn, have a length greater than the blocks in the inner sub-ring (i.e., $x_5<x_6<x_7$), reducing the amount of empty space between adjacent block than if the blocks in all sub-rings were formed with a length $x_5$. As such more of the space in which exemplary ring 1110 is contained is occupied by field producing magnetic material, increasing the field strength in the same amount of space. It should be appreciated that the arrangement in exemplary ring 1110 is merely illustrative and other arrangements of blocks (e.g., number of stacks and number of blocks within each stack) may be used, as the aspects are not limited in this respect.

Figure 11E:
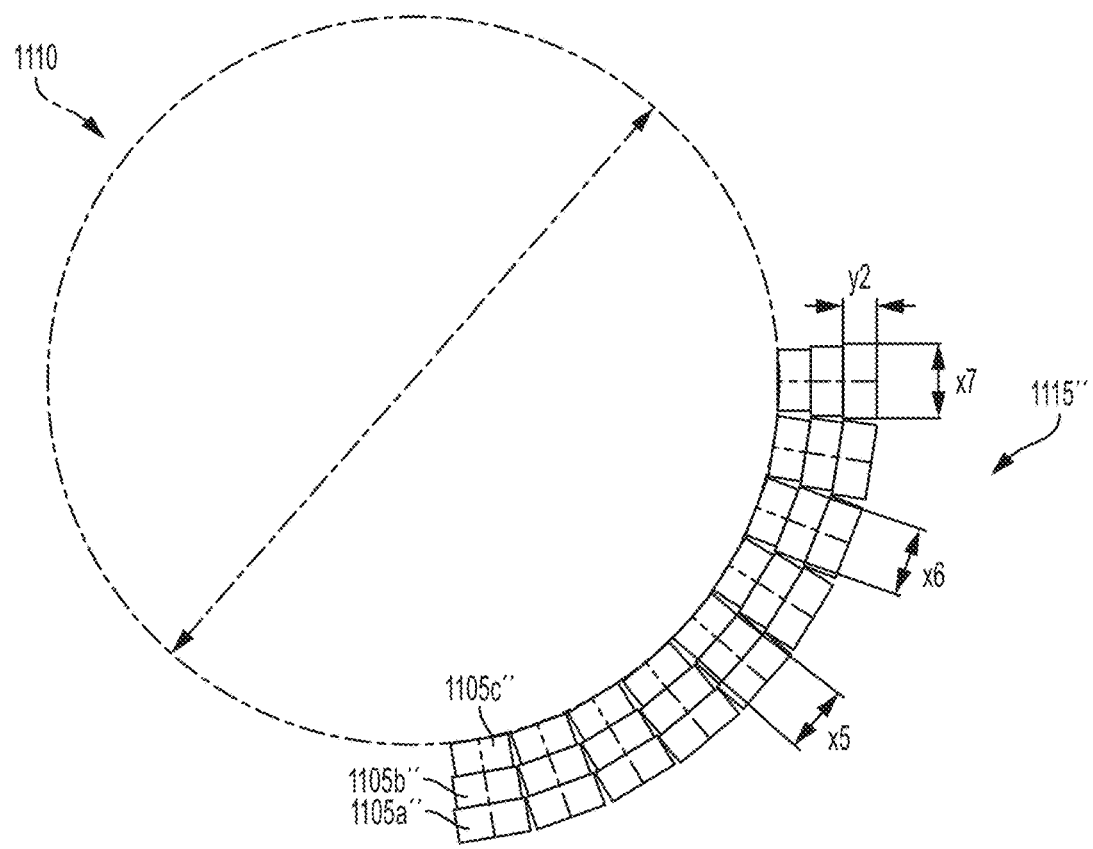
Figure 11F:
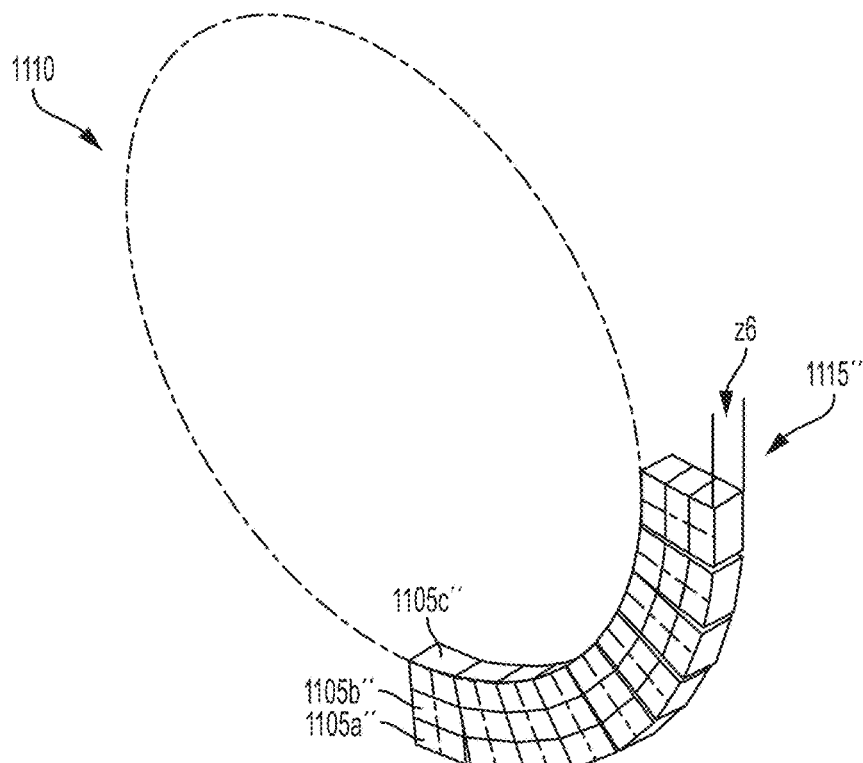
Figure 12A:
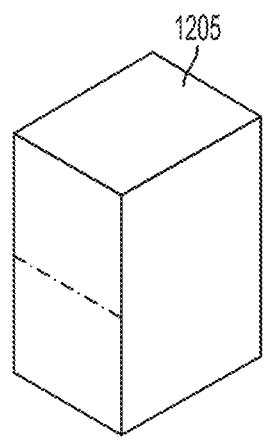
FIGS. 12A-C illustrate exemplary dimensions for permanent magnet blocks for an inner sub-ring of the permanent magnet ring illustrated in FIGS. 11A-F, in accordance with some embodiments.
Figure 12B:
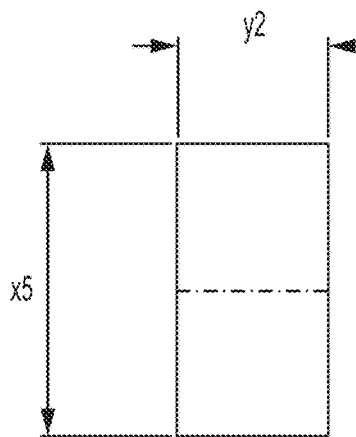
Figure 12C:
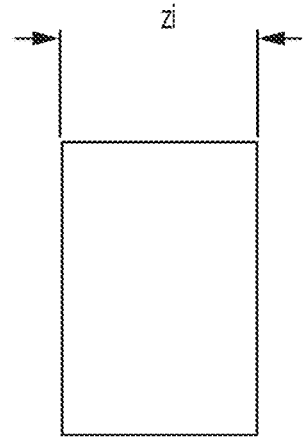
Figure 13A:
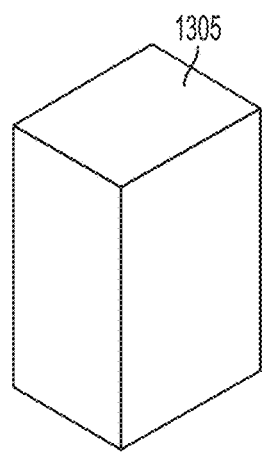
FIGS. 13A-C illustrate exemplary dimensions for permanent magnet blocks for a middle sub-ring of the permanent magnet ring illustrated in FIGS. 11A-F, in accordance with some embodiments.
Figure 13B:
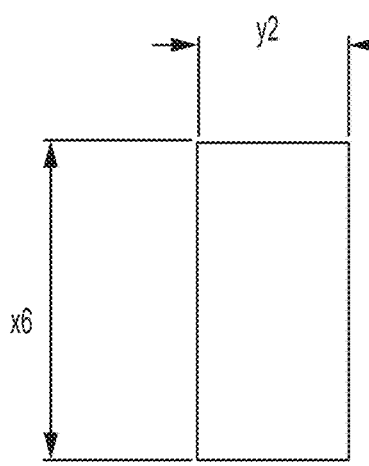
Figure 13C:
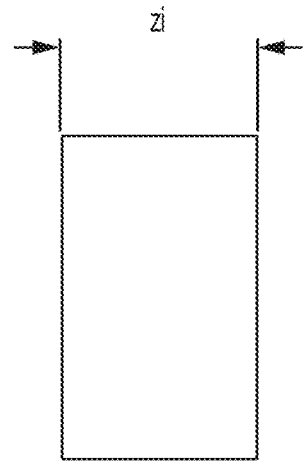
Figure 14A:
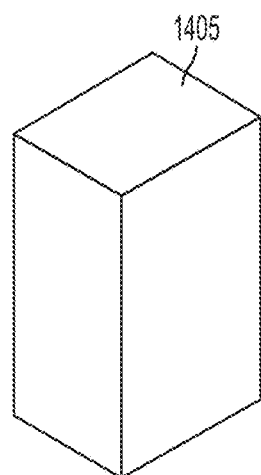
FIGS. 14A-C illustrate exemplary dimensions for permanent magnet blocks for an outer sub-ring of the permanent magnet ring illustrated in FIGS. 11A-F, in accordance with some embodiments.
Figure 14B:
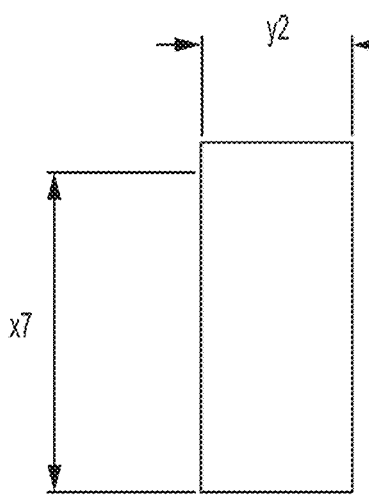
Figure 14C:
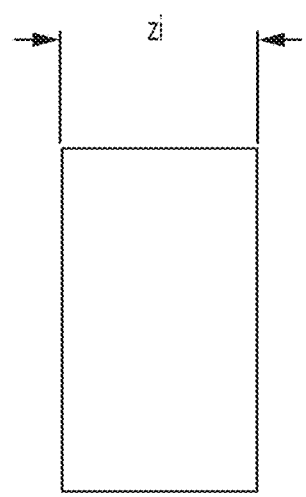

FIGS. 11E and 11F illustrate different views of a portion 1115" of outer ring 1110 in a quadrant nearest the yoke frame (e.g., the portion of ring 310a in quadrant 315a illustrated in FIG. 3B), in accordance with some embodiments. Exemplary portion 1115" of ring 1110 includes a plurality (nine in FIGS. 11E and 11F) of stacks of three blocks each, thus forming three sub-rings of ferromagnetic blocks (e.g., blocks formed of NdFeB, SmCo, etc.). The inner sub-ring is formed of blocks (e.g., exemplary block 1105c") having a length $x_5$, a width $y_2$ and a height (or depth) $z_6$. The middle sub-ring is formed of blocks (e.g., exemplary block 1105b") having a length $x_6$, a width $y_2$ and a height (or depth) $z_6$. The outer sub-ring is formed of blocks (e.g., exemplary block 1105a") having a length $x_7$, a width $y_2$ and a height (or depth) $z_6$. As shown, the blocks in the outer sub-ring have a greater length than blocks in the middle sub-ring which, in turn, have a length greater than the blocks in the inner sub-ring (i.e., $x_5<x_6<x_7$), reducing the amount of empty space between adjacent block than if the blocks in all sub-rings were formed with a length $x_5$. As such more of the space in which exemplary ring 1110 is contained is occupied by field producing magnetic material, increasing the field strength in the same amount of space. It should be appreciated that the arrangement in exemplary ring 1110 is merely illustrative and other arrangements of blocks (e.g., number of stacks and number of blocks within each stack) may be used, as the aspects are not limited in this respect.

FIGS. 12A-C, 13A-C and 14A-C illustrate exemplary dimensions for blocks comprising the inner, middle and outer sub-rings of an outer permanent magnet ring (e.g., exemplary dimensions for blocks 1105a-1105c, 1105a'-1105c' and 1105a"-1105c" forming permanent magnet ring 1110). In particular, exemplary block 1205 illustrated in FIG. 12A (e.g., a block in the inner sub-ring of outer permanent magnet ring 1110 or 310a) may be manufactured to have dimensions $x_5$, $y_2$ and $z_i$, as labeled in FIGS. 12B and 12C. According to some embodiments, $x_5$ is in a range between 34 and 38 millimeters, $y_2$ is in a range between 16 and 20 millimeters and $z_i$ is in a range between 22 and 27 millimeters. Exemplary block 1305 illustrated in FIG. 13A (e.g., a block in the middle sub-ring of outer permanent magnet ring 1110 or 310a) may be manufactured to have dimensions $x_6$, $y_2$ and $z_i$, as labeled in FIGS. 13B and 13C. According to some embodiments, $x_6$ is in a range between 37 and 43 millimeters, $y_2$ is in a range between 16 and 20 millimeters and $z_i$ is in a range between 22 and 27 millimeters. Similarly, exemplary block 1405 illustrated in FIG. 14A (e.g., a block in the outer sub-ring of outer permanent magnet ring 1110 or 310a) may be manufactured to have dimensions $x_7$, $y_2$ and $z_i$, as labeled in FIGS. 14B and 14C. According to some embodiments, $x_7$ is in a range between 40 and 45 millimeters, $y_2$ is in a range between 16 and 20 millimeters and $z_i$ is in a range between 22 and 27 millimeters. It should be appreciated that the dimensions of exemplary blocks 1205, 1305 and 1405 are merely illustrative and the dimensions may be selected as desired and are not limited in this respect. Additionally, blocks may be formed using any one or combination of ferromagnetic material, as the aspects are not limited for use with any particular type of magnetic material. As discussed above, the height of the blocks may be varied to compensate for effects in the homogeneity of the magnetic field resulting from the presence of the yoke. According to some embodiments, $z_i$ is varied depending on which quadrant the block appears in (e.g., whether the block is in quadrant 1115, 1115' or 1115"), further details of which are discussed below.

It should be appreciated that the permanent magnet illustrated in FIG. 3A can be manufactured using any number and arrangement of permanent magnet blocks and are limited to the number, arrangement, dimensions or materials illustrated herein. The configuration of the permanent magnets will depend, at least in part, on the design characteristics of the $B_0$ magnet, including, but not limited to, the field strength, field of view, portability and/or cost desired for the MRI system in which the $B_0$ magnet is intended to operate. For example, the permanent magnet blocks may be dimensioned to produce a magnetic field ranging from 20 mT to 0.1 T, depending on the field strength desired. However, it should be appreciated that other low-field strengths (e.g., up to approximately 0.2 T) may be produced by increasing the dimensions of the permanent magnet, though such increases will also increase the size, weight and cost of the $B_0$ magnet.

As discussed above, the height or depth of the blocks used in the different quadrants may be varied to compensate for effects on the $B_0$ magnetic field resulting from an asymmetric yoke. For example, in the configuration illustrated in FIG. 3A, the position of frame 322 (in particular, legs 325a and 325b) to the permanent magnets 310a and 310b results in magnetic flux being drawn away from regions proximate the frame (e.g., quadrant 315a), reducing the flux density in these regions. To address the resulting non-uniformity in the magnetic field, the height or depth of the blocks in affected regions may be varied (e.g., increased) to generate additional magnetic flux to compensate for the reduction in magnetic flux density caused by the yoke, thereby improving the homogeneity of the $B_0$ magnetic field within the field of view of the $B_0$ magnet.

The inventors have appreciated that the arrangement, dimensions and materials used for the permanent magnet blocks may be chosen to minimize the Lorentz forces produced by the $B_0$ coil during operation of the gradient coils. This technique can be used to reduce vibration and acoustic noise during the operation of the MRI system. According to some embodiments, the design of the permanent magnet blocks are chosen to reduce magnetic field components perpendicular to the $B_0$ field, i.e., parallel to the plane of the gradient coils. According to some embodiments, the outer ring of permanent magnet blocks are designed to reduce the magnetic field components responsible for vibration of the gradient coils during operation in areas outside the field of view of the MRI system, thereby reducing vibration and acoustic noise generated during operation of the MRI system.

Figure 15C:
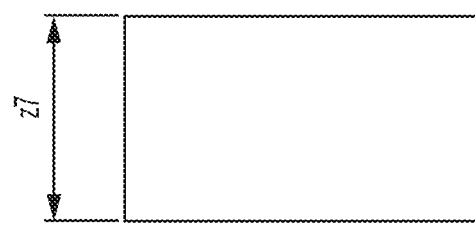
FIGS. 15A-C illustrate views of an exemplary permanent magnet disk, in accordance with some embodiments.
Figure 15B:
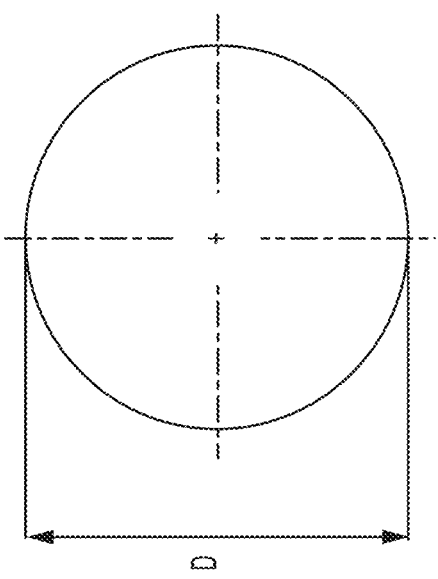
Figure 15A:
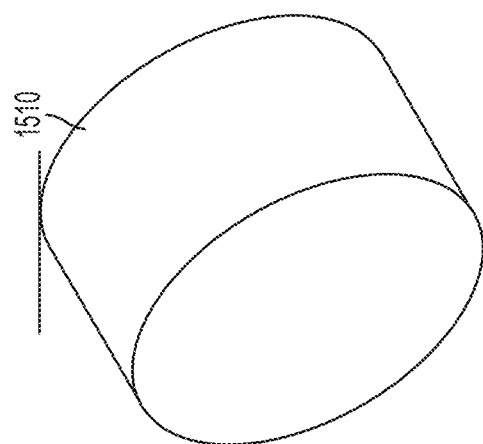

FIGS. 15A-15C illustrate an exemplary permanent magnet disk (e.g., permanent magnet disk 310d illustrated in FIG. 3B), in accordance with some embodiment. Permanent magnet disk 1510 is configured to be placed at center of the permanent magnet (e.g., permanent magnet 310a and/or 310b illustrated in FIG. 3A) to contribute to the $B_0$ field produced by the permanent magnet. Permanent magnet disk 1510 may be formed from any suitable ferromagnetic material (e.g., NdFeB, SmCo, etc.) and have suitable dimensions so that, when magnetized, permanent magnet disk produces a desired magnetic field. Exemplary permanent magnet disk 1510 has a diameter D (e.g., in range between 32 and 36 millimeters) and a thickness $z_7$ (e.g., in range between 18 and 22 millimeters), though any dimensions may be used to satisfy the design requirements of a particular $B_0$ magnet (e.g., to achieve a desired field strength and/or homogeneity).

Figure 16:
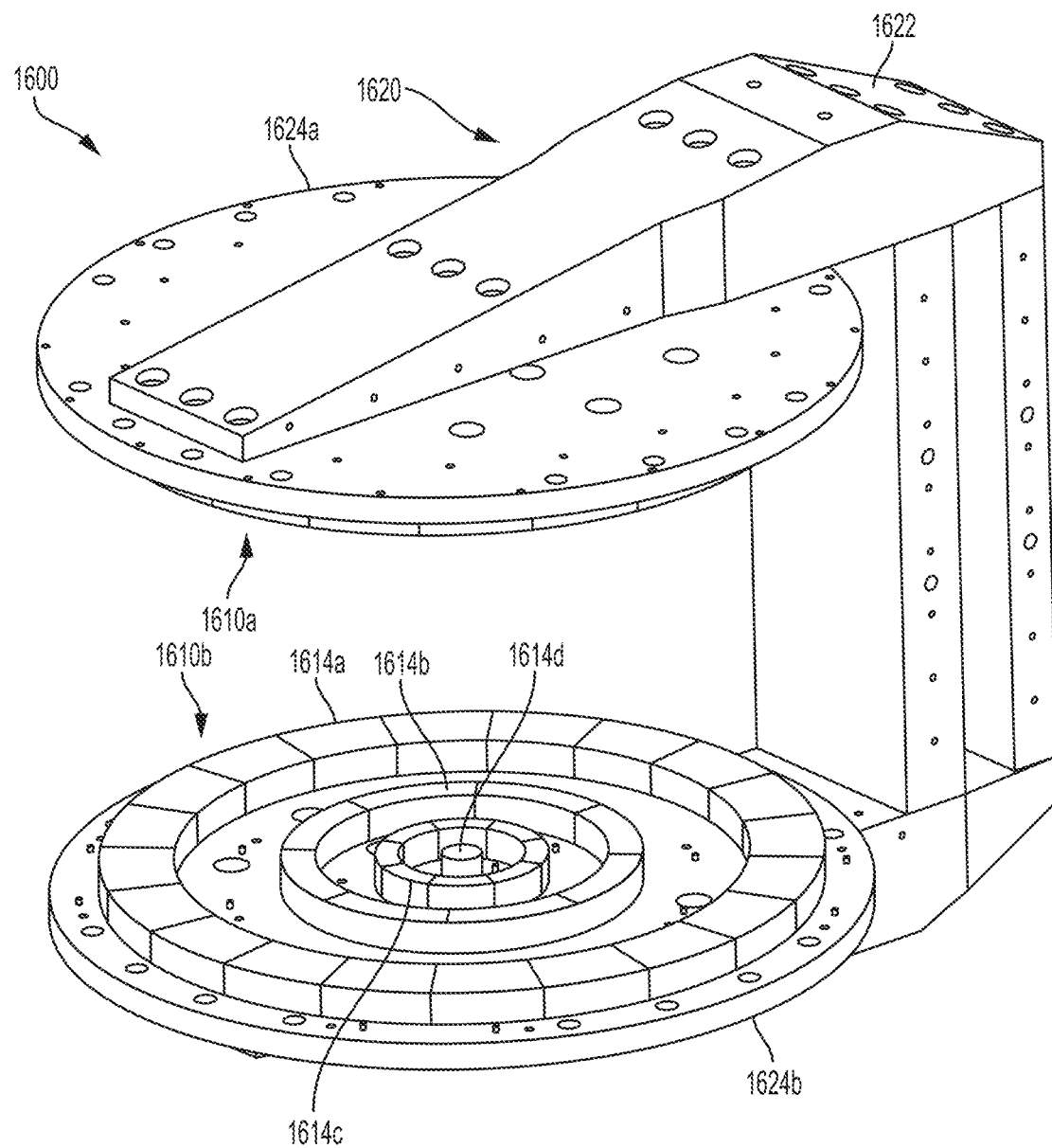
FIG. 16 illustrates a B0 magnet comprising a plurality of permanent magnets, in accordance with some embodiments.

FIG. 16 illustrates a $B_0$ magnet 1600, in accordance with some embodiments. $B_0$ magnet 1600 may share design components with $B_0$ magnet 300 illustrated in FIG. 3A. In particular, $B_0$ magnet 1600 is formed by permanent magnets 1610a and 1610b arranged in a bi-planar geometry with a yoke 1620 coupled thereto to capture electromagnetic flux produced by the permanent magnets and transfer the flux to the opposing permanent magnet to increase the flux density between permanent magnets 1610a and 1610b. Each of permanent magnets 1610a and 1610b are formed from a plurality of concentric permanent magnets, as shown by permanent magnet 1610b comprising an outer ring of permanent magnets 1614a, a middle ring of permanent magnets 1614b, an inner ring of permanent magnets 1614c, and a permanent magnet disk 1614d at the center. Permanent magnet 1610a may comprise the same set of permanent magnet elements as permanent magnet 1610b. The permanent magnet material used may be selected depending on the design requirements of the system (e.g., NdFeB, SmCo, etc. depending on the properties desired).

The permanent magnet rings are sized and arranged to produce a homogenous field of a desired strength in the central region (field of view) between permanent magnets 1610a and 1610b. In particular, in the exemplary embodiment illustrated in FIG. 16, each permanent magnet ring comprises a plurality of circular arc segments sized and positioned to produce a desired $B_0$ magnetic field, as discussed in further detail below. In a similar manner to yoke 320 illustrated in FIG. 3A, yoke 1620 is configured and arranged to capture magnetic flux generated by permanent magnets 1610a and 1610b and direct it to the opposing side of the $B_0$ magnet to increase the flux density in between permanent magnets 1610a and 1610b. Yoke 1620 thereby increases the field strength within the field of view of the $B_0$ magnet with less permanent magnet material, reducing the size, weight and cost of the $B_0$ magnet. Yoke 1620 also comprises a frame 1622 and plates 1624a and 1624b that, in a manner similar to that described above in connection with yoke 1620, captures and circulates magnetic flux generated by the permanent magnets 1610a and via the magnetic return path of the yoke to increase the flux density in the field of view of the $B_0$ magnet. The structure of yoke 1620 may be similar to that described above to provide sufficient material to accommodate the magnetic flux generated by the permanent magnets and provide sufficient stability, while minimizing the amount of material used to, for example, reduce the cost and weight of the $B_0$ magnet.

Figure 17:
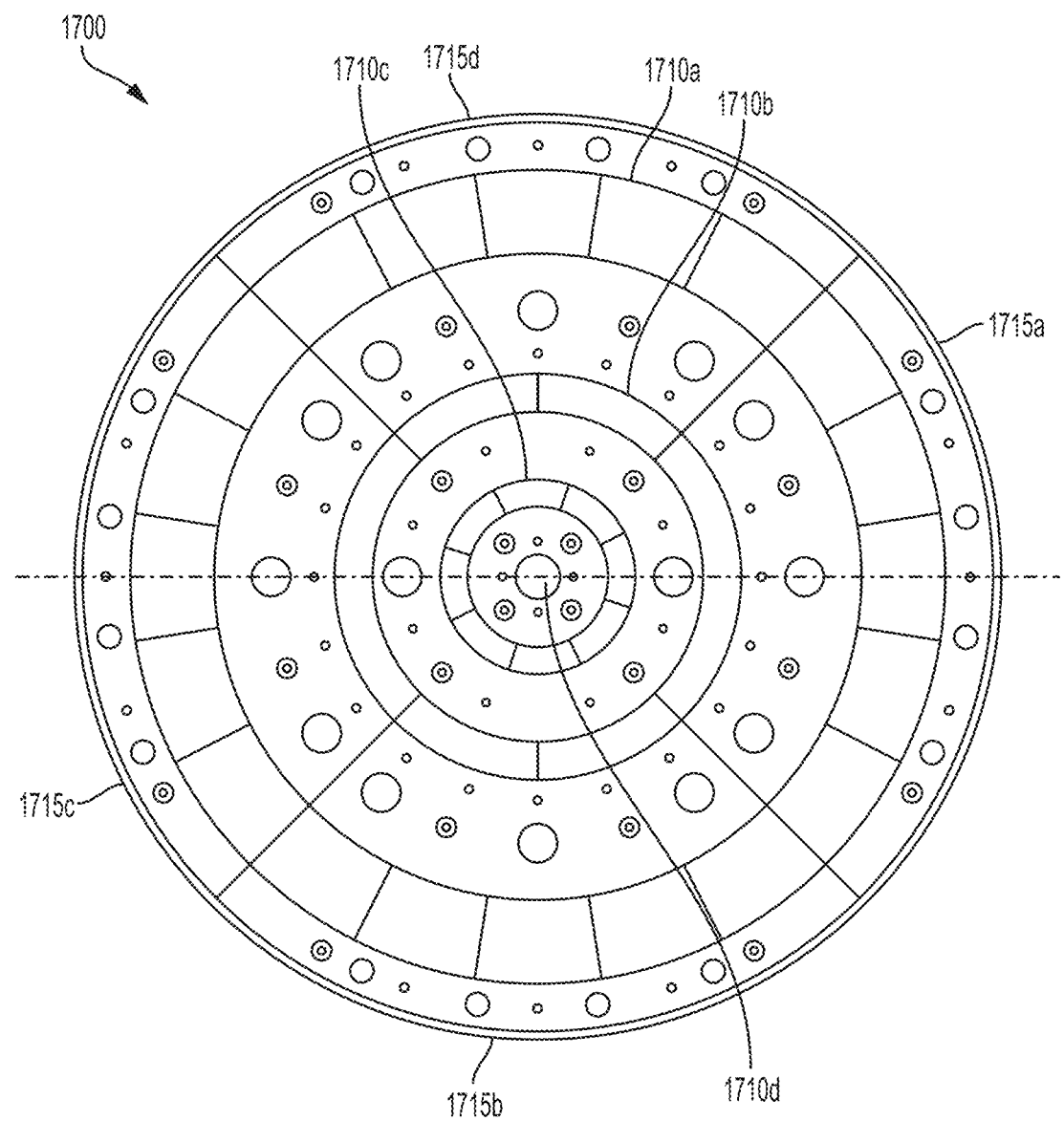
FIG. 17 illustrates a top view of an exemplary configuration of permanent magnet rings forming, in part, the $B_0$ magnet illustrated in FIG. 16.

FIG. 17 illustrates a top-down view of a permanent magnet 1710, which may, for example, be used as the design for permanent magnets 1610a and 1610b of $B_0$ magnet 1600 illustrated in FIG. 16. Permanent magnet 1710 comprises concentric rings 1710a, 1710b, and 1710c, each constructed of a plurality of circular arc segments of ferromagnetic material, and a ferromagnetic disk 1710d at the center. The direction of the frame of the yoke to which permanent magnet is attached is indicated by arrow 22. In embodiments in which the yoke is not symmetric (e.g., yoke 1620), the yoke will cause the magnetic field produced by the permanent magnets for which it captures and focuses magnetic flux to be asymmetric as well, negatively impacting the uniformity of the $B_0$ magnetic field. According to some embodiments, one or more dimensions of the circular arc segments are varied to compensate for the effects of the yoke on the magnetic field produced by the permanent magnet. For example, one or more dimensions of circular arc segments in the four quadrants 1715a, 1715b, 1715c and 1715d labeled in FIG. 17 may be varied to compensate for the effects of the yoke on the $B_0$ magnetic field, as discussed in further detail below.

Figure 18A:
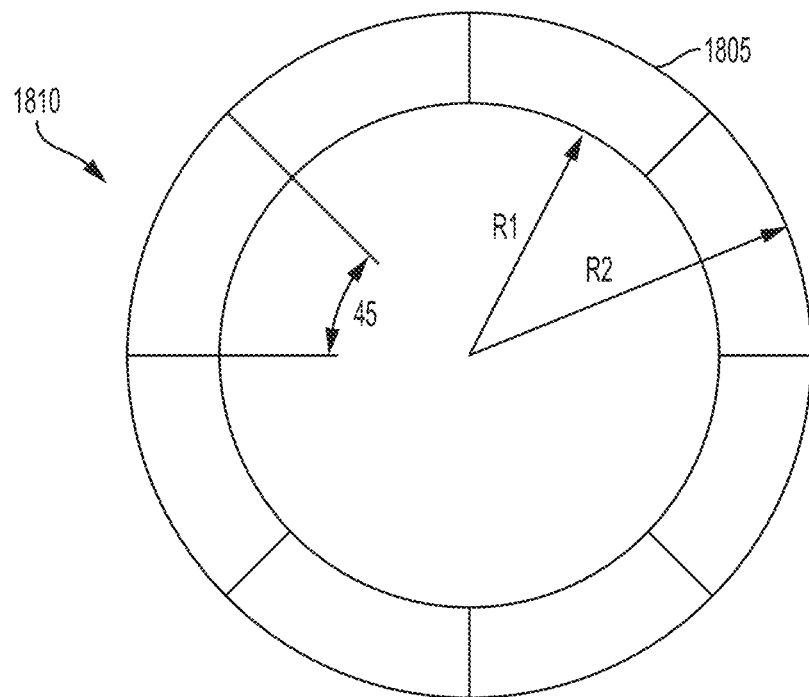
FIGS. 18A and 18B illustrate an exemplary ring of permanent magnet segments for a $B_0$ magnet, in accordance with some embodiments.
Figure 18B:
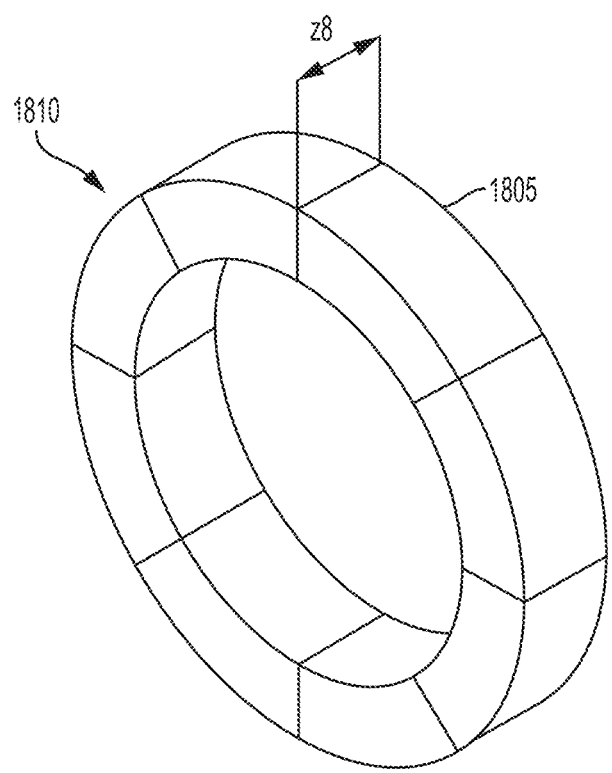

FIGS. 18A and 18B illustrate different views of an inner ring 1810 (e.g., ring 1710c illustrated in FIG. 17), in accordance with some embodiments. Exemplary ring 1810 includes a plurality (eight in exemplary ring 1810 illustrated in FIGS. 18A and 18B) of ferromagnetic circular arc segments (e.g., segments formed of NdFeB, SmCo, etc.), each spanning 45° of the ring. In exemplary ring 1810, the circular arc segments (e.g., exemplary circular arc segment 1805) are dimensioned so as to provide a ring with inner radius R1 and outer radius R2 and a height or depth $z_8$. According to some embodiments, inner ring 1810 has dimensions of R1 between 45-47 mm (e.g., 46.08 mm), R2 between 62-64 mm (e.g., 62.91 mm) and $z_8$ between 22 and 25 mm (e.g., 23.46 mm). It should be appreciated that the number of circular arc segments and the dimensions thereof may be chosen as desired to produce a desired $B_0$ magnetic field (e.g., a desired field strength and/or homogeneity), as the aspects are not limited in this respect.

Figure 18E:
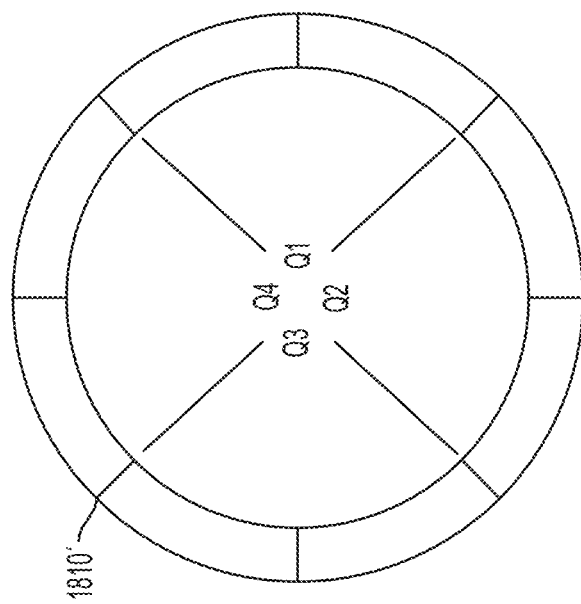
FIG. 18E illustrates a permanent magnet ring for a $B_0$ magnet, in accordance with some embodiments.
Figure 18D:
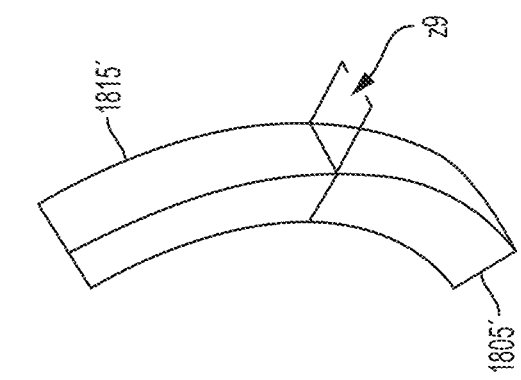
FIGS. 18C and 18D illustrate different views of permanent magnet segments that can be used to form the permanent magnet ring illustrated in FIG. 18E, in accordance with some embodiments.
Figure 18C:
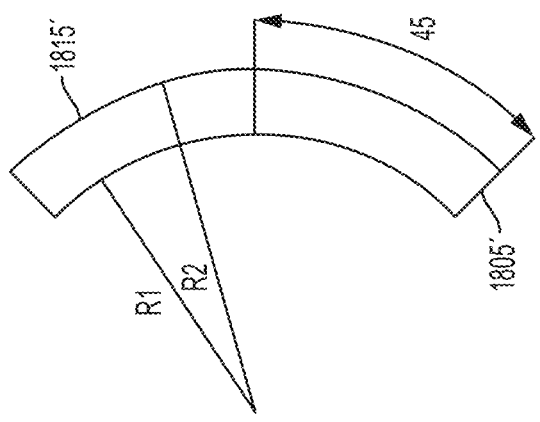

FIGS. 18C and 18D illustrate different views of a segment 1815' that can be used to form middle ring 1810' illustrated in FIG. 18E (e.g., ring 1710b illustrated in FIG. 17). For example, segment 1815' can be used to provide the segments in quadrants Q1-Q4 as illustrated in FIG. 18E (also, e.g., segments in quadrants 1715a-d of ring 1710b illustrated in FIG. 17). Exemplary portion 1815' includes a plurality of ferromagnetic circular arc segments (e.g., segments formed of NdFeB, SmCo, etc.). In FIGS. 18C-18E, two circular arc segments (e.g., exemplary circular arc segment 1805'), each spanning 45°, form a quadrant of ring 1810'. In exemplary portion 1815' of ring 1810', the circular arc segments are dimensioned so as to provide a ring with inner radius R1 and outer radius R2 and a height or depth $z_9$, which dimensions can be chosen for each quadrant to achieve a desired magnetic field, non-limiting examples of which are provided below.

Figure 18H:
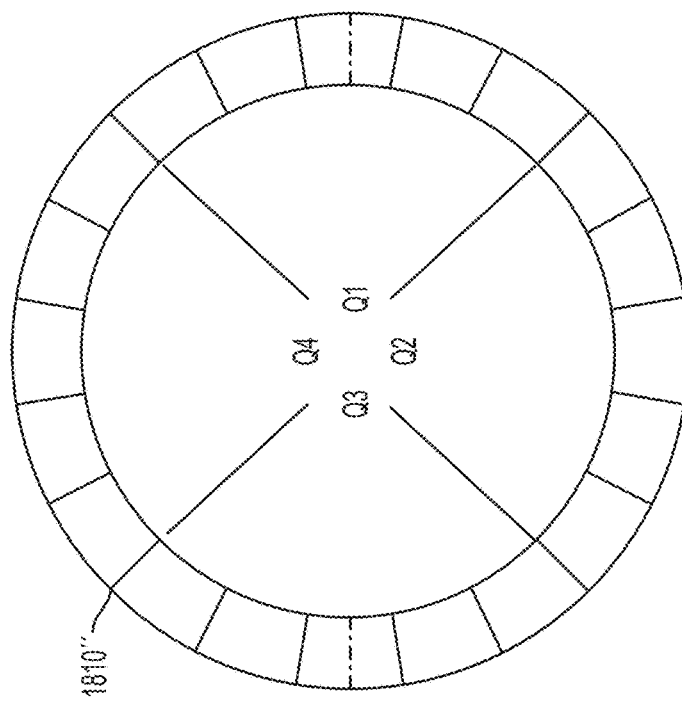
FIG. 18H illustrates a permanent magnet ring for a $B_0$ magnet, in accordance with some embodiments.
Figure 18G:
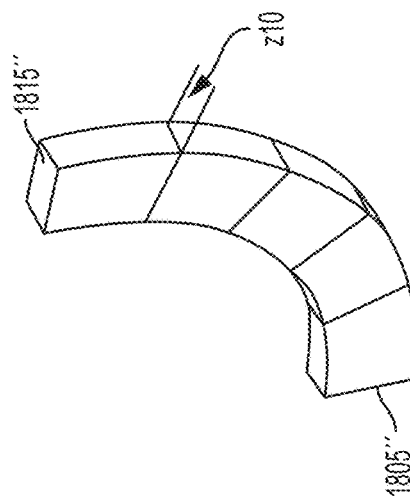
FIGS. 18F and 18G illustrate different views of permanent magnet segments that can be used to form the permanent magnet ring illustrated in FIG. 18H, in accordance with some embodiments.
Figure 18F:
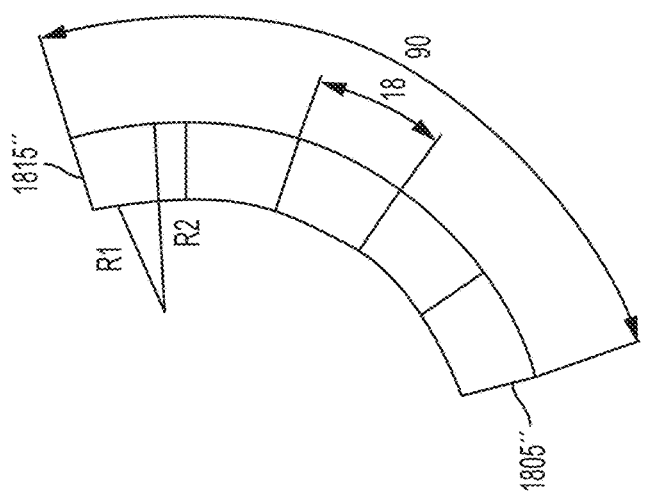

FIGS. 18F and 18G illustrate different views of a segment 1815" that can be used to form outer ring 1810" illustrated in FIG. 18H (e.g., ring 1710a illustrated in FIG. 17). For example, segment 1815" can be used to provide the segments in quadrants Q1-Q4 as illustrated in FIG. 18H (also, e.g., segments in quadrants 1715a-d of ring 1710a illustrated in FIG. 17). Exemplary portion 1815" includes a plurality of ferromagnetic circular arc segments (e.g., segments formed of NdFeB, SmCo, etc.), In FIGS. 18F-18H, five circular arc segments (e.g., exemplary circular arc segment 1805"), each spanning 18° of ring 1810", form a quadrant of ring 1810". In exemplary segment 1815" of ring 1810", the circular arc segments are dimensioned so as to provide a ring with inner radius R1 and outer radius R2 and a height or depth $z_{10}$, which dimensions can be chosen for each quadrant to achieve a desired magnetic field.

As discussed above, the inventors have developed low power, portable low-field MRI systems that can be deployed in virtually any environment and that can be brought to the patient who will undergo an imaging procedure. In this way, patients in emergency rooms, intensive care units, operating rooms and a host of other locations can benefit from MRI in circumstances where MRI is conventionally unavailable. Aspects that facilitate portable MRI are discussed in further detail below.

Figure 19A:
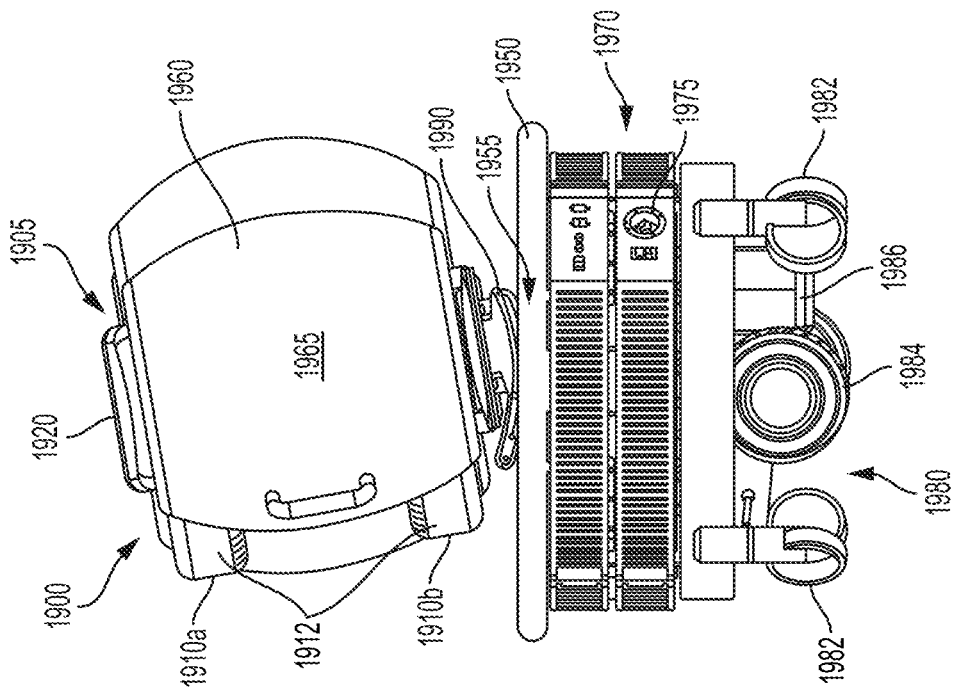
FIGS. 19A and 19B illustrate a portable low-field MRI system, in accordance with some embodiments.
Figure 19B:
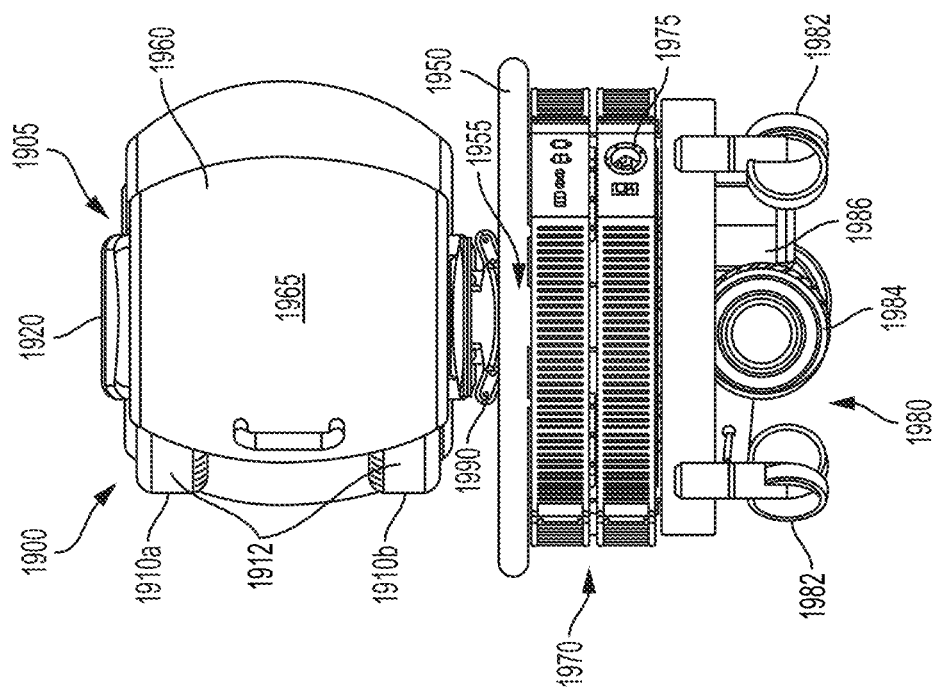

FIGS. 19A and 19B illustrate a low power, portable low-field MRI system, in accordance with some embodiments. Portable MRI system 1900 comprises a $B_0$ magnet 1905 including at least one first permanent magnet 1910a and at least one second permanent magnet 1910b magnetically coupled to one another by a ferromagnetic yoke 1920 configured to capture and channel magnetic flux to increase the magnetic flux density within the imaging region (field of view) of the MRI system. Permanent magnets 1910a and 1910b may be constructed using any suitable technique, including any of the techniques described herein (e.g., using any of the techniques, designs and/or materials described in connection with $B_0$ magnet 300 illustrated in FIG. 3A and/or $B_0$ magnet 1600 illustrated in FIG. 16 and described in the accompanying description thereof). Yoke 1920 may also be constructed using any of the techniques described herein (e.g., using any of the techniques, designs and/or materials described in connection with yokes 320 and 1620 illustrated in FIG. 3A and FIG. 16 and described in the accompanying description thereof). It should be appreciated that, in some embodiments, $B_0$ magnet 1905 may be formed using electromagnets using any of the electromagnet techniques described herein (e.g., using any of the techniques, designs and/or materials described in connection with $B_0$ magnet 200 illustrated in FIGS. 2A and 2B and described in the accompanying description thereof). $B_0$ magnet 1905 may be encased or enclosed in a housing 1912 along with one or more other magnetics components, such as the system's gradient coils (e.g., x-gradient, y-gradient and z-gradient coils) and/or any shim components (e.g., shim coils or permanent magnetic shims), $B_0$ correction coils, etc.

$B_0$ magnet 1905 may be coupled to or otherwise attached or mounted to base 1950 by a positioning mechanism 1990, such as a goniometric stage (examples of which are discussed in further detail below in connection with FIGS. 45A-D and 46A-B), so that the $B_0$ magnet can be tilted (e.g., rotated about its center of mass) to provide an incline to accommodate a patient's anatomy as needed. In FIG. 19A, the $B_0$ magnet is shown level without an incline and, in FIG. 19B, the $B_0$ magnet is shown after undergoing a rotation to incline the surface supporting the patient's anatomy being scanned. Positioning mechanism 1990 may be fixed to one or more load bearing structures of base 1950 arranged to support the weight of $B_0$ magnet 1905.

In addition to providing the load bearing structures for supporting the $B_0$ magnet, base 1950 also includes an interior space configured to house the electronics 1970 needed to operate the portable MRI system 1900. For example, base 1950 may house the power components to operate the gradient coils (e.g., X, Y and Z) and the RF transmit/receive coils. The inventors have developed generally low power, low noise and low cost gradient amplifiers configured to suitably power gradient coils in the low-field regime, designed to be relatively low cost, and constructed for mounting within the base of the portable MRI system (i.e., instead of being statically racked in a separate room of a fixed installment as is conventionally done). Examples of suitable power components to operate the gradient coils are described in further detail below (e.g., the power components described in connection with FIGS. 20-34). According to some embodiments, the power electronics for powering the gradient coils of an MRI system consume less than 50 W when the system is idle and between 100-300 W when the MRI system is operating (i.e., during image acquisition). Base 1950 may also house the RF coil amplifiers (i.e., power amplifiers to operate the transmit/receive coils of the system), power supplies, console, power distribution unit and other electronics needed to operate the MRI system, further details of which are described below.

According to some embodiments, the electronics 1970 needed to operate portable MRI system 1900 consume less than 1 kW of power, in some embodiments, less than 750 W of power and, in some embodiments, less than 500 W of power (e.g., MRI systems utilizing a permanent $B_0$ magnet solution). Techniques for facilitating low power operation of an MRI device are discussed in further detail below. However, systems that consume greater power may also be utilized as well, as the aspects are not limited in this respect. Exemplary portable MRI system 1900 illustrated in FIGS. 19A and 19B may be powered via a single power connection 1975 configured to connect to a source of mains electricity, such as an outlet providing single-phase power (e.g., a standard or large appliance outlet). Accordingly, the portable MRI system can be plugged into a single available power outlet and operated therefrom, eliminating the need for a dedicated power source (e.g., eliminating the need for a dedicated three-phase power source as well as eliminating the need for further power conversion electronics to convert three phase power to single phase power to be distributed to corresponding components of the MRI system) and increasing the availability of the MRI system and the circumstances and locations in which the portable MRI system may be used.

Portable MRI system 1900 illustrated in FIGS. 19A and 19B also comprises a conveyance mechanism 1980 that allows the portable MRI system to be transported to different locations. The conveyance mechanism may comprise one or more components configured to facilitate movement of the portable MRI system, for example, to a location at which MRI is needed. According to some embodiments, conveyance mechanism comprises a motor 1986 coupled to drive wheels 1984. In this manner, conveyance mechanism 1980 provides motorized assistance in transporting MRI system 1900 to desired locations. Conveyance mechanism 1980 may also include a plurality of castors 1982 to assist with support and stability as well as facilitating transport.

According to some embodiments, conveyance mechanism 1980 includes motorized assistance controlled using a controller (e.g., a joystick or other controller that can be manipulated by a person) to guide the portable MRI system during transportation to desired locations. According to some embodiments, the conveyance mechanism comprises power assist means configured to detect when force is applied to the MRI system and to, in response, engage the conveyance mechanism to provide motorized assistance in the direction of the detected force. For example, rail 1955 of base 1950 illustrated in FIGS. 19A and 19B may be configured to detect when force is applied to the rail (e.g., by personnel pushing on the rail) and engage the conveyance mechanism to provide motorized assistance to drive the wheels in the direction of the applied force. As a result, a user can guide the portable MRI system with the assistance of the conveyance mechanism that responds to the direction of force applied by the user. The power assist mechanism may also provide a safety mechanism for collisions. In particular, the force of contact with another object (e.g., a wall, bed or other structure) may also be detected and the conveyance mechanism will react accordingly with a motorized locomotion response away from the object. According to some embodiments, motorized assistance may be eliminated and the portable MRI system may be transported by having personnel move the system to desired locations using manual force.

Portable MRI system 1900 includes slides 1960 that provide electromagnetic shielding to the imaging region of the system. Slides 1960 may be transparent or translucent to preserve the feeling of openness of the MRI system to assist patients who may experience claustrophobia during conventional MRI performed within a closed bore. Slides 1960 may also be perforated to allow air flow to increase the sense of openness and/or to dissipate acoustic noise generated by the MRI system during operation. The slides may have shielding 1965 incorporated therein to block electromagnetic noise from reaching the imaging region. According to some embodiments, slides 1960 may also be formed by a conductive mesh providing shielding 1965 to the imaging region and promoting a sense of openness for the system. Thus, slides 1960 may provide electromagnetic shielding that is moveable to allow a patient to be positioned within the system, permitting adjustment by personnel once a patient is positioned or during acquisition, and/or enabling a surgeon to gain access to the patient, etc. Thus, the moveable shielding facilitates flexibility that allows the portable MRI system to not only be utilized in unshielded rooms, but enables procedures to be performed that are otherwise unavailable. Exemplary slides providing varying levels of electromagnetic shielding are discussed in further detail below.

According to some embodiments, a portable MRI system does not include slides, providing for a substantially open imaging region, facilitating easier placement of a patient within the system, reducing the feeling of claustrophobia and/or improving access to the patient positioned within the MRI system (e.g., allowing a physician or surgeon to access the patient before, during or after an imaging procedure without having to remove the patient from the system). The inventors have developed techniques that facilitate performing MRI with varying levels of electromagnetic shielding, including no or substantially no shielding of the imaging region, including a noise suppression system adapted to suppress electromagnetic noise in the environment. According to some embodiments, portable MRI system 1900 may be equipped with a noise reduction system using one or more of the noise suppression and/or avoidance techniques described herein to, for example, dynamically adapt the noise suppression/cancellation response in concert with the shielding configuration of a given shielding arrangement of the portable MRI system 1900. Thus, portable low field MRI system 1900 can be transported to the patient and/or to a desired location and operated outside specially shielded rooms (e.g., in an emergency room, operating room, NICU, general practitioner's office, clinic) and/or brought bedside directly to the patient wherever located, allowing for MRI to be performed when and where it is needed. To facilitate portable MRI that can be operated in virtually any location, the inventors have developed low power MRI systems that, in accordance with some embodiments, are configured to be powered by main electricity (e.g., single-phase electric power from standard or industrial wall outlets), as discussed in further detail below.

As discussed above, conventional MRI systems consume significant power, requiring dedicated three-phase power sources to operate. In particular, conventional MRI systems that use superconducting material to form the $B_0$ magnet require cryogenic cooling systems that consume substantial power to keep the conductors in a superconducting state. In addition, the power amplifiers used to operate the gradient amplifiers are large power components that draw large amounts of power and are typically stored in a separate room that houses the electronic components of the system. Moreover, power components configured to operate the transmit/receive coil systems of conventional MRI system also consume significant amounts of power. Many conventional high field MRI systems require HVAC systems that also draw substantial amounts of power.

Conventional MRI systems are fixed installments requiring a specialized and dedicated spaces. As a result, the requirement of a dedicated three-phase power connection to operate the MRI system is not a critical limitation for these systems, as it is just one of a number of dedicated and specialized features of a conventional MRI installment. However, requiring a dedicated three-phase power source places significant restrictions on locations at which a portable MRI system can be operated. Accordingly, the inventors have developed a low power MRI system that facilitates portability of the MRI system. For example, in accordance with some embodiments, a low power MRI system is configured to operate using mains power (e.g., single phase electric power from a standard or industrial outlet). Exemplary aspects of a low power MRI system are discussed in further detail below.

According to some embodiments, a low power MRI system comprises a permanent $B_0$ magnet (e.g., any of the permanent magnets discussed herein such as those illustrated in FIGS. 3A and 16). Because a permanent $B_0$ magnet, once magnetized, will produce its own persistent magnetic field, power is not required to operate the permanent $B_0$ magnet to generate its magnetic field. As a result, a significant (often dominant) contributor to the overall power consumption of an MRI system can be eliminated, facilitating the development of an MRI system that can be powered using mains electricity (e.g., via a standard wall outlet or common large household appliance outlets), as discussed in further detail below in connection with exemplary low power MRI systems.

Furthermore, conventional power components adapted to operate a gradient coil system are generally unsuitable for use in low-field MRI due, at least in part to, expense and noise levels and are unsuitable for low power and/or portable MRI due to power consumption, size and weight. For example, while the cost of conventional power components used to operate gradient coils in currently available MRI systems may be acceptable given the relative insignificance compared to the total cost of a high-field MRI installation, this cost may be unacceptably high in the context of a low-field MRI system that is designed as a lower cost alternative. Thus, the cost of a power component conventionally used for high-field MRI may be disproportionately large and therefore not satisfactory for some lower cost low-field MRI systems.

Additionally, the relatively low SNR in the low-field (and particularly in the very-low and ultra-low-field regimes) renders conventional gradient coil power components unsuitable. In particular, conventional power components for driving gradient coils are generally unsuitable for low-field MRI systems because they are not designed to drive the coils with sufficiently low noise. Although the noise injected by such power components may be acceptable in the high SNR regime of high-field MRI systems, such components generally do not provide a sufficiently low level of noise to provide acceptable image quality in a low-field MRI system. For example, conventional power components may exhibit unsatisfactory variation in the output (e.g., ripple) for use in the low-field context, injecting relatively significant noise into the gradient coil system of a low-field MRI system.

Moreover, conventional power components configured to drive the gradient coil system of currently available MRI systems are not designed to be power efficient, consuming large amounts of power. In addition, conventional power components configured to operate the gradient coil system of currently available MRI systems are large, heavy devices, typically racked in a separate room adjacent the MRI device along with the other electronic components. Thus, conventional gradient power components are not suitable for use in a low power, portable MRI system.

The inventors have developed low-noise, low power gradient power component(s) suitable for driving the gradient coil system of a low-field MRI system. In particular, techniques developed by the inventors provide for a low cost, low power, low noise gradient coil system suitable for a low-field, very-low field or ultra-low field MRI system, and more particularly, for a portable MRI system that can operate using standard and/or commonly available power connections. That is, in addition to facilitating a low power MRI system, the gradient coils and gradient coil power components facilitate MRI at lower field strengths not attainable using conventional gradient coil systems due, at least in part, to the low noise operation of the gradient power components. According to some embodiments, the power electronics for powering the gradient coils of an MRI system consume less than 50 W when the system is idle and between 100-300 W when the MRI system is operating (i.e., during image acquisition), allowing for operation from standard wall power, some examples of which are described in further detail below in connection with FIGS. 20-34.

Figure 20:
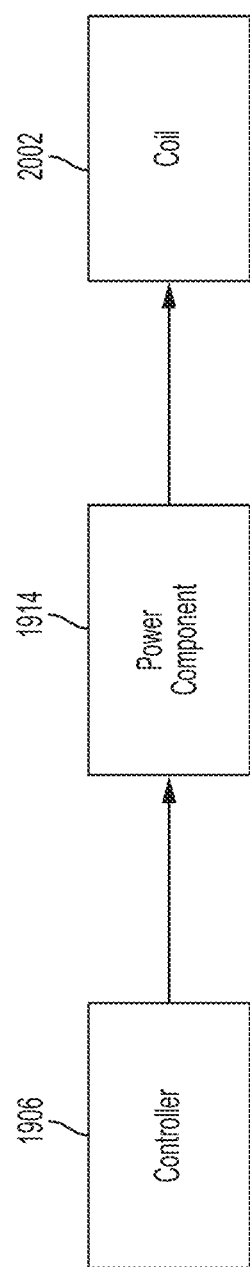
FIG. 20 shows drive circuitry for driving a current through a coil to produce a magnetic field, in accordance with some embodiments of the technology described herein.

FIG. 20 illustrates drive circuitry for driving a current through a coil 2002 of an MRI system to produce a magnetic field in accordance with a desired pulse sequence, according to some embodiments. Power component 1914 drives a current through coil 2002 based on a control signal from the controller 1906. The controller 1906 may produce a control signal to drive power component 1914 based on a pulse sequence implemented by controller 1906 (or provided by one or more other controllers), as discussed above. In some embodiments, coil 2002 may be a gradient coil 1928. However, the techniques described herein are not limited in this respect, as coil 2002 may be a coil of magnet 1922, shim coil 1924, or an RF transmit and/or receive coil 1926.

Power components configured to power gradient coils typically provide relatively high power and typically need to provide precise control over the current provided to the gradient coil so that the desired pulse sequence can be delivered faithfully. Inaccuracies in delivering the commanded current to the gradient coil results in a decrease in signal-to-noise ratio due to differences between the gradient pulse sequence being delivered and the intended (and expected) pulse sequence. Power components configured to drive gradient coils also should to be responsive in delivering the commanded current to the gradient coil, including rapid transition between commanded current levels so as to faithfully produce the current waveforms required by the desired pulse sequences. Accordingly, the inventors have developed power components capable of being controlled to accurately and precisely provide current, with relatively low noise and relatively high efficiency, to one or more gradient coils to faithfully reproduce a desired pulse sequence, some embodiments of which are discussed in further detail below.

In some embodiments, the power component 1914 may be a "current mode" power component that drives a desired current through coil 2002. The desired current may be produced by power component 1914 in response to a current command from controller 1906. In this respect, the power component 1914 may operate as a current source that is controlled by the current command (which may be provided by the controller as a voltage level indicating the current to be provided to coil 2002). Controller 1906 may change the current command such that power component 1914 produces current values that change in accordance with a selected pulse sequence. For example, controller 1906 may command the power component to drive one or more gradient coils in accordance with a pulse sequence comprising a plurality of gradient pulses. For each gradient pulse, the power component may need to ramp up the current provided to a corresponding gradient coil at the rising edge of the gradient pulse and ramp down the current provided to the gradient coil at a falling edge of the gradient pulse. Example operation of a power component configured to drive the gradient coil to provide a plurality of such gradient pulses is described in further detail below.

Figure 21A:
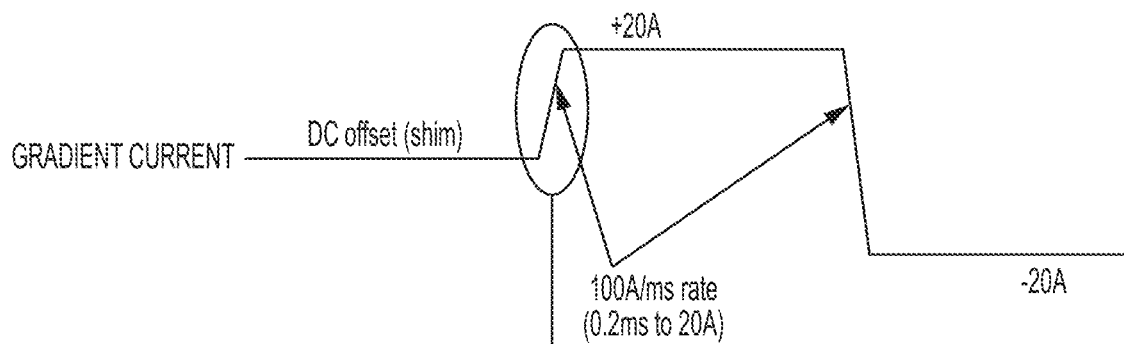
FIG. 21A shows an example of a gradient coil current waveform, in accordance with some embodiments of the technology described herein.

FIG. 21A shows an example of a gradient coil current waveform, according to some embodiments. In this example, the gradient coil current rapidly ramps up at the rising edge of the gradient pulse from 0 A to +20 A within a time interval of 0.2 ms, remains at +20 A for a period of time, then rapidly ramps down at the falling edge of the gradient pulse to −20 A, and remains at −20 A for a period of time. It should be appreciated that the exemplary current to produce a gradient pulse is provided by way of illustration and that different pulse sequences may comprise gradient pulses having different current and/or voltage requirements. Controller 1906 and power component 1914 can be configured to drive one or more gradient coils according to any suitable pulse sequence.

Figure 21B:
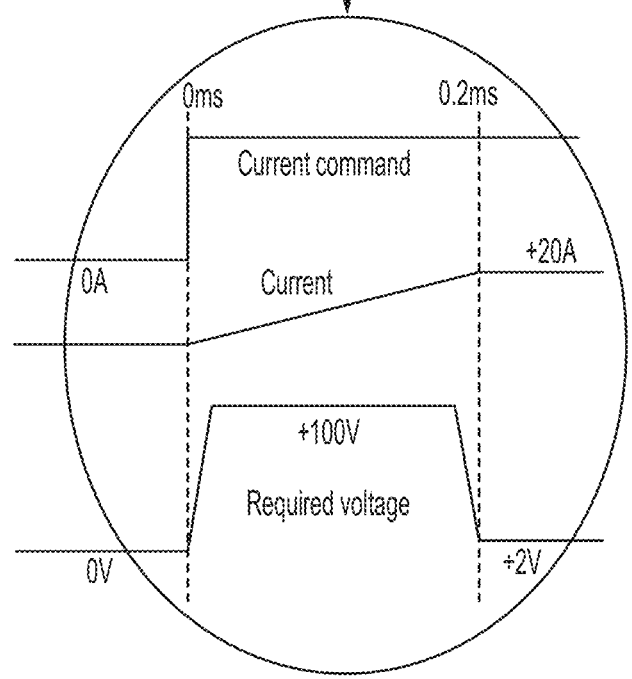
FIG. 21B shows waveforms for the current command, the gradient coil current and the gradient coil voltage before, during and after the rising transition of the gradient coil current waveform shown in FIG. 21A, in accordance with some embodiments of the technology described herein.

FIG. 21B shows waveforms for the current command, the gradient coil current and the gradient coil voltage before, during and after the rising edge of the gradient coil current shown in FIG. 21A. The gradient coil current is the current through the gradient coil. The gradient coil voltage is the voltage across the gradient coil. The current command is a signal representing an amount of current to be driven through the gradient coil by power component 1914. In response to a current command at a time of 0 ms, the current through the gradient coil begins to rise toward the commanded current of +20 A. Since the gradient coil is an inductive load, a relatively large voltage needs to be provided to the gradient coil to rapidly increase the current through the gradient coil. Providing a rapid increase in current through the gradient coil is desirable in MRI applications, as providing fast transitions between gradient coil current values can decrease acquisition times and may be needed to implement certain pulse sequences. As should be appreciated from the exemplary voltages and currents shown in FIGS. 21A and 21B, the power component 1914 may have the capability of driving the gradient coil with relatively high power.

As an example, a gradient coil may have an inductance of 200 μH and a resistance of 100 mΩ Since the rate of change of the current through the gradient coil is proportional to its inductance, a voltage of 100V needs to be provided to the gradient coil to increase its current at a rate of 100 A/ms. However, once the gradient coil current levels off at 20 A, the voltage requirement drops substantially. At this point, since the current is no longer changing, the voltage needed depends upon the resistance of the gradient coil. Since the resistance of the gradient coil is 100 mΩ, the voltage needed to be provided to the gradient coil to maintain the current steady at 20 A is 2V, which is significantly lower than the voltage (100V) needed during the transition between current values. However, these values of current, voltage, inductance and resistance are provided merely by way of example, as any suitable gradient coil designs may be used, which may have different values of inductance and/or resistance. Further, other suitable values of currents, voltages, transition timings, etc. values may be used and/or needed to implement a given pulse sequence.

Since the resistance of the gradient coil may be relatively low (e.g., less than 500 mΩ), in some embodiments the power component 1914 has a relatively low output impedance in order to efficiently supply the commanded current. For example, according to some embodiments, the power component 1914 comprises a linear amplifier configured to power one or more gradient coils (e.g., to provide current to the one or more gradient coils in accordance with a desired pulse sequence). To implement a linear amplifier having a low output impedance, transistors of suitable size may be used having low equivalent series resistance and/or a number of transistors may be connected in parallel to produce a low resistance collectively. Interconnects may be designed to have a relatively low resistance. The output impedance of the linear amplifier may, for example, be less than twice the impedance of the gradient coil, in some embodiments. In some embodiments, the voltage drop across the transistors of the linear amplifier may be relatively low in operation, such as less than 5V, less than 2V, or less than 1V (and greater than 0V). Using an amplifier with a relatively low output impedance may be particularly helpful for driving current through a gradient coil, which may have substantial DC current. A low output impedance can improve efficiency and limit heating of the amplifier. Details of exemplary linear amplifier implementations are discussed in further detail below.

Figure 22A:
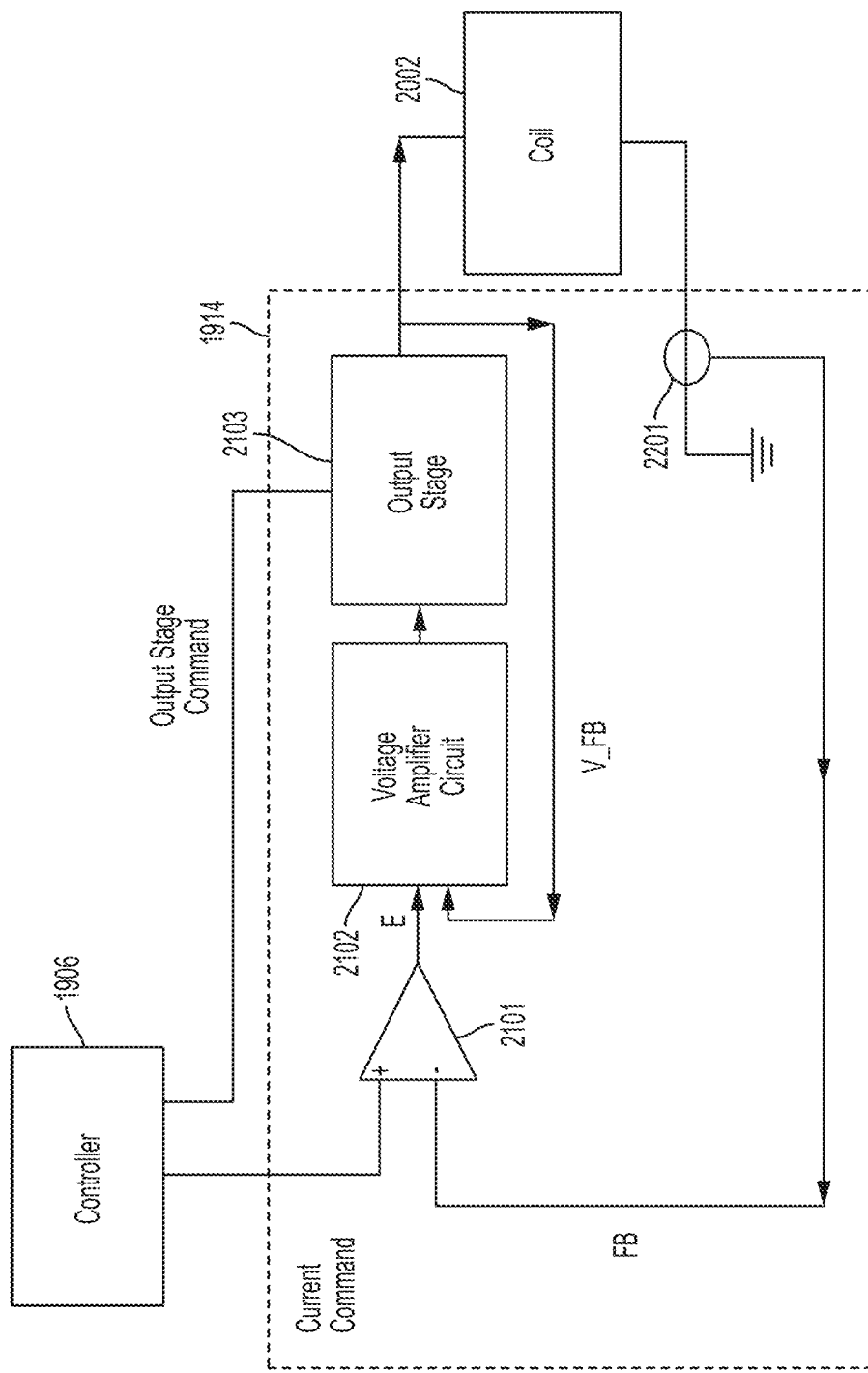
FIG. 22A shows an example of a power component having a current feedback loop and a voltage feedback loop, in accordance with some embodiments of the technology described herein.

FIG. 22A shows an example of a power component 1914 having a current feedback loop and a voltage feedback loop, according to some embodiments. Power component 1914 is configured to provide the current needed to drive one or more gradient coils in accordance with a desired pulse sequence. As such, power component 1914 is designed to be a low noise current source that can be precisely controlled to provide the commanded current waveform needed to drive the one or more gradient coils to faithfully produce the desired gradient magnetic fields. Power component 1914 includes a comparator 2101 that receives a current command from controller 1906 at its non-inverting input terminal and a current feedback signal FB from a current sensor 2201 at its inverting input terminal. The current command may be a voltage value representing the commanded current. The current feedback signal FB may be a voltage value representing the measured current. In some embodiments, a high-quality current sensor may be used to provide an accurate feedback signal FB, which can improve the accuracy of the gradient coil current pulses.

The comparator 2101 produces an error signal E (e.g., a voltage) representing the difference between the current command and the current feedback signal FB. Amplifier circuit 2102 amplifies the error signal to produce an amplified error signal that is provided to the output stage 2103. The output stage 2103 drives coil 2002 based upon the amplified error signal. The current through the coil 2002 is measured by current sensor 2201, and a feedback signal FB is fed back to the comparator 2101, as discussed above. The current feedback loop thereby causes the current through the coil 2002 to be equal to the current commanded by the controller 1906. In this respect, the power component 1914 may operate as a voltage-controlled current source. According to some embodiments, a high accuracy, high precision current sensor 2201 is used to ensure that the current output provided to the gradient coil accurately tracks the current commanded by the controller 1906. As a result, the current provided to power the gradient coil can be held as close to the commanded current as feasible. The power component 1914 also has a voltage feedback loop that provides the output voltage of the output stage 2103 to the input of the voltage amplifier circuit 2102.

Figure 22B:
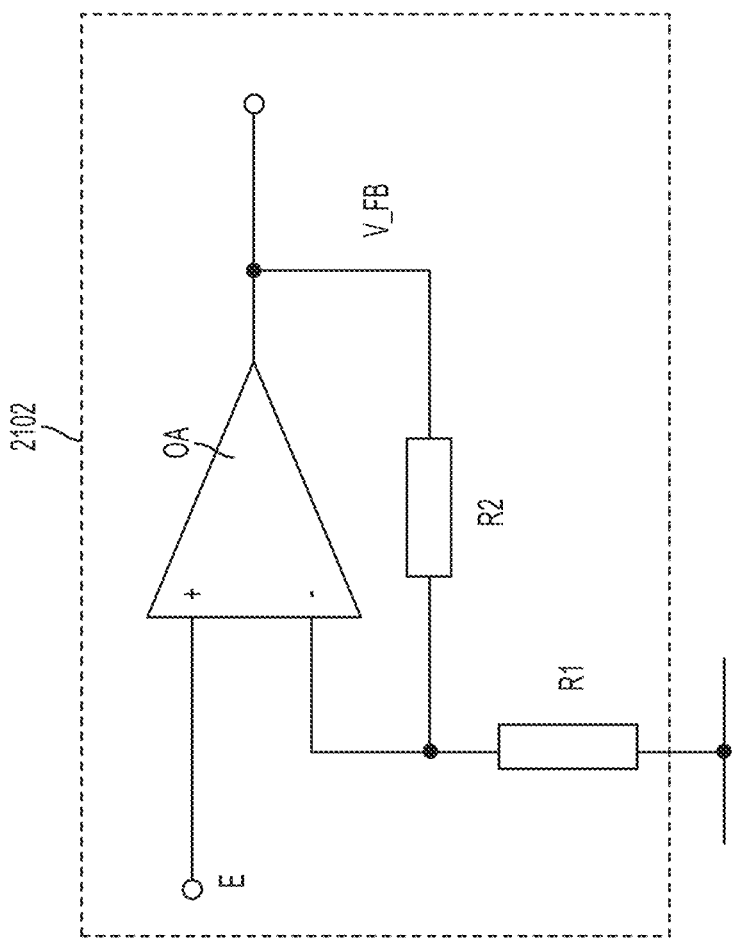
FIG. 22B shows an example of a voltage amplifier, in accordance with some embodiments of the technology described herein.

As illustrated in FIG. 22B, the voltage amplifier circuit 2102 may include an operational amplifier OA that receives the error signal E at its non-inverting input and the voltage feedback signal V_FB at its inverting input. The voltage feedback signal may be provided to the inverting input of the operational amplifier through a resistive voltage divider (e.g., including resistors R1 and R2), which causes the operational amplifier to amplify the input voltage based on the ratio of resistance values in the voltage divider. Any suitable voltage gain may be used for the voltage amplifier, such as gain of 5-15, by way of example. In some embodiments, the voltage gain of the output stage may be one (unity).

As illustrated in FIG. 22A, in some embodiments, the controller 1906 may provide a command to the output stage 2103. The controller 1906 may command the output stage 2103 to produce a power supply voltage suitable for supplying current needed to perform a corresponding portion of a pulse sequence. As an example, the command may cause a power converter of the output stage to begin ramping up the magnitude of a power supply voltage in advance of a gradient coil current pulse. Such a command is discussed in further detail below with reference to FIG. 33D.

In some embodiments, the output stage 2103 is configured to be selectively powered by a plurality of power supply terminals at different voltages. The power supply terminal selected to power the output stage 2103 may be chosen depending on the output voltage produced by the voltage amplifier. For example, when the power component is commanded to produce a relatively high (positive) output voltage the power component may be powered from a relatively high (positive) voltage supply terminal, and when the power component is commanded to produce a relatively low (positive) output voltage, the power component is powered from a relatively low (positive) voltage supply terminal. Accordingly, the efficiency of the power component can be improved by reducing the voltage drop across its transistor(s) when relatively low output voltage is produced. It should be appreciated that any number of supply terminals and voltage levels may be used, as the aspects are not limited in this respect. For example, high, mid and low voltage supply terminals (both positive and negative) may be used, or an even greater number as suitable for a particular design and/or implementation.

Figure 23A:
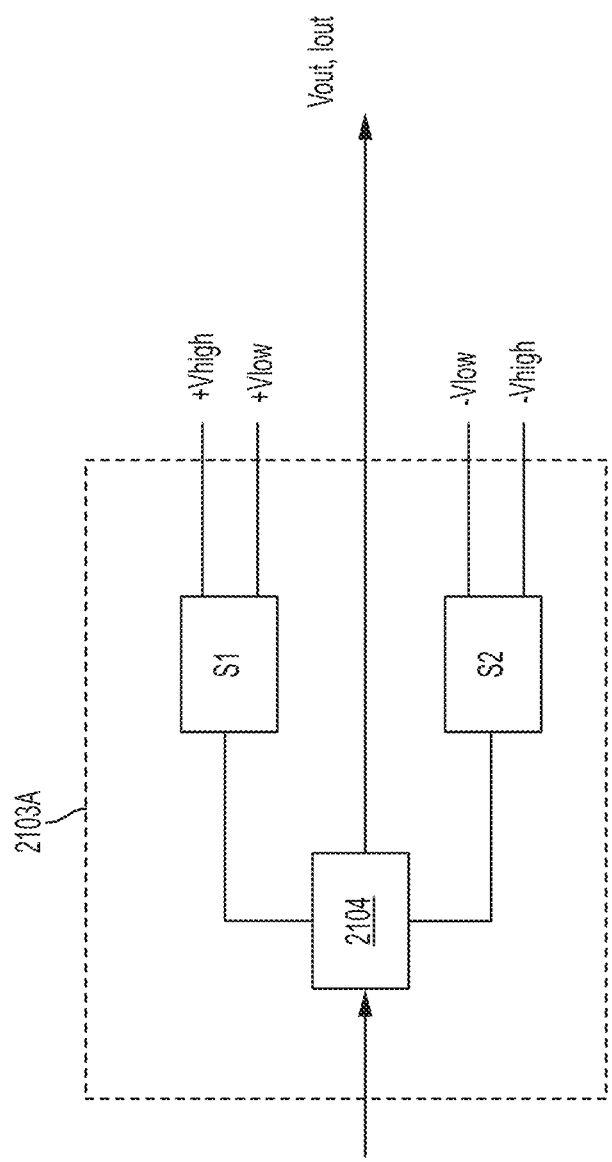
FIGS. 23A and 23B show examples of an output stage that can be powered by different supply terminals depending on the output voltage, in accordance with some embodiments of the technology described herein.
Figure 23B:
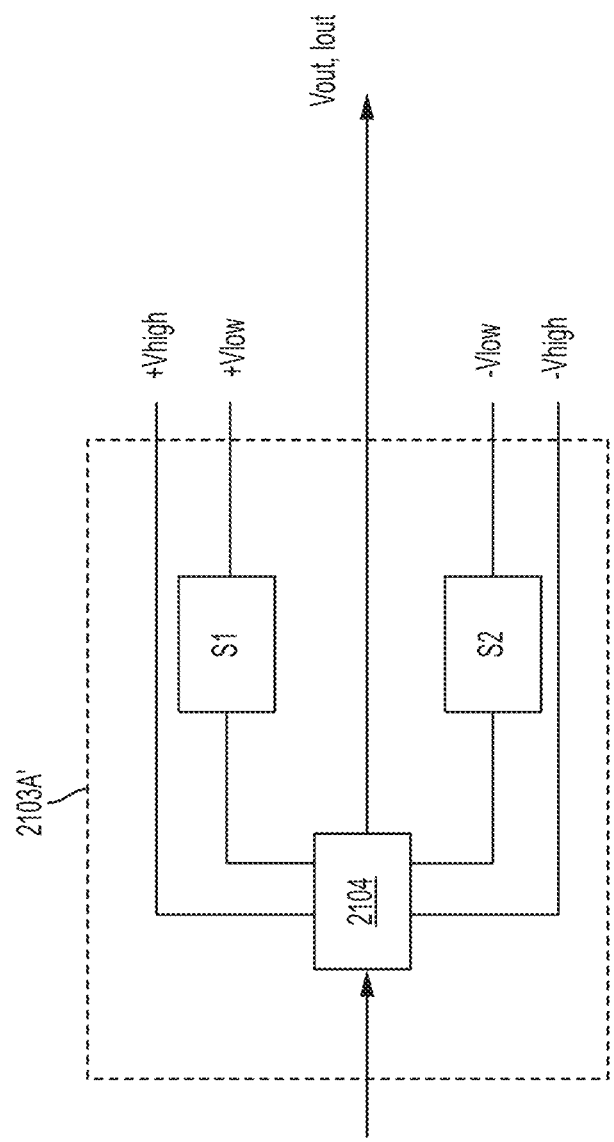

FIG. 23A shows an example of an output stage 2103A having an output Vout, Iout suitable for powering one or more gradient coils of a magnetic resonance imaging system. To improve the power efficiency in powering one or more gradient coils, output stage 2103A can be powered by different supply terminals depending on the output voltage Vout. For example, output stage 2103A can be powered by a plurality of supply terminals of a first polarity (e.g., a plurality of different positive voltages) and/or a plurality of supply terminals of a second polarity (e.g., a plurality of different negative voltages). To facilitate low noise operation, according to some embodiments, output stage 2103A may include a linear amplifier 2104. According to some embodiment, each of the different supply terminals provides a different fixed supply voltage. According to some embodiments, one or more of the different supply terminals produce a variable supply voltage, as discussed in further detail below.

In operation, if a positive output voltage is produced at Vout, switching circuitry S1 connects the high side power input of linear amplifier 2104 to either the high voltage terminal +Vhigh or the low voltage terminal +Vlow depending on the magnitude of the output voltage. If a relatively high output voltage is to be produced (e.g., if the output voltage to be produced exceeds a particular threshold), the switching circuitry S1 connects the high side power input of linear amplifier 2104 to the high voltage terminal +Vhigh. If a relatively low output voltage is to be produced (e.g., if the output voltage to be produced remains below the particular threshold), the switching circuitry S1 connects the high side power input of linear amplifier 2104 to the low voltage terminal +Vlow. Similarly, if a negative output voltage is produced, switching circuitry S2 connects the low side power input of linear amplifier 2104 to either the high voltage terminal −Vhigh or the low voltage terminal −Vlow depending on the magnitude of the output voltage, as discussed above. Any suitable switching circuitry S1 and S2 may be used. Such switching circuitry may include a diode that is passively switched and/or a transistor that is actively switched.

In some embodiments, the high-voltage or low-voltage terminals may be directly connected to the linear amplifier 2104, without an intervening switch S1 or S2. For example, as shown by the exemplary output stage 2103A' illustrated in FIG. 23B, the high voltage terminals +Vhigh and −Vhigh may be directly connected to the linear amplifier 2104, and the low voltage terminals +Vlow and −Vlow may be connected to the linear amplifier 2104 through respective switches S1 and S2. The linear amplifier 2104 may be designed such that it is powered by a low voltage supply terminal unless its voltage is insufficient to supply the output current, in which case the linear amplifier 2104 is powered by the high voltage supply terminal. It should be appreciated that the use of +−Vhigh and +−Vlow is merely exemplary and any number of voltages levels may be used to provide a desired output voltage. For example, one or more intervening voltage levels between +−Vhigh and +−Vlow, respectively, may be used to produce the desired voltage levels.

Figure 24:
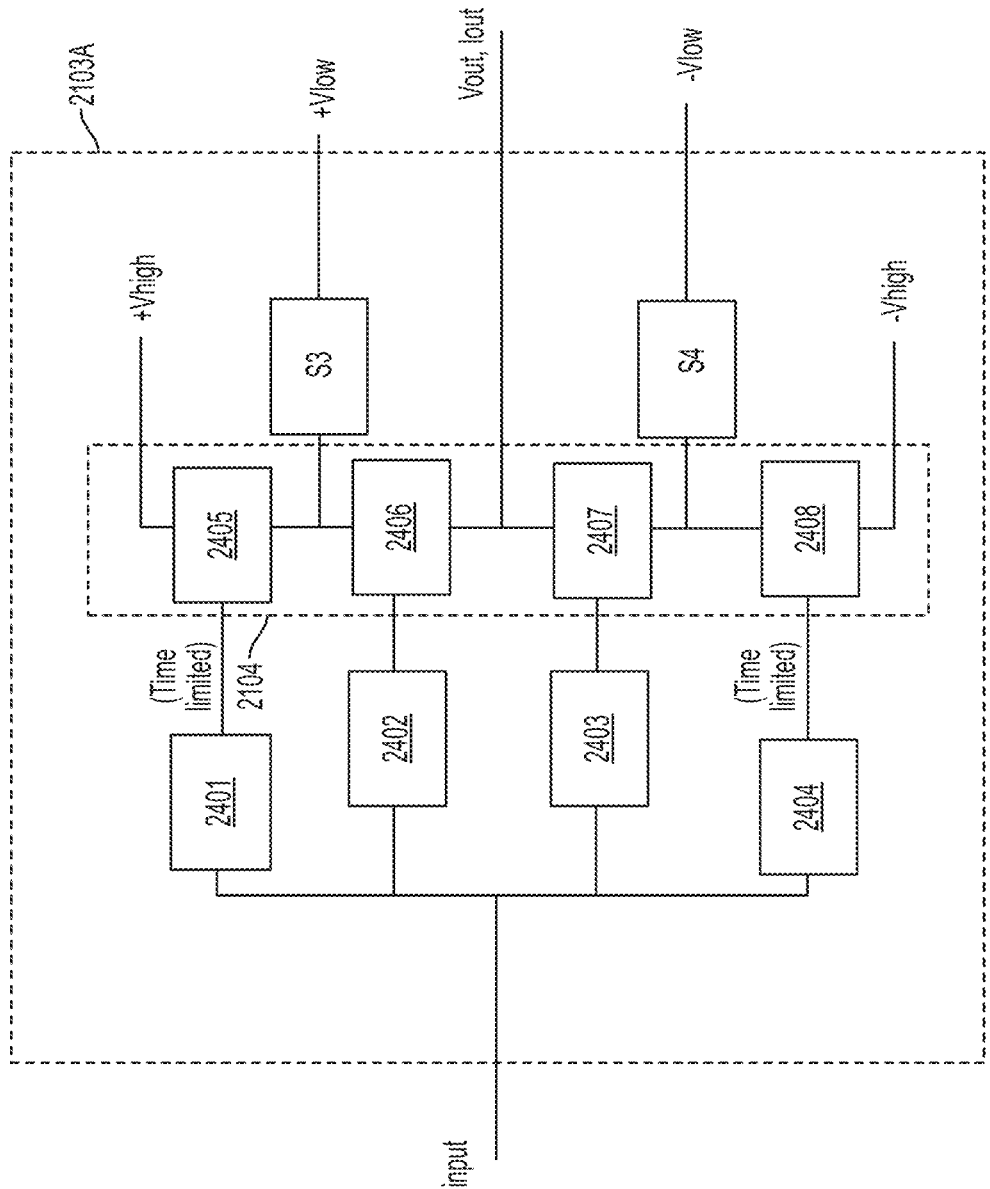
FIG. 24 shows an example of an output stage having a plurality of drive circuits to drive a plurality of transistor circuits connected to high voltage and low voltage supply terminals, in accordance with some embodiments of the technology described herein.

FIG. 24 shows an example of an output stage 2103A having a plurality of drive circuits 2401-2404. Drive circuits 2401-2404 drive a linear amplifier 2104 that includes a plurality of transistor circuits 2405-2408, each including one or more transistors. The linear amplifier 2104 can be connected to the high voltage or low voltage supply terminals depending on the output voltage to be produced.

When a low positive output voltage is to be produced, transistor(s) 2406 are connected to the low voltage terminal +Vlow via switch circuitry S3. Transistor(s) 2405 are turned off by drive circuit 2401 to isolate the transistors 2406 from the high voltage terminal +Vhigh. Drive circuit 2402 drives transistor(s) 2406 as a linear amplifying element, based on the input, to produce an amplified output using the low voltage terminal +Vlow as a source of current.

To provide a high positive output voltage, drive circuit 2401 turns on transistor(s) 2405 to connect the high voltage terminal +Vhigh to the transistors 2406. Switch circuitry S3 may be turned off to isolate transistor(s) 2406 from the low voltage terminal +Vlow. Drive circuit 2402 may drive transistor(s) 2406 fully on, such that transistor(s) 2405 are connected to the output of output stage 2103A. Drive circuit 2401 drives transistor(s) 2405 as a linear amplifying element, based on the input, to produce an amplified output using the high voltage terminal +Vhigh.

Accordingly, the low voltage terminal +Vlow can be used to provide a low output voltage and the high voltage terminal +Vhigh can be used to provide a high output voltage. A negative output voltage may be provided similarly by drive circuits 2403 and 2404, transistor(s) 2407 and 2408, and switch circuitry S4. When a negative output voltage is produced, drive circuits 2401 and 2402 may turn off transistor(s) 2405 and 2406. Similarly, when a positive output voltage is produced, drive circuits 2403 and 2404 may turn off transistor(s) 2407 and 2408.

Transistor(s) 2406 may operate as a linear amplifying element of linear amplifier 2104 for low output voltages and transistor(s) 2405 may operate as a linear amplifying element for high output voltages. In some embodiments, transistor(s) 2406 and 2405 may be biased such that for a transition region between low positive output voltages and high positive output voltages, transistor(s) 2405 and 2406 both act as linear amplifying elements of linear amplifier 2104, i.e., they are neither fully-on nor fully-off. Operating both transistors 2405 and 2406 as linear elements during such transitions may facilitate linear amplifier 2104 having a smooth and continuous transfer function. Transistors 2407 and 2408 may operate similarly to transistors 2405 and 2406 to produce a range of negative output voltages.

In some embodiments, switch circuitry S3 and S4 may be realized by diodes that automatically switch on and off depending on whether the high voltage terminal is being utilized. For example, if switch circuitry S3 includes a diode, the anode may be connected to the terminal +Vlow and the cathode to transistor(s) 2406, such that current can only flow out of terminal +Vlow into the output stage 2103A. However, the techniques described herein are not limited in this respect, as switch circuitry S3 and S4 may be realized using controlled switches, such as transistors, or any other suitable switching circuitry.

In some embodiments, the circuit of FIG. 24 may be used to drive a gradient coil using a pulse sequence as shown in FIG. 21. When the output current is constant, the output voltage (e.g., 2V) may be produced by sourcing current from the low voltage terminal +Vlow. During a transition when the current is changed rapidly, a high output voltage (e.g., 100V) may be produced by sourcing current from the high voltage terminal +Vhigh. Thus, the high voltage terminal may be used during transitions in the output current to provide high output voltages, and the low voltage terminal may be used to provide low output voltages for high efficiency.

According to some embodiments, for example, according to some pulse sequences, the high voltage terminal(s) may only need to be used for a relatively short period of time, so that transistor(s) 2405 (and 2408) may be conducting for only a relatively small duty cycle. Thus, in some embodiments, transistor(s) 2405 (and 2408) may be reduced in size, and/or the number of transistors connected in parallel may be reduced, with respect to transistors 2406 (or 2407), as transistor(s) 2405 (and 2408) will have time to dissipate heat between transitions in the gradient coil current.

In some embodiments, drive circuits 2401 and 2404 may be designed to provide time-limited output signals. Providing time-limited output signals may ensure that transistor(s) 2405 and/or 2408 are turned on only temporarily and not turned on to drive a steady state current. Such a technique may be advantageous if transistor(s) 2405 or 2408 are designed to conduct for only relatively short periods of time, as it can prevent excessive power dissipation by transistor(s) 2405 or 2408.

Figure 25:
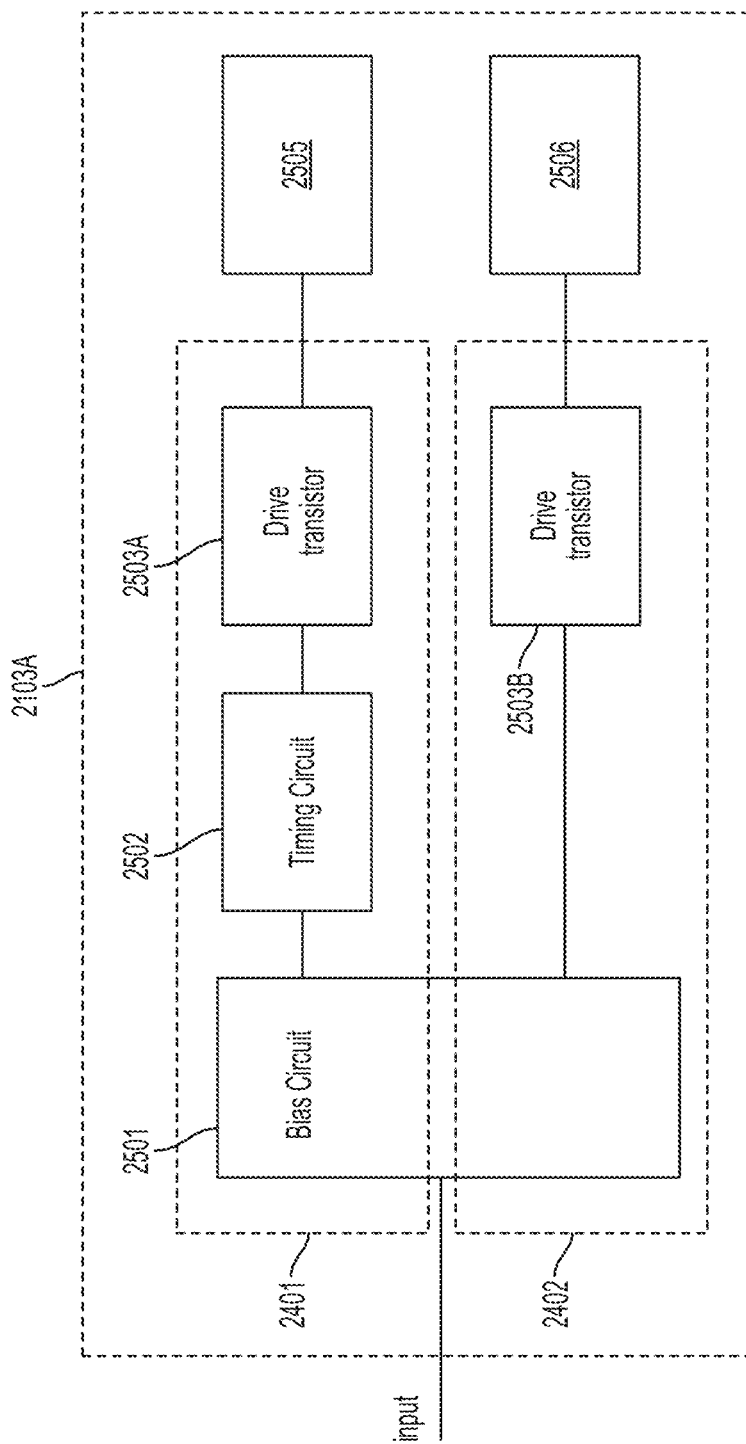
FIG. 25 shows drive circuits including a bias circuit and a timer circuit, in accordance with some embodiments of the technology described herein.

FIG. 25 shows a block diagram of drive circuitry 2401 and 2402, according to some embodiments. Drive circuitry 2401 includes a drive transistor 2503A for driving transistor(s) 2405. Drive circuitry 2402 includes a drive transistor 2503B for driving transistor(s) 2406.

Drive circuitry 2401 and 2402 may include one or more bias circuits 2501 for producing a DC bias on the input voltage provided to the drive transistors 2503A and 2503B. In some embodiments, the bias circuit(s) 2501 may bias drive transistors 2503A and/or 2503B slightly below their turn-on voltages. The inventors have recognized and appreciated that biasing the drive transistors slightly below their turn-on voltages can reduce or eliminate thermal runaway. Advantageously, such a biasing technique may not reduce the linearity of the output stage 2103A. If an operational amplifier OA of voltage amplifier circuit 2102 has a sufficiently high speed, it can respond fast enough to accurately control the output voltage of the output stage despite biasing the drive transistors slightly below their turn-on voltages.

In some embodiments, drive circuitry 2401 may include a timing circuit that causes drive circuit 2401 to produce a time-limited output. Any suitable timing circuit may be used. In the example of FIG. 25, a timing circuit 2502 is connected to the input of output stage 2103A via bias circuit 2501, and limits the amount of time that an input can be provided to the drive transistor 2503A.

In some embodiments, the timing circuit 2502 may be an RC circuit that has an output voltage that decays over time, and turns off drive transistor 2503A when the output of the timing circuit 2502 falls below the turn on voltage of the drive transistor 2503A. The time that transistor(s) 2405 are turned on is limited based on the RC time constant of the RC circuit. However, the techniques described herein are not limited to implementing the timing circuit using an RC circuit, as any suitable timing circuitry may be used, including analog and/or digital circuitry. In some embodiments, drive circuits 2403 and 2404 may be implemented similarly to drive circuits 2402 and 2401, respectively, for negative input and output voltages.

Figure 26:
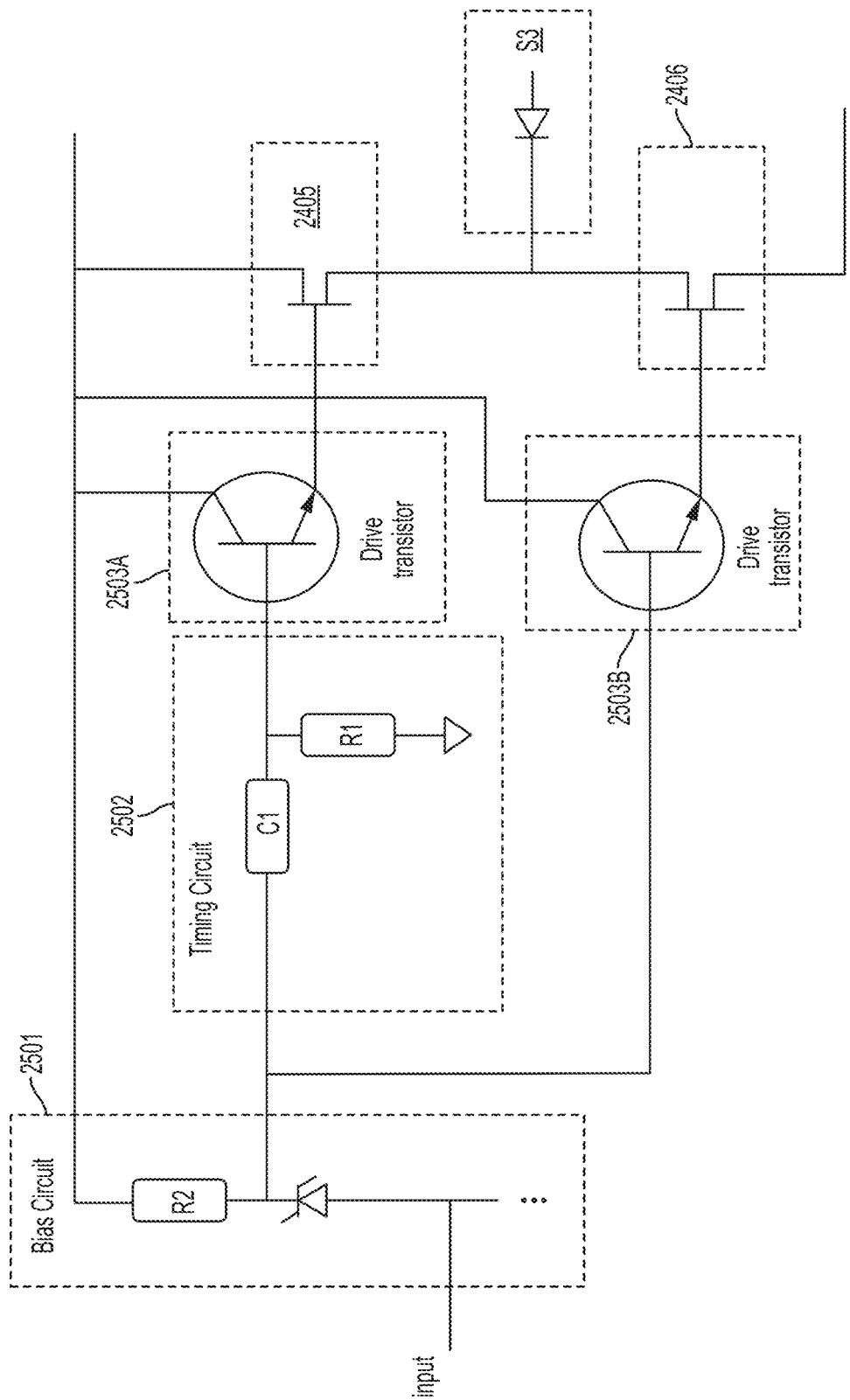
FIG. 26 shows an example implementation of the drive circuits of FIG. 25, in accordance with some embodiments of the technology described herein.

FIG. 26 shows an example implementation of the drive circuits of FIG. 25, in accordance with some embodiments of the technology described herein. As shown in FIG. 26, in some embodiments, the bias circuit 2501 may be realized by a Zener diode in series with a resistor R2, connected between the high voltage terminal +Vhigh and a lower voltage DC terminal (e.g., −Vhigh) below the voltage of +Vhigh. In some embodiments, the bias circuit 2501 may include additional circuitry between the high voltage terminal +Vhigh and the lower voltage DC terminal to provide a DC path for current to flow between them and establish a suitable bias voltage. In some embodiments, the bias circuit 2501 may include another Zener diode and resistor in series with the Zener diode and resistor shown in FIG. 26, for providing bias voltage(s) to the low-side drive circuits 2403 and 2404. However, this is merely by way of example, as any suitable bias circuit may be used. FIG. 26 also illustrates an example of a timing circuit 2502 realized as an RC circuit having a capacitor C1 and a resistor R1. Again, this is merely one example of a timing circuit, as other configurations of timing circuits may be used. Drive transistors 2503A and 2503B are shown as being realized by bipolar junction transistors. However, the techniques described herein are not limited in this respect, as the drive transistors may be realized by any type of transistors. Transistor circuits 2405 and 2406 are shown as MOSFETs, in this example. However, the transistor circuits 2405 and 2406 may be realized by any type of transistors. In some embodiments, transistor circuits 2405 and/or 2406 may have a plurality of transistors connected in parallel. As discussed above, switch circuitry S3 may be realized as a diode, as shown in FIG. 26. However, as discussed above, the techniques described herein are not limited in this respect, as in some embodiments switch circuitry S3 may be realized by a transistor.

Figure 27:
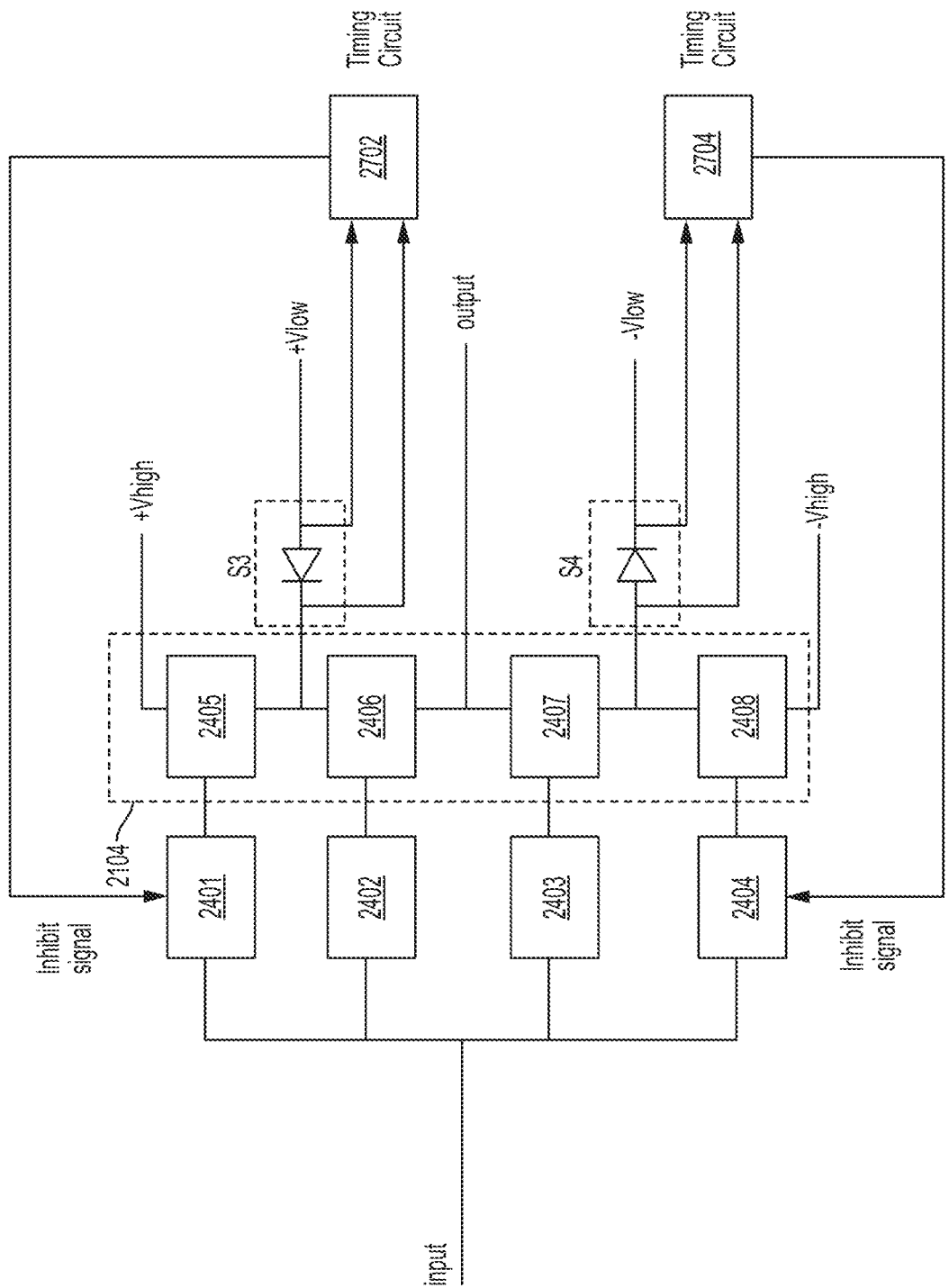
FIG. 27 shows another example of a technique for implementing a timing circuit, according to some embodiments.

FIG. 27 shows another example of a technique for implementing a timing circuit. The inventors have recognized and appreciated that if switch S3 is realized by a diode, the voltage across the diode can be used as a trigger for a timing circuit to limit the amount of time that transistor(s) 2405 are turned on. When a low output voltage is produced by linear amplifier 2104, the diode is forward biased and conducting. When the linear amplifier 2104 produces a high output voltage, transistor(s) 2405 turn on and the diode switches from being forward biased to being reverse biased. The reverse bias voltage can be sensed by timing circuit 2702 as an indication that transistor(s) 2405 are being turned on. In the example of FIG. 27, the voltage across the diode is provided as an input to timing circuit 2702, which produces an inhibit signal to inhibit the operation of drive circuit 2401 after a period of time, thereby limiting the amount of time that transistor(s) 2405 are turned on. Timing circuit 2704 may operate similarly in order to inhibit the operation of drive circuit 2404 after transistor(s) 2408 have been conducting for a period of time.

Figure 28:
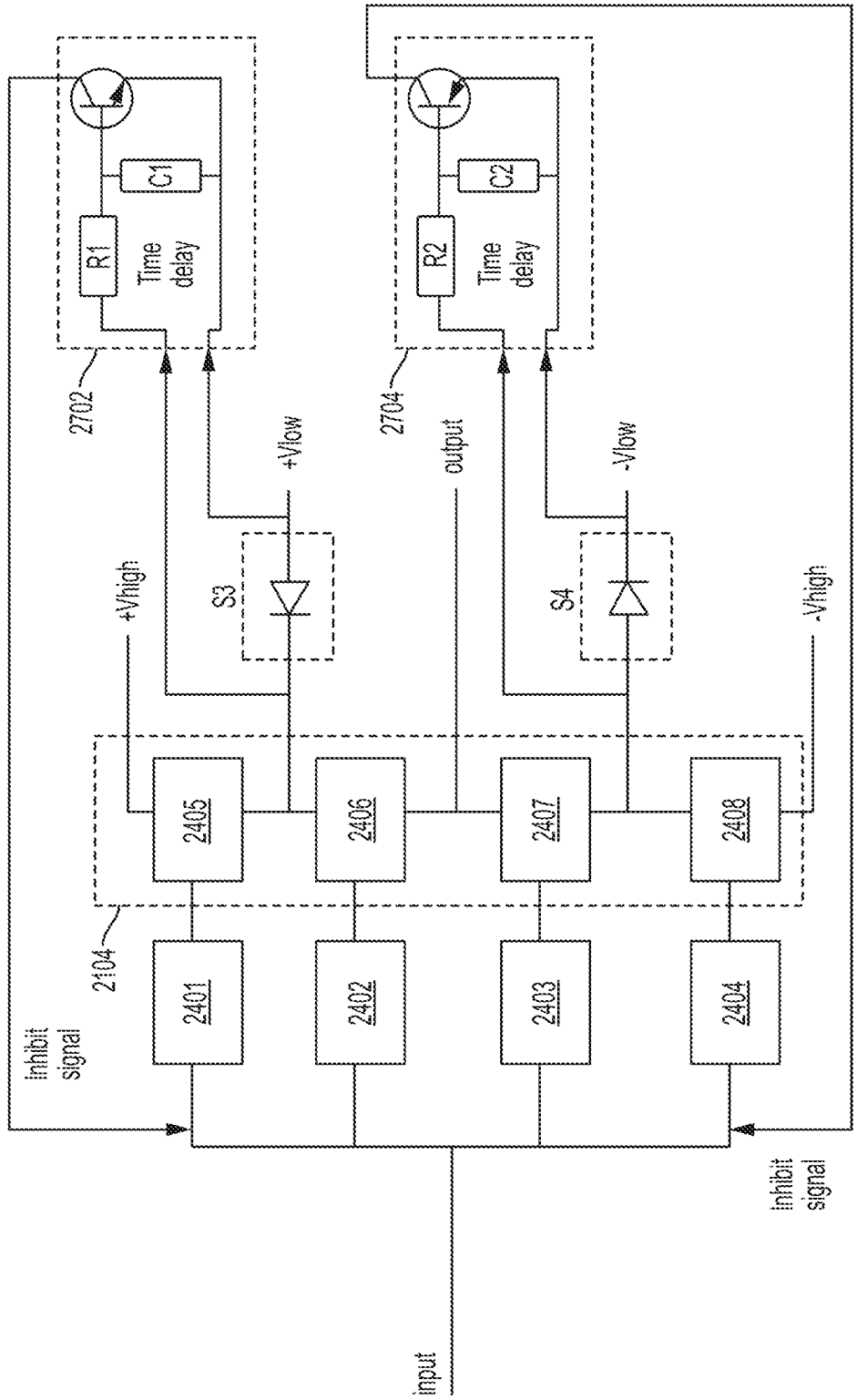
FIG. 28 shows an example of timing circuits realized by an RC circuit and a transistor, according to some embodiments.

FIG. 28 shows an example of timing circuits 2702 and 2704 realized by an RC circuit and a bipolar transistor. In timing circuit 2702, for example, once the diode is reverse biased after a period of time the output of the RC circuit rises to a level where the bipolar transistor turns on. When the bipolar transistor turns on, the input of the drive circuit 2401 is pulled down to +Vlow, which turns off the drive circuit 2401 and transistor(s) 2405.

Figure 29:
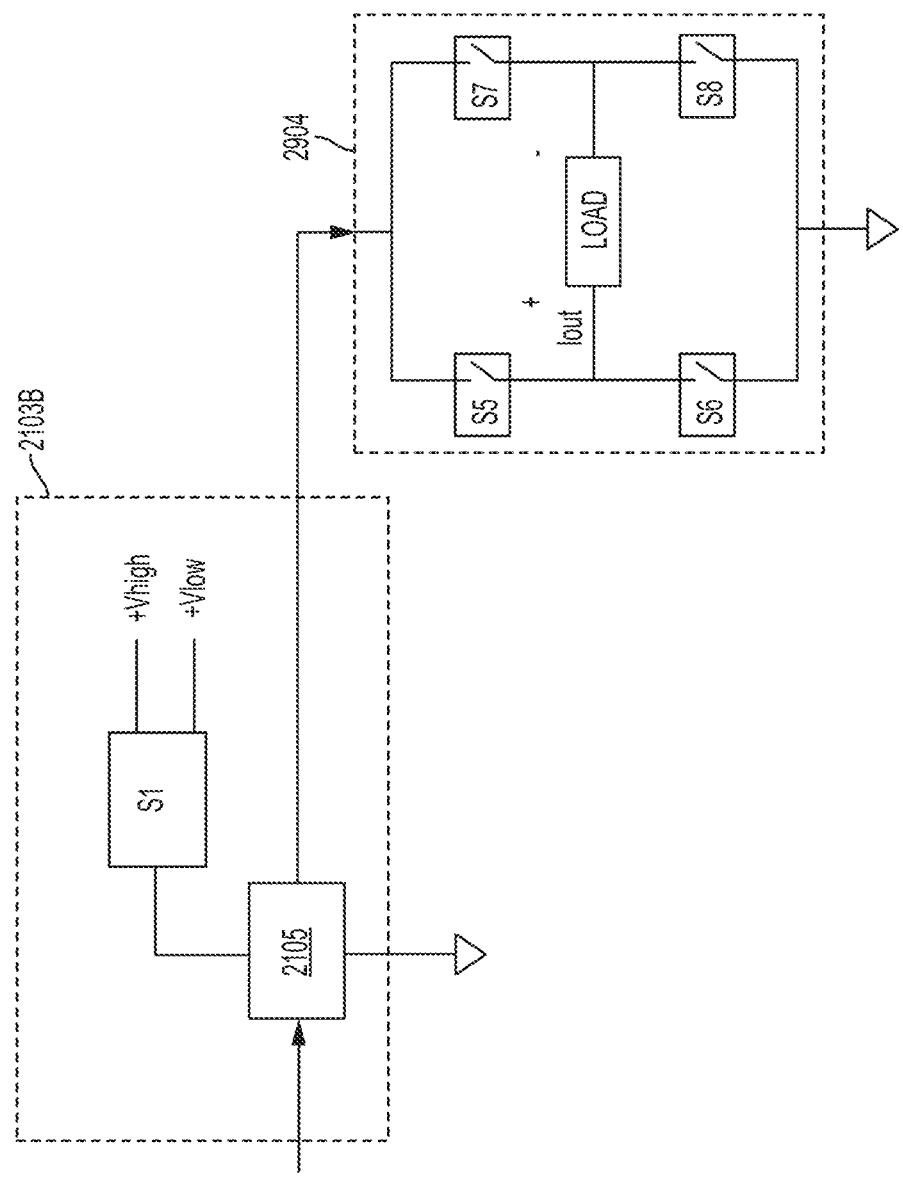
FIG. 29 shows an example of an output stage including a single-ended linear amplifier, according to some embodiments.

Although FIGS. 24, 27 and 28 show a "double-ended" linear amplifier 2104 that may produce a positive output voltage or a negative output voltage, the techniques described herein are not limited in this respect, as in some embodiments a single-ended linear amplifier may be used. FIG. 29 shows an example of an output stage 2103B including a single-ended linear amplifier 2105 that produces only positive output voltages. FIG. 29 schematically illustrates that the single-ended linear amplifier 2105 may be connected to a high positive voltage terminal +Vhigh or a low positive voltage terminal +Vlow by switch S1, depending on the output voltage to be produced. The output stage 2103B may be implemented using the drive circuits 2401, 2402, transistor(s) 2405 and 2406, and associated switch circuit S3 discussed above, in some embodiments.

The output stage 2103B may provide a positive output voltage or a negative output voltage to a load using a polarity-switching circuit 2904. In the example of FIG. 29, polarity-switching circuit 2904 is realized using an H-bridge including switches S5-S8. A positive voltage may be provided to the load by turning on switches S5 and S8 and turning off switches S6 and S7. A negative voltage may be provided to the load by turning on switches S6 and S7 and turning off switches S5 and S8. In some embodiments, the control circuit (not shown) may control switches S5-S8 to produce an output voltage of a suitable polarity. The polarity may be determined by examining the polarity of the current command, the error signal E, or any other suitable signal.

Figure 30:
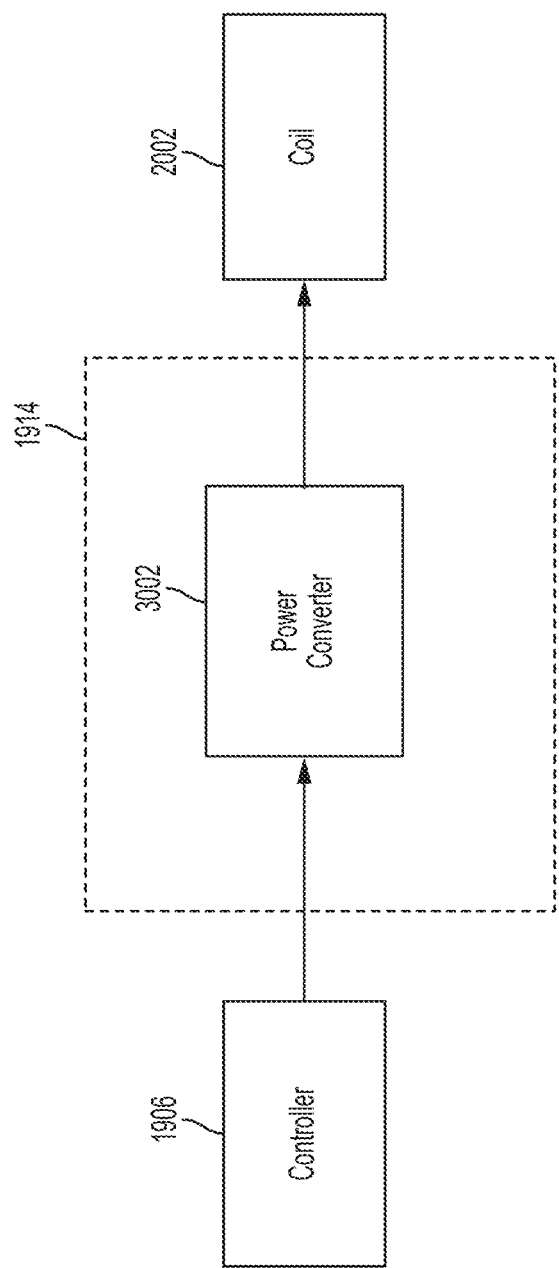
FIG. 30 shows an example of a power component may include a switching power converter, according to some embodiments.

As discussed above, conventional switching converters can introduce a significant amount of switching noise into the system because they switch at frequencies in the range of tens to hundreds of kHz. Such switching noise can interfere with imaging because it is in the same frequency range as MR signals desired to be detected. The inventors have recognized that a power converter having a switching frequency above the Larmor frequency of interest does not interfere with imaging to a significant degree. Accordingly, in some embodiments, power component 1914 may include a switching power converter 3002 that is designed to switch at a relatively high switching frequency, above the Larmor frequency of interest, as shown in FIG. 30. In some embodiments, the switching frequency may be higher than 1 MHz, higher than 10 MHz, higher 30 MHz or higher than 300 MHz.

As discussed above, the inventors have appreciated that providing variable voltage supply terminals facilitates efficient powering of one or more gradient coils of a magnetic resonance imaging system (e.g., a low-field MRI system). In some embodiments, the output stage may be powered by one or more variable voltage supply terminals that are controlled to produce supply voltages close to the desired output voltage. Providing such a variable voltage supply terminal can improve the efficiency of the output stage by limiting the voltage drop across the linear amplifier.

Figure 31:
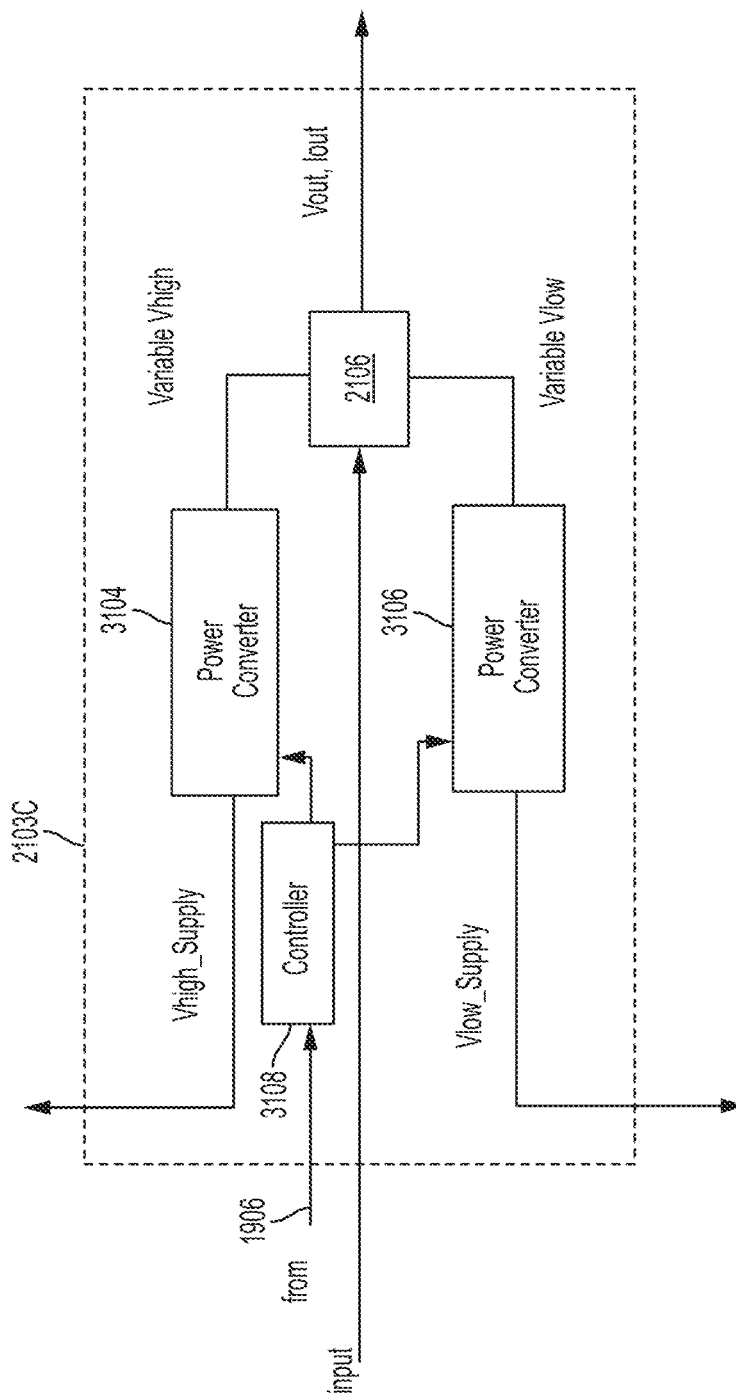
FIG. 31 shows an embodiment of an output stage that may be powered by a variable voltage positive supply terminal and a variable voltage negative supply terminal, according to some embodiments.

FIG. 31 shows an embodiment of an output stage 2103C that may be powered by a variable voltage positive supply terminal and a variable voltage negative supply terminal. The voltages of the supply terminals can be varied depending on the output voltage to reduce the voltage drop across the transistor(s) of the linear amplifier 2106, thus facilitating efficient powering of gradient coil(s) to produce magnetic fields according to a desired pulse sequence. In some embodiments, the voltage of the positive voltage terminal and/or the negative voltage terminal may be provided by power converters 3104 and/or 3106, respectively. The variable output voltages of the power converters 3104 and/or 3106 may be controlled by a controller 3108 based on the desired output voltage of output stage 2103C to maintain the voltages of the positive voltage terminal and/or the negative voltage terminal slightly above (or below, respectively) the output voltage of the output stage, thereby reducing the voltage drop across the transistor(s) of the linear amplifier.

According to some embodiments, controller 3108 controls the variable output voltages of the power converters 3104 and/or 3106 based on the output voltage of linear amplifier 2106. However, the variable output voltages may be controlled in other ways and/or in different relationship to the desired output voltage of output stage 2103C. For example, the variable output voltages may be controlled based on the command (e.g., current command) provided to linear amplifier 2106. As discussed in the foregoing, a controller may be configured to command the linear amplifier to produce output sufficient to drive one or more gradient coils of a magnetic resonance imaging system in accordance with a desired pulse sequence. As such, controller 3108 may be configured to control the variable output voltages of the power converters 3104 and/or 3106 so that the output voltages provided to the linear amplifier are sufficient, without being too excessive and therefore inefficient, to allow the linear amplifier to produce output to power the one or more gradient coils in accordance with the desired pulse sequence. Control of the power converters 3104 and 3106 may be performed in any suitable way, such as by controlling their duty ratio, their frequency, or any other control parameter that can control the output voltage of the power converters. In some embodiments, power converters 3104 and 3106 of FIG. 31 may be switching power converters designed to switch at a relatively high switching frequency, above the Larmor frequency of interest, as discussed above. However, any suitable power converter may be used, as the aspects are not limited in this respect.

Figure 32A:
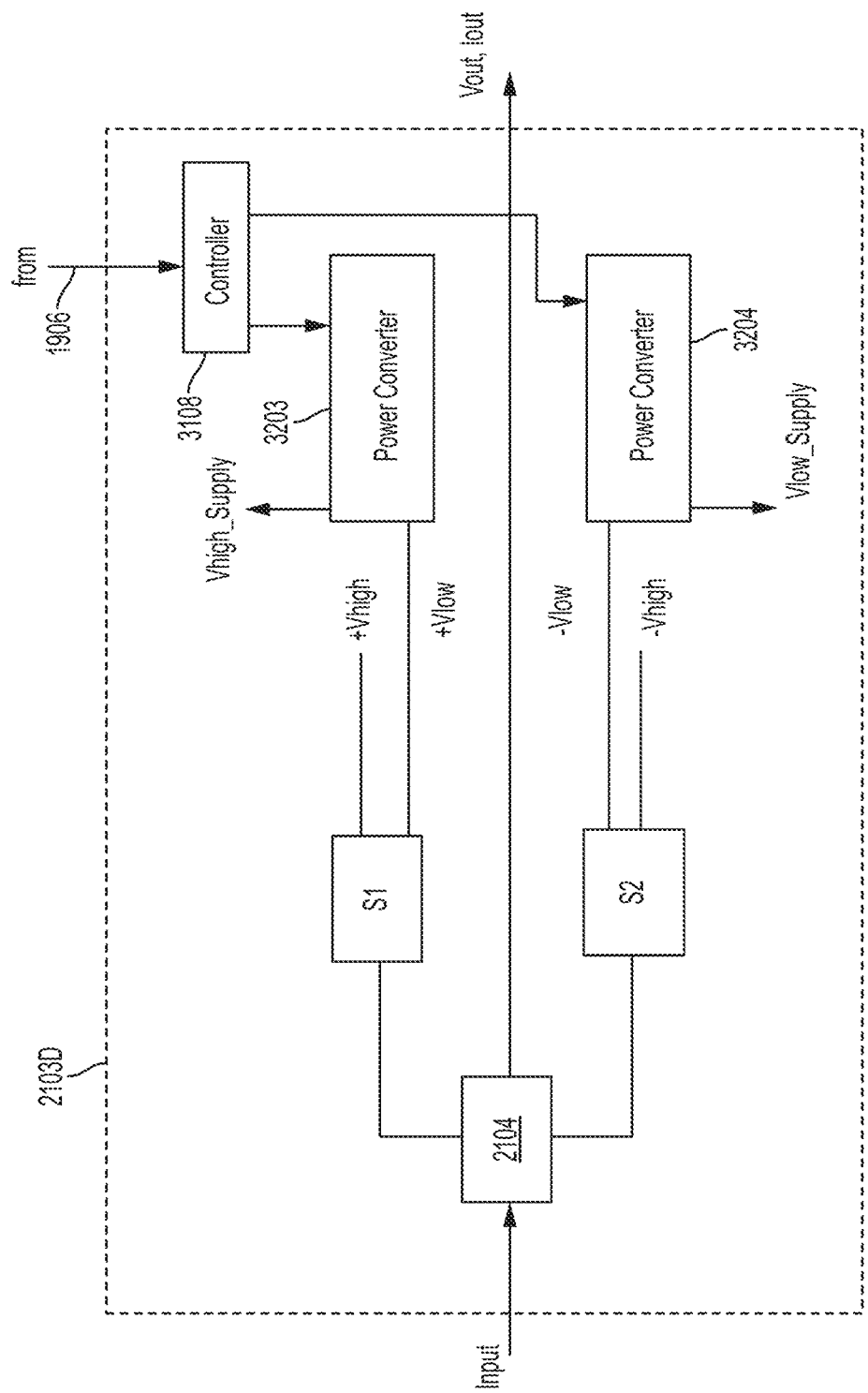
FIG. 32A shows an embodiment similar to that of FIG. 23A with variable low voltage supply terminals.

In some embodiments, both high and low voltage supply terminals (e.g., +Vhigh and +Vlow) may power the linear amplifier, as illustrated in FIGS. 23, 24, and 29, and the voltage of the low voltage supply terminal, the high voltage supply terminal, both, or any supply terminal provided may be variable. FIG. 32A shows an embodiment of an output stage 2103D similar to FIG. 23A with variable low voltage supply terminals. Rather than having low voltage terminals +Vlow and −Vlow at fixed voltages, FIG. 32A shows that +Vlow and −Vlow can have variable voltages. In some embodiments, the variable voltages of +Vlow and −Vlow may be provided by power converters 3203 and 3204, respectively. In some embodiments, power converters 3203 and 3204 may be switching power converters designed to switch at a relatively high switching frequency, above the Larmor frequency of interest, as discussed above. When a relatively low output voltage is to be produced (e.g., in the steady state), current is sourced from the low voltage supply terminals +Vlow or −Vlow. The output voltages +Vlow or −Vlow of the power converters 3203 or 3204 may be controlled by controller 3108 based on the desired output voltage Vout of linear amplifier 2104 to maintain the voltages of the low voltage supply terminals +Vlow or −Vlow slightly above (or below, respectively) the output voltage of the output stage, thereby reducing the voltage drop across the transistor(s) of the linear amplifier in the steady state and reducing power dissipation. When a relatively high output voltage is to be produced, current may be sourced from the high voltage terminals +Vhigh or −Vhigh, which may have fixed voltages.

Figure 32B:
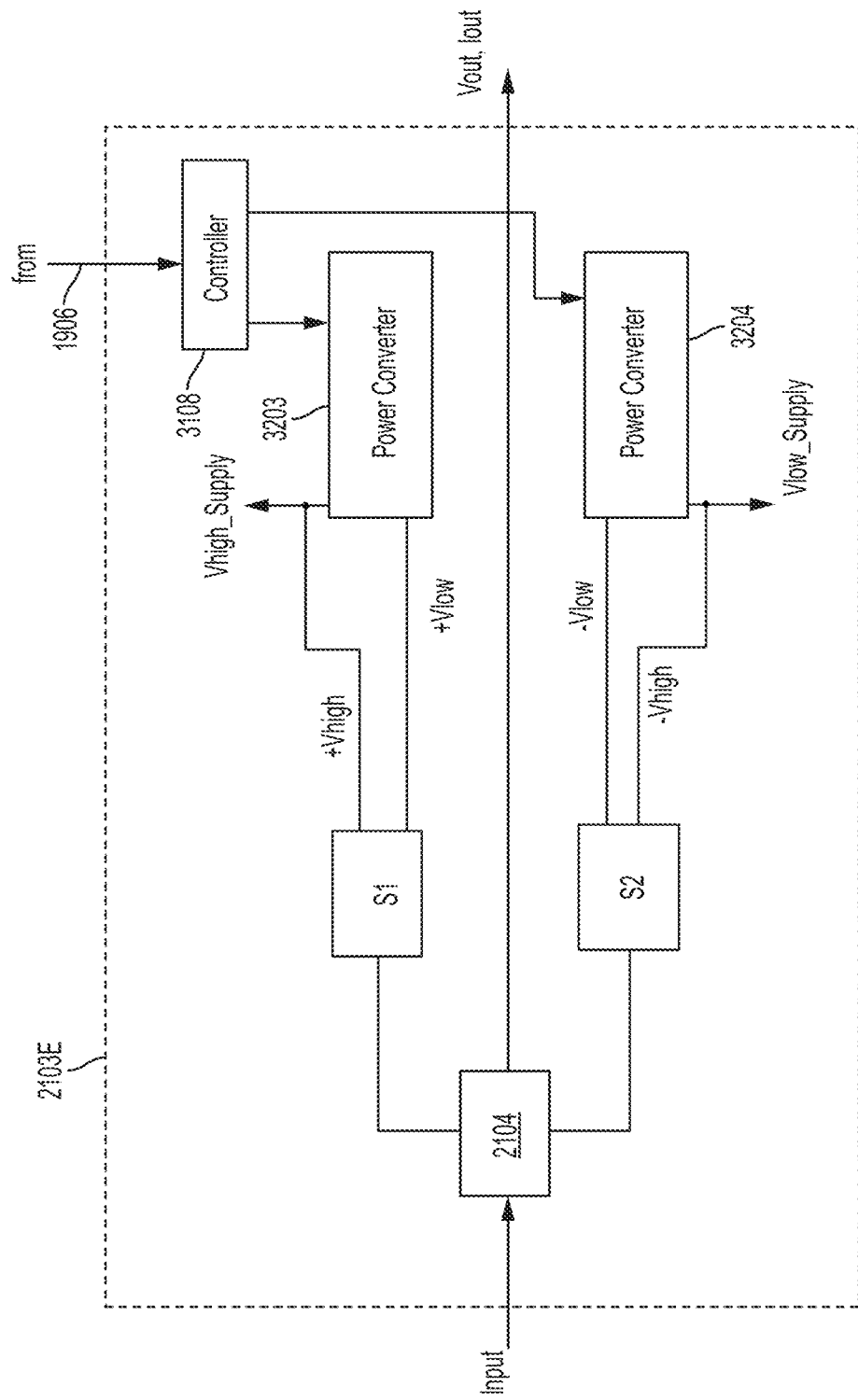
FIG. 32B shows an embodiment in which the high voltage supply terminals are the same as the power supply terminals that supply power to the power converters.

+Vhigh may be a separate terminal from the power supply terminal Vhigh_Supply that supplies power to power converter 3203, as illustrated in FIG. 32A, or may be the same terminal as Vhigh_Supply, as illustrated in FIG. 32B. In FIG. 32B, an example is shown of an output stage 2103E in which +Vhigh is provided from the power supply terminal Vhigh_Supply and −Vhigh is provided from the power supply terminal Vlow_Supply that provides power to power converter 3204. Providing +Vhigh and/or −Vhigh from the existing power supply terminals can avoid the need to produce additional power supply voltages, which can simplify the design and implementation of the output stage.

FIG. 33A shows an example of a gradient coil current waveform, according to some embodiments. The gradient coil current is initially zero, then rapidly ramps up to 10 A in 0.1 ms. The current remains at 10 A for a period of time, then drops back to 0 A. The current remains at 0 A for a period of time before rapidly ramping up to 20 A in 0.2 ms. The current remains at 20 A for a period of time, then drops back to 0 A. It should be appreciated that the amp values and time intervals are merely exemplary for the purposes of illustration, and any suitable values may be used.

FIG. 33B shows the rising transition of the gradient coil current from 0 A to 10 A, the voltage 3302 needed for driving the gradient coil, the voltage of the high voltage supply terminal +Vhigh and the low voltage supply terminal +Vlow. During the transition, current is sourced from the high voltage supply terminal +Vhigh in order to provide a high voltage to the gradient coil to quickly ramp up its current. As the transition occurs, the power converter 3203 begins to ramp up the voltage of the low voltage supply terminal +Vlow from ~0V to a voltage slightly higher than the output voltage necessary to drive the gradient coil with a steady state current of 10 A. Once the steady state current of 10 A is reached, current is sourced from the low voltage supply terminal +Vlow in order to provide high efficiency in the steady state.

FIG. 33C shows the rising transition of the gradient coil current from 0 A to 20 A, the gradient coil voltage, and the voltage of the high voltage supply terminal +Vhigh and the low voltage supply terminal +Vlow. During the transition to 20 A, as with the transition to 10 A, current is sourced from the high voltage supply terminal +Vhigh in order to provide a high voltage to the gradient coil to quickly ramp up its current. As the transition occurs, the power converter 3203 begins to ramp up the voltage of the low voltage supply terminal +Vlow from ~0V to a voltage slightly higher than the output voltage necessary to drive the gradient coil with a steady state current of 20 A. Once the steady state current of 20 A is reached, current is sourced from the low voltage supply terminal +Vlow.

Since the voltage of the low voltage supply terminal +Vlow can be varied, it can be set slightly above the output voltage needed for different steady state current levels. This can improve the efficiency over the case of using a low voltage supply terminal +Vlow having a fixed voltage, as a fixed voltage would need to be designed to handle the maximum steady state current, which may be a higher voltage than necessary for driving lower steady state currents, which can decrease efficiency. As an example, if the +Vlow is set high enough to supply a 20 A steady state gradient coil current, such a voltage is higher than necessary to supply a 10 A steady state gradient coil current, which results in increased voltage drop across the linear amplifier transistor(s) when supplying a 10 A steady state gradient coil current, and higher power dissipation occurs than is necessary. A variable voltage can be set at or near the minimum voltage necessary to supply the commanded steady state gradient coil current, which improves efficiency.

Figure 33D:
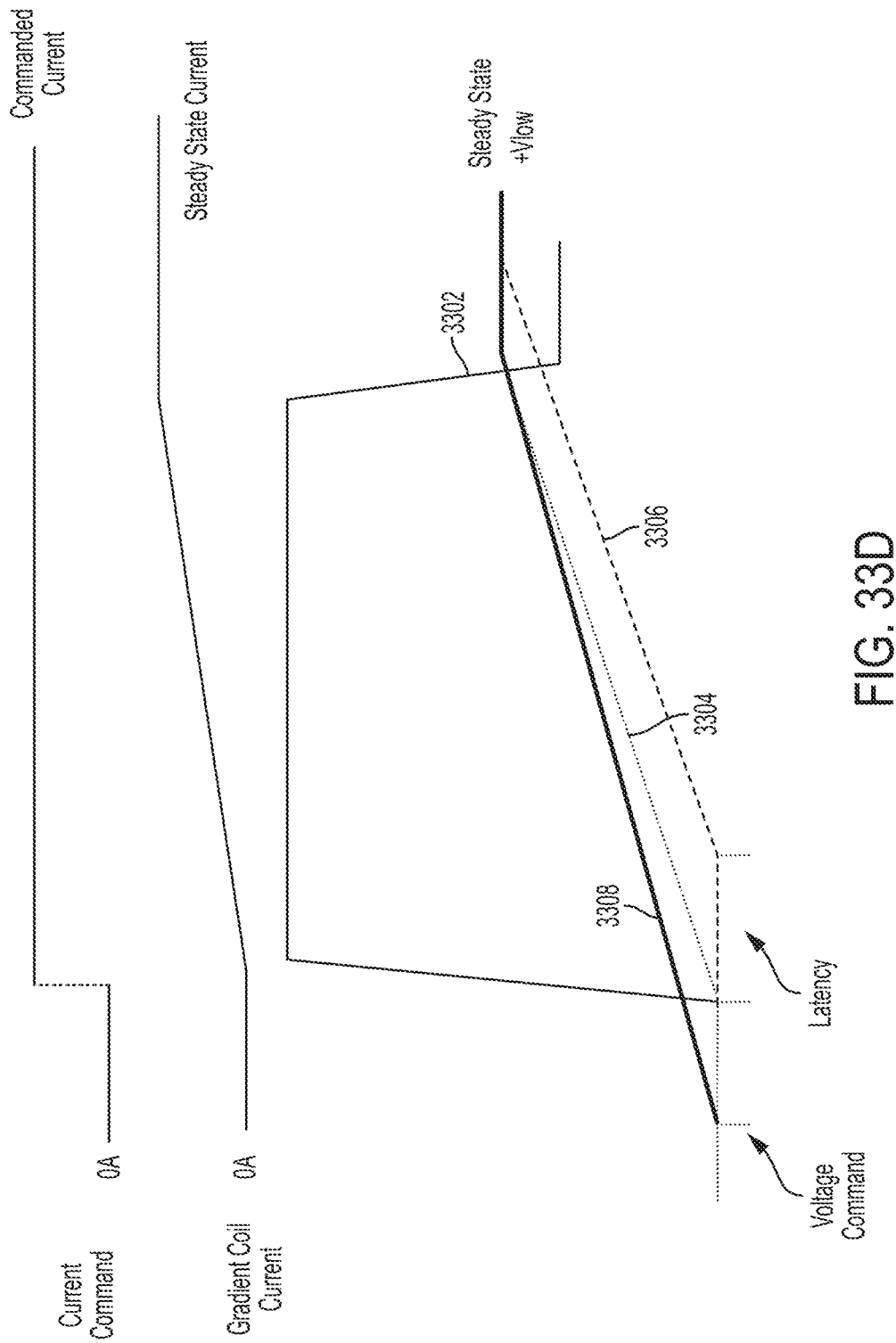

FIG. 33D shows a current command, gradient coil current, the voltage 3302 of the gradient coil needed to supply the current, and several different transition waveforms of the voltage +Vlow. Transition waveform 3304 shows an idealized transition in which the voltage of +Vlow starts ramping up in response to the rising edge of the gradient coil current command, and reaches the steady state value of +Vlow at the same time that the steady state gradient coil current (and voltage values) are reached. However, the inventors have recognized and appreciated that there may be factors preventing the voltage +Vlow from reaching a sufficient voltage level in time for the terminal +Vlow to supply the steady state current. Transition waveform 3306 shows a more realistic transition of +Vlow, which has a period of latency (delay) in responding to the gradient coil current command. As shown in FIG. 33D, the transition waveform 3306 starts ramping up only after a period of time following the rising edge of the current command. The slope of the transition waveform 3306 may be limited, as the power converter 3203 may have an output filter (e.g., a capacitor) that limits the speed with which power converter 3203 can change the voltage of +Vlow. As a result, the transition waveform 3306 may not reach a sufficient voltage level by the time the steady state gradient coil current and voltage are reached, which may result in the low voltage supply terminal +Vlow being unable to supply the steady state current, at least temporarily.

To address this, in some embodiments, the power converter 3203 (or 3204) may begin ramping up the magnitude of the voltage of +Vlow (or −Vlow) before the rising edge of the gradient coil current command. FIG. 33D shows a transition waveform 3308 for +Vlow that starts ramping up before the rising edge of the gradient coil current command. To begin the transition prior to the rising edge of the gradient coil current command, controller 3108 may receive information from controller 1906 regarding an upcoming gradient coil current pulse, and begin ramping up the magnitude of the voltage of +Vlow (or −Vlow) in anticipation of the current pulse. This information may be provided from controller 1906 to controller 3108 in any suitable way. As an example, the controller 1906 may analyze the currently selected gradient coil pulse sequence, determine a power supply voltage level suitable to supply the steady state gradient coil current for the next current pulse, and send a voltage command to controller 3108 in advance of an anticipated current command. The power converter 3203 (or 3204) may then respond to the received voltage command and begin ramping +Vlow (or −Vlow) to the commanded voltage value. As another example of providing the information to the controller 3108, the controller 1906 may send the currently selected pulse sequence or a portion of the pulse sequence to controller 3108. Controller 3108 may then analyze the pulse sequence and send commands to the power converter 3203 (or 3204) to start ramping the voltage +Vlow (or −Vlow) in advance of a gradient coil current pulse. In the example of FIG. 33D, the power converter 3203 starts ramping up the voltage of +Vlow in response to a voltage command provided by controller 1906 to controller 3108 in advance of the rising edge of the current command. As a result, the transition waveform 3308 reaches the level of +Vlow sufficient to supply the steady state current by the time the steady state current level is reached.

Figure 34A:
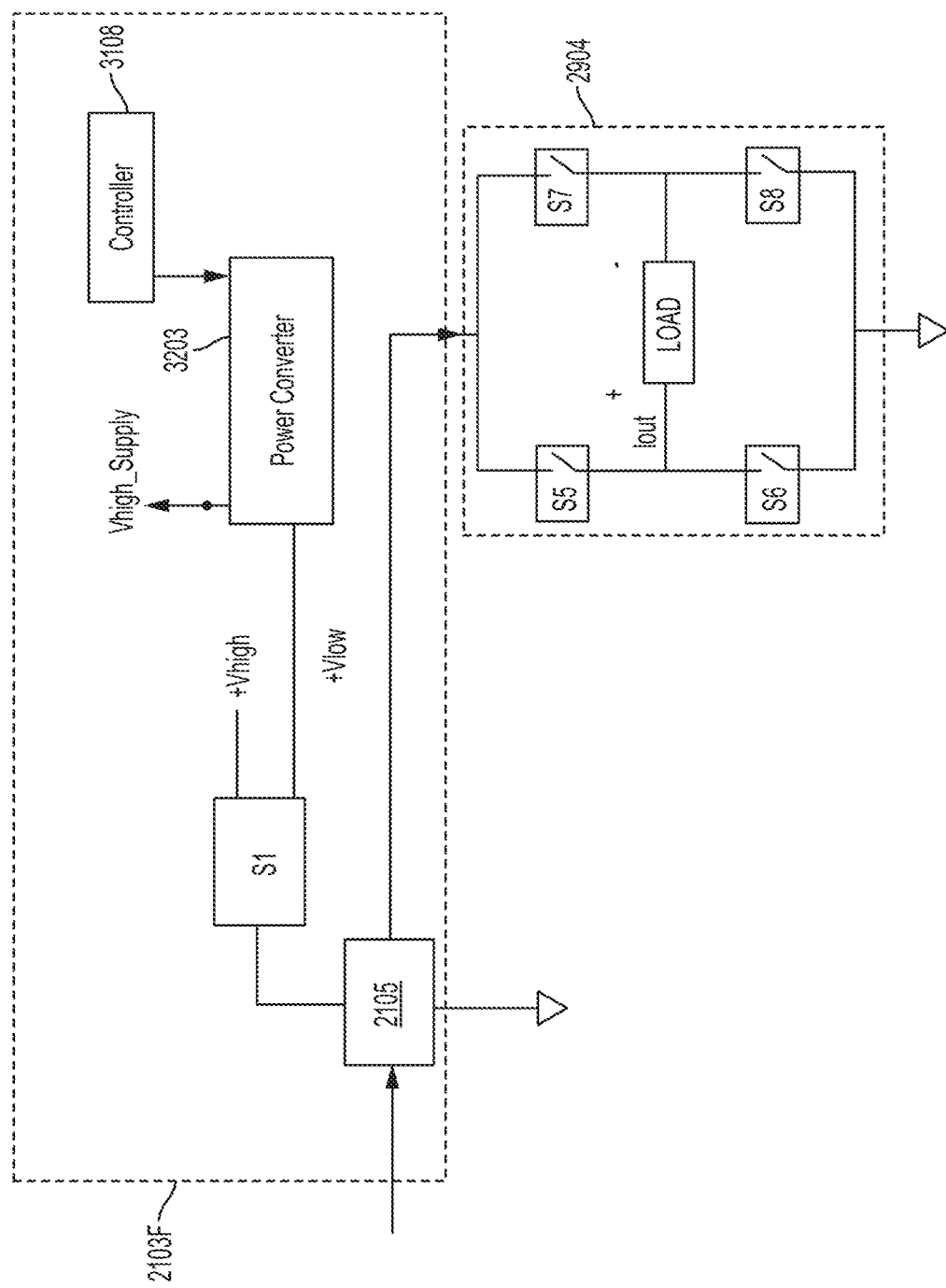
FIG. 34A shows an embodiment similar to that of FIG. 30 with a variable low voltage supply terminal.

FIG. 34A shows an embodiment of an output stage 2103F with a single-ended linear amplifier similar to that of FIG. 29, with a variable low voltage supply terminal +Vlow. As with the embodiment of FIG. 32A, the power converter 3203 supplies a variable voltage to the low voltage supply terminal +Vlow that can be set slightly above the voltage needed to supply the commanded steady state gradient coil current.

Figure 34B:
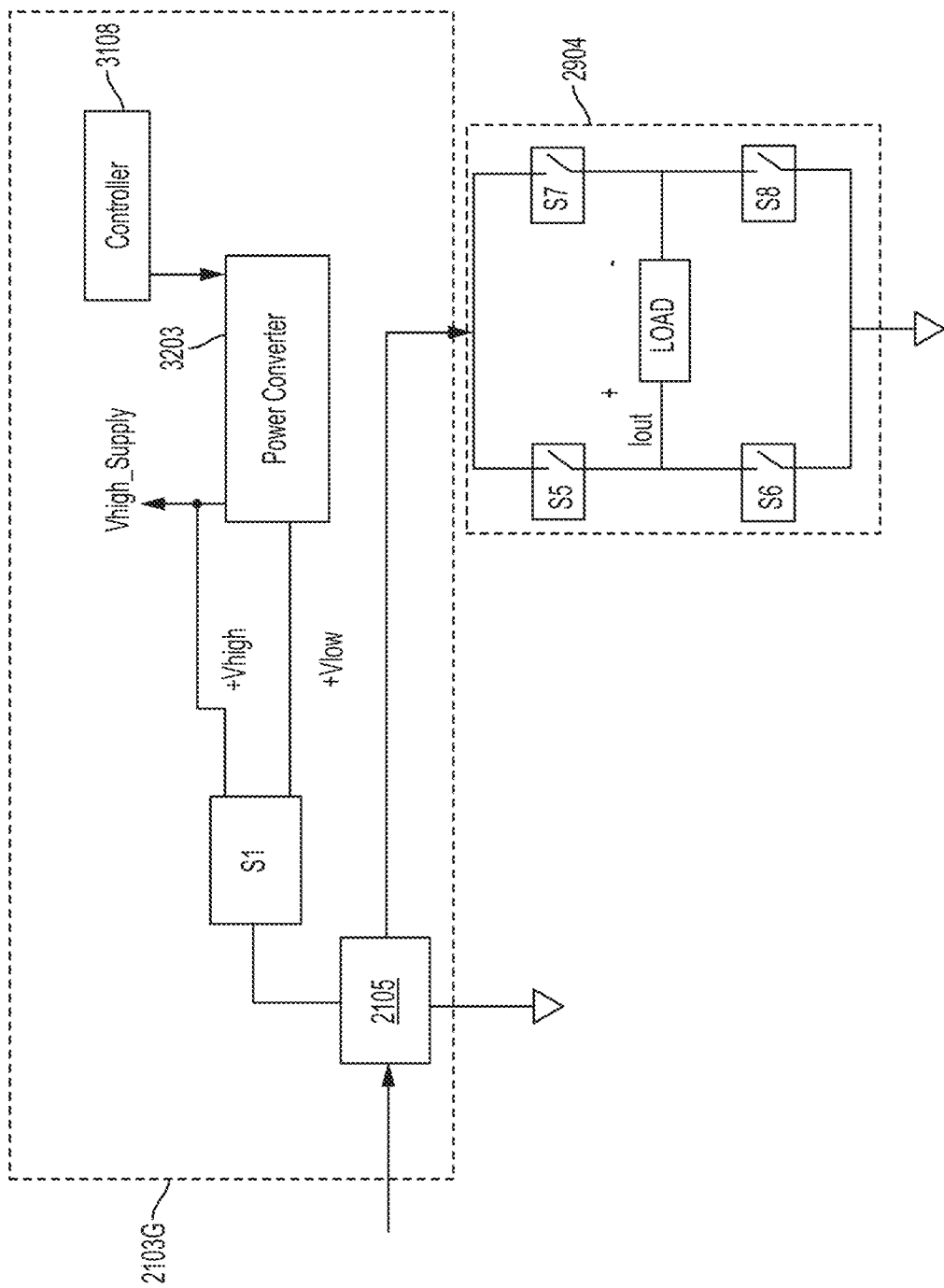
FIG. 34B shows an embodiment in which the high voltage supply terminal is the same as the power supply terminal that supplies power to the power converter.

As discussed above in connection with FIG. 32A and FIG. 32B, the high voltage supply terminal +Vhigh may be a separate terminal from the power supply terminal Vhigh_Supply, as illustrated in FIG. 34A, or may be the same terminal as Vhigh_Supply, as illustrated in FIG. 34B. In FIG. 34B, an example of an output stage 2103G is shown in which +Vhigh is provided from the power supply terminal Vhigh_Supply. Providing the voltage +Vhigh from the existing power supply terminal Vhigh_Supply can avoid the need to produce additional power supply voltages, which can simplify the design and implementation of the output stage.

In some embodiments, both the low voltage supply terminal(s) and the high voltage supply terminal(s) may have variable voltages. For example, the embodiments of FIG. 32 or 29 may be modified such that the high voltage supply terminals +Vhigh and/or −Vhigh are variable voltages produced by power converters. Such power converters may be similar to power converters 3203 and 3204, and may be controlled by the controller 3108, as well. Such an embodiment can be used for any suitable type of imaging, and may be particularly useful for diffusion weighted imaging, for example, where relatively large currents may be needed (e.g., 40 A, 50 A, 70 A, 90 A or more, or any values there between).

In some embodiments, one or more additional power supply terminals may power the linear amplifier. For example, a third power supply terminal may be provided that has a voltage higher than the high voltage supply terminal +Vhigh (e.g., at least 5 times higher or at least 10 times higher, and even as high as 20 or 30 times higher or more, or in any range between such values). Adding a third supply terminal may help improve efficiency in the case where a wide range of voltages need to be produced. Any number of power supply terminals may be provided, as the techniques described herein are not limited in this respect.

Accordingly, using techniques described herein for a low power, low noise amplifier, gradient amplifiers may be configured to operate well within the power budget available using mains electricity (e.g., power delivered from standard wall outlets). According to some embodiments that utilize a linear amplifier design, the power electronics for powering the gradient coils of an MRI system consume between 100-200 W for typical pulse sequences (e.g., bSSFP, FLAIR, etc.) and between 200 W-750 W for more demanding pulse sequences such as DWI. According to some embodiments using switched power converters, the power electronics for powering the gradient coils of an MRI system consume between 50-100 W or less for typical pulse sequences (e.g., bSSFP, FLAIR, etc.) and between 100 W-300 W or less for significantly demanding pulse sequences such as DWI. In addition to low power operation that facilitates operation using standard wall power, the gradient power amplifiers described herein are also configured to be relatively compact in size so that they can be housed within an enclosure (e.g., within base 1950 of the portable MRI systems described in FIGS. 19A and 19B) along with the other electronic components to facilitate portable MRI. According to some embodiments, the gradient amplifiers are designed to be connected to a backplane (e.g., a printed circuit board backplane) that connects the gradient amplifiers to the power source (e.g., wall power) and to the gradient coils of the system, as discussed in further detail below in connection with FIGS. 36 and 37A-D.

The inventors have further developed low power and efficient amplifiers to operate the RF coils of the RF transmit/receive system (e.g., RF power amplifiers to drive one or more transmit/receive coils configured to produce $B_1$ magnetic field pulses to produce an MR response) to facilitate operation of a portable MRI system. According to some embodiments, RF power amplifiers (RFPAs) are configured to operate using mains electricity (e.g., sharing a portion of available main electricity with the other components of the system), such as the power supplied from a single-phase standard wall outlet and/or from a single-phase large appliance outlet. In embodiments of a portable MRI system operating with power supplied from single phase wall power, the RFPAs must share the limited available power with other components (e.g., the exemplary GPAs discussed above, console, on-board computer, cooling fans, etc.) and therefore need to be designed to efficiently make use of the limited power available. The inventors have developed techniques for efficient RFPAs suitable for use in portable MRI powered by mains electricity. According to some embodiments, the maximum input power to the RFPA(s) is approximately 160 W, thereby limiting the average power consumption of the RFPA(s) to a maximum of 160 W. However, the techniques described herein significantly reduce the average power consumption of the RFPA(s), including in circumstances when a given pulse sequence requires higher levels of instantaneous power (e.g., 400 W for DWI pulse sequences), as discussed in further detail below.

Figure 35:
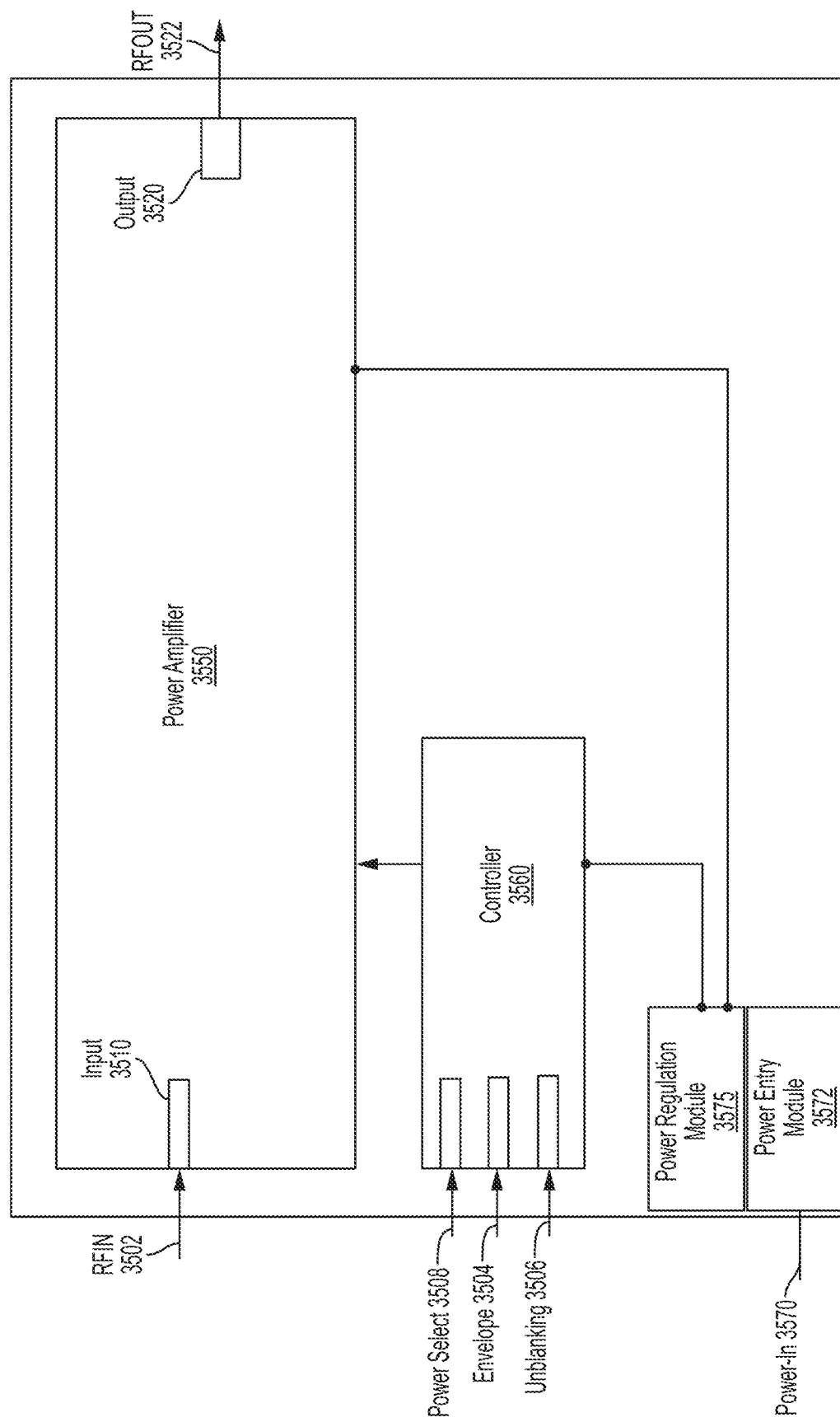
FIG. 35 illustrates a radio frequency power amplifier (RFPA), in accordance with some embodiments.

FIG. 35 is a block diagram of an exemplary low power RFPA, in accordance with some embodiments. RFPA 3500 comprises an input block 3510 that receives an RFIN signal 3502 corresponding to the desired RF signal waveform to be amplified by power amplifier 3550 and provided as RFOUT 3522 at power levels sufficient to operate an RF transmit coil to produce $B_1$ magnetic field pulses according to a desired pulse sequence. Power amplifier 3550 may include any suitable type of amplifier, or combination of amplifier stages, to amplify RFIN 3502 to suitable levels. For example, power amplifier 3550 may comprise one or more class A type amplifiers configured to amplify RFIN 3502 to a desired power level RFOUT 3522 (e.g., maximum 100 W, 400 W, etc. of instantaneous power). Class A amplifiers provide excellent fidelity in amplifying an input signal and therefore facilitate producing an RFOUT waveform 3522 with very little distortion, ensuring that image quality is not degraded by distortion from the RFPA. However, other classes of amplifiers are more power efficient, but generally increase distortion in the course of amplifying an input signal. The inventors have recognized that due to the relatively high Q factor of the RF coils, some additional distortion in the RFOUT 3522 may be tolerated with little, no or acceptable impact on image quality. According to some embodiments, power amplifier 3550 comprises one or more class B, class AB or class BC type amplifiers, etc. Thus, power amplifier 3550 may be made more power efficient by selecting a more efficient class of amplifier provided the increased distortion can be tolerated or compensated for so that image quality is not unsatisfactorily sacrificed. According to some embodiments, power amplifier 3550 includes a plurality of amplification stages that incrementally step up the signal to the desired level for RFOUT 3522.

RFPA 3500 comprises a power entry module 3572 that receives power at power-in 3570, which may correspond to power at a number of different power levels. The power provided at power-in 3570 may be provided by the MRI system's power supplies that deliver DC power converted from AC wall power, as discussed in further detail below in connection with FIG. 36. It should be appreciated that one or more DC-DC power supplies may also be provided to produce desired voltage levels from the DC power provided by the AC-DC power supply or supplies. For example, power-in 3570 may include power lines at +100V, +40V, +23V and −15V provided by, for example, a switched power supply that receives DC power from the AC-DC power supply or supplies. According to some embodiments, a power supply board is included to provide the voltage levels needed for the RFPA. The power supply board may be implemented as a card that is connected to a backplane to receive DC power from the AC-DC power supply and convert the power into desired voltage levels that are delivered to RFPA, which itself may implemented as a board connected to the same backplane, as discussed in further detail below in connection with FIG. 36. Power regulation module 3575 includes regulators that convert the power received by the power entry module 3572 to the voltage levels needed by the RFPA. For example, power regulation module 3575 may include power regulator(s) that provide power lines at +/−5V, +13.8V, +15V and +3.3V to be distributed to controller 3560, power amplifier 3550 and/or any other components of the RFPA requiring power. It should be appreciated that the power distribution arrangement and the power levels needed will depend on the requirements of the particular system, and the above mentioned values are merely exemplary.

In conventional MRI systems, RFPAs typically consume the maximum power required to transmit the $B_1$ magnetic pulse sequences continuously. In particular, even when maximum power is not required for a particular pulse sequence and during intervals when no RF pulses are being produced (e.g., during a transmit quiet period when the MRI system is detecting emitted MR signals), conventional RFPAs still consume maximum power. Because conventional MRI systems are generally not power limited (e.g., conventional MRI systems are powered by a dedicated three-phase power sources), the inefficient use of power consumption is generally acceptable and tolerated. However, an RFPA consuming maximum power may be unsuitable for low power MRI, for example, for a portable MRI system operating from the power supplied by mains electricity (e.g., single-phase wall power). The inventors have developed techniques for more optimal operation of an RFPA from a power consumption perspective, facilitating operation of a portable MRI system using mains electricity.

In FIG. 35, a controller 3560 (e.g., a field programmable gate array (FPGA)) is provided to control various aspects of the operation of RFPA 3500 to reduce power consumption and/or more efficiently use available power, examples of which are described in further detail below. According to some embodiments, an RFPA is configured so that the maximum power drawn by the power amplifier is selectable based on the power requirements of a given pulse sequence. In particular, different image acquisition pulse sequences have different power requirements. For example, a diffusion weighted imaging (DWI) pulse sequence requires significantly more power than a balance steady-state free precession (bSSFP) pulse sequence. Conventionally, RFPAs would be set to provide the power amplification needed for the most demanding pulse sequences (e.g., to draw power according to the most power intensive pulse sequences), such as DWI pulse sequences for example. As a result, during image acquisition of less demanding pulse sequences (e.g., bSSFP), significant excess power is consumed by the RFPAs.

RFPA 3500 is configured so that the power amplification can be selected based upon the requirements of a given pulse sequence (e.g., the power dissipation of the power amplifier can be selected based on the power needed to produce a given pulse sequence). In exemplary RFPA 3500 illustrated in FIG. 35, a power select signal 3508 may be provided to controller 3560 to configure power amplifier 3550 to amplify RFIN 3502 in accordance with the maximum power requirements of a given pulse sequence. For example, for a pulse sequence that requires 50 W, the power select signal 3508 may instruct controller 3560 to bias power amplifier 3550 to dissipate 50 W. Similarly, for a pulse sequence that requires 100 W, the power select signal 3508 may instruct controller 3560 to bias power amplifier 3550 to dissipate 100 W, and for a pulse sequence that requires 400 W, the power select signal 3508 may instruct controller 3560 to bias power amplifier 3550 to dissipate 400 W, etc. In this manner, power amplifier 3550 may be scaled to dissipate power in proportion to the maximum power needs of a given pulse sequence. Thus, because RFPA 3500 is not always consuming power according to the maximum power requirements of the most demanding pulse sequence, significant power reduction may be achieved. According to some embodiments, the power select signal 3508 is set by the console based on the pulse sequence to be used to perform a given image acquisition protocol.

While the power select signal 3508 allows scaling of the power amplifier to the maximum power requirements of a given pulse sequence, excess power will still be consumed during intervals where the pulse sequence does not require maximum power levels, thereby reducing the possible efficiency of the RFPA. To address this drawback, the inventors have developed techniques to dynamically scale power dissipation of the power amplifier in accordance with the changing needs of a given pulse sequence. According to some embodiments, the power consumed by the RFPA is dynamically adjusted based on the needs of the signal being amplified. For example, as illustrated in FIG. 35, controller 3560 may receive an envelope signal 3504 corresponding to the amplitude of the RFIN 3502 waveform to provide an indication of the instantaneous power levels needed to produce the desired RF pulse sequence. Based on envelope 3504, controller 3560 may be configured to dynamically bias amplifier 3550 in correspondence to the changing envelope of the RFIN waveform (e.g., by changing the biasing points on the amplifier transistors in correspondence with envelope signal 3504). As a result, the envelope or magnitude of RFIN 3502 may be tracked by controller 3560 via envelope signal 3504 to dynamically bias the power amplifier accordingly, thus limiting the power dissipation of power amplifier 3550 to the contemporaneous power needs of the pulse sequence and significantly reducing excess power consumed by RFPA 3500. In this manner, power amplifier 3550 can be scaled to draw power in accordance with the instantaneous or substantially instantaneous power needs of the transmitted pulse sequence.

As discussed above, a pulse sequence typically defines the timing of both RF and gradient magnetic field pulses as well as defining the time periods during which the receive coils are detecting MR pulses (e.g., so-called transmit quiet periods). Thus, pulse sequences will have repeated intervals of time when no RF magnetic field pulses are being transmitted. The inventors recognized that if the power amplifier remains on during these intervals (e.g., during transmit quiet periods), power will be consumed even though no RF magnetic field pulses are being transmitted. According to some embodiments, one or more power consuming components of the RFPA are turned off during periods when no RF magnetic field pulses are being produced by the RF transmit coil(s) (e.g., during transmit quite periods such as during MR signal detection and/or during some portions of gradient pulse sequences generation) to prevent the RFPA from consuming power unnecessarily.

As an example, in exemplary RFPA 3500, controller 3560 receives an unblanking signal 3506 that indicates transmit quiet periods of the current pulse sequence. In response to the unblanking signal 3506 indicating a transmit quiet period, controller 3560 is configured to turn off power amplifier 3550 to the extent possible to conserve power (e.g., logic and bias circuits and any other circuitry that consumes power and can be turned off or disconnected may be shut down by controller 3560). When the unblanking signal 3506 changes state to indicate that an RF magnetic field pulse is to be produced, controller 3560 turns on the power amplifier 3550 so that the RF magnetic field pulse can be produced and transmitted by the RF coil(s). Unblanking signal 3506 may be provided by the console or main controller of the MRI system to indicate transmit quiet periods of the pulse sequence of an image acquisition procedure. In many pulse sequences, intervals when RF magnetic field pulses are transmitted may be as little as 10% of the pulse sequence. As such, disabling the power amplifier during the significant transmit quiet periods may result in relatively significant power savings.

It should be appreciated that one or a combination of the above described techniques may be used to reduce the power consumption of the RFPA to facilitate low power MRI, as the aspects are not limited in this respect. In particular, an RFPA need not include each of the power saving techniques described above, but instead can employ one or more of these techniques. For example, a RFPA may include a mechanism that allows selection of discrete power levels depending on the pulse sequence (e.g., via power select signal 3508), a mechanism to scale the power of the power amplifier according to the instantaneous (or approximately instantaneous) power needs of the RF pulses (e.g., by tracking the envelope 3504 of the RF pulse waveform) and/or a mechanism to disable the power amplifier during transmit quite periods (e.g., via unblanking signal 3506). Using one or more of the techniques described above, the RFPA(s) may consume less than the 160 W input power even when producing demanding pulse sequences such as DWI that require intervals of instantaneous power that exceed the input power (e.g., 400 W of instantaneous power). According to some embodiments, the RFPA(s) of a portable MRI system consume 65 W or less during image acquisition and, according to some embodiments, the RFPA (s) may consume 50 W or less (e.g., 25-30 W or less) during operation depending on the pulse sequences produced, thus conserving available wall power for the other components of the system (e.g., GPAs, computer, console, fans, etc.). Other power savings techniques may be used in addition or in the alternative, as the aspects are not limited in this respect.

The above described components facilitate low power operation of an MRI system allowing for a portable MRI system that can be operated using mains electricity (e.g., single-phase "wall power" delivered at standard and/or large appliance outlets). In addition to low power consumption, aspects of portability of an MRI system may be enhanced by a compact design where electronic components used to operate the MRI system are contained on or within a standalone unit along with the magnetics components of the system. Incorporating the power conversion and distribution system, the electronic components (e.g., power amplifiers, console, on-board computer, thermal management, etc.) and the magnetics components of the MRI system on or within a single self-contained device, facilitates portable MRI. As discussed above, conventional MRI systems typically have a separate room for the power components, which must therefore deliver power to the magnetics components of the MRI system via cables connecting the power components to the MRI device located in a specially shielded room. Not only is this arrangement fixed to a dedicated space, but the cabling required to connect the power components to the magnetics components is responsible for significant power losses. As discussed above in connection with FIGS. 19A and 19B, to facilitate portability, the inventors have developed a power system that is contained within a housing that supports or on which the magnetics components of the MRI system are located to provide a standalone, portable MRI system that can be brought to any location having access to wall power, some examples of which are described in further detail below.

Figure 36:
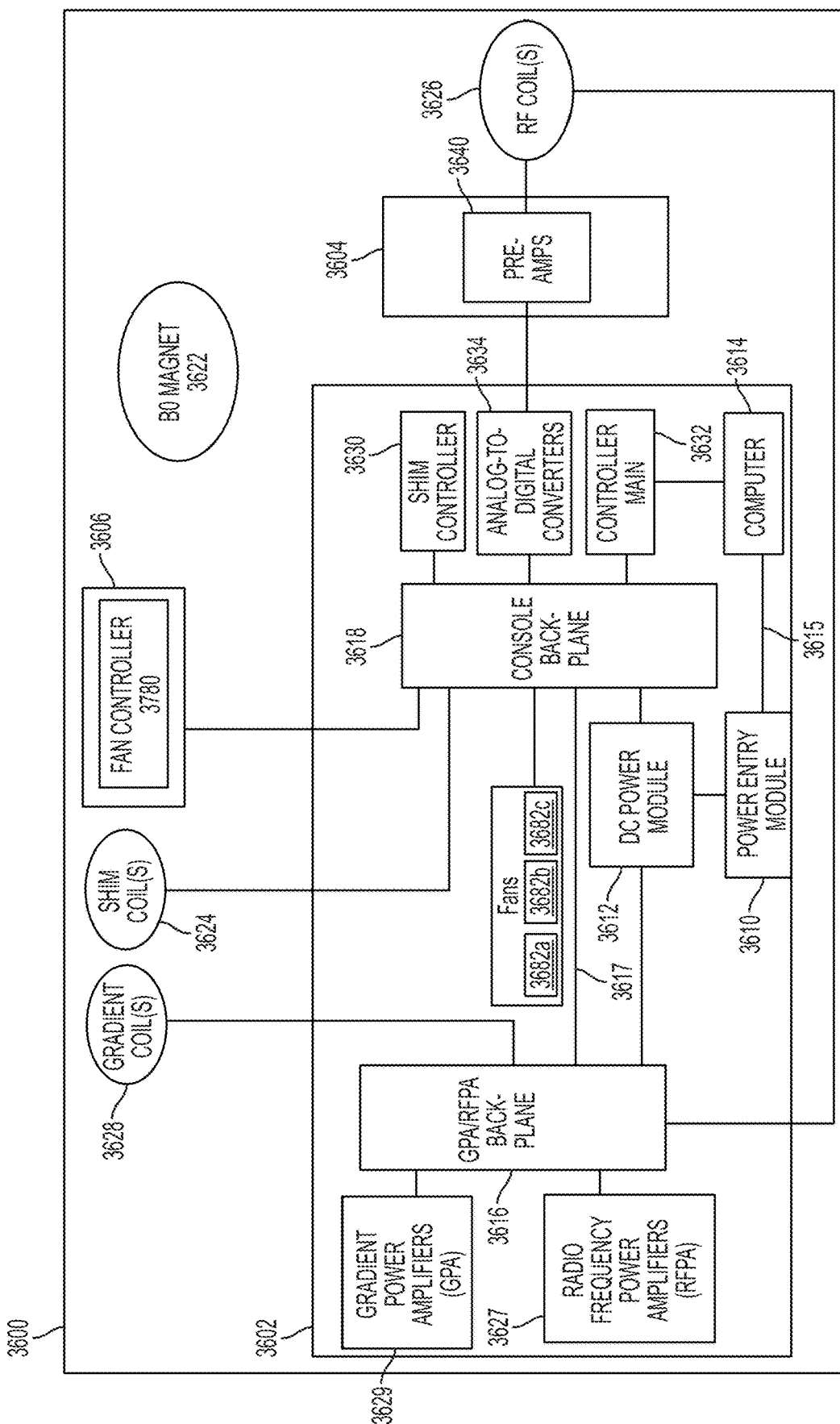
FIG. 36 illustrates a housing for electronic components of a portable MRI system, in accordance with some embodiments.

FIG. 36 illustrates a block diagram of components of a portable MRI system 3600, including the magnetics components (e.g., $B_0$ magnet 3622, gradient coils 3628, RF coil(s) 3626 and, optionally, shim coils 3624), a power conversion and distribution system configured to receive power from a mains electricity source (e.g., a single-phase wall outlet) and the electronic components used to operate the magnetics components and control the operation of the portable MRI system. In FIG. 36, portable MRI system 3600 includes an electronics enclosure 3602, a preamplifier enclosure 3604 and a fan board enclosure 3606. Electronics enclosure 3602 may be positioned below and/or arranged to support the magnetics components of the MRI system (e.g., the $B_0$ magnet, gradient coils, RF coils, shim coils, etc.) to provide a single, integrated standalone and portable MRI system (e.g., enclosure 3602 may form, in part, a base for the portable MRI system 3600, similar to base 1950 located below the magnetics components in portable MRI system 1900 illustrated in FIGS. 19A and 19B). Electronics enclosure 3602 contains a power entry module 3610 and DC power conversion module 3612 for converting power from an AC source (e.g., a wall outlet) and supplying DC power to the electronics system described in further detail below. According to some embodiments, power entry module 3610 provides a power connection configured to receive mains electricity, for example, single-phase power from a wall outlet (e.g., a single-phase outlet providing approximately between 110 and 120 volts at approximately 50-60 Hertz and rated at 15, 20 or 30 amperes, approximately between 210 and 250 volts at approximately 50-60 Hertz and rated at 15, 20 or 30 amperes, depending on the national or regional power standard delivered from wall outlets in the geographic location in which the MRI system is deployed).

Power entry module 3610 may be adapted to filter received mains electricity delivered in accordance with the corresponding power standard so that the AC power is suitable for input to DC power module 3612. DC power module 3612 may comprise one or more power supplies to convert AC power to DC power that can be distributed at voltage levels needed by the various electronics components of portable MRI system 3600. DC power module 3612 may include, for example, one or more commercial power supplies configured to receive AC power as an input and supply DC power as an output. Commercial power supplies are available that are configured to receive a wide variety of AC power. For example, available power supplies are capable of receiving AC power in a range from approximately 85V to approximately 265V in a frequency range from 50-60 Hz and configured to convert the AC input to deliver approximately 1600 W of DC power (e.g., 380V, 4.2 A DC power). The AC input range on such exemplary commercial power supplies makes it suitable for use with the most common, if not all, mains electricity sources worldwide. Thus, according to some embodiments, the MRI system can be configured to be essentially agnostic to different wall power standards, allowing the MRI system to be operated from wall power comprehensively across different regions and/or countries, requiring only a change to the plug type required by the particular outlet.

DC power module 3612 may include one or more AC-DC power supplies and/or one or more DC-DC power converters configured to deliver power to one or more backplanes at levels required by the different electronic components of the MRI system (e.g., power amplifiers, console, controllers, thermal management, on-board computer, etc.), as discussed in further detail below. Individual electronic components may further include one or more power regulators to transform power distributed by the backplanes to desired levels needed for the respective electronic components. It should be appreciated that by providing low power electronic components having power demands that do not exceed the available power provided by mains electricity, power circuitry for transforming three-phase power to single-phase power can be eliminated, facilitating a simplified power entry module 3610, reducing the size, cost and complexity of the power circuitry of the MRI system.

The electronics system illustrated in FIG. 36 comprises backplanes 3616 and 3618 coupled to DC power module 3612 and configured to distribute operating power at desired levels to various hardware components of the electronics system. Backplane 3616 is configured to provide power to GPAs 3629 (e.g., any of the low power, low noise GPAs described above in connection with FIGS. 20-34), RFPAs 3627 (e.g., RFPAs using any of the techniques described in connection with low power RFPA 3500 illustrated in FIG. 35) and gradient coil(s) 3660. Backplane 3616 therefore provides the connections to deliver power to the power amplifiers (e.g., GPA 3629 and RFPA 3627) from DC power module 3612 and provides the connections to deliver amplified power to the corresponding magnetics components (e.g., gradient coils 3628 and RF coil(s) 3626) from the respective power amplifiers. According to some embodiments, backplane 3616 has multiple inputs to receive power at different power levels for distribution to the power amplifiers. According to some embodiments, backplane 3616 has inputs to receive power from DC power module 3612 at +/−48V at 4 A, +/−15V at 50 A and +48V at 3 A for distribution to the power amplifiers. However, it should be appreciated that the above power inputs to the backplane are merely exemplary, and the number of power inputs as well as the voltage and amplitude levels of the power inputs will depend on the specific design needs of a given implementation. According to some embodiments, backplane 3616 is a printed circuit board, allowing for distribution of power using PCB power connectors, eliminating the need for expensive, bulky and lossy cable bundles between the power source and the electronic components.

Backplane 3618 is configured to provide power to various controllers including main controller 3632, shim controller 3630 and fan controller 3780, various electronic components such as analog-to-digital converter (ADC) circuitry 3634, preamplifiers 3640 and magnetics component such as shim coil(s) 3624. According to some embodiments, backplane 3618 comprises an input to receive power from DC power module 3612 at +48V, 4 A for distribution to the components connected to the backplane. According to some embodiments, backplane 3618 includes a DC-DC converter to convert the 48V from DC power module 3612 to 12V for distribution to one or more of the connected components (e.g., main controller 3632). As with backplane 3616, backplane 3618 may be a printed circuit board to distribute power without the cable bundles used in conventional MRI power systems to connect the power source to the electronic components, which may be located at relatively long distances. In the embodiment illustrated in FIG. 36, backplanes 3616 and 3618 are connected via connector 3617 to allow communication between the backplanes and components connected thereto. It should be appreciated that the components connected to the backplanes may be designed as boards or "cards" configured to connect to slots in the respective backplanes. However, one or more connected components can be implemented in a different manner, as the aspects are not limited in this respect.

The use of backplane(s) (e.g., exemplary backplanes 3616 and 3618) provides a number of advantages. As discussed above, backplanes allow electronic components (e.g., power amplifiers, computers, console, controllers, etc.) to be connected to the backplane using PCB connectors (e.g., slots) to eliminate the long cabling conventionally used to connect the power source to the electronic components, thus reducing the size, complexity, cost and power losses that accompanies conventional cabling systems. In addition, because the magnetics components are located proximate the electronic components (e.g., located directly above enclosure 3602), any necessary cabling connecting the magnetics to the backplanes will be significantly reduced in size from the cables used in conventional MRI, which typically had to connect power components and other electronic components to magnetics components located in separate rooms. Given these short distances, cables such as ribbon cables can be used to connect the backplanes to the magnetics components to facilitate compact, simple and power efficient connection between electronic and magnetics components of the MRI system. Moreover, the use of backplanes allows electronic components, such as power amplifiers (e.g., GPAs 3629 and RFPA 3627), to be removed and replaced without needing to disconnect the magnetics components from the respective backplane.

Electronics enclosure 3602 also contains RFPA(s) 3627 and GPAs 3629, which in addition to being significantly lower power due to the low-field strengths involved in the low-field and very low-field regimes, may also incorporate one or more of the low power techniques discussed herein (e.g., as discussed above in connection with the GPAs illustrated in FIGS. 20-34 and/or the RFPAs discussed above in connection with FIG. 35. In some embodiments, RFPA 3627 and/or GPA 3629 may comprise a plurality of amplification stages using FETs or other suitable switching components. In embodiments that include multiple amplification stages for one or both of RFPA 3627 and GPA 3629, each of the amplification stages may be associated with electromagnetic shielding configured to shield the stage from electromagnetic interference. In contrast to large amplifier designs commonly used with conventional MRI systems, which require the use of large shielding structures, power amplifiers (e.g., RFPAs 3627, GPAs 3629) designed in accordance with some embodiments employ smaller and/or simpler electromagnetic shielding structures, further reducing the size, complexity and cost of a portable MRI system.

Additionally, the low power amplifiers (e.g., GPAs 3629 and RFPAs 3627) and lower drive currents for the gradient and RF coils may also simplify thermal management of the MRI system. For example, the low power electronic and magnetics components, in accordance with some embodiments, may be cooled using an air-cooled thermal management system. For example, low power MRI system 3600 includes a fan controller 3780 to control one or more fans (e.g., fans 3682a, 3682b, 3682c) to provide air to cool power components of the system that are co-located in electronics enclosure 3602 and/or the magnetics components of the system. An enclosure 3606 for fan controller 3780 may be located outside electronics enclosure 3602, for example, adjacent to or integrated with the housing for the magnetics components (see e.g., FIG. 37D) or, according to some embodiments, may be located within electronics enclosure 3602. Conventional high power systems often require water-based cooling systems that not only increase the size, cost and complexity of the system, but require a water source to operate the MRI system. Eliminating the need for water-based cooling facilitates portability of the MRI system because the thermal management system can be operated from the electrical power source (e.g., mains electricity), removing the need for an external water source and removing water circulation equipment from the MRI system.

Electronics enclosure 3602 also includes a main controller 3632 (e.g., a console) configured to provide control signals to drive the operation of the various other components (e.g., RF coils, gradient coils, etc.) of the portable MRI system to provide console control in real-time or near real-time. For example, main controller 3632 may be programmed to perform the actions described in connection controller 106 illustrated in FIG. 1. Many conventional MRI systems include a console controller implemented as a specialized high-performance computer to perform similar functions. In some embodiments, main controller 3632 is implemented using a field-programmable gate array (FPGA), which has substantially fewer power requirements compared to the high-performance console computers used in conventional MRI systems, contributing to the reduction in cost, complexity and power consumption of a portable MRI system. In the embodiment illustrated in FIG. 36, main controller 3632 is connected to computer 3614 (e.g., a personal computer grade processor and memory system) to communicate between the two components. Computer 3614 may include its own power converter and power supply and may therefore have a separate connection to 3615 to power entry module 3610.

Portable MRI system 3600 also includes pre-amplifiers 3640 located in a pre-amplifier enclosure 3604 to receive signals from RF coil(s) 3626. Pre-amplifiers 3640 are coupled to analog-to-digital converter (ADC) circuitry 3634 located within electronics enclosure 3602. ADCs 3634 receive analog signals from RF coils 3626 via pre-amplifier circuitry 3640 and convert the analog signals to digital signals that can be processed by computer 3614, including by transmitting signals to an external computer, for example, via a wireless connection (e.g., transmitting digital signals to a smartphone, tablet computer, notepad, etc. used by an operator to initiate and/or control the imaging protocol). RF coil(s) 3626 may include one or more noise coils, one or more RF receive coils configured to detect MR signals and/or one or more RF coils that operate as both noise coils and RF receive coils. Accordingly, signals received from RF coil(s) 3626 may include signals representing electromagnetic noise and/or signals representing MR data. Techniques for utilizing these signals in a noise reduction system to facilitate operation of the portable MRI system outside of specially shielded rooms are discussed in further detail below (e.g., in connection with FIGS. 41A-D and 42). Enclosure 3604 for preamplifiers 3640 may be located outside electronics enclosure 3602, for example, adjacent to or integrated with the housing for the magnetics components (see e.g., FIG. 37D) or, according to some embodiments, may be located within electronics enclosure 3602.

As discussed above, MR data received from coils(s) 3626 may be processed by computer 3614 to suppress noise or otherwise prepare the MR data for image reconstruction. According to some embodiments, MR data is transmitted to one or more external computers to perform image reconstruction (e.g., MR data may be transmitted wirelessly to a mobile device and to secure server(s) in the cloud, or MR data may be transmitted directly to one or more servers for further processing). Alternatively, image reconstruction may be performed by computer 3614. The inventors have recognized that off-loading computation intensive processing (e.g., image reconstruction and the like) to one or more external computers reduces the power consumption of the on-board computer 3614 and eliminates the need to use an on-board computer with significant processing power, reducing the cost and power consumption of such implementations.

Electronics enclosure 3602 also provides containment for shim controller 3630 configured to control the operation of one or more shim coil(s) 3624 to improve the field homogeneity in an imaging field of view. Due to the lower output currents required to control the operation of shim coil(s) 3624 in a low-field MRI system, the electronics used to implement shim controller 3630 may be smaller and/or simpler in similar ways described above for RFPA 3627 and GPA 3629. For example, simple low-power switches may be used to reduce the size and complexity of the shim controller, thereby facilitating the implementation of a portable MRI system. As discussed above, electronics enclosure 3602 may form, in part, the base of portable MRI system 3600, the base supporting the magnetics components of the MRI system. For example, electronics enclosure 3602 may form, in part, a base similar to base 1950 of portable MRI system 1900 illustrated in FIGS. 19A and 19B. Accordingly, the components of an MRI system can be co-located on or within a standalone unit to provide portable MRI system 3600.

Figure 37A:
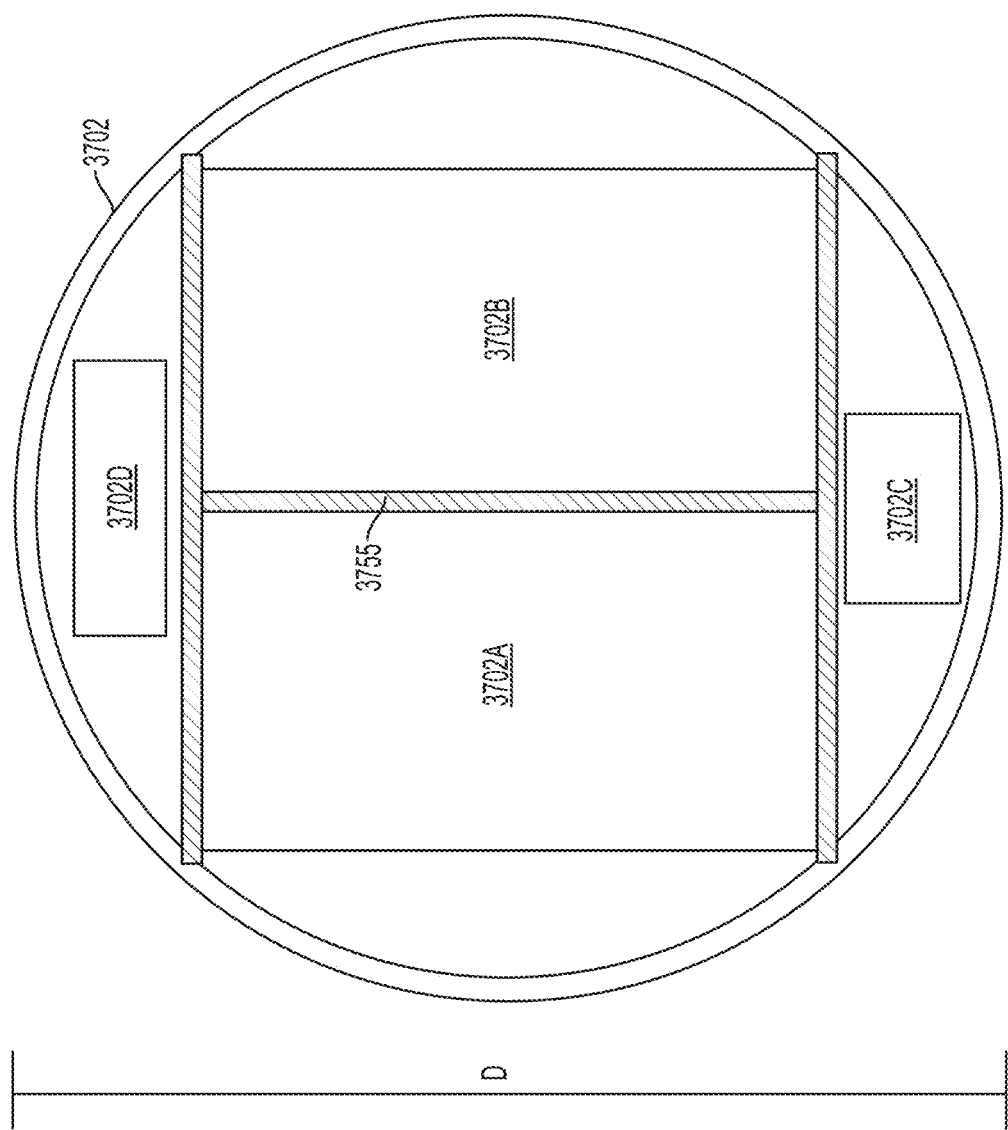
FIG. 37A illustrates a circular housing for electronic components of a portable MRI system, in accordance with some embodiments.
Figure 37B:
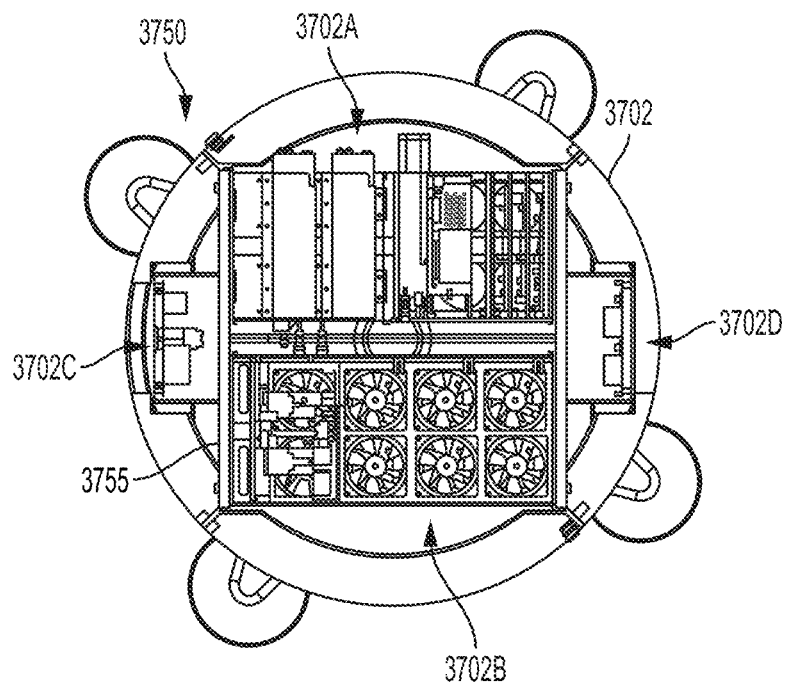
FIGS. 37B and 37C illustrate views of a base comprising a housing for electronics components of a portable MRI system, in accordance with some embodiments.
Figure 37C:
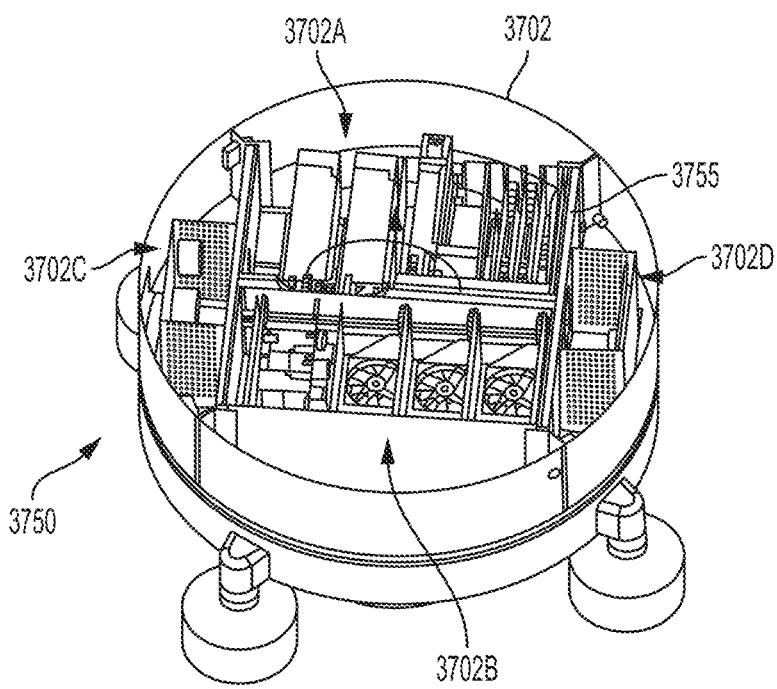
Figure 37D:
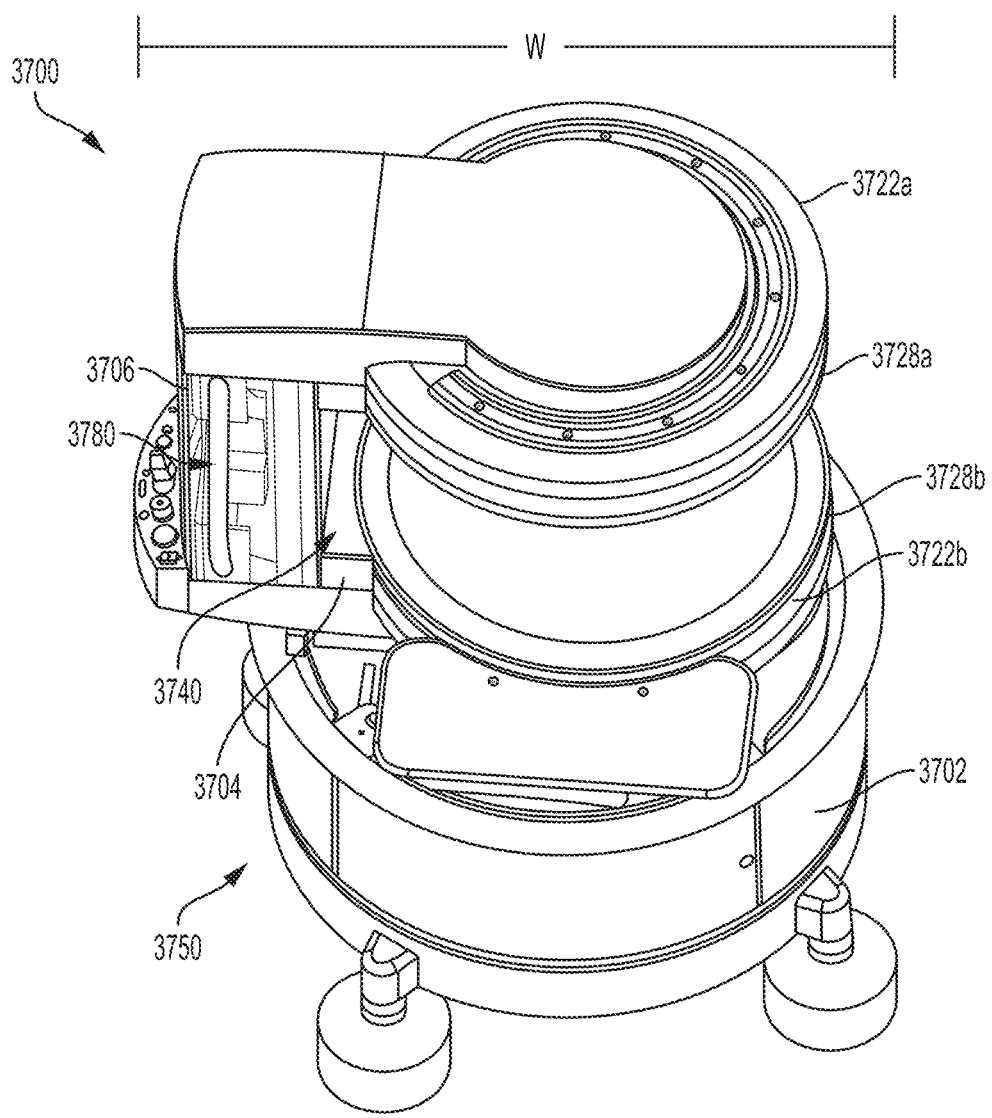
FIG. 37D illustrates a portable MRI system, in accordance with some embodiments.

FIGS. 37A-D illustrate an exemplary arrangement of components of a portable MRI system. In particular, FIG. 37A illustrates a circular housing 3702 that forms a part of base 3750 of portable MRI system 3700 (shown in FIG. 37D). Housing 3702 may house the components described in connection with electronics enclosure 3602 illustrated in FIG. 36. Housing 3702 comprises a chassis or frame 3755 configured to secure the electronic components and provide support for the magnetics components positioned on top of base 3750, as shown in FIG. 37D. Frame 3755 separates housing 3702 into a number of partitions, including partition 3702A that houses a first backplane to connect the power source to the power amplifiers and to connect the power amplifiers to the corresponding magnetics components, and partition 3702B that houses a second backplane to connect the power source to the various controllers (e.g., a computer, main controller/console, shim controller, etc.) and to ADCs for digitizing signals from the RF coils. Partitions 3702A and 3702B may, for example, house the electronic components illustrated in enclosure 3602 in FIG. 36, except for the power entry which is located in partition 3702C in FIG. 37A. Additionally, housing 3702 includes a partition 3702D for a motor that provides a power assist to facilitate transporting or moving the portable MRI system to different locations. For example, portable MRI system 3700 may include one or more motorized wheels that can be engaged when moving portable MRI system 3700 to different locations, as discussed in further detail below in connection with FIGS. 39A and 39B. Housing 3702 is manufactured having a diameter D, which may be chosen to facilitate moving the portable MRI system in typical spaces where the MRI system may be utilized (e.g., in emergency rooms, intensive care units, operating rooms, etc.). According to some embodiments, housing 3702 has a diameter in a range between 25 and 40 inches. For example, exemplary housing 3702 may have a diameter of approximately 32 inches to allow for relative ease in maneuvering the system in spaces where the portable MRI system is intended to be operated.

FIGS. 37B and 37C illustrate different views of circular housing 3702 as part of a base 3750 of portable MRI system 3700. The views in FIGS. 37B and 37C show the arrangement of electronic components within partitions 3702A-C formed by frame 3755, with the backplanes located between partitions 3702A and 3702B. FIG. 37D illustrates a portable MRI device 3700 showing the magnetics components arranged atop base 3750. In particular, magnets 3722a and 3722b form, at least in part, a $B_0$ magnet and gradient coils 3728a and 3728b provide X-gradient, Y-gradient and Z-gradient coils for portable MRI system 3700. As shown, portable MRI system may have a maximum horizontal width W that facilitates the maneuverability of the system within the facilities in which the MRI system is used. According to some embodiments, the maximum horizontal dimension of a portable MRI system is in a range between 40 and 60 inches and, more preferably, in a range between 35 and 45 inches. For example, exemplary portable MRI system 3700 has a maximum horizontal width of approximately 40 inches.

Figure 38A:
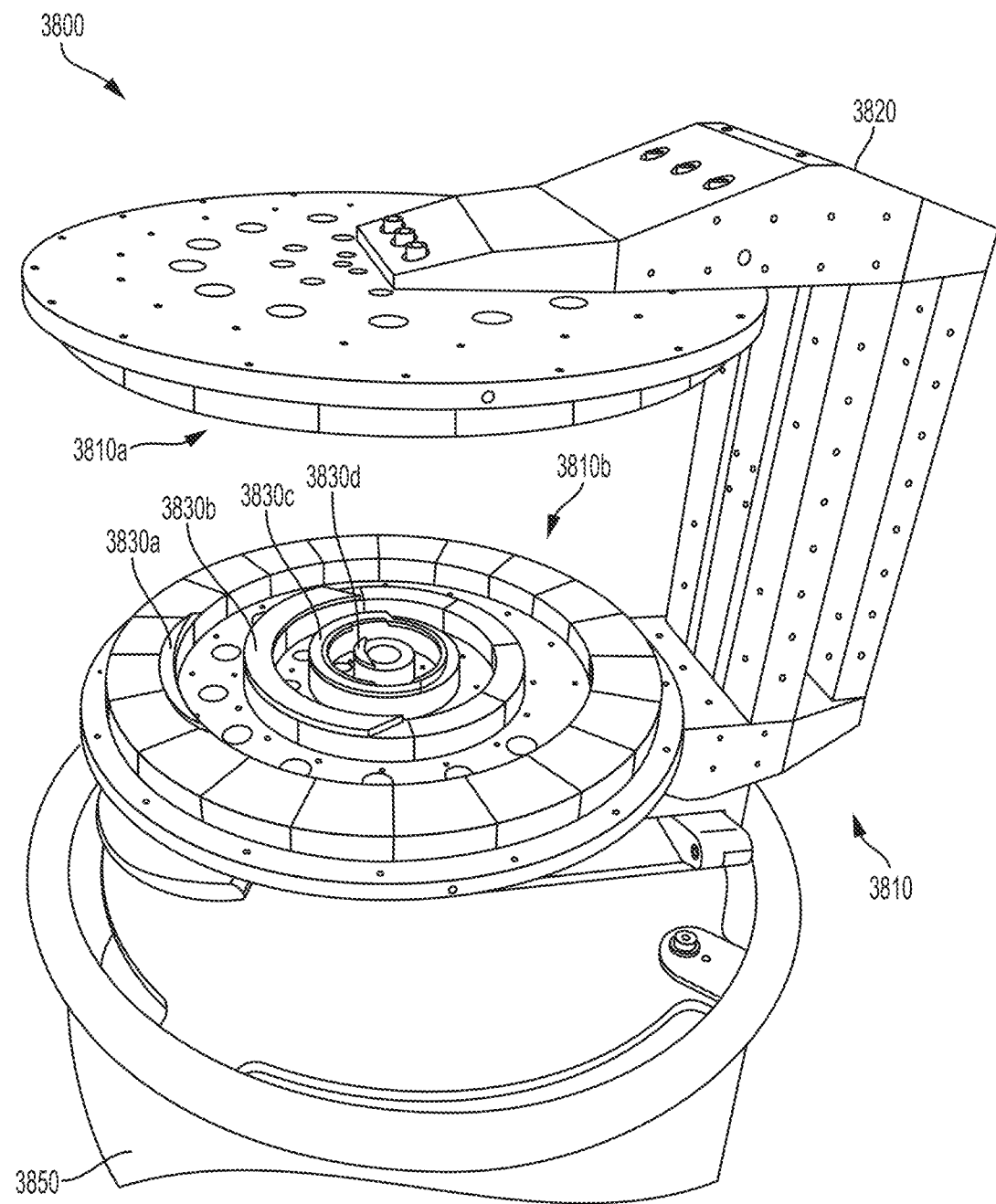
FIG. 38A illustrates permanent magnet shims for a $B_0$ magnet of a portable MRI system, in accordance with some embodiments.
Figure 38B:
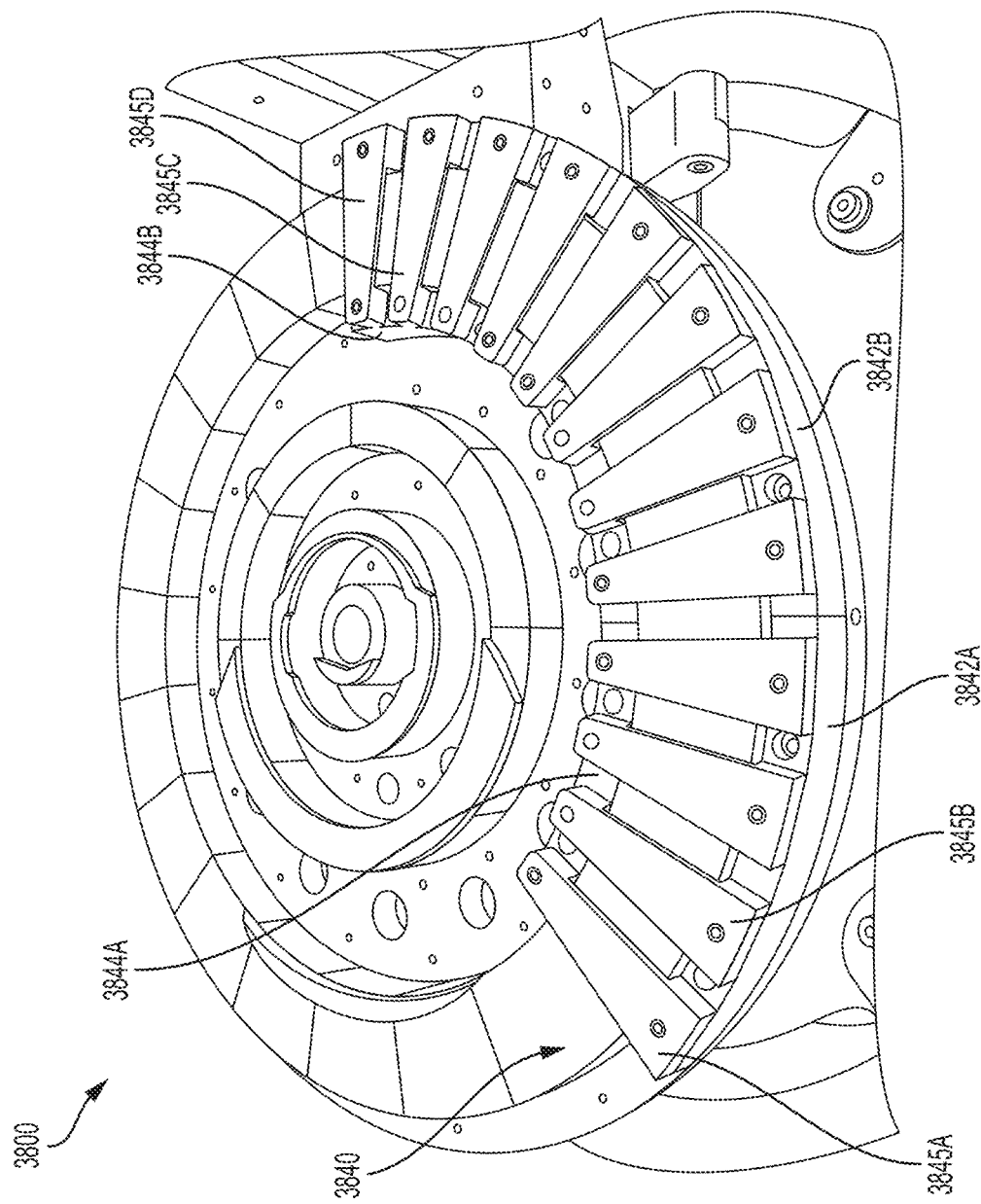
FIGS. 38B and 38C illustrate vibration mounts for gradient coils of a portable MRI system, in accordance with some embodiments.
Figure 38C:
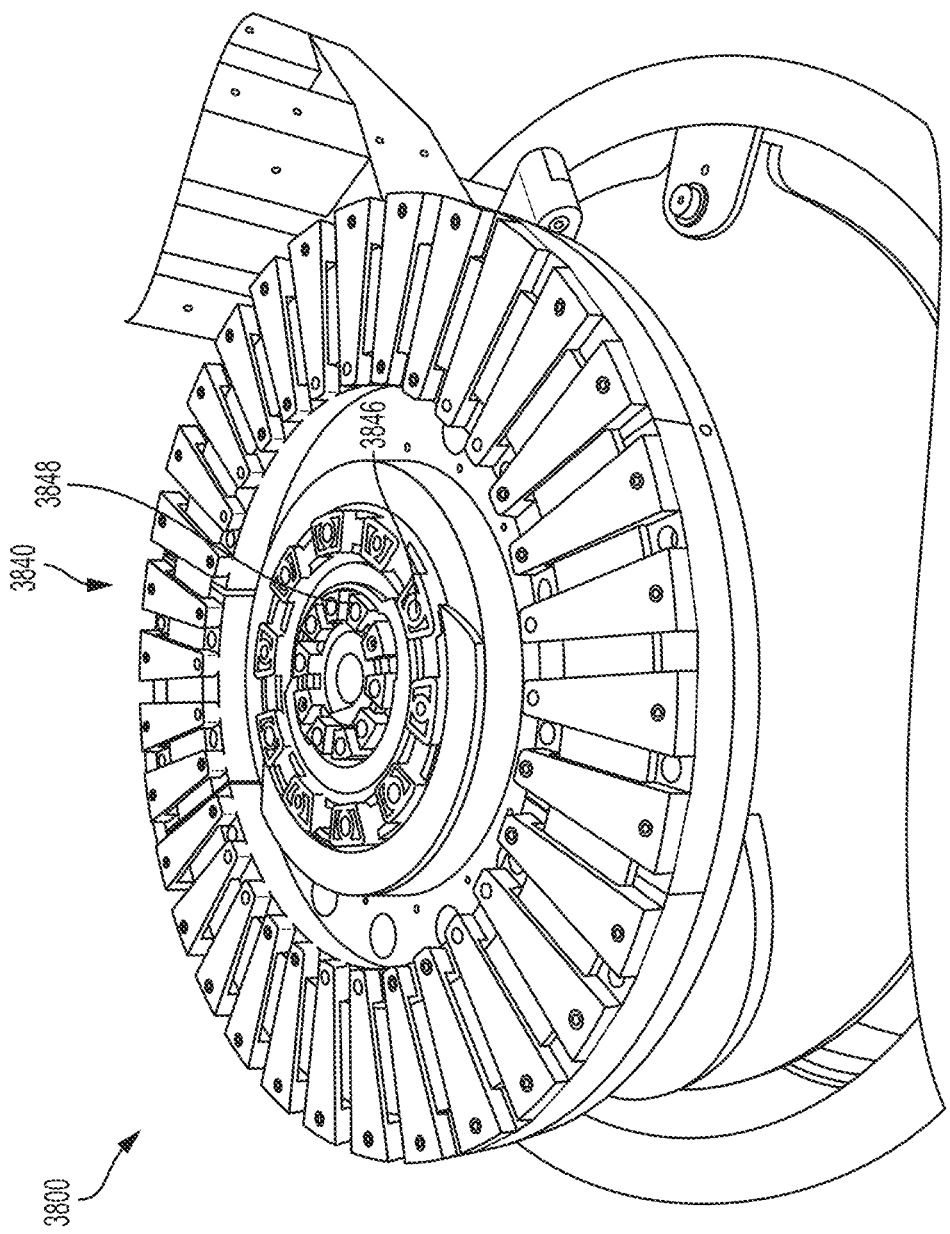
Figure 38D:
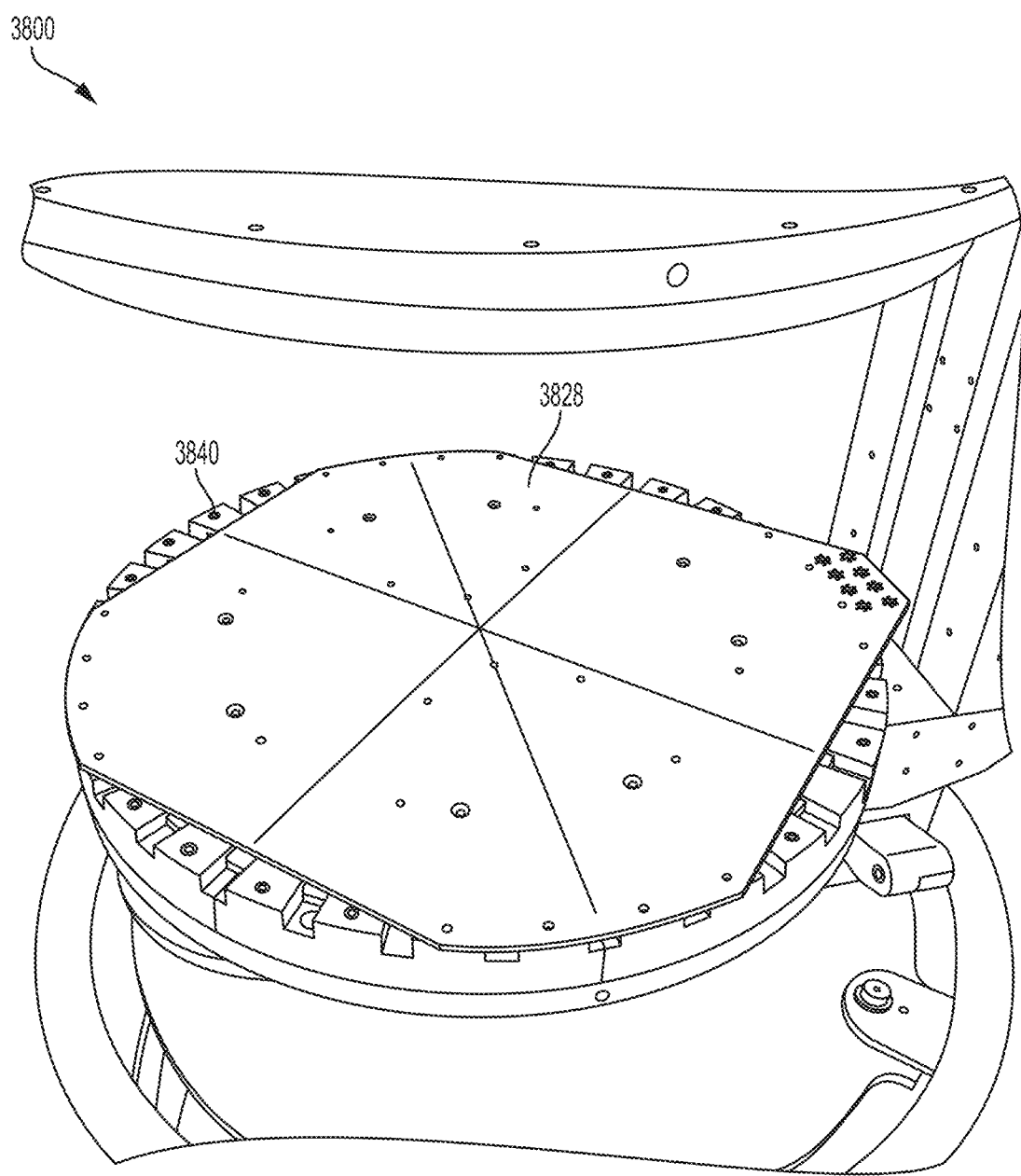
FIG. 38D illustrates a laminate panel comprising gradient coils fastened to the vibration mounts illustrated in FIGS. 38B and 38C.
Figure 38E:
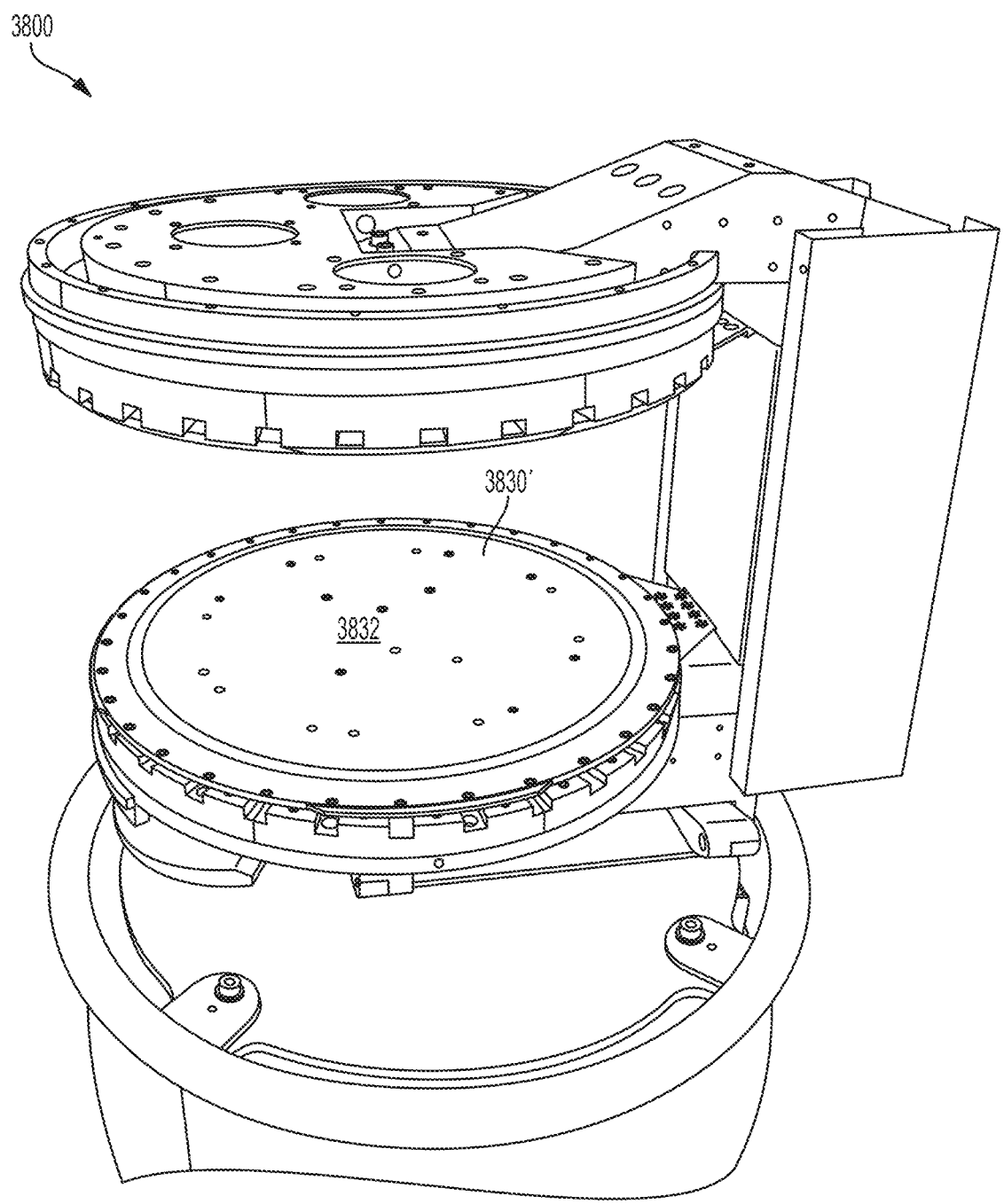
FIG. 38E illustrates exemplary shims for a $B_0$ magnet of a portable MRI system, in accordance with some embodiments.
Figure 38F:
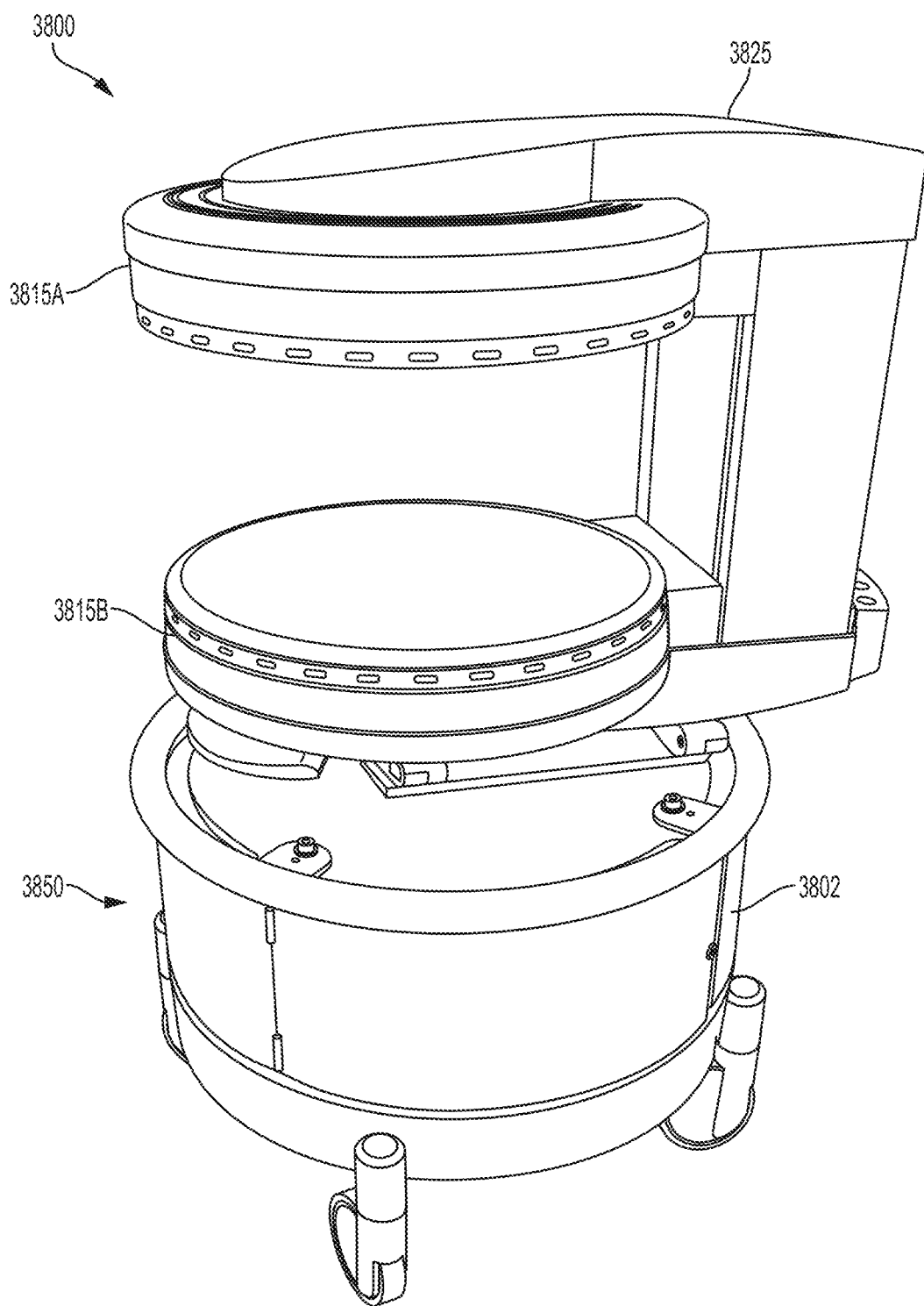
FIG. 38F illustrates a portable MRI system, in accordance with some embodiments.

FIGS. 38A-F illustrate a number of exemplary steps in constructing a portable MRI system 3800. In FIG. 38A, a $B_0$ magnet 3810 comprising upper permanent magnet 3810a, lower permanent magnet 3810b and yoke 3820 is mounted atop a base 3850, a portion of which is illustrated in FIG. 38A (the full base 3850 is illustrated in FIG. 38F). The upper and lower permanent magnets 3810a and 3810b are formed from a plurality of concentric rings of permanent magnet blocks, for example, similar to the permanent magnets rings described in connection with FIGS. 16-18, though any configuration of permanent magnet rings may be used. $B_0$ magnet 3810 and yoke 3820 may be constructed to be relatively light weight, for example, using the techniques and materials described above in connection with FIGS. 3-18 so that the total weight of the completed portable MRI system 3800, as shown in FIG. 38F, weighs less than 1,500 hundred pounds and, more preferably, less than 1000 pounds. Accordingly, portable MRI system 3800 may be transported to different locations by personnel, with or without motor assist capabilities, examples of which are described in further detail below.

$B_0$ magnet 3810 may be configured to produce a $B_0$ magnetic field in the very low field strength regime (e.g., less than or equal to approximately 0.1 T). For example, portable MRI system 3800 may be configured to operate at a magnetic field strength of approximately 64 mT, though any low-field strength may be used. $B_0$ magnetic field strengths in the very low-field regime facilitate a 5-Gauss line (e.g., the perimeter outside of which the fringe magnetic field from the $B_0$ magnet is 5 Gauss or less) that remains close to the portable MRI system. For example, according to some embodiments, the 5-Gauss line has a maximum dimension of less than seven feet and, more preferably, less than 5 feet and, even more preferably, less than 4 feet. In addition to using very low field strengths, shielding may be provided to reduce the volume of the region inside the 5-Gauss line, as discussed in further detail below.

As shown in FIG. 38A, provided on top of one or more of the permanent magnet rings are permanent magnet shims 3830 configured to improve the profile of the $B_0$ magnetic field produced by $B_0$ magnet 3810. As discussed above, one exemplary technique for addressing the relatively low SNR characteristic of the low-field regime is to improve the homogeneity of the $B_0$ field by the $B_0$ magnet. In general, a $B_0$ magnet requires some level of shimming to produce a $B_0$ magnetic field with a profile (e.g., a $B_0$ magnetic field at the desired field strength and/or homogeneity) satisfactory for use in MRI. In particular, production factors such as design, manufacturing tolerances, imprecise production processes, environment, etc., give rise to field variation that produces a $B_0$ field having unsatisfactory profile after assembly/ manufacture. For example, after production, exemplary $B_0$ magnets 200, 300 and/or 1600 described above may produce a $B_0$ field with an unsatisfactory profile (e.g., inhomogeneity in the $B_0$ field unsuitable for imaging) that needs to be improved or otherwise corrected, typically by shimming, to produce clinically useful images.

Shimming refers to any of various techniques for adjusting, correcting and/or improving a magnetic field, often the $B_0$ magnetic field of a magnetic resonance imaging device. Similarly, a shim refers to something (e.g., an object, component, device, system or combination thereof) that performs shimming (e.g., by producing a magnetic field). Techniques for facilitating more efficient and/or cost effective shimming for a $B_0$ magnet for MRI are described in U.S. application Ser. No. 15/466,500 ('500 application), titled "Methods and Apparatus for Magnetic Field Shimming," and filed on Mar. 22, 2017, which is herein incorporated by reference in its entirety.

Exemplary permanent magnet shims 3830a, 3830b, 3830c and 3830d may be provided, for example, using any of the shimming techniques described in the '500 application. In particular, the configuration or pattern (e.g., shape and size) of permanent magnet shims 3830a-d may be determined by computing a magnetic field correction and determining a magnetic pattern for the permanent magnet shims to provide, at least in part, the magnetic field correction. For example, permanent magnet shims 3830a-d may compensate for effects on the $B_0$ magnetic field resulting from asymmetric yoke 3820. For example, the pattern of the permanent magnet shims 3830a-d may be determined to mitigate and/or substantially eliminate non-uniformity in the $B_0$ magnetic field resulting from the effects of yoke 3820 and/or more compensate for other non-uniformities in the $B_0$ magnetic field resulting from, for example, imperfect manufacturing processes and materials to improve the profile (e.g., strength and/or homogeneity) of the $B_0$ magnet. It should be appreciated that in the embodiment illustrated in FIG. 38A, permanent magnetic 3810a also has permanent magnet shims provided thereon that are not visible in the view illustrated in FIG. 38A.

FIGS. 38B and 38C illustrate a vibration mount for the gradient coils of portable MRI system 3800. As illustrated in FIG. 38B, vibration mount 3840 includes portions positioned over the outer permanent magnet ring and fastened into place. In particular, circular arc segments 3842, of which exemplary circular arc segments 3842A and 3842B are labeled, are affixed to the frame on the outside of the outer permanent magnet ring and corresponding circular arc segments 3844, of which exemplary circular arc segments 3844A and 3844B are labeled, are affixed to the frame on the inside of the outer permanent magnet ring. Slats 3845, of which exemplary slats 3845A-D are labeled, are fastened to the circular arc segments 3842 and 3844 to form a vibration mount on which the gradient coils are mounted, as illustrated in FIG. 38D. As shown in FIG. 38C, additional circular arc segments 3846 and 3848 are arranged between the inner permanent magnet rings to facilitate fastening the gradient coils to vibration mount 3840. FIG. 38C illustrates a completed vibration mount 3840 configured so that the gradient coils (e.g., a laminate panel on which gradient coils are fabricated) can be fastened to the frame of the $B_0$ magnet to provide spacing between the gradient coils and the permanent magnet shims and rings of the $B_0$ magnet 3810, and to provide vibration damping to reduce the acoustic noise and vibration of the gradient coils during operation. It should be appreciated that in the embodiment illustrated in FIGS. 38B-C, a vibration mount is also provided on the upper permanent magnet that is not visible in the view illustrated in FIGS. 38B and 38C.

FIG. 38D illustrates a laminate panel 3828 having gradient coils fabricated thereon fastened to vibration mount 3840. For example, laminate panel 3828 may have one or more x-gradient coils, one or more y-gradient coils and/or one or more z-gradient coils patterned into one or more layers of laminate panel 3828. One or more other magnetics components may also be fabricated on laminate panel 3828, such as one or more shim or correction coils for the $B_0$ magnet 3810. Techniques for fabricating magnetics components on laminate panels is described in U.S. Pat. No. 9,541,616 ('616 Patent), titled "Low-Field Magnetic Resonance Imaging Methods and Apparatus," issued Jan. 10, 2017, which is herein incorporated by reference in its entirety. It should be appreciated that in the embodiment illustrated in FIG. 38D, a laminate panel comprising one or more gradient coils (e.g., gradient coils for the X, Y and Z directions) is also fastened to the vibration mount provided on the upper permanent magnet that is not visible in the view illustrate in FIG. 38D to provide the gradient magnetic fields needed for MRI.

FIG. 38E illustrates additional permanent magnet shims 3830' affixed over the laminate panel 3828 illustrated in FIG. 38D. Permanent magnet shim 3830' may provide fine shimming for the $B_0$ magnet. In particular, using any of the techniques described in the '500 application incorporated herein, the magnetic pattern of permanent magnet shim 3830' may be determined by computing a magnetic field correction and determining a magnetic pattern for the permanent magnet shim to provide, at least in part, the magnetic field correction. The patterned permanent magnet shim 3830 may be affixed to a substrate 3832 so that it can be secured to the portable MRI system on top of the laminate panel (e.g., using any of the techniques for patterning described in the '500 application). In this manner, permanent magnet shims 3830 illustrated in FIG. 38A may provide a coarse shimming and permanent magnet shim 3830' may provide a finer shim to improve the profile of the $B_0$ magnetic field produced by $B_0$ magnet 3810 (e.g., to correct for a $B_0$ offset and/or to improve the homogeneity of the $B_0$ magnetic field). It should be appreciated that in the embodiment illustrated in FIG. 38E, another permanent magnet shim may be affixed to the frame over the laminate panel on the upper permanent magnet that is not visible in the view shown in FIG. 38E to correct and/or improve the profile of the $B_0$ magnetic field produced by permanent magnet 3810. The shims provided (e.g., permanent magnet shims 3830, 3830' and/or shim coils fabricated on the laminate panels along with the gradient coils) facilitates a homogeneous $B_0$ magnetic field suitable for obtaining clinically useful images (e.g., the images illustrated in FIGS. 47-50 below).

FIG. 38F illustrates portable MRI system 3800 with housings or outer coverings over the magnetics components illustrated in FIGS. 38A-E. In particular, housing 3815A and 3815B provide covering for the $B_0$ permanent magnet 3810, permanent magnet shims 3830 and 3830', and laminate panel 3828 comprising the gradient coils for the system for the upper and lower portions of the $B_0$ magnet, respectively. Housing 3825 provides a covering for yoke 3828 and, according to some embodiments, houses preamplifiers (e.g., preamplifiers 3640 and 3740 illustrated in FIGS. 36 and 37D, respectively) and a fan controller (e.g., fan controller 3780 and 3780 illustrated in FIGS. 36 and 37D, respectively) that controls the thermal management for the system. The magnetics components of portable MRI system 3800 are supported by base 3850 comprising a housing 3802 for housing the electronic components of the portable MRI system (e.g., the electronic components discussed above configured to operate using mains electricity, such as from a standard wall outlet). Portable MRI system 3800 may be sized as discussed above to facilitate maneuverability of the portable MRI system 3800 so that the system can be brought to the patient. In addition, portable low field MRI system 3800 may be constructed of materials and designed to be light weight, preferably less than 1,500 pounds and, more preferably, less than 1,000 pounds.

As discussed above, a factor in developing a portable MRI system is the ability to operate the MRI system in generally unshielded, partially shielded environments (e.g., outside of specially shielded rooms or encompassing cages or tents). To facilitate portable MRI that can be flexibly and widely deployed and that can be operated in different environments (e.g., an emergency room, operating room, office, clinic, etc.), the inventors have developed noise reduction systems comprising noise suppression and/or avoidance techniques for use with MRI systems in order to eliminate or mitigate unwanted electromagnetic noise, reduce its impact on the operation of the MRI systems and/or to avoid bands in the electromagnetic spectra where significant noise is exhibited.

Performance of a flexible low-field MRI systems (e.g., a generally mobile, transportable or cartable system and/or a system that can be installed in a variety of settings such as in an emergency room, office or clinic) may be particularly vulnerable to noise, such as RF interference, to which many conventional high field MRI systems are largely immune due to being installed in specialized rooms with extensive shielding. To facilitate low field MRI systems that can be flexibly and widely deployed, the inventors have developed noise reduction systems that employ one or more noise suppression techniques for use with low-field MRI systems in order to eliminate or mitigate unwanted noise or to reduce its impact on the operation of the low-field systems.

According to some embodiments, noise suppression and/or avoidance techniques are based on noise measurements obtained from the environment. The noise measurements are subsequently used to reduce the noise present in MR signals detected by the low-field MRI system (e.g., a system having a $B_0$ field of approximately 0.2 T or less, approximately 0.1 T or less, approximately 50 mT or less, approximately 20 mT or less, approximately 10 mT or less, etc.) during operation, either by suppressing the environmental noise, configuring the low-field MRI system to operate in a frequency band or bin having less noise, using signals obtained from multiple receive coils, or some combination therewith. Thus, the low-field MRI system compensates for noise present in whatever environment the system is deployed and can therefore operate in unshielded or partially shielded environments so that MRI is not limited to specialized shielded rooms.

Noise suppression techniques developed by the inventors, examples of which are descried in further detail below, facilitate operation of MRI systems outside shielded rooms and/or that have varying levels of device level shielding of the imaging region of the system. Accordingly, MRI systems employing one or more of the noise suppression techniques described herein may be employed where needed and in circumstances where conventional MRI is unavailable (e.g., in emergency rooms, operating rooms, intensive care units, etc.). While aspects of these noise suppression techniques may be particularly beneficial in the low-field context where extensive shielding may be unavailable or otherwise not provided, it should be appreciated that these techniques are also suitable in the high-field context and are not limited for use with any particular type of MRI system.

Using the techniques described herein, the inventors have developed portable, low power MRI systems capable of being brought to the patient, providing affordable and widely deployable MRI where it is needed. FIGS. 39A and 39B illustrate views of a portable MRI system, in accordance with some embodiments. Portable MRI system 3900 comprises a $B_0$ magnet 3910 formed in part by an upper magnet 3910*a* and a lower magnet 3910*b* having a yoke 3920 coupled thereto to increase the flux density within the imaging region. The $B_0$ magnet 3910 may be housed in magnet housing 3912 along with gradient coils 3915 (e.g., any of the gradient coils described in U.S. application Ser. No. 14/845,652, titled "Low Field Magnetic Resonance Imaging Methods and Apparatus" and filed on Sep. 4, 2015, which is herein incorporated by reference in its entirety). According to some embodiments, $B_0$ magnet 3910 comprises an electromagnet, for example, an electromagnet similar to or the same as electromagnet 210 illustrated in FIG. 2. According to some embodiments, $B_0$ magnet 3910 comprises a permanent magnet, for example, a permanent magnet similar to or the same as permanent magnet 300 illustrated in FIG. 3A or permanent magnet 1600 illustrated in FIG. 16.

Portable MRI system 3900 further comprises a base 3950 housing the electronics needed to operate the MRI system. For example, base 3950 may house the electronics discussed above in connection with FIGS. 36-38, including power components configured to operate the MRI system using mains electricity (e.g., via a connection to a standard wall outlet and/or a large appliance outlet). For example, base 3970 may house low power components, such as those described herein, enabling at least in part the portable MRI system to be powered from readily available wall outlets. Accordingly, portable MRI system 3900 can be brought to the patient and plugged into a wall outlet in the vicinity.

Portable MRI system 3900 further comprises moveable slides 3960 that can be opened and closed and positioned in a variety of configurations. Slides 3960 include electromagnetic shielding 3965, which can be made from any suitable conductive or magnetic material, to form a moveable shield to attenuate electromagnetic noise in the operating environment of the portable MRI system to shield the imaging region from at least some electromagnetic noise. As used herein, the term electromagnetic shielding refers to conductive or magnetic material configured to attenuate the electromagnetic field in a spectrum of interest and positioned or arranged to shield a space, object and/or component of interest. In the context of an MRI system, electromagnetic shielding may be used to shield electronic components (e.g., power components, cables, etc.) of the MRI system, to shield the imaging region (e.g., the field of view) of the MRI system, or both.

The degree of attenuation achieved from electromagnetic shielding depends on a number of factors including the type of material used, the material thickness, the frequency spectrum for which electromagnetic shielding is desired or required, the size and shape of apertures in the electromagnetic shielding (e.g., the size of the spaces in a conductive mesh, the size of unshielded portions or gaps in the shielding, etc.) and/or the orientation of apertures relative to an incident electromagnetic field. Thus, electromagnetic shielding refers generally to any conductive or magnetic barrier that acts to attenuate at least some electromagnetic radiation and that is positioned to at least partially shield a given space, object or component by attenuating the at least some electromagnetic radiation.

It should be appreciated that the frequency spectrum for which shielding (attenuation of an electromagnetic field) is desired may differ depending on what is being shielded. For example, electromagnetic shielding for certain electronic components may be configured to attenuate different frequencies than electromagnetic shielding for the imaging region of the MRI system. Regarding the imaging region, the spectrum of interest includes frequencies which influence, impact and/or degrade the ability of the MRI system to excite and detect an MR response. In general, the spectrum of interest for the imaging region of an MRI system correspond to the frequencies about the nominal operating frequency (i.e., the Larmor frequency) at a given $B_0$ magnetic field strength for which the receive system is configured to or capable of detecting. This spectrum is referred to herein as the operating spectrum for the MRI system. Thus, electromagnetic shielding that provides shielding for the operating spectrum refers to conductive or magnetic material arranged or positioned to attenuate frequencies at least within the operating spectrum for at least a portion of an imaging region of the MRI system.

In portable MRI system 3900 illustrated, the moveable shields are thus configurable to provide shielding in different arrangements, which can be adjusted as needed to accommodate a patient, provide access to a patient and/or in accordance with a given imaging protocol. For example, for the imaging procedure illustrated in FIG. 40A (e.g., a brain scan), once the patient has been positioned, slides 4060 can be closed, for example, using handle 4062 to provide electromagnetic shielding 4065 around the imaging region except for the opening that accommodates the patient's upper torso. In the imaging procedure illustrated in FIG. 40B (e.g., a scan of the knee), slides 4060 may be arranged to have openings on both sides to accommodate the patient's legs. Accordingly, moveable shields allow the shielding to be configured in arrangements suitable for the imaging procedure and to facilitate positioning the patient appropriately within the imaging region.

Figure 40A:
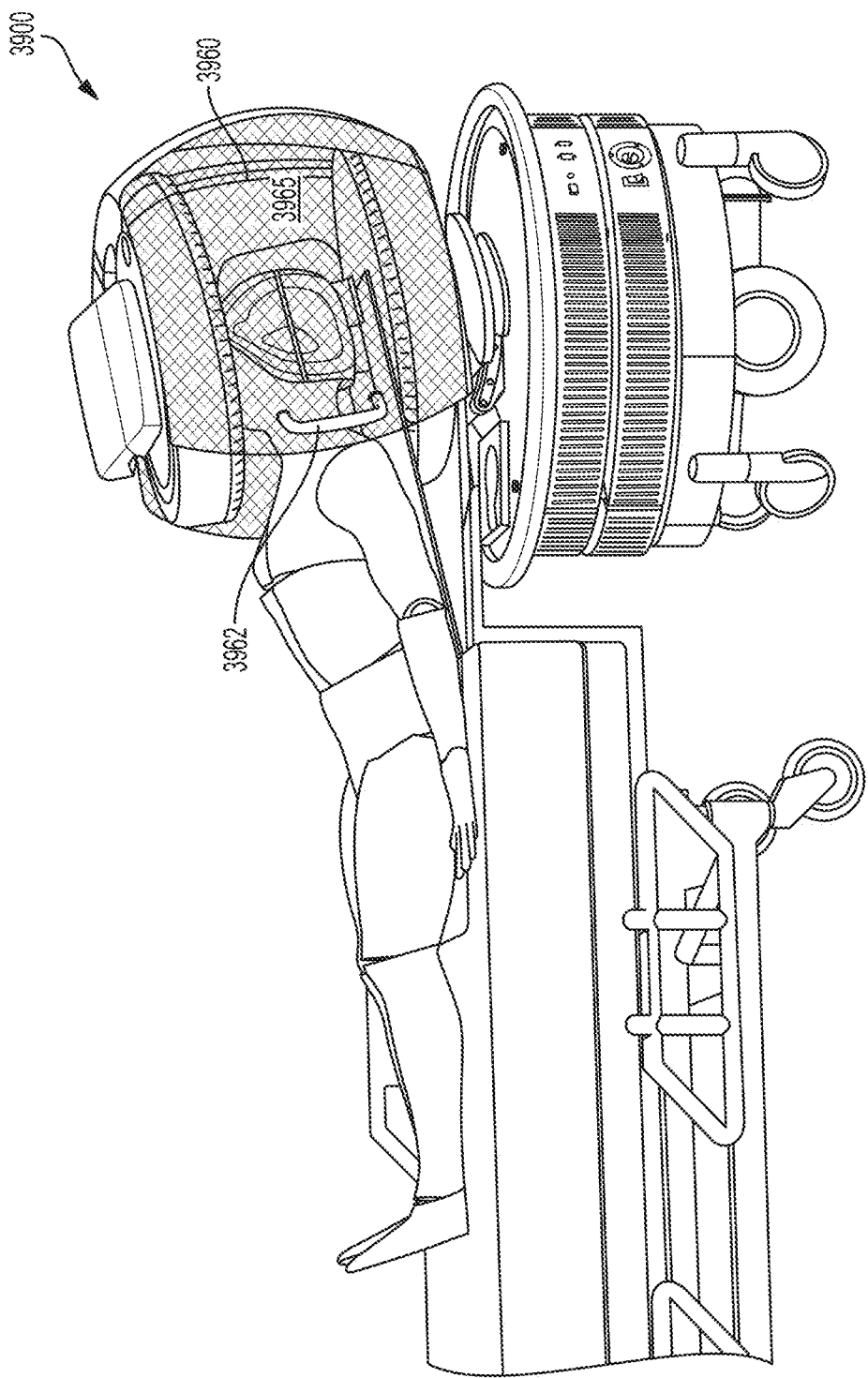
FIG. 40A illustrates a portable MRI system performing a scan of the head, in accordance with some embodiments.
Figure 40B:
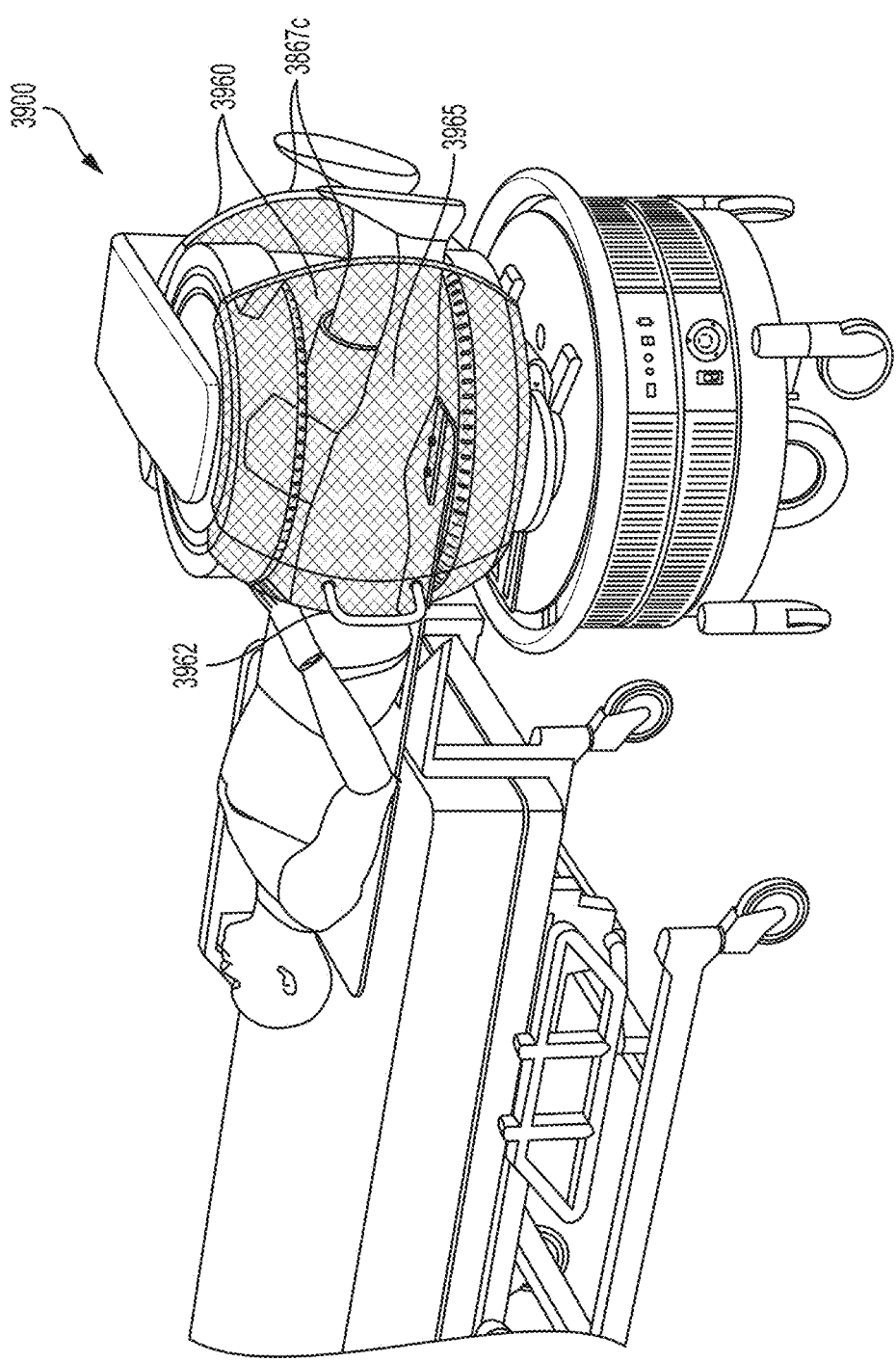
FIG. 40B illustrates a portable MRI system performing a scan of the knee, in accordance with some embodiments.

As discussed above, a noise reduction system comprising one or more noise reduction and/or compensation techniques may also be performed to suppress at least some of the electromagnetic noise that is not blocked or sufficiently attenuated by shielding 3965. In particular, as discussed in the foregoing, the inventors have developed noise reduction systems configured to suppress, avoid and/or reject electromagnetic noise in the operating environment in which the MRI system is located. According to some embodiments, these noise suppression techniques work in conjunction with the moveable shields to facilitate operation in the various shielding configurations in which the slides may be arranged. For example, when slides 4060 are arranged as illustrated in FIG. 40B, increased levels of electromagnetic noise will likely enter the imaging region via the openings. As a result, the noise suppression component will detect increased electromagnetic noise levels and adapt the noise suppression and/or avoidance response accordingly. Due to the dynamic nature of the noise suppression and/or avoidance techniques developed by the inventors, the noise reduction system is configured to be responsive to changing noise conditions, including those resulting from different arrangements of the moveable shields. Thus, a noise reduction system in accordance with some embodiments may be configured to operate in concert with the moveable shields to suppress electromagnetic noise in the operating environment of the MRI system in any of the shielding configurations that may be utilized, including configurations that are substantially without shielding (e.g., configurations without moveable shields), as discussed in further detail below.

To ensure that the moveable shields provide shielding regardless of the arrangements in which the slides are placed, electrical gaskets may be arranged to provide continuous shielding along the periphery of the moveable shield. For example, as shown in FIG. 39B, electrical gaskets 3967a and 3967b (see also FIG. 45C) may be provided at the interface between slides 3960 and magnet housing to maintain to provide continuous shielding along this interface. According to some embodiments, the electrical gaskets are beryllium fingers or beryllium-copper fingers, or the like (e.g., aluminum gaskets), that maintain electrical connection between shields 3965 and ground during and after slides 3960 are moved to desired positions about the imaging region. According to some embodiments, electrical gaskets 3967c are provided at the interface between slides 3960, as illustrated in FIG. 40B, so that continuous shielding is provided between slides in arrangements in which the slides are brought together. Accordingly, moveable slides 3960 can provide configurable shielding for the portable MRI system.

To facilitate transportation, a motorized component 3980 is provide to allow portable MRI system to be driven from location to location, for example, using a control such as a joystick or other control mechanism provided on or remote from the MRI system. In this manner, portable MRI system 3900 can be transported to the patient and maneuvered to the bedside to perform imaging, as illustrated in FIGS. 40A and 40B. As discussed above, FIG. 40A illustrates a portable MRI system 4000 that has been transported to a patient's bedside to perform a brain scan. FIG. 40B illustrates portable MRI system 4000 that has been transported to a patient's bedside to perform a scan of the patient's knee.

The portable MRI systems described herein (e.g., MRI systems illustrated in FIGS. 19 and 39-40) may be operated from a portable electronic device, such as a notepad, tablet, smartphone, etc. For example, tablet computer 3975 may be used to operate portable MRI system to run desired imaging protocols and to view the resulting images. Tablet computer may be connected to a secure cloud to transfer images for data sharing, telemedicine and/or deep learning on the data sets. Any of the techniques of utilizing network connectivity described in U.S. application Ser. No. 14/846,158, titled "Automatic Configuration of a Low Field Magnetic Resonance Imaging System," filed Sep. 4, 2015, which is herein incorporated by reference in its entirety, may be utilized in connection with the portable MRI systems described herein.

Figure 39C:
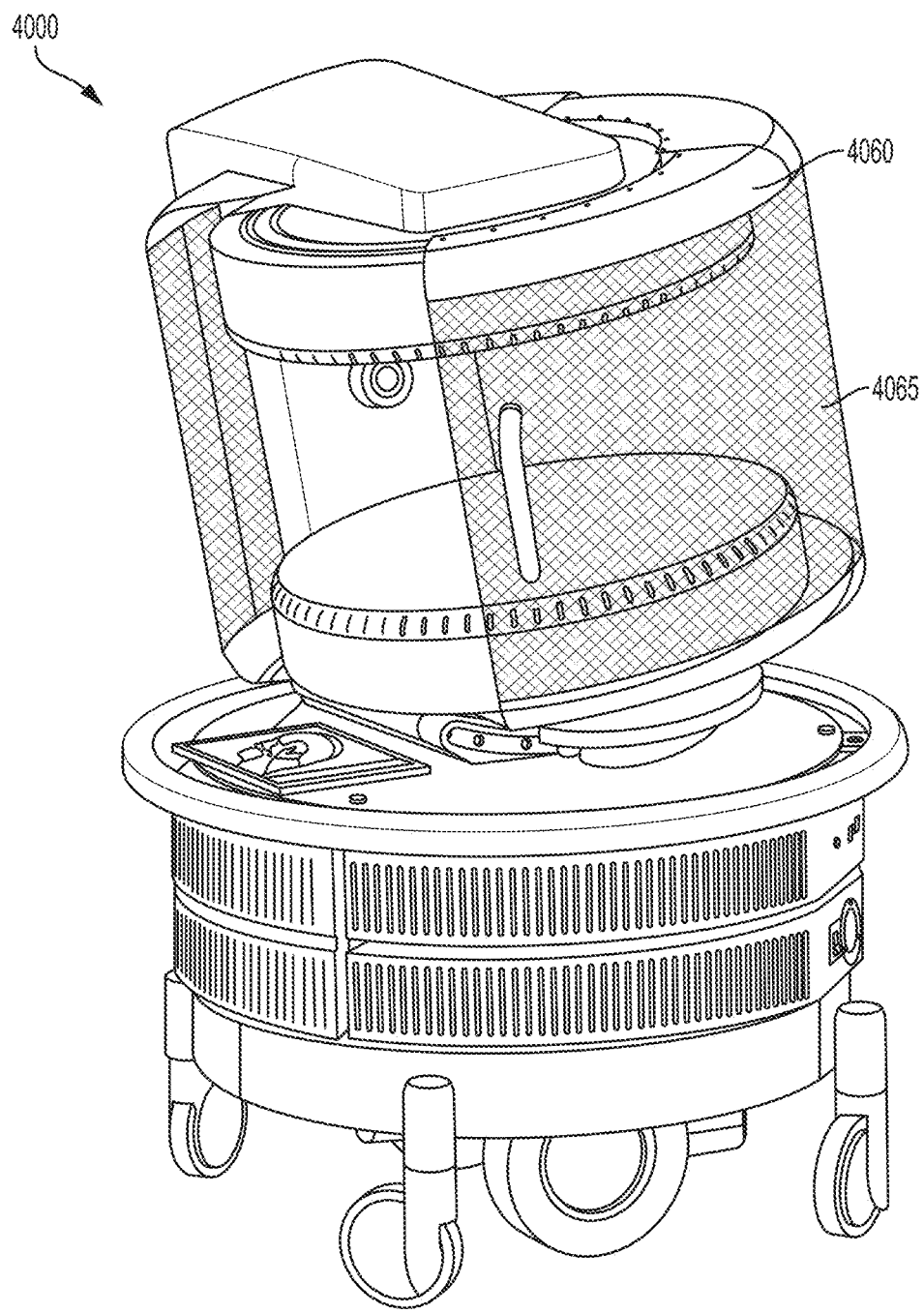
FIG. 39C illustrates another example of a portable MRI system, in accordance with some embodiments.

FIG. 39C illustrates another example of a portable MRI system, in accordance with some embodiments. Portable MRI system 4000 may be similar in many respects to portable MRI systems illustrated in FIGS. 16, 39A and 39B. However, slide 4060 are constructed differently, as is shielding 3965', resulting in electromagnetic shields that are easier and less expensive to manufacture. As discussed above, a noise reduction system may be used to allow operation of a portable MRI system in unshielded rooms and with varying degrees of shielding about the imaging region on the system itself, including no, or substantially no, device-level electromagnetic shields for the imaging region, as discussed in further detail below (e.g., in connection with FIGS. 41A-D and 42).

It should be appreciated that the electromagnetic shields illustrated in FIGS. 39-40 are exemplary and providing shielding for an MRI system is not limited to the example electromagnetic shielding described herein. Electromagnetic shielding can be implemented in any suitable way using any suitable materials. For example, electromagnetic shielding may be formed using conductive meshes, fabrics, etc. that can provide a moveable "curtain" to shield the imaging region. Electromagnetic shielding may be formed using one or more conductive straps (e.g., one or more strips of conducting material) coupled to the MRI system as either a fixed, moveable or configurable component to shield the imaging region from electromagnetic interference, some examples of which are described in further detail below. Electromagnetic shielding may be provided by embedding materials in doors, slides, or any moveable or fixed portion of the housing. Electromagnetic shields may be deployed as fixed or moveable components, as the aspects are not limited in this respect.

Accordingly, aspects of the technology described herein relate to improving the performance of low-field MRI systems in environments where the presence of noise, such as RF interference, may adversely impact the performance of such systems. In some embodiments, a low-field MRI system may be configured to detect noise (e.g., environmental electromagnetic noise, internal system noise, radio frequency interference, etc.) and, in response, adapt the low-field MRI system to reduce the impact of the noise on the operation of the system. The low-field MRI system may be configured to reduce the impact of the noise by suppressing noise in the RF signal obtained by the RF receive coil, by generating RF signals that destructively interfere with noise in the environment (e.g., RF interference), by adjusting characteristics of the magnetic fields produced (e.g., adjusting the magnetic field strength of the B0 magnet) and/or received by the low-field MRI system so that the transmit/receive coils operate in a frequency band satisfactorily free from interference, or using a combination of these techniques.

According to some embodiments, noise suppression techniques described herein allow a MRI system to be operated in unshielded or partially shielded environments and/or with or without device level shielding of the imaging region (e.g., shielding provided on the low-field MRI device itself to shield the imaging region from electromagnetic interference), at least in part by adapting noise compensation to the particular environment in which the MRI system is deployed. As a result, deployment of an MRI system is not confined to specially shielded rooms or other customized facilities and instead can be operated in a wide variety of environments.

In some embodiments, a system may be configured to obtain information about noise in the system's environment or within the system itself (e.g., RF interference) and suppress noise in the RF signal measured by the RF receive coil based, at least in part, on the obtained information. The system may be configured to obtain information about noise in the environment by using one or more auxiliary sensors. The term "auxiliary" is used to differentiate between a sensor or detector capable of detecting noise and the primary receive channel that receives MR signals for use in MRI. It should be appreciated that, in some embodiments, an auxiliary sensor may also receive one or more MR signals. For example, the low-field MRI system may comprise one or more auxiliary RF receive coils positioned proximate to the primary transmit/receive coil(s), but outside of the field of view of the B0 field, to detect RF noise without detecting MR signals emitted by a subject being imaged. The noise detected by the auxiliary RF coil(s) may be used to suppress the noise in the MR signal obtained by the primary RF coil of the MRI system.

Such an arrangement has the ability to dynamically detect and suppress RF noise to facilitate the provision of, for example, a generally transportable and/or cartable low-field MRI system that is likely to be subjected to different and/or varying levels of RF noise depending on the environment in which the low-field MRI system is operated. That is, because noise suppression is based on the current noise environment, techniques described herein provide noise suppression capability specific to the particular environment in which the system is deployed. The simplistic approach of subtracting samples of noise obtained by one or more auxiliary sensors from the signal measured by the primary receive coil(s) generally provides unsatisfactory noise suppression, even if the gain of the noise detected by the auxiliary sensor(s) is adjusted. The primary receive coil(s) and the auxiliary sensor(s) may measure different noise signals because the primary coil(s) and the auxiliary sensor(s) may be in different locations, have different orientations, and/or may have different physical characteristics (e.g., may have a different number of coil turns, may differ in size, shape, impedance, or may be a different type of sensor altogether).

Different locations and/or orientations of the primary coil(s) and the auxiliary sensor(s) may lead to differences in the characteristics of the noise signals received by the primary coil and the auxiliary sensor. Different physical characteristics between the primary coil(s) and auxiliary sensor(s) may lead to frequency-dependent differences between noise signals received by the primary coil(s) and auxiliary sensor(s). As a result, subtracting the noise signal measured by one or more auxiliary sensors from the signal measured by the primary coil(s) may not adequately suppress noise detected by the primary coil(s). Even if the noise signal measured by the auxiliary sensor(s) were scaled by a constant in an attempt to compensate for differences in the gain of the noise signals received by the primary coil(s) and auxiliary sensor(s), such compensation would not account for frequency-dependent differences in the noise signals.

Some noise suppression techniques employ a transform to suppress noise in the RF signal received by one or more primary receive coil(s) of a low-field MRI system. According to some embodiments, the transform operates to transform a noise signal received via one or multiple auxiliary sensors (e.g., one or more auxiliary RF coils and/or other types of sensors described herein) to an estimate of the noise received by the primary receive coil (or multiple primary receive coils). In some embodiments, noise suppression may comprise: (1) obtaining samples of noise by using the one or more auxiliary sensor(s); (2) obtaining samples of the MR data using the primary RF coil; (3) determining a transform; (4) transforming the noise samples using the transform; and (5) subtracting the transformed noise samples from the obtained MR data to suppress and/or eliminate noise.

The transform may be estimated from multiple (e.g., at least ten, at least 100, at least 1000, etc.) calibration measurements obtained using the auxiliary sensor(s) and primary coil(s). Multiple calibration measurements allow for estimating the transform with high accuracy. The transform may be computed in the time domain, frequency domain or a combination of both. According to some embodiments, a transform may be estimated from the plurality of calibration measurements. Multiple calibration measurements allow for estimating the amplitude and phase of the transform for a plurality of frequency bins across the frequency spectrum for which the transform is defined. For example, when processing signals using a K-point DFT (e.g., where K is an integer equal to 128, 256, 512, 1024 etc.), multiple measurements may allow for estimating the amplitude and phase of the transform for each of the K frequency bins.

In some embodiments, multiple auxiliary receive coils may be used as auxiliary sensors to suppress noise received by the primary transmit/receive coil(s) of a low-field MRI system. For example, in some embodiments, a low-field MRI system may include multiple RF coils positioned/configured to sense the MR signal emitted by the subject being imaged (e.g., multiple "primary" coils) and/or multiple coils positioned/configured to receive noise data, but to detect little or no MR signal (e.g., multiple "auxiliary" coils). Such an arrangement facilitates detection and characterization of multiple noise sources to suppress a variety of noise that may be present in a given environment. Multiple primary receive coils may also be used that factor into the noise characterization techniques described herein, as well as being used to accelerate image acquisition via parallel MR, or in other suitable ways, as discussed in further detail below.

In some embodiments, multiple auxiliary sensors may be used to perform noise compensation when there are multiple sources of noise in the environment of the low-field MRI system. For example, one or more auxiliary RF coils and/or one or more other types of sensors may be used to obtain information about the noise environment resulting from noise produced by multiple sources, which information in turn may be used to process the RF signal received by the primary receive coil(s) in order to compensate for the noise produced by multiple sources. For example, in some embodiments, a multichannel transform may be estimated from calibration measurements obtained using multiple auxiliary sensors and the primary RF coil(s), as described in more detail below. The multichannel transform may represent the relationships among the noise signals captured by the primary RF coil(s) and each of the multiple auxiliary sensors. For example, the transform may capture correlation among the noise signals received by the multiple auxiliary sensors. The transform may also capture correlation among the noise signals receive by the multiple auxiliary sensors and the noise signal received by the primary RF coil(s).

In some embodiments, multiple auxiliary sensors may be used to perform noise suppression by: (1) obtaining samples of noise by using multiple auxiliary sensors; (2) obtaining samples of the MR data using the primary RF coil(s); (3) obtaining a multichannel transform; (4) transforming the noise samples using the multichannel transform; and (5) subtracting the transformed noise samples from the obtained MR data to suppress and/or eliminate noise.

In some embodiments, the multichannel transform may be estimated from multiple (e.g., at least ten, at least 100, at least 1000, etc.) calibration measurements. According to some embodiments, multiple calibration measurements are used to estimate the amplitude and phase of the transform for a plurality of frequency bins across which the multichannel transform is defined. For example, when processing signals using a K-point DFT (e.g., where K is an integer equal to 128, 256, 512, 1024 etc.), multiple calibration measurements may allow for estimating the amplitude and phase of the multichannel transform for each of the K frequency bins.

According to some embodiments, the MR signal detected by one or more primary receive coils may also be utilized to characterize the noise to suppress or eliminate noise from the MR data. In particular, the inventors have recognized that by repeating MR data acquisitions using the same spatial encoding (e.g., by repeating a pulse sequence with the same operating parameters for the gradient coils), the "redundant" data acquired can be used to characterize the noise. For example, if a pulse sequence is repeated with the same spatial encoding multiple times, the MR data obtained should in theory be the same. Thus, the difference in the signals acquired from multiple acquisitions using the same spatial encoding can be presumed to have resulted from noise. Accordingly, multiple signals obtained from using the same spatial encoding may be phase shifted and subtracted (or added) to obtain a measure of the noise.

According to some embodiments, noise characterized in this manner can be used to compute a transform or included as a channel in a multi-channel transform, as discussed in further detail below. Alternatively, noise characterized in this manner can be used alone or in combination with other techniques to suppress noise from acquired MR signals. For example, a noise estimate obtained based on multiple MR signals obtained using the same spatial encoding may be used to suppress noise without computing a transform, as other suitable techniques may be used.

According to some embodiments, one or more sensors (e.g., one or more RF coils or other sensors capable of detecting electromagnetic fields) may be used to assess the noise background in a spectrum of interest to assess which band within the spectrum is cleanest from a noise perspective so that the transmit/receive coil(s) may be configured to operate in the identified frequency band. Accordingly, in some embodiments, a low-field MRI system may be adapted by adjusting the transmit/receive coil(s) to operate at a frequency band having less interference relative to other frequency bands in which the transmit/receive coil(s) can be configured to operate. For example, one or more auxiliary RF coils may be configured to monitor noise across multiple frequency bands over which the primary RF coil could operate and, the primary RF coil may be configured to operate at the frequency band having the least amount of noise, as determined by the measurements obtained using the auxiliary RF coils. In particular, an auxiliary RF coil may be a wideband RF coil configured to measure the noise level (e.g., noise floor) across a wide band of frequencies. Based on the noise measured across a frequency band of interest, the primary transmit/receive coil(s) (e.g., which may be a narrowband coil) may be configured to operate in a band determined to have less noise than other frequency bands. Alternatively, multiple sensors may be provided, each measuring noise levels in a respective frequency band. The primary transmit/receive coil(s) may then be configured to operate in the frequency band determined to have the least amount of noise present.

A significant source of interference for a low-field MRI system may be one or more power lines (e.g., power cords) supplying power to the low-field MRI system. Accordingly, in some embodiments, a low-field MRI system is configured to measure directly any interference due to the power line(s) and use the measurements to suppress or cancel such interference. For example, in some embodiments, a low-field MRI system may include one or more sensors coupled to a power line of the system to measure any RF signals produced or carried by the power line, and the measurements obtained by the sensor(s) may be used as part of the noise suppression techniques described herein (e.g., to further characterize the noise environment and facilitate estimation of a comprehensive transform).

In some embodiments, a low-field MRI system may include an antenna capacitively coupled to one of the power lines of the system and may be configured to use measurements obtained by the antenna to suppress noise in the RF signal received by the primary RF coil of the low-field MRI system. Such an antenna may be of any suitable type and, for example, may comprise a thin metal sheet wrapped around the power line and/or one or more capacitors coupled to the power line. A low-field MRI system may include multiple such antenna to detect noise resulting from any desired number of power lines supplying power to the system (or that otherwise impact the system) including, for example, hot lines carrying single-phase, two-phase, or three-phase power. In some instances, a low-field MRI system may include such an antenna for a ground wire. As another example, a low-field MRI system may include a sensor inductively coupled to a power line or multiple respective power lines (e.g., by use of a toroid or any other suitable method) to measure RF signals carried by the power line such that these measurements may be used to suppress noise in the RF signal measured by the primary RF coil of the low-field MRI system.

In some embodiments, a sensor's measurements of interference due to a power line may be used to suppress noise in the RF signal measured by the primary RF receive coil by estimating a transform between the primary RF receive coil and the sensor. This may be done in any suitable way and, for example, may be done using the techniques described herein for estimating a transform between the primary RF receive coil and an auxiliary RF receive coil. For example, noise characterized in this manner may be used to estimate a transform alone or may be a channel in a multi-channel transform. Noise characterized by a sensor coupled to one or more power lines may be utilized in other manners (e.g., used directly to suppress noise), as the aspects are not limited in this respect.

According to some embodiments, noise in the environment may be detected by coupling one or more sensors to one or more electromagnetic interference (EMI) shields. For example, a sensor may be connected inductively or capacitively between one or more EMI shields and ground to detect the EMI captured by the shield. Noise characterized in this manner may be used to suppress or eliminate noise from MR signals detected by the primary receive coil(s). For example, noise characterized by coupling a sensor to one or more EMI shields may be used to estimate a transform alone, or may be used as a channel in a multi-channel transform. Noise characterized by a sensor coupled to one or more EMI shields may be utilized in other manners, as the aspects are not limited in this respect.

Referring again to FIG. 1, MRI system 100 includes controller 106 (also referred to as a console) having control electronics to send instructions to and receive information from power management system 110. Controller 106 may be configured to implement one or more pulse sequences, which are used to determine the instructions sent to power management system 110 to operate the magnetic components 120 in a desired sequence. For example, in a low-field MRI system, controller 106 may be configured to control power management system 110 to operate the magnetic components 120 in accordance with a balance steady-state free precession (bSSFP) pulse sequence, a low-field gradient echo pulse sequence, a low-field spin echo pulse sequence, a low-field inversion recovery pulse sequence, and/or any other suitable pulse sequence. Controller 106 may be implemented as hardware, software, or any suitable combination of hardware and software, as aspects of the disclosure provided herein are not limited in this respect.

In some embodiments, controller 106 may be configured to implement a pulse sequence by obtaining information about the pulse sequence from pulse sequences repository 108, which stores information for each of one or more pulse sequences. Information stored by pulse sequences repository 108 for a particular pulse sequence may be any suitable information that allows controller 106 to implement the particular pulse sequence. For example, information stored in pulse sequences repository 108 for a pulse sequence may include one or more parameters for operating magnetics components 120 in accordance with the pulse sequence (e.g., parameters for operating the RF transmit and receive coils 126, parameters for operating gradient coils 128, etc.), one or more parameters for operating power management system 110 in accordance with the pulse sequence, one or more programs comprising instructions that, when executed by controller 106, cause controller 106 to control system 100 to operate in accordance with the pulse sequence, and/or any other suitable information. Information stored in pulse sequences repository 108 may be stored on one or more non-transitory storage media.

As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information.

Computing device 104 may be any electronic device that may process acquired MR data and generate one or more images of the subject being imaged. In some embodiments, computing device 104 may be a fixed electronic device such as a desktop computer, a server, a rack-mounted computer, or any other suitable fixed electronic device that may be configured to process MR data and generate one or more images of the subject being imaged. Alternatively, according to some embodiments of a low-field MRI system, computing device 104 may be a portable device such as a smart phone, a personal digital assistant, a laptop computer, a tablet computer, or any other portable device that may be configured to process MR data and generate one or more images of the subject being imaged. In some embodiments, computing device 104 may comprise multiple computing devices of any suitable type, as the aspects are not limited in this respect. A user 102 may interact with workstation 104 to control aspects of the low-field MR system 100 (e.g., program the system 100 to operate in accordance with a particular pulse sequence, adjust one or more parameters of the system 100, etc.) and/or view images obtained by the low-field MR system 100.

Figure 41A:
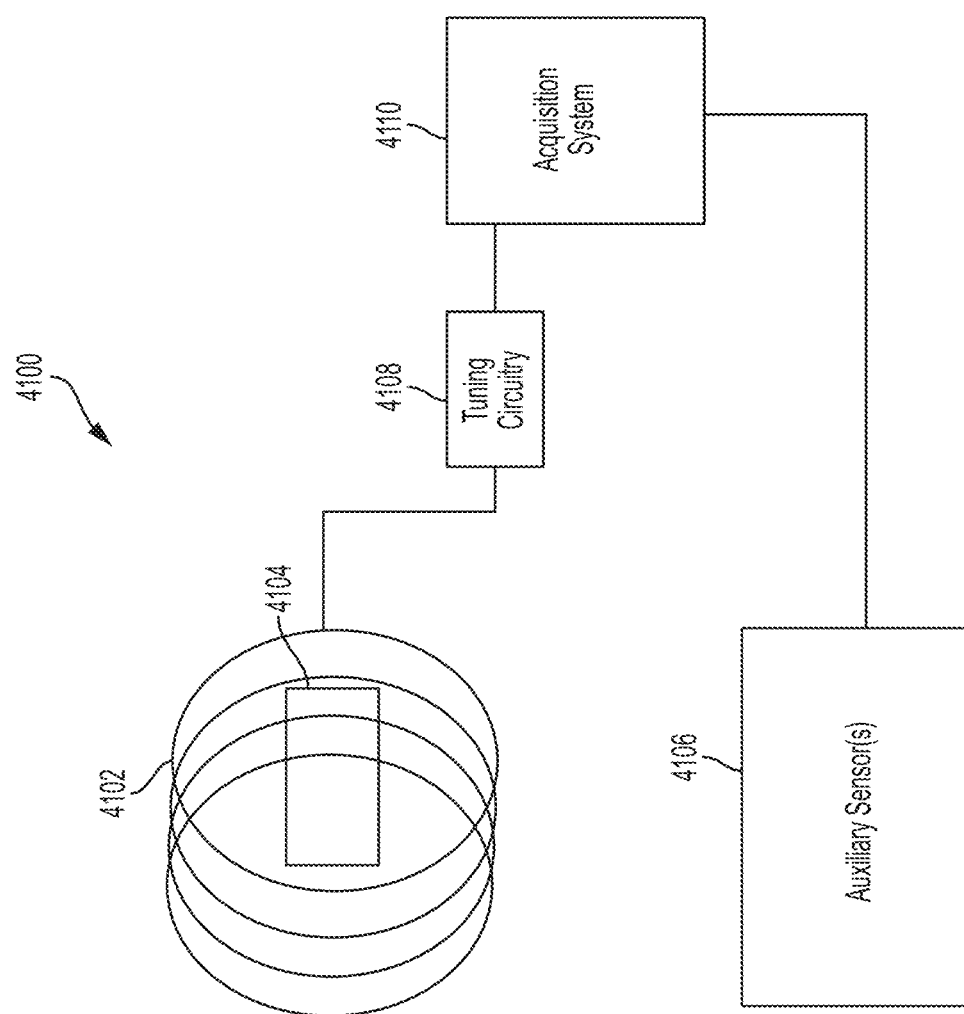

FIG. 41A shows illustrative components of a portion of an example of a MRI system that may be used for performing noise suppression, in accordance with some embodiments of the technology described herein. For example, transmit/receive system 4100 may form at least part of the transmit/receive equipment (e.g., transmit/receive coils 126, one or more controllers, etc.) of a low-field MRI system, such as any of the exemplary systems described in the above incorporated co-filed patent applications. Transmit/receive system 4100 is configured to detect MR signals emitted from excited atoms of a subject 4104 being imaged, and to characterize noise in the environment to suppress or remove the characterized noise from the detected MR signals, as discussed in further detail below.

As shown in FIG. 41A, transmit/receive system 4100 comprises a primary RF receive coil 4102 configured to measure MR signals emitted by the subject 4104 in response to an excitation pulse sequence (e.g., a pulse sequence selected from pulse sequence repository 108 and executed by controller 102). The excitation pulse sequence may be produced by primary RF receive coil 4102 and/or by one or more other transmit RF coils arranged proximate subject 4104 and configured to produce suitable MR pulse sequences when operated. Primary receive coil 4102 may be a single coil or may be a plurality of coils, which, in the latter case, may be used to perform parallel MRI. Tuning circuitry 4108 facilitates operation of primary receive coil 4102 and signals detected by RF coil(s) 4102 are provided to acquisition system 4110, which may amplify the detected signals, digitize the detected signals, and/or perform any other suitable type of processing.

Transmit/receive system 4100 also includes auxiliary sensor(s) 4106, which may include any number or type of sensor(s) configured to detect or otherwise measure noise sources in the environment and/or environmental noise produced by the MRI system itself. The noise measured by auxiliary sensor(s) 4106 may be characterized and used to suppress noise in the MR signal detected by primary RF coil(s) 4102 using techniques described in further detail below. After acquisition system 4110 processes the signals detected by RF coil(s) 4102 and auxiliary sensor(s) 4106, acquisition system 4110 may provide the processed signals to one or more other components of the MRI system for further processing (e.g., for use in forming one or more MR images of subject 4104). Acquisition system 4110 may comprise any suitable circuitry and may comprise, for example, one or more controllers and/or processors configured to control the MRI system to perform noise suppression in accordance with embodiments described herein. It should be appreciated that components illustrated in FIG. 41A may be configured to detect MR signals generated by a MRI system and, for example, the RF coils may be similar or the same as those described in the above incorporated co-field applications, or may be any other suitable type of coil.

In some embodiments, auxiliary sensor(s) 4106 may include one or more auxiliary coils 4206 configure to measure noise from one or more noise sources in the environment in which the MRI system is operating, as shown in FIG. 41B. In some instances, the auxiliary RF coil(s) 4206 may be constructed to be substantially more sensitive to ambient noise than to any noise generated by the coil itself. For example, the auxiliary RF coil 4206 may have a sufficiently large aperture and/or a number of turns such that the auxiliary coil is more sensitive to noise from the environment than to noise generated by the auxiliary coil itself. In some embodiments, auxiliary RF coil(s) 4206 may have a larger aperture and/or a greater number of turns than primary RF coil(s) 4102. However, auxiliary RF coil(s) 4206 may be the same as primary RF coil in this respect and/or may differ from primary RF coil(s) 4102 in other respects, as the techniques described herein are not limited to any particular choice of coils. For example, in some embodiments, an auxiliary sensor of a different type is used in place of an RF coil type sensor, as discussed in further detail below.

In the illustrative embodiment of FIG. 41B, auxiliary RF coil(s) 4206 is/are located a distance 4205 apart from primary RF coil 4102. The distance 4205 may be selected such that auxiliary coil(s) 4206 is/are sufficiently far away from the sample 4104 to avoid sensing MR signals emitted by the sample during imaging, but otherwise arranged as close as possible to the primary RF coil 4102 so that auxiliary coil(s) 4206 detect noise similar to the noise detected by primary coil(s) 4102. In this manner, the noise from one or more noise sources measured by auxiliary coil(s) 4206 and characterized using techniques discussed herein (e.g., by using the detected noise to calculate, at least in part, a transform that can be used to suppress and/or eliminate noise present on detected MR signals) may be representative of the noise detected by primary coil(s) 4102. It should be appreciated that auxiliary coil(s) 4206 need not be RF coils, but may be any type of sensor capable of detecting or measuring noise in the environment that may impact the performance of the MRI system, as the techniques described herein are not limited for use with any particular type of sensor.

Figure 41C:
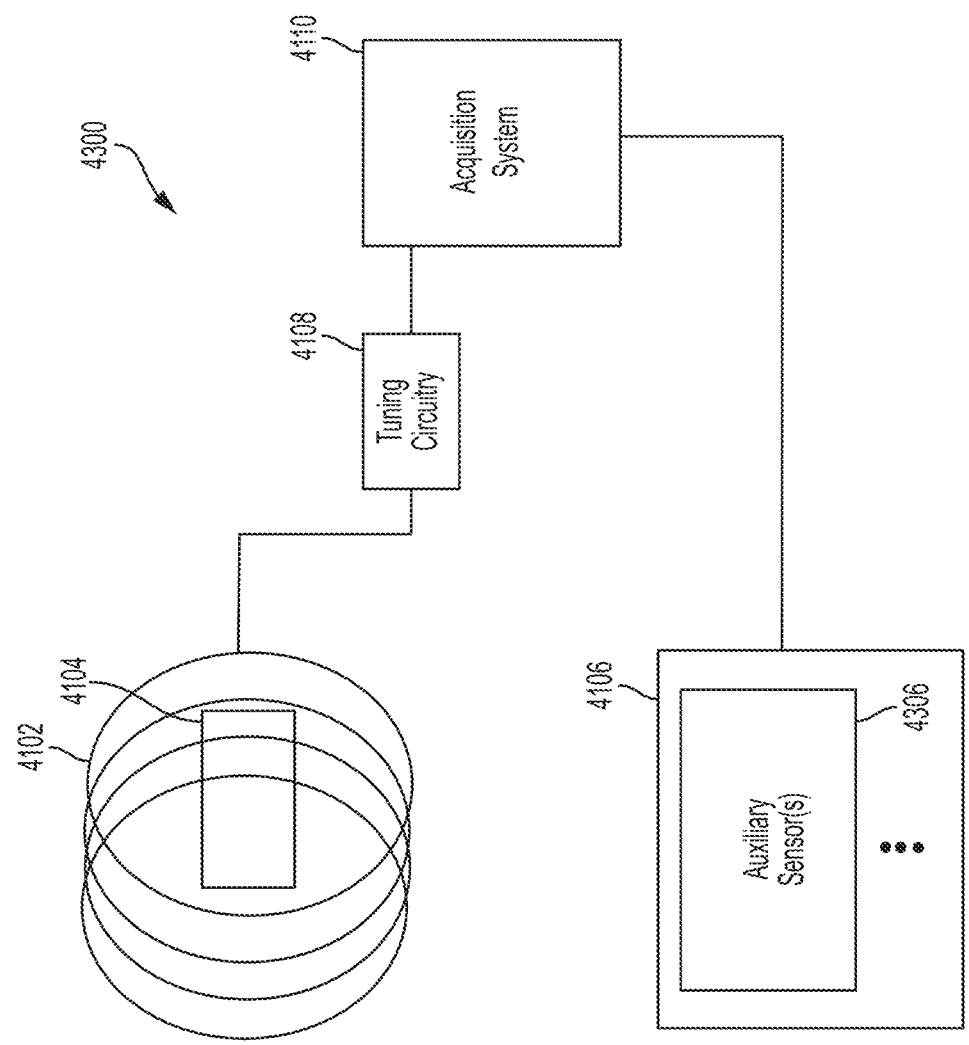

According to some embodiments, auxiliary sensor(s) 4106 may include one or more auxiliary sensors 4306 configure to measure noise by coupling sensor(s) to one or more components of the MRI system, as schematically shown in FIG. 41C. For example, auxiliary sensors 4306 may include one or more sensors coupled to one or more components of the MRI system or otherwise arranged to detect noise produced by the MRI system. As discussed above, power cables are frequently a source of noise that can have a negative impact on the operation of the MRI system and, in particular, may produce noise that is detected by the one or more primary coils. According to some embodiments, auxiliary sensor(s) 4306 include one or more sensors coupled (e.g., capacitively or inductively) to one or more power cables of the system to detect noise produced therefrom. The detected noise may be characterized and used to suppress noise from detected MR signals, for example, by using the detected noise to produce, at least in part, a transform that characterizes noise detected by the auxiliary sensor(s) 4306, or by being directly applied to detected MR signals.

As discussed above, the low-field regime may facilitate systems that can be utilized in a wide variety of circumstances and/or that can be generally transported from one location to another. As a result, low-field MRI systems will frequently operate outside of specially shielded rooms. Thus, some low-field MRI systems may utilize partial shielding of one or more components of the system to prevent at least some EMI from reaching the shielded components. The inventors have appreciated that by coupling one or more sensors to one or more EMI shields (e.g., a Faraday cage of one or more components or the like) of the system, the noise absorbed by the one or more EMI shields can be measured, characterized and used to suppress and/or eliminate noise from detected MR signals. According to some embodiments, auxiliary sensor(s) 4306 include one or more sensors coupled between one or more EMI shields and ground to measure noise absorbed by the EMI shield that can be used to facilitate noise suppression. For example, the noise detected from the EMI shield may be used to compute, at least in part, a transform that can be utilized in suppressing and/or eliminating noise from detected MR signals. It should be appreciated that auxiliary sensor(s) 4306 may include any other type of sensor capable of detecting noise, as the aspects are not limited in this respect.

According to some embodiments, auxiliary sensor(s) 4106 include the primary coil(s) itself as illustrated in FIG. 41D, wherein the primary RF coil(s) are labeled both as primary receive coil 4102 and auxiliary sensor 4406 for the system, as the primary RF coil(s) may perform both roles in some circumstances. As discussed above, the inventors have recognized that certain pulse sequences facilitate using the signals acquired from the primary coil(s) to also suppress noise thereon. A pulse sequence refers generally to operating transmit coil(s) and gradient coil(s) in a prescribed sequence to induce an MR response. By repeating the same pulse sequence using the same spatial encoding, "redundant" MR signals can be obtained and used to estimate noise present in the MR signals.

To address the relatively low signal-to-noise ratio (SNR) of low-field MRI, pulse sequences have been utilized that repeat MR data acquisitions using the same spatial encoding (e.g., by repeating a pulse sequence with the same operating parameters to drive the gradient coils in the same manner). The MR signals obtained over multiple acquisitions are averaged to increase the SNR. For example, a balanced steady-state free precession (bSSFP) pulse sequence may be used to rapidly obtain MR data over multiple acquisitions, which acquisitions are then averaged together to increase the SNR. The term "average" is used herein to describe any type of scheme for combining the signals, including absolute average (e.g., mean), weighted average, or any other technique that can be used to increase the SNR by combining MR data from multiple acquisitions. Because the bSSFP pulse sequence does not require waiting for the net magnetization to realign with the $B_0$ field between successive MR data acquisitions (e.g., successive acquisitions may be obtained without needing to wait for the transverse magnetization vector to decrease to 0), multiple acquisitions may be rapidly obtained. However, any pulse sequence can be used to perform multiple acquisitions at the same location, as the aspects are not limited in this respect.

The inventors have appreciated that the MR data obtained during multiple acquisitions performed using the same spatial encoding may be used to suppress and/or eliminate noise from the detected MR signal. As discussed above, when multiple acquisitions are performed by repeating the pulse sequence with the same spatial encoding, the MR signals obtained should be the same or nearly the same and the differences can be attributed to noise. As such, phase shifting the MR signal obtained over multiple acquisitions and computing the difference between the signals provides a means for evaluating the noise corrupting the MR data. The difference may be obtained by phase shifting and either adding or subtracting the phase shifted MR signals depending on the type of pulse sequence utilized. For example, the bSSFP pulse sequence flips the polarity of the pulse sequence on subsequent acquisitions so that the difference may be computed by adding MR signals that have been appropriately shifted in phase. However, MR signals obtained using other pulse sequences that do not flip the polarity may be subtracted after being appropriately phase shifted to obtain the difference between multiple MR acquisitions. Because multiple acquisitions (e.g., 10, 20, 50, 100, 150 or more) obtained using the same spatial encoding may already be performed (and averaged) in the low-field context to achieve sufficiently large SNR, using one or more of the acquisitions to compute a noise estimate will not substantially increase acquisition times, if at all.

The computed noise (e.g., the difference between MR signals obtained over multiple acquisitions with the same spatial encoding) can be used to suppress and/or eliminate the noise in the detected MR signal. According to some embodiments, the noise computed according to the above described technique may be used to, at least in part, determine a transform that can be used to suppress and/or eliminate noise in the manner discussed in further detail below. However, noise computed by determining the difference between multiple MR acquisitions can be utilized in other ways to suppress and/or eliminate noise, as the aspects are not limited in this respect. For example, noise computed based on determining the difference between multiple MR acquisitions obtained from the same location may be directly applied to detected MR signals or applied after further processing. It should be appreciated that the noise computed by comparing multiple acquisitions obtained using the same spatial encoding can be used to dynamically suppress and/or eliminate noise from the detected MR signals. In this way, noise cancellation dynamically adapts to changing noise conditions in the environment.

As discussed above, noise detected by one or more auxiliary sensors, some examples of which are described in the foregoing, may be used to characterize the noise from one or more noise sources and suppress and/or eliminate noise from detected MR signals. According to some embodiments, the noise detected by one or more auxiliary sensors is used to determine a transform that can be used to transform detected noise to an approximation of the noise detected by the one or more primary receive coils. According to some embodiments, noise detected by one or more auxiliary sensors is applied to detected MR signals to suppress noise without using a transform.

As a non-limiting example, a noise suppression component (e.g., acquisition system 4110 illustrated in FIGS. 41A-D) may suppress noise in a signal $s_{pri}(t)$, detected by primary RF coil 4102, by using the signal $s_{aux}(t)$, detected by auxiliary sensor 4106, and a primary-to-auxiliary sensor (PA) transform $H_{PA}(\omega)$ via the following expression:

$$s_{comp}(t) = s_{pri}(t) - \mathcal{F}^{-1}\{H_{PA}(\omega)S_{aux}(\omega)\}, \quad (1)$$

where $S_{aux}(\omega)$ is the Fourier transform of $s_{aux}(t)$, $\mathcal{F}^{-1}\{\ \}$ is the inverse Fourier transform operator, and $s_{comp}(t)$ is the noise-suppressed signal. It should be appreciated that the noise compensation calculation of Equation (1) may be implemented in any of numerous ways and, for example, may be implemented in the frequency domain or in the time domain, as the noise suppression techniques described herein are not limited in this respect. Exemplary techniques for estimating a PA transform are described in more detail below.

Figure 42:
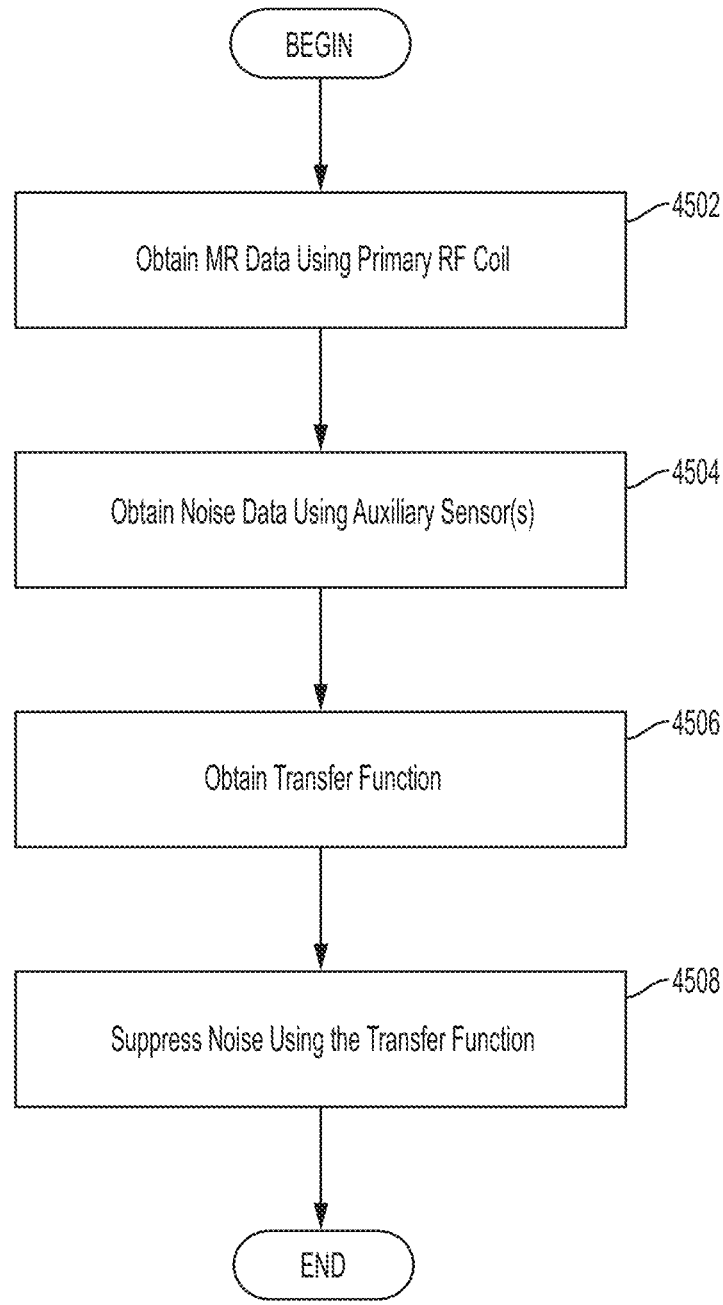
FIG. 42 is a flowchart of an illustrative process for performing noise reduction, in accordance with some embodiments.

FIG. 42 is a flowchart of an illustrative process 4501 for performing noise suppression, in accordance with some embodiments of the technology described herein, including a detailed description of a technique for determining an exemplary transform, first with respect to a transform between an auxiliary sensor and a primary receive coil, followed by a description of a transform between multiple auxiliary sensors and a primary receive coil (multi-channel transform). It should be appreciated that a single or multi-channel transform may be computed for any number of receive coils so that noise cancellation in this respect can be performed using any number and type of auxiliary sensor and any number and type of receive coil. Process 4501 may be performed by components of any suitable MRI system and, for example, may be performed by components of MRI system 100 described with reference to FIG. 1 and the associated components illustrated in FIGS. 41A-D.

Process 4501 begins at acts 4502 and 4504, where a MRI system obtains MR data by using a primary RF coil (e.g., RF coil 4102) and obtains noise data using one or more auxiliary sensors (e.g., one or more RF coils 4206 and/or one or more other sensors 4106, 4306, 4406, etc.). As discussed above, any number of auxiliary sensors of any type may be used to characterize the noise in the environment of the MRI system. To illustrate aspects of the noise suppression techniques, the case of a primary RF coil and an auxiliary sensor is first considered. The primary RF coil and auxiliary sensor may operate to obtain MR and noise data substantially simultaneously such that the noise data acquired by the auxiliary sensor may be used to suppress noise in the MR data acquired by the primary RF coil.

The signal obtained by the primary RF coil may comprise both noise and an MR signal emitted by the sample being imaged. For example, if $s_{pri}(t)$ represents the total signal measured by the primary RF coil, then $s_{pri}(t)$ may be expressed as:

$$s_{pri}(t) = m_{pri}(t) + n_{pri}(t),$$

where $m_{pri}(t)$ and $n_{pri}(t)$ represent the MR signal and noise components of the total signal measured by the primary RF coil. Assuming that the auxiliary sensor measures a negligible amount of MR signal (due to the placement of the auxiliary sensor relative to the primary RF coil and the sample being imaged), the signal measured by the auxiliary sensor contains mostly ambient RF noise. For example, if $s_{aux}(t)$ represents the total signal measured by the auxiliary sensor, then $s_{aux}(t)$ may be expressed according to:

$$s_{aux}(t) = n_{aux}(t),$$

where $n_{aux}(t)$ is noise measured by the auxiliary sensor.

As discussed above, the noise components of the signals measured by the primary RF coil and auxiliary sensor may be different (e.g., $n_{pri}(t)$ may be different from $n_{aux}(t)$) due to physical differences between the primary coil and auxiliary sensor as well as differences in location and orientation. However, the inventors have appreciated that a relationship between the noise signals measured by the primary coil and the auxiliary sensor may be established since both measure noise from one or more common sources. Such a relationship may be, in some embodiments, represented by a primary to auxiliary transform. For example, the relationship may be represented by a primary to auxiliary transform $H_{PA}(\omega)$ as detailed below.

For example, in some embodiments, each of the noise signals $n_{pri}(t)$ and $n_{aux}(t)$ may contain noise from several independent sources including, but not limited to, noise from one or more sources in the environment of the low-field MRI system, noise generated by the primary RF coil and/or the auxiliary sensor, and noise generated by one or more other components of the MRI system (e.g., noise generated by tuning circuitry, acquisition system, power cables, etc.). Thus, for example, the noise signals $n_{pri}(t)$ and $n_{aux}(t)$ may be expressed as:

$$n_{pri}(t)=c_{pri}(t)+u_{pri}(t), \text{ and}$$

$$n_{aux}(t)=c_{aux}(t)+u_{aux}(t) \cong c_{aux}(t),$$

where $c_{pri}(t)$ and $c_{aux}(t)$ represent correlated noise (i.e., the signals $c_{pri}(t)$ and $c_{aux}(t)$ are correlated) generated by one or more common noise sources detected by the primary coil and the auxiliary sensor, respectively, and where $u_{pri}(t)$ and $u_{aux}(t)$ represent uncorrelated noise detected by the primary coil and auxiliary sensors, respectively (e.g., noise generated by the primary coil and auxiliary sensor themselves). As described above, in some embodiments, the auxiliary sensor may be configured such that it is more sensitive to noise from the environment than noise generated by the sensor itself. For example, the auxiliary sensor may be an auxiliary RF coil having a sufficiently large aperture and/or number of turns. As such, $c_{aux}(t)$ may be substantially larger than $u_{aux}(t)$ so that $n_{aux}(t) \cong c_{aux}(t)$.

Each of the noise signals $c_{pri}(t)$ and $c_{aux}(t)$ can be expressed in relation to the common noise source(s) through a respective measurement transform. For example, in the Fourier domain, the Fourier transforms $C_{pri}(\omega)$ and $C_{aux}(\omega)$ of noise signals $c_{pri}(t)$ and $c_{aux}(t)$ can be expressed as:

$$C_{pri}(\omega)=H_{pri}(\omega)C_s(\omega)$$

$$C_{aux}(\omega)=H_{aux}(\omega)C_s(\omega)$$

where $C_s(\omega)$ is the Fourier transform of a common noise source and $H_{pri}(\omega)$ and $H_{aux}(\omega)$ respectively represent the channel between the common noise source and the primary receive coil and auxiliary sensor. Combining the above equations yields:

$$C_{pri}(\omega) = H_{PA}(\omega)C_{aux}(\omega),$$

where $$H_{PA}(\omega) = \frac{H_{pri}(\omega)}{H_{aux}(\omega)},$$

is the primary-to-auxiliary transform.

Returning to the discussion of process 4501, after the MR and noise signals are acquired at acts 4502 and 4504, process 4501 proceeds to act 4506, where a primary-to-auxiliary (PA) transform is obtained. In some embodiments, the PA transform may have been previously estimated so that obtaining the PA transform at act 4506 comprises accessing a representation of the PA transform (e.g., a frequency-domain or a time-domain representation of the PA transform). In other embodiments, obtaining the PA transform at act 4506 may comprise estimating and/or updating the estimate of the transform. Techniques for estimating a PA transform are described in more detail below.

Next, at act 4508, the noise data obtained at act 4504 and the PA transform obtained at act 4506 may be used to suppress or cancel noise in the MR data obtained at act 4502. This may be done using Equation (1) described above, using any equivalent formulation of Equation (1) (e.g., the entire calculation may be performed in the frequency domain), or in any other suitable way.

As described above, a primary-to-auxiliary transform may be used to suppress noise in the MR data acquired by a primary RF coil in a MRI system such as a low-field MRI system. In some embodiments, the primary-to-auxiliary transform may be estimated from calibration measurements obtained by the primary RF coil and the auxiliary sensor. This may be done in any suitable way. For example, the PA transform may be estimated from calibration measurements obtained when no MR signal is present or when the strength of the MR signal is small relative to the strength of the noise detected by the primary RF coil. As another example, the PA transform may be estimated from calibration measurements obtained when an MR signal is present (e.g., during operation of the MRI system). Any suitable number of calibration measurements may be used (e.g., at least 100, 100-1000, at least 1000, etc.). When more measurements are used, the PA transform may be estimated at a higher resolution (e.g., at more frequency values) and/or with increased fidelity with respect to the actual noise environment. The PA transform may be estimated using a least-squares estimation technique or any other suitable estimation technique, as the techniques described herein are not limited to any particular computational method.

According to some embodiments, a PA transform comprises a PA transform that is estimated from the calibration measurements. As one non-limiting example, when the signal acquired by the primary coil at times $\{t_k\}$ does not contain any MR signal or when the strength of the MR signal is small relative to the strength of the noise detected by the primary RF coil, then $s_{pri}(t_k)=n_{pri}(t_k)$, so that the discrete Fourier transform of $s_{pri}(t_k)$ is given by:

$$S_{pri}(\omega_k)=C_{pri}(\omega_k)+U_{pri}(\omega_k),$$

where $C_{pri}(\omega_k)$ is the discrete Fourier transform of $C_{pri}(t_k)$ and $U_{pri}(\omega_k)$ is the discrete Fourier transform of $u_{pri}(t_k)$. Since $C_{pri}(\omega_k)=H_{PA}(\omega_k)S_{ref}(\omega_k)$, the discrete Fourier transform of the signal received at the primary coil may be represented as a function of the discrete Fourier transform of the signal received at the auxiliary sensor according to:

$$S_{pri}(\omega_k)=H_{PA}(\omega_k)S_{aux}(\omega_k)+U_{pri}(\omega_k) \quad (2)$$

Equation (2) represents a set of independent equations, one for each frequency component, $\omega_k$. Since both $U_{pri}$ and $H_{PA}$ are unknown, it may not be possible to determine $H_{PA}$ from a single calibration measurement. If M calibration measurements (e.g., at least 10, at least 100, at least 1000 calibration measurements) are made such that multiple examples of $S_{pri}$ and $S_{aux}$ for each frequency component are obtained, then the PA transform can be determined despite the unknown $U_{pri}$, via any suitable estimation technique, for example, via least squares estimation. This is so because multiple measurements may be used to average out the uncorrelated noise. Given M calibration measurements, a least squares estimator for the PA transform may be obtained by considering the following matrix equation for each frequency component $\omega_k$, $$\begin{bmatrix} S_{pri}(\omega_k)_1 \\ \vdots \\ S_{pri}(\omega_k)_M \end{bmatrix} = H_{PA}(\omega_k) \begin{bmatrix} S_{aux}(\omega_k)_1 \\ \vdots \\ S_{aux}(\omega_k)_M \end{bmatrix},$$

which can be solved according to:

$$H_{PA}(\omega_k) = \left\{ \begin{bmatrix} S_{aux}(\omega_k)_1 \\ \vdots \\ S_{aux}(\omega_k)_M \end{bmatrix}^T \begin{bmatrix} S_{aux}(\omega_k)_1 \\ \vdots \\ S_{aux}(\omega_k)_M \end{bmatrix} \right\}^{-1} \begin{bmatrix} S_{aux}(\omega_k)_1 \\ \vdots \\ S_{aux}(\omega_k)_M \end{bmatrix}^T \begin{bmatrix} S_{pri}(\omega_k)_1 \\ \vdots \\ S_{pri}(\omega_k)_M \end{bmatrix}.$$

As may be appreciated from the foregoing, the above-described estimator uses multiple measurements (i.e., M noise signals measured by each of the primary and auxiliary coils) to estimate the value of the primary-to-auxiliary transform for multiple frequency bins. This results in significantly improved estimates of the PA transform as compared to techniques which rely on a single measurement (i.e., a single signal measured by each of the primary and auxiliary coils) to estimate the transform. Such single-measurement techniques may include scaling and time-shifting the reference signal before subtraction, which would correct for a difference in phase between the noise signal as received at a primary coil and an auxiliary coil, but (unlike the multiple measurement technique described herein) would not correct for frequency-dependent phase differences.

Another single-measurement technique may include scaling and phase adjusting the auxiliary noise signal in the frequency domain before subtracting it from the signal received at the primary coil. This could be accomplished by using the discrete Fourier transform (DFT) of the signals received by a primary coil and an auxiliary coil. The optimal scaling and phase shift can be determined by a least-squares fit across multiple frequency bins. For example, if $S_{pri}(\omega_k)$ is the DFT of the signal measured on the primary receive coil and $S_{aux}(\omega_k)$ is the DFT of the signal measured on an auxiliary coil at the same time, an average scaling and phase shift SPF for a subset of frequency bins (in the range of [k1,k2]) may be computed according to:

$$SPF = \frac{\sum_{k1}^{k2} S_{aux}(\omega_k) S_{pri}(\omega_k)}{\sum_{k1}^{k2} S_{aux}(\omega_k) S_{aux}(\omega_k)}.$$

Although this single-measurement technique may be used to create a frequency-dependent correction, the method requires a tradeoff between frequency resolution of the correction and accuracy of the estimation of the scaling and phase offset. In particular, this "averaging across frequency bins of a single measurement" technique results in poor (e.g., high-variance, biased) estimation of a PA transform. In contrast, the above-described multiple measurement technique provides for an unbiased and low-variance estimator.

As described above, the inventors have appreciated that the use of multiple coils may facilitate improved MRI in a number of ways, including more robust noise detection and/or cancellation, accelerated image acquisition, etc. In embodiments where multiple primary receive coils and/or multiple auxiliary sensors are used, all of the sensors may be the same type or may be of different types. For example, in circumstances where one or more RF coils are used as sensors, none, some, or all of the coils may be shielded. As another example, the coils can have different sensitivities. When other types of sensors are used, at least some of the characteristics of the sensors and the primary receive coil(s) may necessarily be different, though some may be similar or the same.

In some embodiments, multiple auxiliary RF coils and/or primary RF coils may be used to accelerate imaging. For example, multiple RF coils used to sense noise from the same or different noise sources may also be used to perform parallel MR. In this manner, multiple RF coils may provide both noise characterization functions as well as accelerated image acquisition via their use as parallel receive coils.

In some embodiments, as described above, multiple sensors may be used to perform noise compensation in the presence of multiple noise sources. In an environment having N correlated noise sources, where N is an integer greater than one, the Fourier transforms $C_{pri}(\omega)$ and $C_{aux}(\omega)$ of noise signals $c_{pri}(t)$ and $c_{aux}(t)$, received by a primary coil and an auxiliary sensor can be expressed as:

$C_{pri}(\omega) = H_{pri,1}(\omega)C_1(\omega) + H_{pri,2}(\omega)C_2(\omega) + \ldots + H_{pri,N}(\omega)C_N(\omega)$ $C_{aux}(\omega) = H_{aux,1}(\omega)C_1(\omega) + H_{aux,2}(\omega)C_2(\omega) + \ldots + H_{aux,N}(\omega)C_N(\omega),$ where $C_j(\omega)$; $1 \leq j \leq N$, is a Fourier transform of a noise signal from the $j^{th}$ noise source, $H_{pri,j}(\omega)$ is a transform between the primary coil and the $j^{th}$ noise source, and $H_{aux,j}(\omega)$ is a transform between the auxiliary sensor and the $j^{th}$ noise source. When the ratio $H_{pri,j}(\omega)/H_{aux,j}(\omega)$ is different for one or more noise sources, it may not be possible to perform high quality noise compensation by using only a single auxiliary sensor. However, multiple auxiliary sensors may be used to perform noise compensation in this circumstance as described below.

Described below is a non-limiting example of how multiple auxiliary sensors may be used to perform noise compensation for multiple different noise sources. Without loss of generality, suppose a MR system has a primary coil and P auxiliary sensors (where P is any integer greater than or equal to 1). Further, suppose that the MR system is deployed in an environment in which there are N different noise sources (where N is an integer greater than or equal to 1). Let $H_{ij}(\omega)$ denote the transform between the $i^{th}$ auxiliary sensor (where $1 \leq i \leq P$) and the jth noise source (where $1 \leq j \leq N$). The following set of equations relate the Fourier transforms of the signals received by the auxiliary sensors to the Fourier transforms of the noise signals produced by the noise sources:

$$\begin{bmatrix} H_{11} & \cdots & H_{1N} \\ \vdots & \ddots & \vdots \\ H_{P1} & \cdots & H_{PN} \end{bmatrix} \begin{bmatrix} C_1 \\ \vdots \\ C_N \end{bmatrix} = \begin{bmatrix} C_{aux,1} \\ \vdots \\ C_{aux,P} \end{bmatrix},$$

where $C_{aux,i}$; $1 \leq i \leq P$, is a Fourier transform of the signal received at the ith auxiliary sensor, $C_j(\omega)$; $1 \leq j \leq N$ is a Fourier transform of a noise signal from the $j^{th}$ noise source, and where the dependence of all the terms on frequency is not shown explicitly (the ($\omega$) is suppressed for brevity), though it should be appreciated that all the terms in the above matrix equation are functions of frequency.

When the number of auxiliary sensors is greater than or equal to the number of noise sources (i.e., P>=N), the above matrix equation may be solved for the noise signals according to:

$$\begin{bmatrix} C_1 \\ \vdots \\ C_N \end{bmatrix} =$$

-continued $$\left\{\begin{bmatrix} H_{11} & \cdots & H_{1N} \\ \vdots & \ddots & \vdots \\ H_{P1} & \cdots & H_{PN} \end{bmatrix}^T \begin{bmatrix} H_{11} & \cdots & H_{1N} \\ \vdots & \ddots & \vdots \\ H_{P1} & \cdots & H_{PN} \end{bmatrix}\right\}^{-1} \begin{bmatrix} H_{11} & \cdots & H_{1N} \\ \vdots & \ddots & \vdots \\ H_{P1} & \cdots & H_{PN} \end{bmatrix}^T \begin{bmatrix} C_{aux,1} \\ \vdots \\ C_{aux,P} \end{bmatrix}.$$

If such a solution exists, the correlated noise measured on the primary receive coil may be expressed in relation to the measurements obtained by all of the auxiliary sensors according to:

$$C_{pri} = [H_{pri,1} \quad \cdots \quad H_{pri,N}]$$

$$\left\{\begin{bmatrix} H_{11} & \cdots & H_{1N} \\ \vdots & \ddots & \vdots \\ H_{P1} & \cdots & H_{PN} \end{bmatrix}^T \begin{bmatrix} H_{11} & \cdots & H_{1N} \\ \vdots & \ddots & \vdots \\ H_{P1} & \cdots & H_{PN} \end{bmatrix}\right\}^{-1} \begin{bmatrix} H_{11} & \cdots & H_{1N} \\ \vdots & \ddots & \vdots \\ H_{P1} & \cdots & H_{PN} \end{bmatrix}^T \begin{bmatrix} C_{aux,1} \\ \vdots \\ C_{aux,P} \end{bmatrix}.$$

A multi-channel transform $H_{MPA}$ may be defined according to:

$$H_{MPA} = [H_{PA,1} \quad \cdots \quad H_{PA,P}] = [H_{pri,1} \quad \cdots \quad H_{pri,N}]$$

$$\left\{\begin{bmatrix} H_{11} & \cdots & H_{1N} \\ \vdots & \ddots & \vdots \\ H_{P1} & \cdots & H_{PN} \end{bmatrix}^T \begin{bmatrix} H_{11} & \cdots & H_{1N} \\ \vdots & \ddots & \vdots \\ H_{P1} & \cdots & H_{PN} \end{bmatrix}\right\}^{-1} \begin{bmatrix} H_{11} & \cdots & H_{1N} \\ \vdots & \ddots & \vdots \\ H_{P1} & \cdots & H_{PN} \end{bmatrix}^T.$$

It may then be seen that the noise measured by the primary receive coil is a linear combination of the noise signals measured on all the auxiliary coils:

$$C_{pri} = [H_{PA,1} \quad \cdots \quad H_{PA,P}] \begin{bmatrix} C_{aux,1} \\ \vdots \\ C_{aux,P} \end{bmatrix}. \quad (3)$$

Thus, given noise signals measured by P auxiliary sensors (e.g., the Fourier transforms of which are given by $C_{aux,i}$ for $1 \leq i \leq P$), the above equation may be used to estimate the noise signal received at the primary receive coil (e.g., the Fourier transform of which is given by $C_{pri}$). In turn, the estimated noise signal may be subtracted from the overall signal measured by the primary receive coil (which signal would have both an MR signal component and a noise component) to perform noise suppression.

However, to use the above equation (3), an estimate of the multichannel primary-to-auxiliary transform $H_{MPA} = [H_{PARC,1} \cdots H_{PARC,P}]$ is needed. This may be achieved in any suitable way and, in some embodiments, may be done by making multiple measurements using the primary receive coil and the auxiliary sensors (e.g., at a time when there is no MR signal present) and using these measurements to estimate the multichannel primary-to-auxiliary transform. For example, given M measurements of noise signals at each of the P auxiliary sensors and the primary receive coil, the $H_{MPA}$ may be estimated for each frequency component $\omega_k$ (where k is an index over frequency bins) using least squares estimation according to:

$$\begin{bmatrix} H_{PA,1}(\omega_k) \\ \vdots \\ H_{PA,P}(\omega_k) \end{bmatrix} =$$

$$\left\{\begin{bmatrix} S_{aux,1}(\omega_k)_1 & \cdots & S_{aux,P}(\omega_k)_1 \\ \vdots & \ddots & \vdots \\ S_{aux,1}(\omega_k)_M & \cdots & S_{aux,P}(\omega_k)_M \end{bmatrix}^T \begin{bmatrix} S_{aux,1}(\omega_k)_1 & \cdots & S_{aux,P}(\omega_k)_1 \\ \vdots & \ddots & \vdots \\ S_{aux,1}(\omega_k)_M & \cdots & S_{aux,P}(\omega_k)_M \end{bmatrix}\right\}^{-1} \times$$

$$\begin{bmatrix} S_{aux,1}(\omega_k)_1 & \cdots & S_{aux,P}(\omega_k)_1 \\ \vdots & \ddots & \vdots \\ S_{aux,1}(\omega_k)_M & \cdots & S_{aux,P}(\omega_k)_M \end{bmatrix}^T \begin{bmatrix} S_{pri}(\omega_k)_1 \\ \vdots \\ S_{pri}(\omega_k)_M \end{bmatrix},$$

where $S_{aux,i}(\omega_k)_m$ represents the value of the kth frequency bin of the Fourier transform of the mth measured signal obtained by the ith auxiliary sensor, and where $S_{pri}(\omega_k)_m$ represents the value of the kth frequency bin of the Fourier transform of the mth measured signal obtained by the primary receive coil. This least-squares approach provides the most complete correction when the columns of the following matrix are as orthogonal as possible to one another:

$$\begin{bmatrix} H_{11} & \cdots & H_{1N} \\ \vdots & \ddots & \vdots \\ H_{P1} & \cdots & H_{PN} \end{bmatrix}.$$

Put another way, each auxiliary sensor may detect some or all of the different noise sources in a unique way from other auxiliary sensors. In order to correct for the presence of near field sources, multiple sensors may be placed in different locations to be more or less sensitive to some of the noise sources. In some embodiments, multiple sensors may be oriented orthogonally to one another (e.g., one sensor may be oriented in an "X" direction, another sensor may be oriented in the "Y" direction, and another sensor may be oriented in a "Z" direction). In this way, each vector of the time varying interference fields may be captured. It may also be beneficial to use one or more antennas as an auxiliary sensor to provide another orthogonal measurement.

It should be appreciated that the techniques described herein facilitate detecting noise in the environment of an MRI system using any number and/or type of sensor suitable for detecting noise produced by respective noise sources. As a result, noise from a variety of sources that may impact the performance of the MRI system may be detected and used to suppress and/or eliminate noise from MR signals detected by the MRI system during operation. Because techniques described herein operate on the particular noise environment of the MRI system, a noise reduction system employing noise suppression techniques described herein facilitate deployment of an MRI system wherever the system may be needed, eliminating the requirement that the system be installed in specially shielded rooms. The ability to dynamically adapt to changing noise environments facilitates development of MRI systems that can be deployed in generally noisy environments, including environments where noise sources may change over time. Because techniques described herein can be utilized during operation of the MRI system, the noise environment can be characterized dynamically so that it reflects the same noise environment to which the system is currently being exposed. These noise suppression and/or avoidance techniques permit the MRI system to operate in almost any environment and to dynamically adapt to and compensate for electromagnetic noise present, enabling a portable MRI system that can be transported to wherever the patient is located to perform the needed diagnostic, surgical or monitoring procedure.

A noise reduction system may include additional techniques to increase the SNR of a portable MRI system by reducing system noise, for example, by reducing inductive coupling between adjacent or neighboring RF coils in a multi-coil transmit/receive system. According to some embodiments, multiple coils can be used to both improve SNR and to facilitate noise suppression. For example, a collection of RF coils, which may be either RF signal coils (e.g., primary RF coils), RF noise coils (e.g., auxiliary RF coils) or both, may be arranged at different locations and orientations to detect a comprehensive RF field that can be characterized and compensated for using any of the noise suppression techniques discussed herein. According to some embodiments, a portable MRI system comprises multiple transmit/receive coils to improve the SNR of image acquisition. For example, a portable MRI system may comprise 2, 4, 8, 16, 32 or more RF receive coils to improve the SNR of MR signal detection.

Figure 43A:
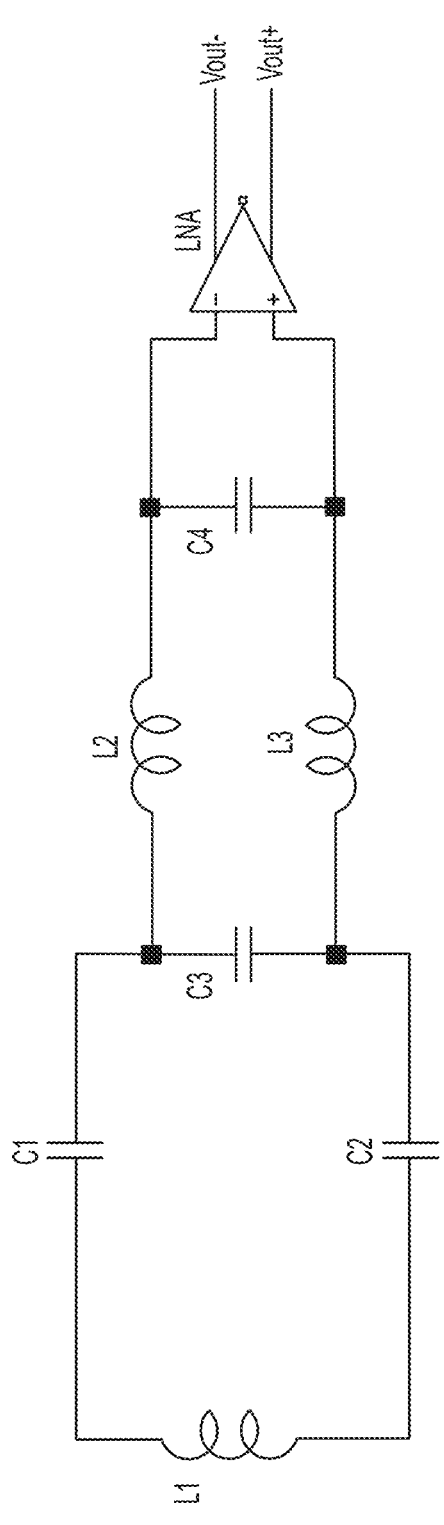
FIG. 43A-B illustrate respective examples of decoupling circuits configured to reduce inductive coupling between radio frequency coils in a multi-coil transmit/receive system, in accordance with some embodiments.
Figure 43B:
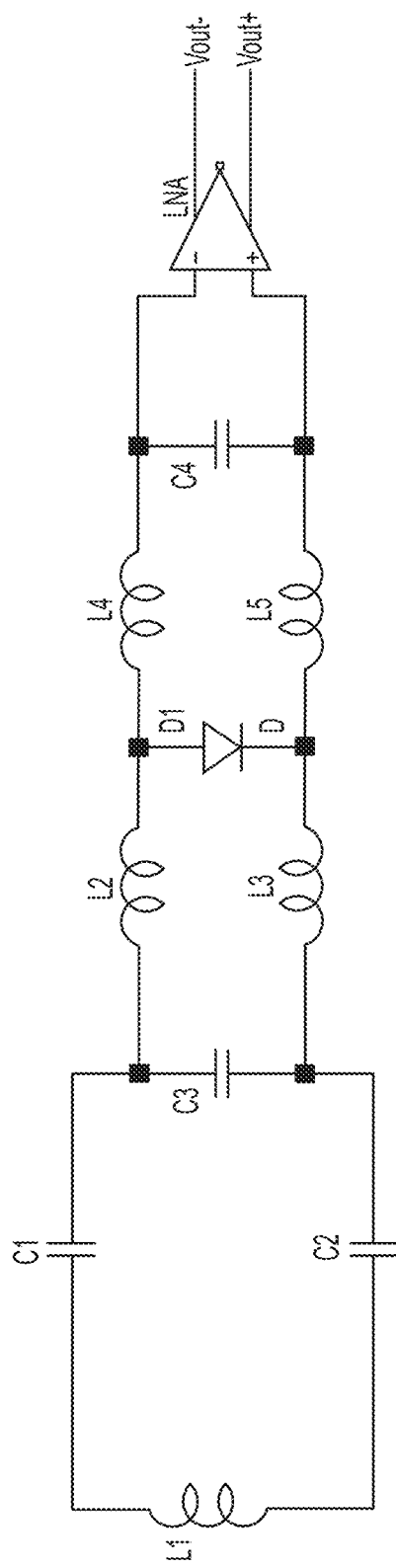

In general, RF coils are tuned to increase coil sensitivity at a frequency of interest. However, inductive coupling between adjacent or neighboring coils (e.g., RF coils sufficiently proximate one another) degrades the sensitivity of tuned coils and significantly reduces the effectiveness of the collection of RF coils. Techniques for geometrically decoupling neighboring coils exist but place strict constraints on coil orientation and position in space, reducing the ability of the collection of RF coils to accurately detect the RF field and, as a consequence, degrading the noise rejection performance. To address the negative impact of inductive coupling between coils, the inventors have utilized coil decoupling techniques that reduce the inductive coupling between radio frequency coils in multi-coil transmit/receive systems. For example, FIGS. 43A and 43B illustrate passive decoupling circuits configured to reduce inductive coupling between radio frequency coils in a multi-coil transmit/receive system, in accordance with some embodiments. Passive decoupling circuit 4300a may be configured to decouple RF noise coils, for example, RF noise coils positioned outside the field of view of the MRI system that are not subjected to the relatively intense transmit $B_1$ field produced by the RF transmit system (i.e., one or more RF transmit coils). In this context, inductor L1 represents an RF coil configured to detect electromagnetic noise in the environment that is tuned by the circuit formed by capacitors C1, C2 and C3. Capacitors and inductors are arranged to provide a balanced differential circuit to reduce common mode noise. The tank circuit formed by L2, L3, C3 and C4 is configured to have a high impedance to ensure that the current through L1 remains small. Appropriate selection of the values for the L-C network ensures that the current passing through L1, while remaining small, has sufficient SNR for measurement at the differential output (Vout−, Vout+) of the LNA to characterize electromagnetic noise in the environment with adequate sensitivity. Equivalent impedance at the LNA input is given by:

$$Z_{eq} = \left(\frac{C_4}{C_3}\right)^2 R$$

In the above equation, R is the equivalent losses of the primary inductance L1. Capacitor and inductor values can be chosen to attain optimal noise impedance of the LNA used for detection. FIG. 43B illustrates a passive decoupling circuit 4300b configured to decouple RF coils that may be subjected to $B_1$ transmit fields. In particular, L1 may represent an RF signal coil within the field of view of the MRI system. Passive decoupling network 4300b may be similar to passive decoupling network 4300a in some respects, but differs in that diode D1, capacitor C3 and inductors L2 and L3 operate as a transmit/receive switch that isolates the RF coil (represented as inductor L1) from the LNA when RF signals are being transmitted by one or more RF transmit coils. Specifically, the L-C network is divided into two network portions by the transmit/receive switch to protect sensitive electronics during RF transmit cycles. During a transmit pulse, diode D1 is turned on to create a short circuit, isolating the RF signal coil from the receive electronics. The resulting L-C network provides a tank circuit with a high impedance that ensures that the current in L1 remains small. During receive cycles, diode D1 is turned off and the RF coil is connected to the LNA and tuned by the resulting balanced tank circuit configured to limit the current through L1, while allowing for sufficient signal to be detected at the differential outputs of the LNA. Thus, the RF coil is connected to a first tank circuit during transmit cycles and a second tank circuit during receive cycles of a pulse sequence. Equivalent impedance at the LNA input is then:

$$Z_{eq} = \left(\frac{L_4}{L_2}\right)^2 R$$

Conventional decoupling circuits often use PIN diodes to isolate the receive electronics from the RF signal coil. However, PIN diodes suitable for performing this function in a decoupling circuit require approximately 1 A of current to turn the diode on. As an example, a transmit/receive coil system having eight receive coils may require on the order of 8 A of current to decouple the receive coils from the RF signal coil(s) for each transmit and receive cycle of an image acquisition pulse sequence. Accordingly, over the span of an image acquisition protocol, substantial power is consumed by the decoupling circuits of the RF transmit/receive system. The inventors recognized that PIN diodes could be replaced by Gallium Nitride (GaN) field effect transistors (FETs) to reduce the power consumption of the RF transmit/receive system. In particular, GaN FETs require on the order of milliamps to turn on, reducing the power consumption by several orders of magnitude. In addition, the capacitance of the GaN FETs when turned on are small compared to PIN diodes, reducing negative impact on the balanced circuit. According to some embodiments, diode D1 in decoupling circuit 4300b is replaced with one or more GaN FETs, thereby reducing the power consumption of the RF transmit/receive system.

Figure 43C:
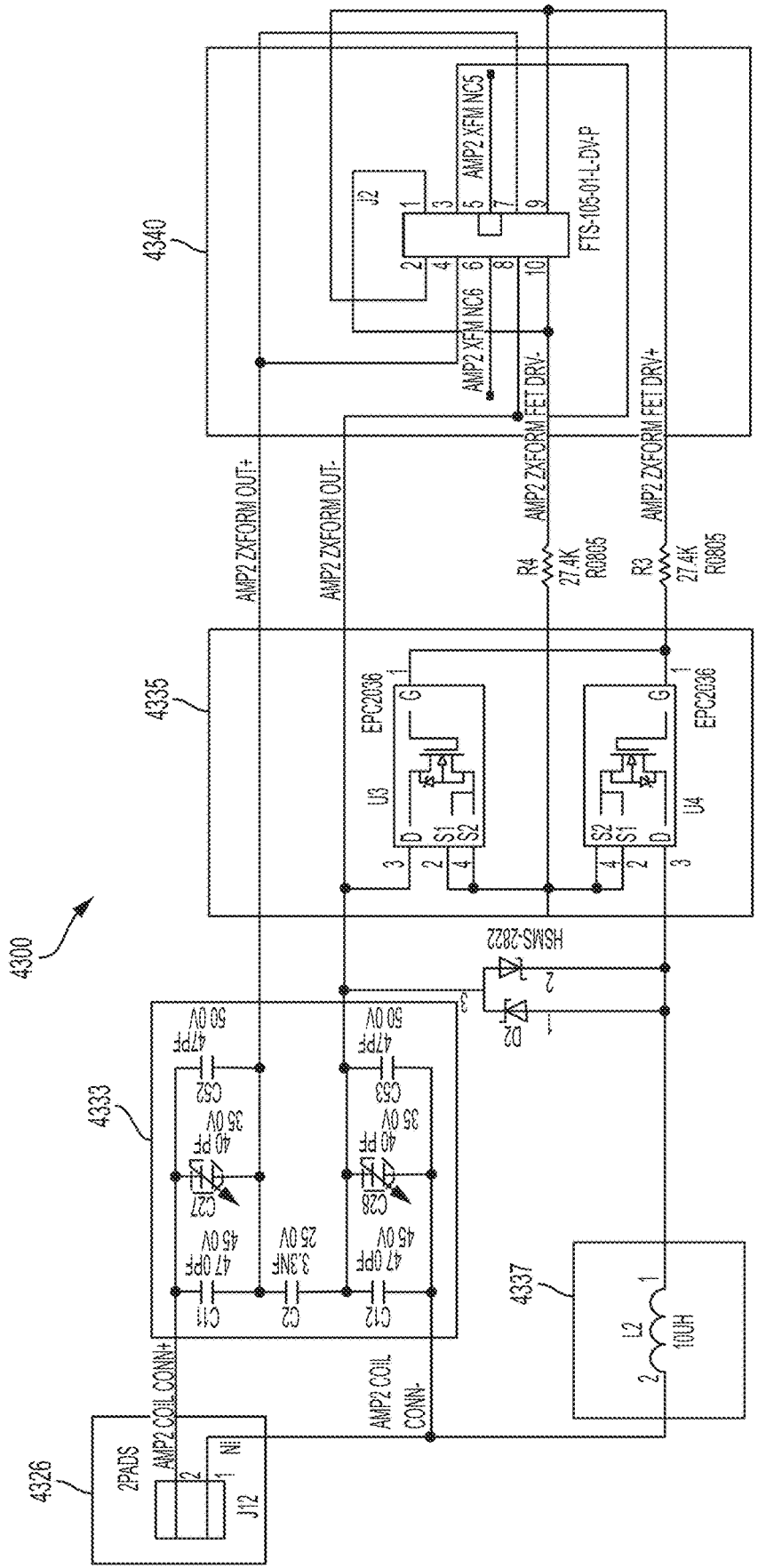
FIG. 43C illustrates a decoupling circuit using Gallium Nitride (GaN) field effect transistors (FETs) to couple and decouple a receive coil, in accordance with some embodiments.

FIG. 43C illustrates a circuit 4300 for a RF receive coil 4326 using GaN FETs 4335 to couple and decouple the receive electronics from the RF coil, in accordance with some embodiments. In FIG. 43C, a receive coil 4326 is connected to a resonant circuit 4333 and to receive circuitry 4340 (e.g., preamplifiers such as linear amplifiers) configured to receive and deliver signals detected by receive coil 4326. During transmit cycles (e.g., during transmission of RF pulses by one or more RF transmit coils), receive coil 4326 is detuned to protect receive circuitry 4340, which could be damaged if RF transmit signals from RF transmit coil(s) were to couple to receive coil 4326 and propagate to receive circuitry 4340. As discussed above, conventional circuits often employ PIN diodes to detune or decouple the receive coil from the receive circuitry. Circuit 4300 includes decoupling circuitry that uses GaN FETs 4335 to detune receive coil 4326 so as to decouple the receive coil from receive circuitry 4340. In particular, during transmit cycles, GaN FETs 4326 are turned on (i.e., closed to create a short circuit between terminals) to switch inductor 4337 into the circuit to detune resonant circuit 4333 so that RF transmit pulses do not couple to receive coil 4326. During receive cycles, GaN FETs 4335 are turned off (i.e., opened to create an open circuit between terminals) to remove inductor 4337 from resonant circuit 4333 so that receive coil will couple to MR signals emitted in response to the RF transmit pulses. As discussed above, GaN FETs require substantially less power to turn on compared to conventional diodes such as PIN diodes, conserving power on each transmit/receive cycle (e.g., reducing the power consumption from approximately 1 A to milliamps for each receive coil in the RF transmit/receive system).

Figure 43D:
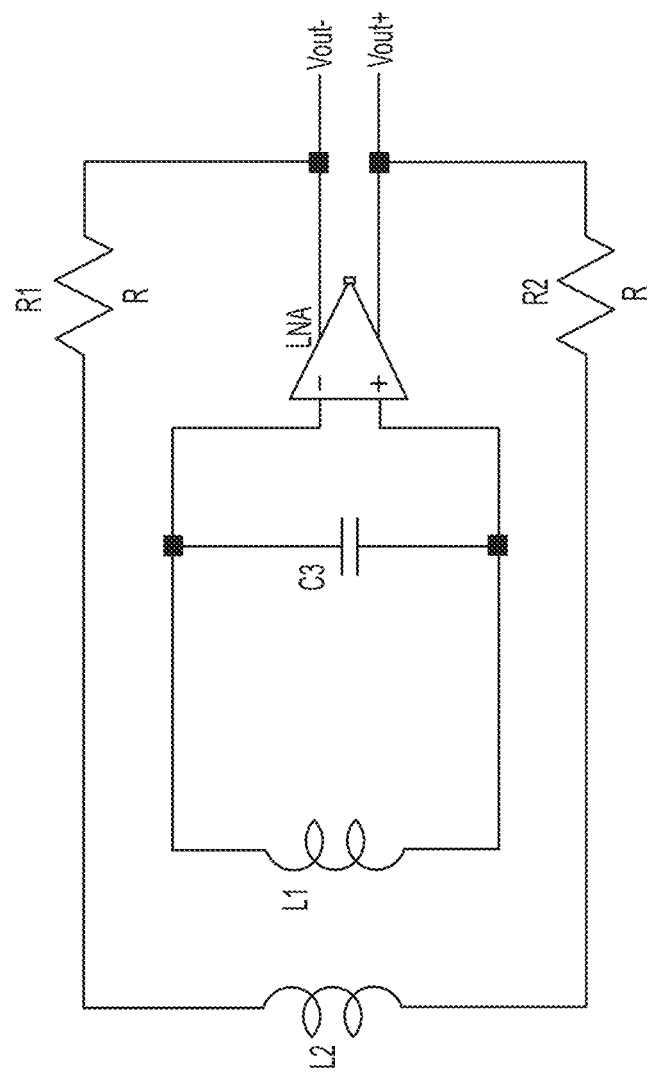
FIG. 43D illustrates an active decoupling circuit, in accordance with some embodiments.

FIG. 43D illustrates an active decoupling circuit configured to reduce inductive coupling between radio frequency coils in a multi-coil transmit/receive system, in accordance with some embodiments. In the decoupling circuit illustrated in FIG. 43D, inductor L1 represents an RF coil configured to measure an NMR signal. The RF coil is tuned via capacitor C3 connected in parallel to L1, and the differential outputs Vout−, Vout+ of the LNA measure the NMR signal sensed by the RF coil. The differential output of the LNA are also fed back to a second inductor L2 via resistors R1 and R2. The feedback circuit causes current flowing through inductor L2 to couple negative flux into L1 in response to signals, thus reducing the current flowing through L1 and consequently mitigating the inductive coupling effect on other nearby RF coils. L2 may be provided at a desired distance from L1 and the resistor values of R1 and R2 can be chosen so that the current through L2 achieves the desired current reduction in L1. Decoupling circuit 4300c reduces the number of circuit elements required, thereby reducing the cost and complexity of the decoupling circuit.

The use of decoupling circuits, such as the decoupling circuits illustrated in FIGS. 43A, 43B, 43C and 43D facilitates increasing SNR and mitigates the impact of inductive coupling on the noise rejection performance of a noise reduction system in a multi-coil transmit/receive system. In addition, the decoupling circuit illustrated in FIG. 43C provides a low power transmit/receive switch that reduces the power consumption of decoupling and coupling the RF receive coils during transmit and receive cycles, respectively, via the use of GaN FETs (e.g., instead of PIN diodes and the like). Accordingly, the RF coil system may be operated with reduced power consumption. It should be appreciated that other decoupling circuits may be used, as the aspects are not limited in this respect.

According to some embodiments, noise from various sources are characterized using a combination of the above described techniques to determine a multi-channel transform that can be used to suppress or eliminate noise from the various noise sources. Noise measurements may be obtained during operation of the MRI system so that a multi-channel transform may be determined dynamically, allowing for noise suppression that adapts to the changing noise environment of the MRI system. However, noise in the environment may be characterized upon system start-up, when the system is moved to a different location and/or upon the occurrence of any event, and the characterized noise used to suppress and/or eliminate noise in acquired MR signals, as the techniques described herein can be applied as desired. Any other noise suppression techniques may also be utilized to facilitate operation of an MRI system outside a specially shielded room, tent or enclosure and/or where shielding of the imaging region is otherwise limited or absent, thus allowing for portable MRI.

It should be appreciated that these noise suppression techniques facilitate detecting noise in the environment of an MRI system using any number and/or type of sensor suitable for detecting noise produced by respective noise sources. As a result, noise from a variety of sources that may impact the performance of the MRI system may be detected and used to suppress and/or eliminate noise from MR signals detected by the MRI system during operation. Because these techniques operate on the particular noise environment of the MRI system, a noise reduction system employing these noise suppression techniques facilitate deployment of an MRI system wherever the system may be needed, eliminating the requirement that the system be installed in specially shielded rooms. The ability to dynamically adapt to changing noise environments facilitates development of MRI systems that can be deployed in generally noisy environments, including environments where noise sources may change over time. Because the described noise suppression techniques can be utilized during operation of the MRI system, the noise environment can be characterized dynamically so that it reflects the same noise environment to which the system is currently being exposed. These noise suppression and/or avoidance techniques permit the MRI system to operate in almost any environment and to dynamically adapt to and compensate for electromagnetic noise present, enabling a portable MRI system that can be transported to wherever the patient is located to perform the needed diagnostic, surgical or monitoring procedure.

It should be further appreciated that a noise reduction system may include any one or more noise suppression, rejection and/or avoidance techniques described herein (e.g., one or more of dynamic noise suppression, rejection and/or avoidance techniques, one or more decoupling circuits to reduce inductive coupling, etc.) to facilitate operation of the portable MRI system in virtually any room and with virtually any device-level shielding configuration. As discussed above, conventional MRI systems operate in specially shielded rooms that provide an encompassing shielded space. As a result, MRI systems operating in specially shielded rooms have shielding for substantially 100% of the imaging region. MRI systems that operate within moveable tents or cages also have comprehensive shielding of the imaging region that endeavors to provide as close to 100% shielding of the imaging region as is practicable. To achieve portability, MRI systems according to some embodiments are configured to operate outside specially shielded rooms, tents or cages with varying levels of device-level shielding (e.g., shielding some fraction of the imaging region), including no, or substantially no, shielding of the imaging region.

The amount of electromagnetic shielding for an imaging region can be viewed as a percentage of the maximum solid angle, subtending the imaging region from its center, for which shielding is provided. Specifically, providing shielding for 100% of an imaging region means that electromagnetic shielding for at least the operating spectrum is provided over the maximum solid angle $4\pi$ steradian (sr) about the imaging region. Similarly, providing shielding for less than 75% of the imaging region means that electromagnetic shielding for at least the operating spectrum provides less than 0.75 (4π) sr solid angle coverage of the imaging region, and so on. Accordingly, a specially shielded room provides shielding for substantially 100% of the imaging region for an MRI system deployed within the shielded room because shielding is provided over substantially the maximum solid angle of 4π sr. Similarly, moveable tents or cages are designed to provide shielding for as close to as 100% of the imaging region as is practicable.

The percentage of electromagnetic shielding of an imaging region of an MRI system refers to the total amount of shielding that protects the imaging region, including electromagnetic shielding provided via specially-shielded rooms, tents, cages, etc., as well as device-level electromagnetic shielding (e.g., electromagnetic shields coupled to the housing of the MRI device that provide electromagnetic shielding for the imaging region). Thus, the portable MRI systems illustrated in FIGS. 16, 39A-C, 40A and 40B, when operated outside of specially-shielded rooms or cages, have less than 100% shielding of their respective imaging regions and, in some configurations, have substantially less than 100% shielding. Providing shielding for less than 100% of the imaging region is referred to herein as providing shielding for a fraction of the imaging region, which fraction may be quantified by a specific percentage or percentage range. For example, the electromagnetic shields illustrated in FIGS. 16, 39A-C, 40A and 40B may be adjusted to provide shielding for different fractions of the imaging region (e.g., varying degrees of shielding), such as at least between approximately 85% and approximately 50% (e.g., at approximately 85% or less, approximately 75% or less, approximately 65% or less, etc.).

It should be understood that providing shielding for a fraction of the imaging region refers to instances in which providing less than 100% shielding is intentional and/or by design (e.g., to provide access to or accommodate a patient in an MRI system operated outside a specially shielded room, tent or cage). In practice, shielding techniques are often imperfect and therefore may provide less than 100% shielding even though the intent is to provide 100% shielding for the imaging region (at least for the operating spectrum). For example, doors that are left open or ajar in specially shielded rooms, gaps in tents that go unnoticed, or openings that are not fully closed during imaging, etc., may result in less than 100% shielding even though the intent is to provide full coverage. Imperfect shielding material or construction may also result in unintentionally having less than 100% shielding. Providing shielding for a fraction of the imaging region should not be interpreted to cover these situation, as it refers to circumstances where the fractional coverage is intentional and/or by design.

Figure 44C:
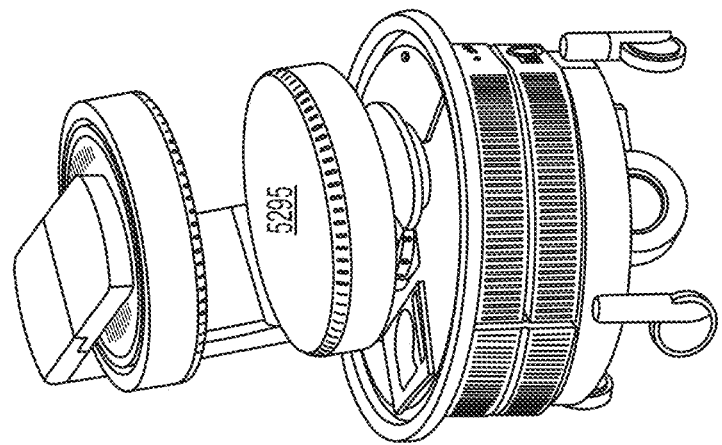
FIGS. 44A-C illustrate a portable MRI system having different amounts of device-level shielding about the imaging region, in accordance with some embodiments.
Figure 44B:
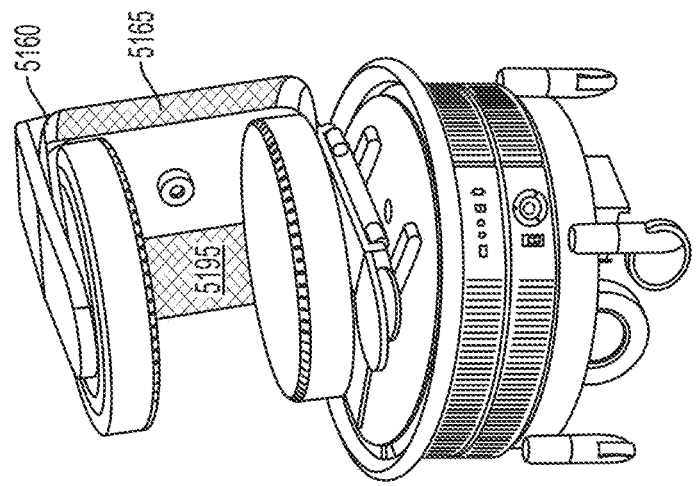
Figure 44A:
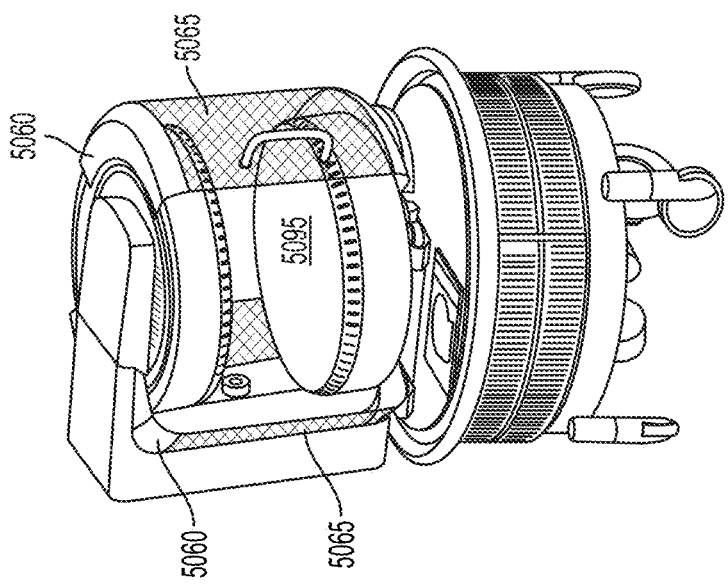

FIGS. 44A-C illustrate a portable MRI system having different amounts of device-level shielding about the imaging region, in accordance with some embodiments. FIG. 44A illustrates a portable MRI system having shields 5065 that partially shield the imaging region 5095. For example, shields 5065 may be incorporated into slides 5060 that can be configured and positioned as desired to provide shielding around approximately 50% of the opening to imaging region 5095. FIG. 44B illustrates another example of a portable MRI system having shield 5165 that provides a lesser degree of shielding for imaging region 5195. For example, slide 5160 may be positioned as desired to provide shielding around approximately 25% of the opening to imaging region 5195. FIG. 44C illustrates an example of a portable MRI system without shields around the imaging region 5295, providing an alternative having substantially no device-level shielding for the open imaging region.

Figure 44D:
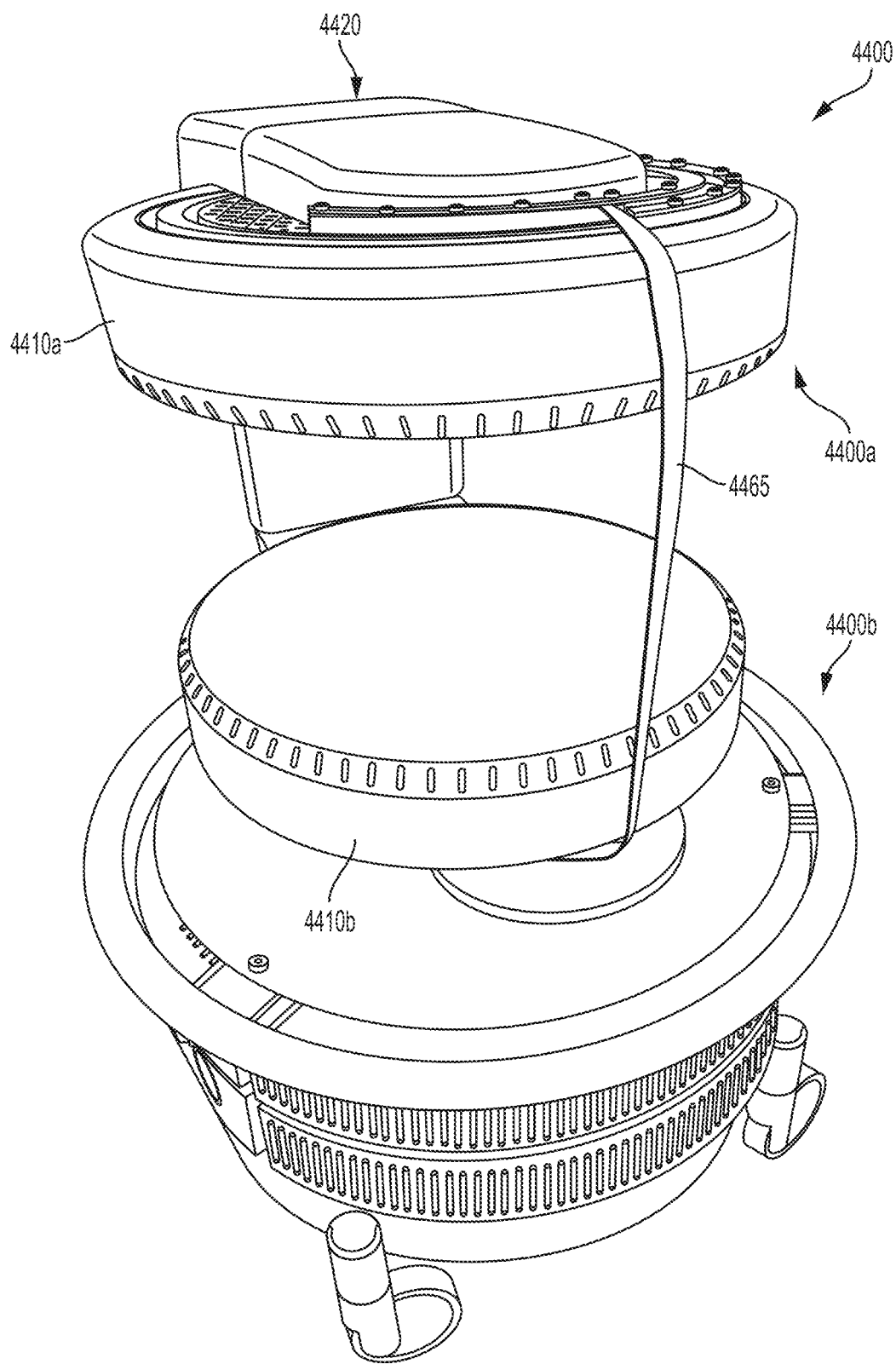
FIG. 44D illustrates a portable MRI system utilizing a conductive strip to provide electromagnetic shielding for the imaging region, in accordance with some embodiments.

FIG. 44D illustrates a portable MRI system 4400 utilizing a further technique for electromagnetic shielding of the imaging region of the system, in accordance with some embodiments. In particular, in the embodiment illustrated in FIG. 44D, shielding from electromagnetic interference is achieved via one or more conductive strips connecting upper and lower portions of the $B_0$ magnet of the portable MRI system to form a conductive loop that counteracts at least some electromagnetic radiation that would otherwise result in interference. In the embodiment illustrated in FIG. 44D, conductive strip 4465 is electrically coupled to upper portion 4400a, lower portion 4400b and may also be connected to ground. In the embodiment illustrated in FIG. 44D, conductive strip 4465 is formed by a conductive braid, providing a flexible strip of material that can be coupled to the $B_0$ magnet with relative ease and convenience. However, conductive strip 4465 may be constructed or composed of any conductive material in any suitable form, some examples of which are described in further detail below.

The exemplary portable MRI system 4400 illustrated in FIG. 44D includes a ferromagnetic yoke 4420 that provides a magnetic path between upper magnet 4410a and lower magnet 4410b to capture and direct the magnetic field produced by the respective magnets to increase the magnetic flux density within the imaging region. In particular, similar to the exemplary yokes described in connection with FIGS. 2A-B, 3A and 16, yoke 4420 comprises a frame and upper and lower plates formed using a suitable ferromagnetic material or combination of materials (e.g., iron, steel, etc.). The upper and lower plates are coupled to the upper and lower magnets, respectively, to form a "magnetic circuit" that captures at least some of the magnetic field produced by the magnets and directs the captured magnetic fields via the "magnetic circuit" to increase the flux density within the imaging region of the MRI device.

The inventors have recognized that coupling conductive strip 4465 to the plates of the yoke forms a conductive loop in which current is induced by electromagnetic radiation propagating in directions through the conductive loop. This induced current will in turn produce an electromagnetic field that counteracts at least some of the electromagnetic radiation that induced the current and/or electromagnetic radiation similarly propagating through the loop. In this manner, electromagnetic interference can be reduced by the counteracting electromagnetic field produced by current induced in the conductive loop formed by the conductive strip 4465 and yoke 4220. Accordingly, the suppression of electromagnetic interference may be improved by the addition of further conductive strips forming additional conductive loops to produce counteracting electromagnetic fields when ambient electromagnetic radiation induces current in the respective conductive loop. In particular, as more conductive loops are added at different orientations, the resulting conductive loops will be responsive to more of the electromagnetic radiation present in the environment.

It should be appreciated that any number of conductive strips may be attached or affixed to the $B_0$ magnet to provide electromagnetic shielding. According to some embodiments, one or more additional strips 4465 connecting components of the $B_0$ magnet to ground may be provided about the imaging region to increase the amount of shielding arranged to protect the imaging region from electromagnetic interference (e.g., to increase the percentage of electromagnetic shielding for the imaging region). For example, a conductive strip shield may be attached every 180°, every 90°, every 45°, every 30° or at any other interval, either regularly or irregularly spaced about the imaging region, to provide a desired degree of electromagnetic shielding. It should be appreciated that any number of conductive strips may be used to achieve a desired percentage of shielding and/or to deliver a desired compromise between openness of the imaging region and comprehensiveness of the shielding for the imaging region, as discussed in further detail below.

While the conductive strip 4465 illustrated in FIG. 44D is made from a flexible material, one or more conductive strips may be formed in other ways, for example, as a rigid conductive strip, bar, rod or handle (or other suitable geometry) that electrically connects the magnets forming the $B_0$ magnet of the MRI system to ground. In this respect, one or more conductive strips may be arranged to serve as a handle to assist in moving the portable MRI system, to facilitate rotating the device or to assist in tilting the $B_0$ magnet (e.g., in conjunction with a goniometric member, examples of which are described in connection with FIGS. 45-47 below) in addition to providing electromagnetic shielding. It should be appreciated that different types of conductive strips may be used in combination (e.g., one or more flexible strips and/or one or more rigid strips) to provide electromagnetic shielding for the MRI system, as the aspects are not limited in this respect.

According to some embodiments, one or more conductive strips are configured to be removable so that conductive strips can be added and removed as desired, facilitating configurable strip shielding that provides a flexible approach to accommodate different operating environments, different imaging circumstances and/or different levels of claustrophobic affliction or unease of the patient. To facilitate configurable shielding in this respect, the housing for the magnets may include a plurality of fastening mechanisms (e.g., snaps, connectors, inserts or other mechanisms) that allow for removable attachment of conductive strips to the housing and that electrically couple the magnets to the conductive strips and to ground when a conductive strip shield is connected to the housing via a respective fastening mechanism. Fastening mechanisms may be arranged at any desired location and at any number of locations to provide flexibility in where and how many conductive strips may be attached to the device. Additionally, the fastening mechanisms themselves may be made to be moveable so that one or more conductive strips coupled to the system via the fastening mechanisms may be adjusted (e.g., rotated about the imaging region). In this manner, conductive strips may be added, removed and/or their positions adjusted as needed to provide a desired shielding configuration in a desired amount (e.g., to provide shielding for a desired percentage of the imaging region).

Providing a plurality of fastening mechanisms that allow removable strips to be attached and removed at a number of locations about the imaging region allows the imaging region to remain essentially open while positioning a patient within the imaging region. After the patient has been positioned within the imaging region, a desired number of conductive strips may be attached to the $B_0$ magnet via the plurality of fastening mechanisms to achieve a desired degree of shielding, to address the electromagnetic environment in which the MRI system is operating, to facilitate a particular imaging protocol and/or to accommodate a patient who may be susceptible to claustrophobia (e.g., conductive strips may be added only while the patient remains comfortable with the openness of the MRI system). Accordingly, strip shielding techniques may provide a flexible, configurable approach to electromagnetic shielding, facilitating the ability to deploy portable MRI systems in a variety of environments and for a variety of applications and circumstances.

There are a number of benefits to reducing the shielding provided around the imaging region (e.g., using any of the shielding techniques described herein), including a reduction in cost and complexity of the system and improvements in accessibility to the imaging region both with respect to positioning a patient for imaging, as well as increased accessibility for medical personnel who may need to perform other tasks requiring access to the patient while the patient remains positioned within the system. In addition, reducing the shielding around the imaging region maximizes the openness of the MRI system to improve the experience of patients who are susceptible to feelings of claustrophobia. In this manner, the applicability of portable MRI may be further increased from a cost and/or flexibility perspective.

According to some embodiments, device-level shields are removable such that the amount of shielding provided may be selected in view of the particular circumstances, such as the required accessibility to the patient and/or imaging region for a given procedure, the severity of a patient's claustrophobia, the particular noise environment, etc. For example, slides carrying shields may be configured to be attached and removed from the $B_0$ magnet, allowing for a portable MRI device to be selectively and dynamically configured as desired (e.g., to allow a portable MRI system to be configured with the amount of shielding and accessibility illustrated in FIGS. 40 and 44A-C, which have three, two, one and zero slides/shields attached, respectively). In this manner, a portable MRI device can take advantage of the shielding and accessibility aspects of the different possible configurations, allowing the portable MRI to be optimized in this respect for given procedures and/or particular patients. According to other embodiments, the number of shields or the amount of shielding for a given portable MRI system may be fixed, which may allow for reductions in cost and complexity, but may also decrease the flexibility of the system from a shielding/accessibility perspective.

As discussed above, the inventors have developed noise reduction systems that allow a portable MRI device to operate in different noise environments (e.g., in unshielded or partially shielded rooms) and to operate with varying amounts of device-level shielding. A portable MRI system may include a noise reduction system that includes any one or combination of the noise suppression, avoidance and/or reduction techniques described herein, as the aspects are not limited in this respect. For example, a noise reduction system may employ one or more of the noise suppression and/or avoidance techniques described herein, allowing for dynamic noise suppression and/or avoidance that compensates for a given noise environment and/or that works in concert with the variable amounts of device-level shielding provided by portable MRI systems having configurable shields (e.g., the portable MRI systems illustrated in FIGS. 40 and 44A-C), including no or substantially no device-level shielding about the imaging region. A noise reduction system may also include coil decoupling networks to reduce the noise resulting from inductive coupling between radio frequency coils in multi-coil transmit/receive systems at any level of shielding provided. It should be appreciated that a noise reduction system may include any one or combination of techniques described herein, as the aspects are not limited in this respect.

As shown in FIGS. 16, 39A-C, 40A and 40B, the portable MRI is configured so that the $B_0$ magnet can be tilted at a desired incline. In many instances, a patient may not be able to lie flat, for example, due to risks associated with increased hydrostatic pressure in the brain. The inventors have developed a portable MRI device having a positioning mechanism that allows the $B_0$ magnet to be rotated, for example, about its center of mass. Thus, if a patient or a particular portion of a patient's anatomy needs to be supported at an incline, the positioning mechanism can be engaged to rotate or tilt the $B_0$ magnet to achieve the desired incline. According to some embodiments, the positioning mechanism can be manually engaged to rotate or tilt the $B_0$ magnet by hand, facilitating quick and easy configuring of the MRI system at the desired incline.

Figure 45A:
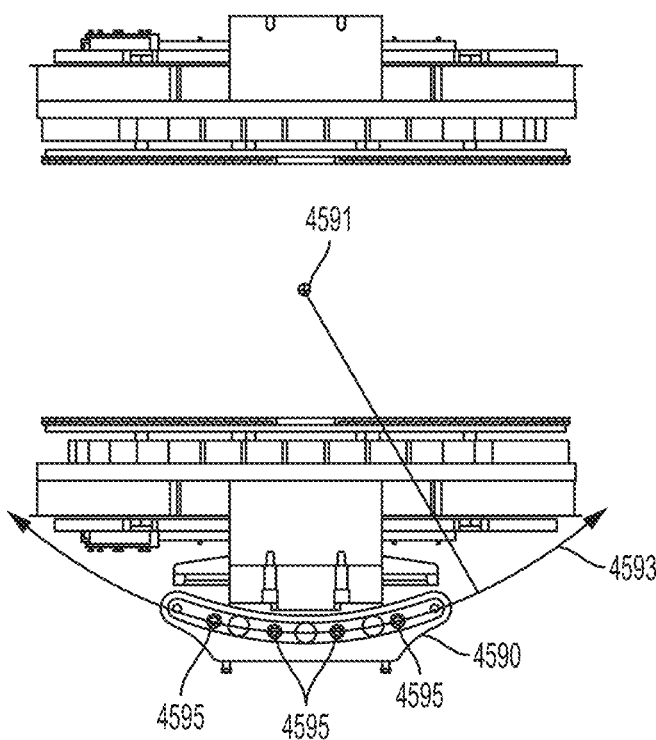
FIGS. 45A-45D illustrate different views of a positioning mechanism, in accordance with some embodiments.

FIGS. 45A-45D illustrate different views of a positioning mechanism that employs a positioning goniometer or goniometric stage 4590 that allows the magnet to be rotated about a fixed axis (e.g., the axis through or near the center of mass of the $B_0$ magnet). As illustrated in FIG. 45A, a goniometric stage 4590 is rotatably coupled to the bottom of a lower portion of the $B_0$ magnet to allow the $B_0$ magnet to be rotated about its center of mass 4591, as shown by direction arrows 4593 in FIG. 45A. Goniometric stage 4590 includes a number of holes or bores 4595 configured to accommodate a locking member (e.g., a locking pin) that locks the mechanism in place at a desired angle, as discussed in further detail below. Rotating the $B_0$ magnet via goniometric stage 4590 effects a tilt that provides an inclined supporting surface for the patient anatomy being imaged, as illustrated in FIG. 40A.

Figure 45B:
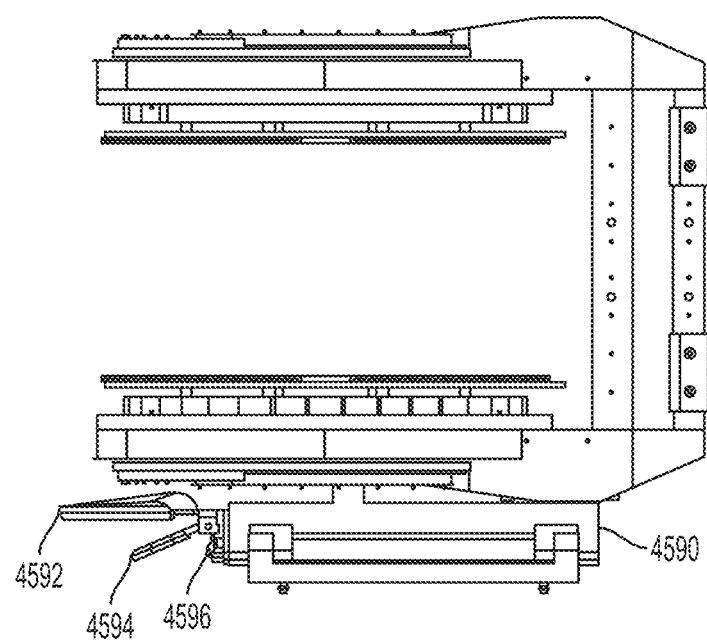
Figure 45C:
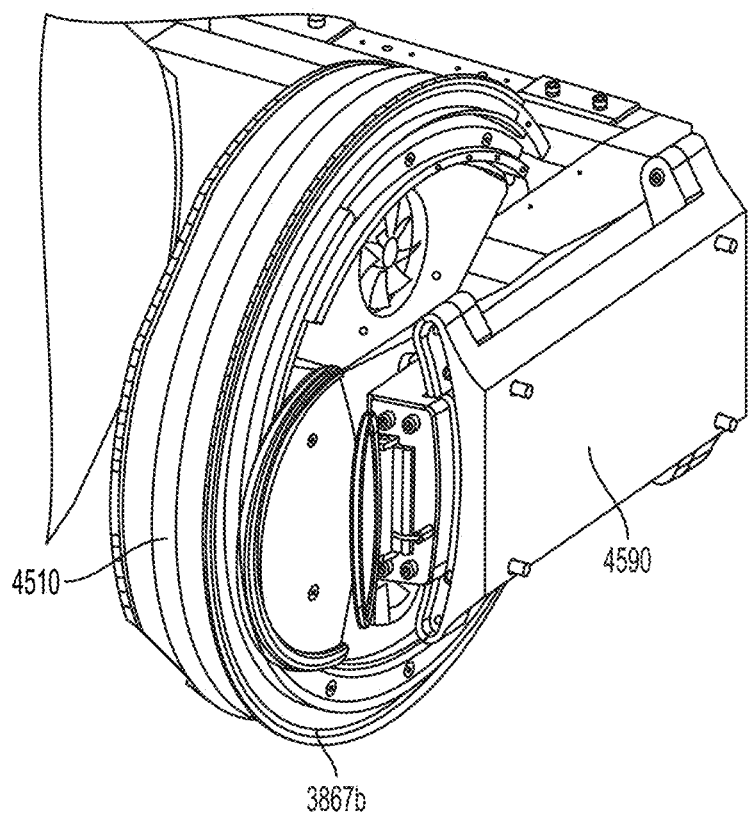
Figure 45D:
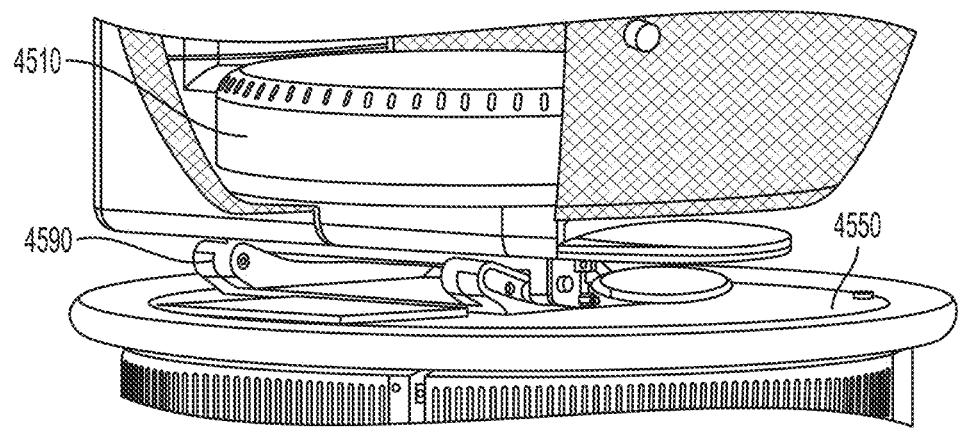

FIG. 45B illustrates a side view of the $B_0$ magnet and the goniometric stage 4590. Goniometric stage 4590 includes a release mechanism 4594 that engages and disengages a locking pin 4596 from holes provided on a fixed or stationary member of the goniometric stage 4590 (e.g., holes 4595 illustrated in FIG. 45A). To rotate the $B_0$ magnet, release mechanism 4594 is pressed in an upward direction to disengage the locking pin 4596 from the hole in which it is currently positioned. For example, handle 4592 allows a user to place a hand on the handle and squeeze release mechanism 4594 towards the handle to release the locking pin 4596, as discussed in further detail below in connection with FIGS. 46A and 46B. With the locking pin 4596 disengaged, the $B_0$ magnet may then be rotated or tilted to the desired incline using handle 4592. Once the $B_0$ magnet has been rotated to the desired angle, release mechanism 4594 may be released so that the locking pin 4596 engages with a corresponding hole at the new position, locking the mechanism in place at the desired angle. FIGS. 45C and 45D illustrate the goniometric stage 4590 coupled to the bottom side of the lower magnet apparatus 4510 and base 4550.

Figure 46A:
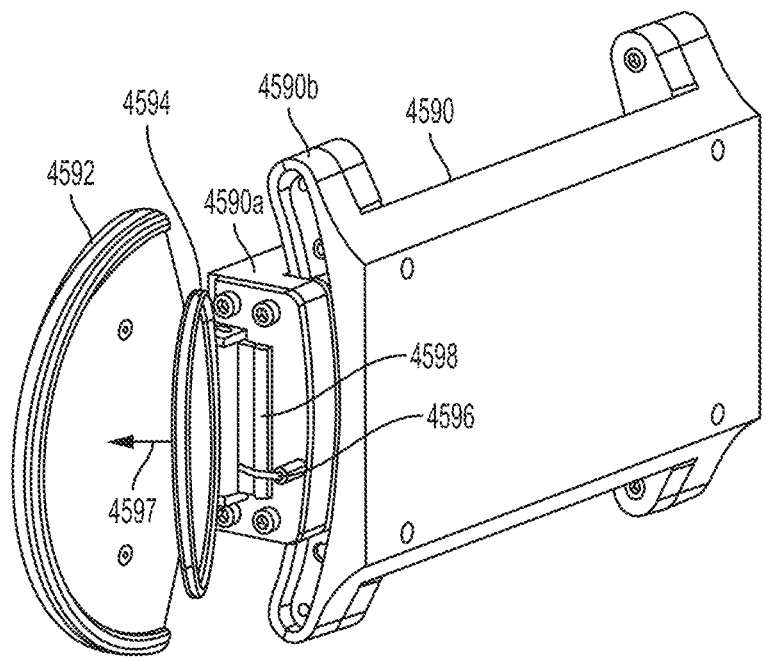
FIGS. 46A and 46B illustrate exemplary components of a positioning mechanism, in accordance with some embodiments.
Figure 46B:
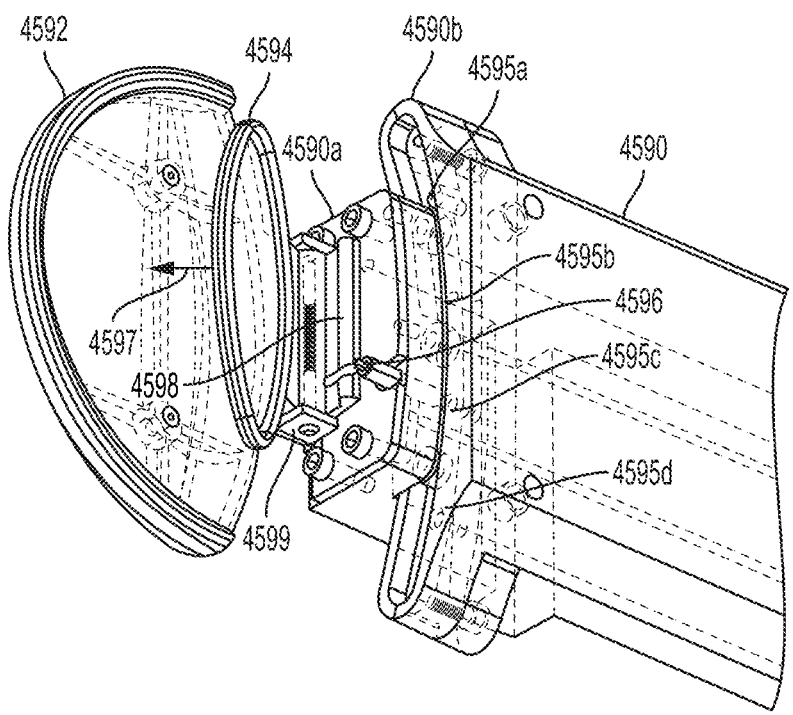

FIGS. 46A and 46B illustrate a closer view of the exemplary goniometric stage 4590 discussed in the foregoing. As shown, release mechanism 4594 is rotatably coupled to moveable stage component 4590a via axle 4599. When force is applied to release mechanism 4594 in the direction shown by arrow 4597 (e.g., by gripping handle 4592 and release mechanism 4594 with a hand and squeezing or lifting the release mechanism towards the handle), release mechanism 4594 rotates about axle 4599 and raises portion 4598 to lift locking pin 4596 out of hole 4595c in which it is currently positioned. When locking pin 4596 is lifted from the hole as shown by the phantom lines in FIG. 46B, moveable stage component 4590a is released from its locked position and allowed it to slide within stationary stage component 4590b. When the moveable stage component 4590a is moved to its desired location, release mechanism 4594 can be release to lock moveable stage component 4590a into the desired position. For example, a spring mechanism may be coupled to the locking pin so that when release mechanism 4594 is released, the spring force causes the locking pin 4596 to return to its locked position. While exemplary goniometric stage 4590 includes four holes (e.g., holes 4595a, 4595b, 4595c and 4595d), any number of holes at any location may be provided to provide a desired granularity to the angles at which the $B_0$ magnet can be positioned, as the aspects are not limited in this respect. It should be appreciated that goniometric stage 4590 allows the $B_0$ magnet to be rotated without movement of the center of mass, permitting the magnet to be rotated by hand. However, other mechanisms that rotate the center of mass may also be used, as the aspects are not limited in this respect.

Figure 47:
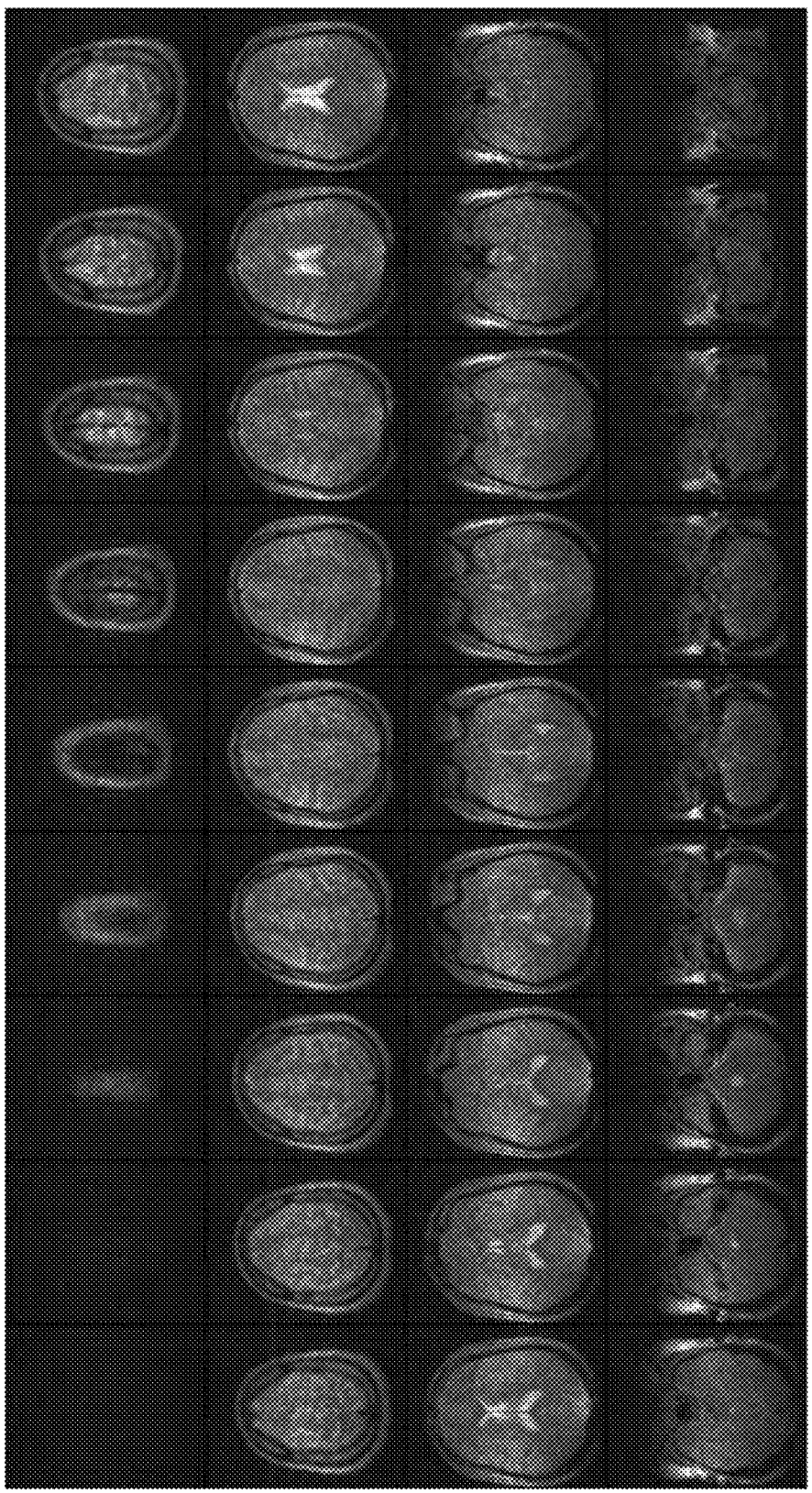
FIGS. 47-50 illustrate images obtained using the low-field MRI systems described herein, in accordance with some embodiments.
Figure 48:
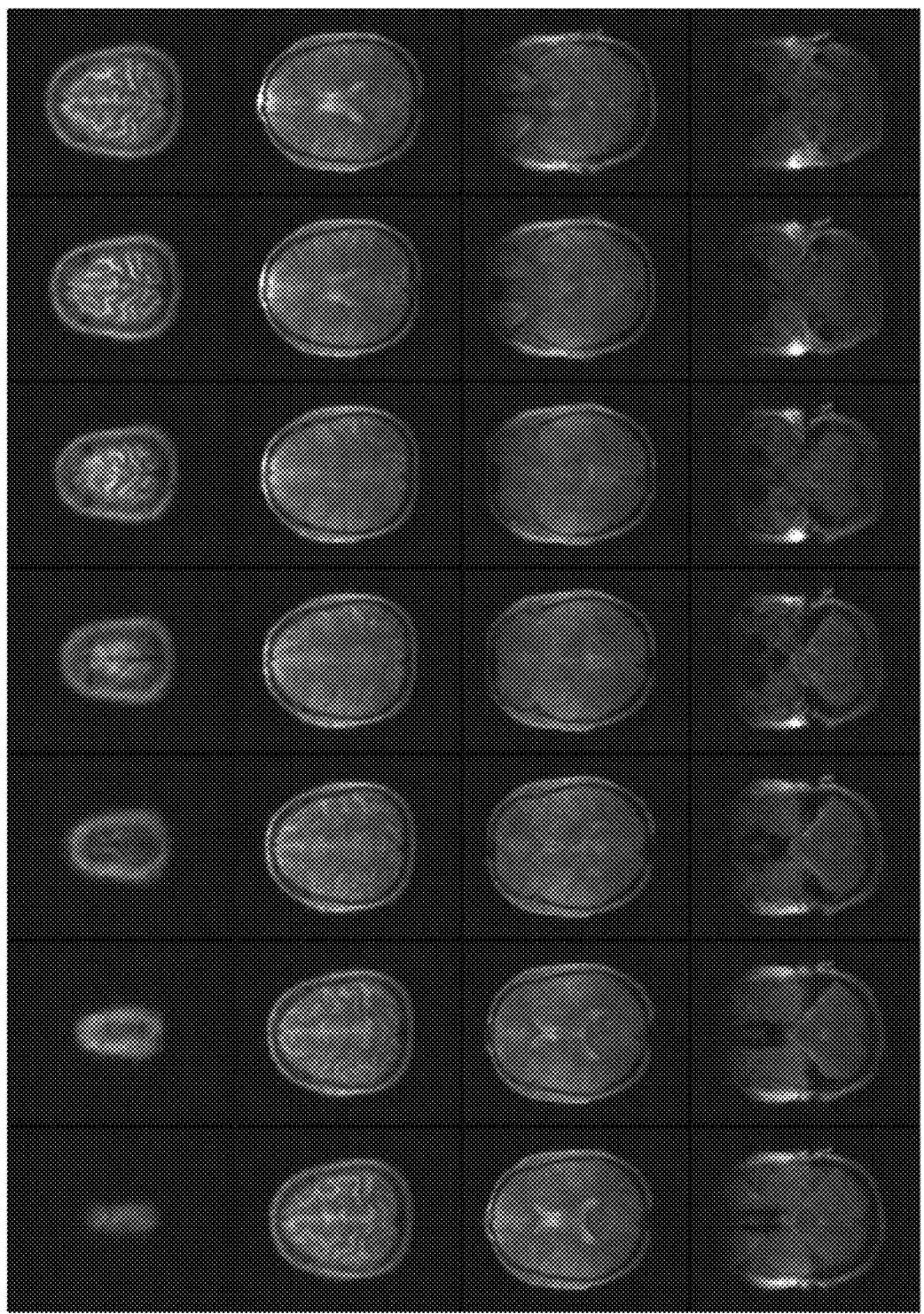
Figure 49:
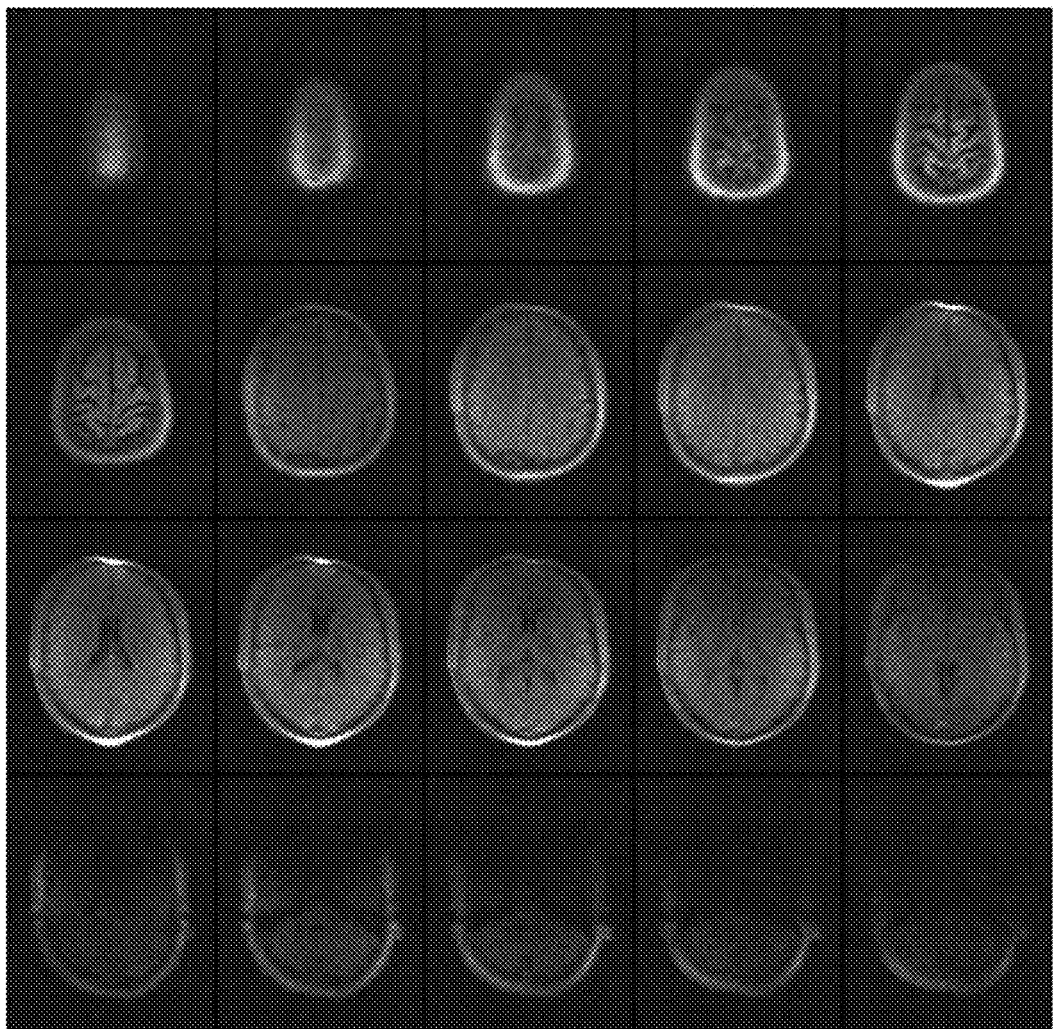
Figure 50:
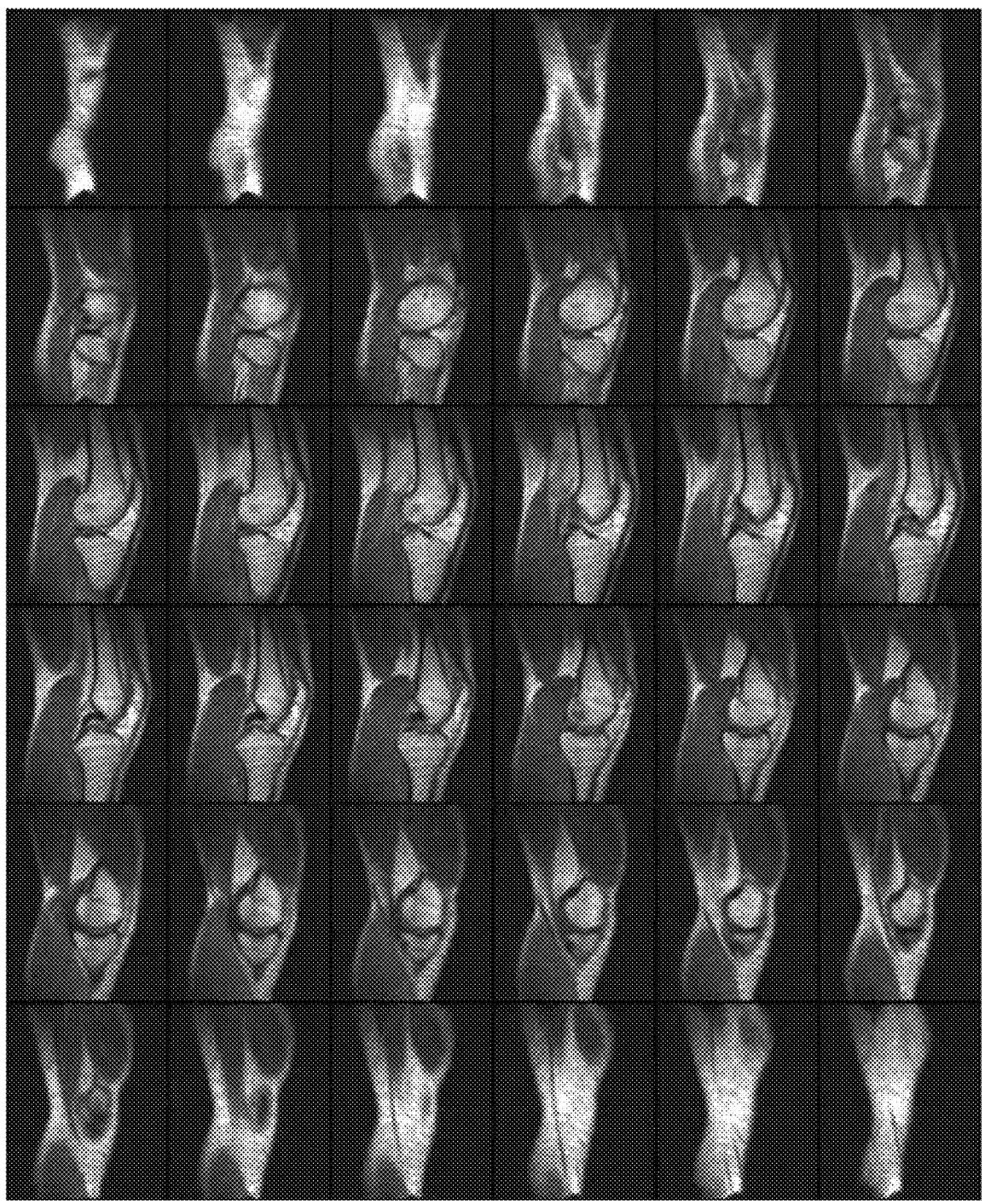

FIG. 47 illustrates the results of a 3 minute brain scan using a portable MRI system incorporating aspects of the techniques described herein (e.g., low field MRI system 1900, 3900, 4000, etc.) operating with a $B_0$ magnetic field having a field strength of approximately 50 mT. The proton density images were obtained using a balanced steady state free precession (bSSFP) pulse sequence and have 2.4×2.2×5 mm resolution. FIG. 48 illustrates the results of a 14 minute brain scan from a portable MRI system operating at a field strength of approximately 50 mT using a bSSFP pulse sequence. The resolution of the proton density images in FIG. 47 is 1.7×1.7×4 mm. FIG. 49 illustrates the result of a 15 minute brain scan from a portable MRI system operating at a field strength of approximately 50 mT using a T2 fluid-attenuated inversion recovery (FLAIR) pulse sequence. The resolution of the T2 images in FIG. 49 are 2×2×5 mm. FIG. 50 illustrates a 15 minute scan of the knee using a portable MRI system operating at approximately 50 mT using a bSSFP pulse sequence. The resolution of the proton density images in FIG. 50 is 1.7×1.7×3 mm.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media)

(e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-discussed function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A yoke for capturing and directing at least some of a $B_0$ magnetic field generated by a magnetic resonance imaging system, the yoke comprising:
   a first plate comprising ferromagnetic material;
   a second plate comprising ferromagnetic material and positioned opposite the first plate such that an imaging region exists therebetween; and
   a frame comprising ferromagnetic material,
      wherein the frame is coupled to the first plate and the second plate to provide a path for at least some of the $B_0$ magnetic field between the first plate and the second plate,
      wherein the frame comprises a first support and a second support, each comprising ferromagnetic material and spaced apart from one another by a gap, the second support being disposed at a greater distance from the imaging region than the first support.

2. The yoke of claim 1, wherein the frame further comprises a first arm portion comprising ferromagnetic material coupled to the first plate and a second arm portion comprising ferromagnetic material coupled to the second plate, and wherein the first and second supports are coupled between the first arm portion and the second arm portion.

3. The yoke of claim 2, wherein the frame is substantially C-shaped.

4. The yoke of claim 2, wherein the first arm portion and the second arm portion each comprise a tapered portion over which a thickness of the respective arm portion varies.

5. The yoke of claim 1, wherein the gap is an air gap.

6. The yoke of claim 1, wherein the first plate and the second plate are substantially circular.

7. A magnetic resonance imaging system, comprising:
   the yoke of claim 1; and
   at least one $B_0$ magnet configured to produce the $B_0$ magnetic field.

8. The magnetic resonance imaging system of claim 7, wherein the at least one $B_0$ magnet comprises:
   at least one first $B_0$ magnet coupled to the first plate; and
   at least one second $B_0$ magnet coupled to the second plate.

9. The magnetic resonance imaging system of claim 8, wherein the at least one first $B_0$ magnet and the at least one second $B_0$ magnet each comprises a permanent $B_0$ magnet.

10. The magnetic resonance imaging system of claim 8, wherein the at least one first $B_0$ magnet, the at least one second $B_0$ magnet, and the yoke together weigh less than or equal to approximately 600 kilograms and greater than or equal to approximately 450 kilograms.

11. An apparatus for providing a $B_0$ magnetic field for a magnetic resonance imaging system, the apparatus comprising:
   at least one $B_0$ magnet configured to produce a magnetic field to contribute to the $B_0$ magnetic field for the magnetic resonance imaging system; and
   a yoke configured to capture and direct at least some of the magnetic field generated by the $B_0$ magnet to increase magnetic flux density within an imaging region of the magnetic resonance imaging system, the yoke comprising:
      a first plate comprising ferromagnetic material;
      a second plate comprising ferromagnetic material and disposed opposite the first plate such that the imaging region exists therebetween;
      a frame comprising ferromagnetic material,
         wherein the frame is coupled to the first plate and the second plate to provide a path for at least some of the magnetic field produced by the $B_0$ magnet between the first plate and the second plate,
         wherein the frame comprises a first support and a second support, each comprising ferromagnetic material and spaced apart from one another by a gap, the second support being disposed at a greater distance from the imaging region than the first support.

12. The apparatus of claim 11, wherein the frame further comprises a first arm portion comprising ferromagnetic material coupled to the first plate and a second arm portion comprising ferromagnetic material coupled to the second plate, and wherein the first and second supports are coupled between the first arm portion and the second arm portion.

13. The apparatus of claim 12, wherein the frame is substantially C-shaped.

14. The apparatus of claim 12, wherein the first arm portion and the second arm portion each comprise a tapered portion over which a thickness of the respective arm portion varies.

15. The apparatus of claim 11, wherein the gap is an air gap.

16. The apparatus of claim 11, wherein the first plate and the second plate are substantially circular.

17. The apparatus of claim 11, wherein the at least one $B_0$ magnet comprises:
   at least one first $B_0$ magnet coupled to the first plate; and
   at least one second $B_0$ magnet coupled to the second plate.

18. The apparatus of claim 17, wherein the at least one first $B_0$ magnet and the at least one second $B_0$ magnet each comprises a permanent $B_0$ magnet.

19. The apparatus of claim 17, wherein the at least one first B0 magnet, the at least one second B0 magnet, and the yoke together weigh less than or equal to approximately 600 kilograms and greater than or equal to approximately 450 kilograms.

20. A magnetic resonance imaging system, comprising:
   the apparatus of claim 11;
   a plurality of gradient coils configured to, when operated, generate magnetic fields to provide spatial encoding of emitted magnetic resonance signals;
   at least one radio frequency transmit coil; and
   a power system comprising one or more power components configured to provide power to the magnetics system to operate the magnetic resonance imaging system.

21. An apparatus for providing a $B_0$ magnetic field for a magnetic resonance imaging system, the apparatus comprising:
- a first $B_0$ magnet and a second $B_0$ magnet arranged relative to one another so that an imaging region is provided therebetween;
- a first plate comprising ferromagnetic material coupled to the first $B_0$ magnet;
- a second plate comprising ferromagnetic material coupled to the second $B_0$ magnet; and
- a frame comprising ferromagnetic material coupled to the first plate and the second plate, the frame comprising a first support and a second support, each comprising ferromagnetic material and spaced apart from one another by a gap, the second support being disposed at a greater distance from the imaging region than the first support.

22. The apparatus of claim 21, wherein the frame further comprises a first arm portion comprising ferromagnetic material coupled to the first plate and a second arm portion comprising ferromagnetic material coupled to the second plate, and wherein the first and second supports are coupled between the first arm portion and the second arm portion.

23. The apparatus of claim 22, wherein the frame is substantially C-shaped.

24. The apparatus of claim 22, wherein the first arm portion and the second arm portion each comprise a tapered portion over which a thickness of the respective arm portion varies.

25. The apparatus of claim 21, wherein the gap is an air gap.

26. The apparatus of claim 21, wherein the first plate and the second plate are substantially circular.

27. The apparatus of claim 11, further comprising:
- a first plurality of $B_0$ magnets coupled to the first plate and comprising the first $B_0$ magnet; and
- a second plurality of $B_0$ magnets coupled to the second plate and comprising the second $B_0$ magnet.

28. The apparatus of claim 27, wherein the first plurality of $B_0$ magnets and the second plurality of $B_0$ magnets each comprise a permanent $B_0$ magnet.

29. The apparatus of claim 27, wherein the first plurality of $B_0$ magnets, the second plurality of $B_0$ magnets, the first plate, the second plate, and the frame together weigh less than or equal to approximately 600 kilograms and greater than or equal to approximately 450 kilograms.

30. The apparatus of claim 21, further comprising a yoke, the yoke comprising:
- the first and second plates; and
- the frame,
- wherein the yoke is configured to capture and direct at least some of the magnetic field generated by the first and second $B_0$ magnets to increase magnetic flux density within the imaging region.

\* \* \* \* \*